(12) United States Patent  
Feinberg et al.

(10) Patent No.: US 11,560,583 B2
(45) Date of Patent: Jan. 24, 2023

(54) HETEROLOGOUS CAROTENOID PRODUCTION IN MICROORGANISMS

(71) Applicant: KnipBio, Inc., Lowell, MA (US)

(72) Inventors: Lawrence F. Feinberg, Lowell, MA (US); Daniel R. Smith, Lowell, MA (US); Bonnie D. McAvoy, Lowell, MA (US); Catherine J. Pujol-Baxley, Lowell, MA (US); Christopher J. Marx, Lowell, MA (US)

(73) Assignee: KNIPBIO, INC., Lowell, MA (US)

( * ) Notice: Subject to any disclaimer, the term of this patent is extended or adjusted under 35 U.S.C. 154(b) by 490 days.

(21) Appl. No.: 16/618,048

(22) PCT Filed: May 31, 2018

(86) PCT No.: PCT/US2018/035505  
§ 371 (c)(1),  
(2) Date: Nov. 27, 2019

(87) PCT Pub. No.: WO2018/222946  
PCT Pub. Date: Dec. 6, 2018

(65) Prior Publication Data  
US 2020/0149083 A1 May 14, 2020

Related U.S. Application Data

(60) Provisional application No. 62/513,892, filed on Jun. 1, 2017.

(51) Int. Cl.  
*C12N 15/09* (2006.01)  
*C12P 23/00* (2006.01)  
(Continued)

(52) U.S. Cl.  
CPC ............ *C12P 23/00* (2013.01); *A23K 20/179* (2016.05); *A23K 50/80* (2016.05); *A61K 9/0056* (2013.01);  
(Continued)

(58) Field of Classification Search  
CPC ..................................................... C12N 15/09  
See application file for complete search history.

(56) References Cited

U.S. PATENT DOCUMENTS 3,891,504 A 6/1975 Schocher  
5,429,939 A 7/1995 Misawa et al.  
(Continued)

FOREIGN PATENT DOCUMENTS

EP 0747483 B1 3/2004  
EP 1780281 A1 5/2007  
(Continued)

OTHER PUBLICATIONS

Pasamontes et al., "Isolation and characterization of the carotenoid biosynthesis genes of *Flavobacterium* sp. strain R1534," Gene 185:35-41, 1997.*

(Continued)

*Primary Examiner* — Rosanne Kosson  
(74) *Attorney, Agent, or Firm* — FisherBroyles, LLP; Jill Jacobson

(57) ABSTRACT

Non-naturally occurring microorganisms are provided that produce C40 carotenoid compound(s), utilizing exogenously added enzyme activities. Methods of producing C40 carotenoid compounds in microbial cultures, and feed and nutritional supplement compositions that include the C40 carotenoid compounds produced in the microbial cultures, are also provided.

12 Claims, 9 Drawing Sheets  
Specification includes a Sequence Listing.

(51) Int. Cl.

| | |
|---|---|
| A23K 20/179 | (2016.01) |
| A23K 50/80 | (2016.01) |
| A61K 9/00 | (2006.01) |
| A61K 31/122 | (2006.01) |
| B01D 3/00 | (2006.01) |
| C12N 15/74 | (2006.01) |

(52) U.S. Cl.
CPC ............ *A61K 31/122* (2013.01); *B01D 3/001* (2013.01); *C12N 15/74* (2013.01)

(56) References Cited

U.S. PATENT DOCUMENTS

| | | | |
|---|---|---|---|
| 5,466,599 | A | 11/1995 | Jacobson et al. |
| 5,530,188 | A | 6/1996 | Ausich et al. |
| 5,530,189 | A | 6/1996 | Ausich et al. |
| 5,545,816 | A | 8/1996 | Ausich et al. |
| 5,656,472 | A | 8/1997 | Ausich et al. |
| 5,691,190 | A | 11/1997 | Girard et al. |
| 6,087,152 | A | 7/2000 | Hohmann et al. |
| 6,124,113 | A | 9/2000 | Hohmann et al. |
| 6,207,409 | B1 | 3/2001 | Hohmann et al. |
| 6,291,204 | B1 | 9/2001 | Pasamontes et al. |
| 6,613,543 | B2 | 9/2003 | Hohmann et al. |
| 6,929,928 | B2 | 8/2005 | Cheng et al. |
| 6,969,595 | B2 | 11/2005 | Brzostowicz et al. |
| 7,064,196 | B2 | 6/2006 | Cheng et al. |
| 7,232,666 | B2 | 6/2007 | Sharpe et al. |
| 7,422,873 | B2 | 9/2008 | Stead et al. |
| 7,932,077 | B2 | 4/2011 | Damude et al. |
| 2003/0003528 | A1 | 1/2003 | Brzostowicz et al. |
| 2004/0078846 | A1 | 4/2004 | Desouza et al. |
| 2005/0019852 | A1 | 1/2005 | Cheng et al. |
| 2005/0124033 | A1 | 6/2005 | Sharpe et al. |
| 2005/0227311 | A1 | 10/2005 | Cheng et al. |
| 2005/0287625 | A1 | 12/2005 | Miler et al. |
| 2006/0003403 | A1 | 1/2006 | Tang et al. |
| 2006/0035312 | A1 | 2/2006 | Cheng et al. |
| 2006/0053513 | A1 | 3/2006 | Steiger et al. |
| 2006/0162020 | A1 | 7/2006 | Sauer et al. |
| 2007/0065903 | A1 | 3/2007 | Dicosimo et al. |
| 2007/0226814 | A1 | 9/2007 | Kly et al. |
| 2007/0238149 | A1 | 10/2007 | Chen et al. |
| 2008/0216756 | A1 | 9/2008 | Horsfall |
| 2009/0202672 | A1 | 9/2009 | Hartnell |
| 2009/0298146 | A1 | 12/2009 | Choi et al. |
| 2012/0156718 | A1 | 6/2012 | Flachmann et al. |
| 2015/0191712 | A1 | 7/2015 | Bott et al. |
| 2015/0315599 | A1 | 11/2015 | Shetty et al. |

FOREIGN PATENT DOCUMENTS

| | | | |
|---|---|---|---|
| EP | 2199399 | A1 | 6/2010 |
| EP | 2471919 | A1 | 7/2012 |
| WO | 2015/021352 | A2 | 2/2015 |
| WO | 2017/083351 | A1 | 5/2017 |
| WO | 2018/106549 | A1 | 6/2018 |
| WO | 2018/222946 | A1 | 12/2018 |

OTHER PUBLICATIONS

Humbelin et al., "Genetics of isoprenoid biosynthesis in Paracoccus zeaxanthinifaciens," Gene 297:129-139, 2002.*
Misawa, N., et al., Production of Beta-Carotene in Zymomonas mobilis and Agrobacterium tumefaciens by Introduction of the Biosynthesis Genes from Erwinia uredovora, Applied and Environmental Microbiology, 57 (6):1847-1849, 1991.
Sedkova, N., et al., Diversity of Carotenoid Synthesis Gene Clusters from Environmental Enterobacteriaceae Strains, Applied and Environmental Microbiology, 71(12):8141-8146, 2005.
Van Dien, S., et al., Genetic Characterization of the Carotenoid Biosynthetic Pathway in Methylobacterium extorquens AM1 and Isolation of a Colorless Mutant, Applied and Environmental Microbiology, 69(12):7563-7566, 2003.
Van Dien, S., et al., Methylobacterium extorquens AM1 and Isolation of a Colorless Mutant, Applied and Environmental Microbiology 69(12):7563-7566, 2003.
Wang, X., et al., Astaxanthin-Rich Algal Meal and Vitamin C Inhibit Helicobacter pylori Infection in BALB/cA Mice, Antimicrobial Agenta and Chemotherapy 44(9):2452-2457, 2000.
Wang, C., et al., Directed evolution of metabolically engineered *Escherichia coli* for carotenoid production, Biotechnol. Progr. 16(6):922-926, 2000.
Welander, P., et al., Hopanoids Play a Role in Membrane Integrity and pH Homeostasis in Rhodopseudomonas palustris TIE-1, Journal of Bacteriology 191(19):61415-6156, 2009.
Ye, R., et al., Construction of the astaxanthin biosynthetic pathway in a methanotrophic bacterium *Methylomonas* sp. strain 16a, J Ind Microbiol 34:289-299, 2007.
Zeeshan, M., et al., The longest polyene, Organic Letters 14(21):5496-5498, 2012.
Albrecht, M., et al., Metabolic engineering of the terpenoid biosynhtetic pathway of *Escherichia coli* for production of the carotenoids Beta-carotene and zeaxanthin, Biotechnology Letters 21:791-795, 1999.
Alcaino, J. et al., Carotenoid Distribution in Nature, Subcellular Biochemistry 79:3-33, 2016.
Altshcul, S. et al., Basic Local Alignment Search Tool, J. Mol. Biol. 215:403-410, 1990.
Berry, A. , et al., *Paracoccus zeaxanthinifaciens* sp. nov., a zeaxanthin-producing bacterium, International Journal of Systematic and Evolutionary Microbiology 53:231-238, 2003.
Britton, G., The biosynthesis of carotenoids: a progress report, Pure & Appl. Chem. 63(1):101-108, 1991.
Chew, B., et al., A comparison of the anticancer activities of dietary beta-carotene, canthaxanthin and astaxanthin in mice in vivo, Anticancer Res. 19(3A):1849-1853, 1999.
Chi, S., et al., Assembly of functional photosystem complexes in Rhodobacter sphaeroides incorporating carotenoids from the spiriloxanthin pathway. Biochimica et Biophysica Acta, 1847:189-201, 2015.
Chou, H.-H., et al., PLoS Genetics, 5(9):e1000652, 2009.
Chubiz, L., et al., A novel pair of inducible expression vectors for use in Methylobacterium extorquens, BMC Research Notes 6:183, 2013.
D'Argenio, D., et al., *Drosophila* as a Model Host for Pseudomonas aeruginosa Infection, J. Bacteriol. 183 (4):1466-1471, 2001.
Delaney, N., et al., Development of an Optimized Medium, Strain and High-Throughput Culturing Methods for Methylobacterium extorquens, PLoS One 8(4):e62957, 2013.
Englund, E., et al., Production of Isoprenoids in Synechocystis PCC 6803, 11th Workshop on Cyanobacteria, Washington University in St. Louis, Aug. 7-11, 2013.
Englund, E., Production of Squalene in *Synechocystis* sp. PCC 6803, PLOS ONE 9(3):e90270, 2014.
Farmer, W. et al., Precursor balancing for metabolic engineering of lycopene productionin *Escherichia coli*, Biotechnol. Prog. 17:57-61, 2001.
Foss, P., et al., Carotenoids in diets for salmonids. I.Pigmentation of rainbow trout with the individual optical isomers of astaxanthin in comparison with canthaxanthin, Aquaculture 41(3):213-26, 1984.
Giovannucci, E., et al.,Intake of carotenoids and retinol in relation to risk of prostate cancer, J. Natl. Cancer Inst. 87(23):1767, 1995.
Henikoff, S., et al., Amino acid substitution matrices from protein blocks, Proc. Natl. Acad. Sci. USA, 89:10915-10919, 1992.
Henke, N., et al., Production of the Marine Carotenoid Astaxanthin by Metabolically Engineered Corynebacterium glutamicum, Marine Drugs 14:124, 2016.
Higgins, D., et al., CLUSTAL: a package for performing multiple sequence alignment on a microcomputer, Gene 73:237-244, 1988.
Higuera-Ciapara, I., et al., Astaxanthin: a review of its chemistry and applications, Crit Rev Food Sci Nutr 46 (2):185-196, 2006.
Jyonouchi, H., et al., Studies of immunomodulating actions of carotenoids. I. Effects of beta-carotene and astaxanthin on murine

(56) References Cited

OTHER PUBLICATIONS lymphocyte functions and cell surafce marker expression in in vitro culture systems, Nutr Cancer 16(2):93-105, 1991.

Kalinowski, C., et al., Effect of different carotenoid sources and their dietary levels on red porgy (*Pagrus pagrus*) growth and skin colour. Aquaculture 244(1-40:223-231, 2005.

Karlin, S., et al., Applications and statistics for multiple high-scoring segments in molecular sequences, Proc. Natl. Acad. Sci. USA, 90: 5873-5877, 1993.

Kim, Y., et al., Composition of corn dry=grind ethanol by-products: DDGS, wet cake, and thin stillage, Bioresource Technology 99(12):5165-5176, 2008.

Kim, S., et al., The astaxanthin dideoxyglycoside biosynthesis pathway in *Sphingomonoas* sp. PB304, Appliled Microbiol Biotechnol, DOI 10.1007/s00253-014-6050-7, 2014.

Kwon, S.-K., et al., Genomic Makeup of the Marine Flavobacterium Nonlabeens (Donghaeana) dokdonensis and Identification of a Novel Class of Rhodopsins, Genome Biol. Evol. 5(1):187-199, 2013.

Lee, J., et al., Cloning and characterization of the astaxanthin biosynthesis gene cluster from the marine bacterium Paracoccus haeundaensis, Gene 370:86-95, 2006.

Lee, M.-C., et al., Asymmetric, Bimodal Trade-Offs During Adaptation of Methylbacterium to Distinct Growth Substrates, Evolution 63:2816-2830, 2009.

Makino, T., et al., Characterization of Cyanobacterial Carotenoid Ketolase CrtW and Hydroxylase CrtR by Commplementation Analysis in *Escherichia coli*, Plant Cell Physiol. 49(12):1867-1878, 2008.

Marx, C., et al., Broad-Host-Range cre-lox System for Antibiotic Marker Recycling in Gram-Negative Bacteria, BioTechniques 33(5):1062-1067, 2002.

Marx, C., et al., Development of improved versatile broad-host-range vectors for use in methylotrophs and other Gram-negative bacteria, Microbiology 147:2065-2075, 2001.

Marx, C., Development of a broad-host-range sacB-based vector for unmarked allelic exchange, BMC Research Notes, doi:10.1186/1756-0500-1-1, 2008.

Marx, C., et al., Novel Methylotrophy Genes of Methylobacterium extorquens AM1 Identified by using Transposon Mutagenesis Including a Putative Dihydromethanopterin Reductase, J. Bacteriol. 185(2):669-673, 2003.

Matthews, S., et al., Astaxanthin binding protein in Atlantic salmon, Comp. Biochem. Physiol. 144(2):206-214, 2006.

Miki, W., Biological functions and acativities of animal carotenoids, Pure Appl. Chem 63(1):141-146, 1991.

Misawa, N., Metabolic Engineering for production of carotenoids in non-carotenogenic bacteria and yeasts, J. Biotechnol. 59(3):169-181, 1998.

Miura, Y., et al., Production of the Carotenoids Lycopene, Beta-Carotene, and Astaxanthin in the Food Yeast Candida utilis, Appl Environm. Microbiol 64(4):1226-1229, 1998.

Nishida, Y., et al., Elucidation of a Carotenoid Biosynthesis Gene Cluster Encodihng a Novel EnzyAme, 2,2'-Beta-Hydroxylase, from *Brevundimonas* sp., Strain SD212 and Combinatorial Biosynthesis of New or Rare Xanthophylls, Applied and Environmental Microbiology 71(8):4286-4296.

Pasamontes, L., et al., Isolation and characterization of the carotenoid biosynthesis genes of *Flavobacterium* sp. strain R1534, Gene 185:35-41, 1997.

Scaife, M., et al., Characterization of Cyanobacterial Beta-Carotene Ketolase and Hydroxylase Genes in *Escherichia coli*, and Their Application for Astaxanthin Biosynthesis, Biotehnology and Bioengineering 103(5):944-955, 2009.

Rust, M., et al.. The Future of Aquafeeds, NOAA Technical memorandum NMFS F/SPO-124, 2011.

Pearson, W., et al., Improved tools for biological sequence comparison, Proc. Natl. Acad. Sci.USA, 85:2444-2448, 1988.

Shahidi, F., et al., Carotenoid Pigments in Seafoods and Aquaculture, Critical Reviews in Food Science and Nutrition 38(1):1-67, 1998.

Sharpe, P., et al., Use of Transposon Promoter-Probe Vectors in the Metabolic Engineering of the Obligate Methanotroph *Mthylomonas* sp. Strain 16a for Enhanced C40 Carotenoid Synthesis, Applied and Environmental Microbiology 73(6):1721-1728, 2007.

Sivy, T., et al., Evidence of Isoprenoid Precursor Toxicity in Bacillus subtilis, Bioscience, Biotechnology, and Biochemistry 75(12):2376-2383, 2011.

Sliwka, H.-R., et al., Superlative catotenoids, Acta ABP Biochimica Polonica 59(1):17-20, 2012.

Tang, X.-S., et al., Improvement of a CrtO-type of beta-carotene ketolase for canthxanthin production in *Methylomonas* sp., Metabolic Engineering 9:348-354, 2007.

Tlusty, M., et al., A transdisciplinary approach to the initial validation of a single cell protein as an alternatiae protein source for use in aquafeeds, PeerJ, DOI 10.7717/peerj.3170, 2017.

Tao, L., et al., Novel Carotenoid Oxidase Involved in Biosynthesis of 4,4'-Diapolycopene Dialdehyde, Applied and Environmental Microbiology 71(6):3294-33-1, 2005.

Tao, L., et al., Expression of bacterial hemoglobin genes to improve astaxanthin production in a methanotrophic bacteirum *Methylomonas* sp., Appl Micriobiol Biotechnol 74:625-633, 2007.

* cited by examiner

SEQUENCE LISTING

<160> NUMBER OF SEQ ID NOS: 52

<210> SEQ ID NO 1
<211> LENGTH: 6760
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 1

| acccacgctc | accggctcca | gatttatcag | caataaacca | gccagccgga | agggccgagc | 60 |
| gcagaagtgg | tcctgcaact | ttatccgcct | ccatccagtc | tattaatatc | cccgtgtcgg | 120 |
| acctgcaggg | gggggggga | aagccacgtt | gtgtctcaaa | atctctgatg | ttacattgca | 180 |
| caagataaaa | atatatcatc | atgaacaata | aaactgtctg | cttacataaa | cagtaataca | 240 |
| aggggtgtta | tgagccatat | tcaacgggaa | acgtcttgct | cgaggccgcg | attaaattcc | 300 |
| aacatggatg | ctgatttata | tgggtataaa | tgggctcgcg | ataatgtcgg | gcaatcaggt | 360 |
| gcgacaatct | atcgattgta | tgggaagccc | gatgcgccag | agttgtttct | gaaacatggc | 420 |
| aaaggtagcg | ttgccaatga | tgttacagat | gagatggtca | gactaaactg | gctgacggaa | 480 |
| tttatgcctc | ttccgaccat | caagcatttt | atccgtactc | ctgatgatgc | atggttactc | 540 |
| accactgcga | tccccgggaa | aacagcattc | caggtattag | aagaatatcc | tgattcaggt | 600 |
| gaaaatattg | ttgatgcgct | ggcagtgttc | ctgcgccggt | tgcattcgat | tcctgtttgt | 660 |
| aattgtcctt | ttaacagcga | tcgcgtattt | cgtctcgctc | aggcgcaatc | acgaatgaat | 720 |
| aacggtttgg | ttgatgcgag | tgattttgat | gacgagcgta | atggctggcc | tgttgaacaa | 780 |
| gtctggaaag | aaatgcataa | gcttttgcca | ttctccaccg | gattcagtcgt | cactcatggt | 840 |
| gatttctcac | ttgataacct | tattttttgac | gaggggaaat | taataggttg | tattgatgtt | 900 |

```
ggacgagtcg gaatcgcaga ccgataccag gatcttgcca tcctatggaa ctgcctcggt    960
gagttttctc cttcattaca gaaacggctt tttcaaaaat atggtattga taatcctgat   1020
atgaataaat tgcagtttca tttgatgctc gatgagtttt tctaatcaga attggttaat   1080
tggttgtaac actggcagag cattacgctg acttgacggg acggaatatt attgaagcat   1140
ttatcagggt tattgtctca tgagcggata catatttgaa tgtatttaga aaaataaaca   1200 aatagggggtt ccgcgcacat ttccccgaaa agtgccacct gacgtctaga tctgaattca   1260
gctgtacaat tggtaccatg gatgggaggg cagcaggtgg gaaagcgggc agtgagcgca   1320
acgcaattaa tgtgagttag ctcactcatt aggcacccca ggctttacac tttatgcttc   1380
cggctcgtat gttgtgtgga attgtgagcg gataacaatt tcacacagga aacagctatg   1440
accatgatta cgccaagcta tttaggtgac actatagaat actcaagcta tgcatcaagc   1500
ttggtaccga gctcggatcc actagtaacg gccgccagtg tgctggaatt cgcccttcac   1560
ctgctgccag tacatatgct gcagctcgag cggccgcggg ccctacgtac gcgtgttaac   1620
cggtgagctc actagaggat ccagccgacc aggctttcca cgcccgcgtg ccgctccatg   1680
tcgttcgcgc ggttctcgga aacgcgctgc cgcgtttcgt gattgtcacg ctcaagcccg   1740
tagtcccgtt cgagcgtcgc gcagaggtca gcgagggcgc ggtaggcccg atacggctca   1800
tggatggtgt ttcgggtcgg gtgaatcttg ttgatggcga tatggatgtg caggttgtcg   1860
gtgtcgtgat gcacggcact gacgcgctga tgctcggcga agccaagccc agcgcagatg   1920
cggtcctcaa tcgcgcgcaa cgtctccgcg tcgggcttct ctcccgcgcg aagctaacc   1980 agcacgtgat aggtcttgtc ggcctcggaa cgggtgttgc cgtgctgggt cgccatcacc   2040
tcggccatga cagcgggcag ggtgtttgcc tcgcagttcg tgacgcgcac gtgacccagg   2100
cgctcggtct tgccttgctc gtcggtgatg tacttcacca gctccgcgaa gtcgctcttc   2160
ttgatggagc gcatggggac gtgcttggca atcacgcgca ccccccggcc gttttagcgg   2220
ctaaaaaagt catggctctg ccctcgggcg gaccacgccc atcatgacct tgccaagctc   2280
gtcctgcttc tcttcgatct tcgccagcag ggcgaggatc gtggcatcac cgaaccgcgc   2340
cgtgcgcggg tcgtcggtga gccagagttt cagcaggccg cccaggcggc caggtcgcc   2400 attgatgcgg gccagctcgc ggacgtgctc atagtccacg acgcccgtga ttttgtagcc   2460
ctggccgacg gccagcaggt aggccgacag gctcatgccg gccgccgccg ccttttcctc   2520
aatcgctctt cgttcgtctg gaaggcagta caccttgata ggtgggctgc ccttcctggt   2580
tggcttggtt tcatcagcca tccgcttgcc ctcatctgtt acgccggcgg tagccggcca   2640
gcctcgcaga gcaggattcc cgttgagcac cgccaggtgc gaataaggga cagtgaagaa   2700
ggaacacccg ctcgcgggtg ggcctacttc acctatcctg cccggctgac gccgttggat   2760
acaccaagga aagtctacac gaaccctttg gcaaaatcct gtatatcgtg cgaaaaagga   2820
tggatatacc gaaaaaatcg ctataatgac cccgaagcag ggttatgcag cggaaaagcg   2880
ctgcttccct gctgttttgt ggaatatcta ccgactggaa acaggcaaat gcaggaaatt   2940
actgaactga ggggacaggc gagagacgat gccaaagagc tacaccgacg agctggccga   3000
gtgggttgaa tcccgcgcgg ccaagaagcg ccggcgtgat gaggctgcgg ttgcgttcct   3060
ggcggtgagg gcggatgtcg aggcggcgtt agcgtccggc tatgcgctcg tcaccatttg   3120
ggagcacatg cgggaaacgg ggaaggtcaa gttctcctac gagacgttcc gctcgcacgc   3180
caggcggcac atcaaggcca agcccgccga tgtgcccgca ccgcaggcca aggctgcgga   3240
acccgcgccg gcacccaaga cgccggagcc acggcggccg aagcaggggg gcaaggctga   3300
```

```
aaagccggcc cccgctgcgg ccccgaccgg cttcaccttc aacccaacac cggacaaaaa    3360
ggatccccaa ttctcatgtt tgacagctta tcatcgataa gctttaatgc ggtagtttat    3420
cacagttaaa ttgctaacgc agtcaggcac cgtgtatgaa atctaacaat gcgctcatcg    3480
tcatcctcgg caccgtcacc ctggatgctg taggcatagg cttggttatg ccggtactgc    3540
cgggcctctt gcgggatatc ggcattttct tttgcgtttt tatttgttaa ctgttaattg    3600
tccttgttca aggatgctgt ctttgacaac agatgttttc ttgcctttga tgttcagcag    3660
gaagcttggc gcaaacgttg attgtttgtc tgcgtagaat cctctgtttg tcatatagct    3720
tgtaatcacg acattgtttc ctttcgcttg aggtacagcg aagtgtgagt aagtaaaggt    3780
tacatcgtta ggatcaagat ccattttttaa cacaaggcca gttttgttca gcggcttgta    3840
tgggccagtt aaagaattag aaacataacc aagcatgtaa atatcgttag acgtaatgcc    3900
gtcaatcgtc atttttgatc cgcgggagtc agtgaacagg taccatttgc cgttcatttt    3960
aaagacgttc gcgcgttcaa tttcatctgt tactgtgtta gatgcaatca gcggtttcat    4020
cactttttc agtgtgtaat catcgtttag ctcaatcata ccgagagcgc cgtttgctaa    4080
ctcagccgtg cgtttttat cgcttttgcag aagttttttga cttcttgac ggaagaatga    4140
tgtgcttttg ccatagtatg ctttgttaaa taaagattct tcgccttggt agccatcttc    4200
agttccagtg tttgcttcaa atactaagta tttgtggcct ttatcttcta cgtagtgagg    4260
atctctcagc gtatggttgt cgcctgagct gtagttgcct tcatcgatga actgctgtac    4320
attttgatac gtttttccgt caccgtcaaa gattgattta taatcctcta caccgttgat    4380
gttcaaagag ctgtctgatg ctgatacgtt aacttgtgca gttgtcagtg tttgtttgcc    4440
gtaatgttta ccggagaaat cagtgtagaa taaacggatt tttccgtcag atgtaaatgt    4500
ggctgaacct gaccattctt gtgtttggtc ttttaggata gaatcatttg catcgaattt    4560
gtcgctgtct ttaaagacgc ggccagcgtt tttccagctg tcaatagaag tttcgccgac    4620
ttttgatag aacatgtaaa tcgatgtgtc atccgcattt ttaggatctc cggctaatgc    4680
aaagacgatg tggtagccgt gatagtttgc gacagtgccg tcagcgtttt gtaatggcca    4740
gctgtcccaa acgtccaggc cttttgcaga agagatattt ttaattgtgg acgaatcgaa    4800
ttcaggaact tgatattttt catttttttg ctgttcaggg atttgcagca tatcatggcg    4860
tgtaatatgg gaaatgccgt atgtttcctt atatggcttt tggttcgttt ctttcgcaaa    4920
cgcttgagtt gcgcctcctg ccagcagtgc ggtagtaaag gttaatactg ttgcttgttt    4980
tgcaaacttt ttgatgttca tcgttcatgt ctcctttttt atgtactgtg ttagcggtct    5040
gcttcttcca gccctcctgt ttgaagatgg caagttagtt acgcacaata aaaaaagacc    5100
taaaatatgt aagggtgac gccaaagtat acactttgcc ctttacacat ttaggtctt    5160
gcctgcttta tcagtaacaa acccgcgcga tttactttc gacctcattc tattagactc    5220
tcgtttggat tgcaactggt ctattttcct cttttgtttg atagaaaatc ataaaaggat    5280
ttgcagacta cgggcctaaa gaactaaaaa atctatctgt ttcttttcat tctctgtatt    5340
ttttatagtt tctgttgcat gggcataaag ttgccttttt aatcacaatt cagaaaatat    5400
cataatatct catttcacta ataatagtg aacggcaggt atatgtgatg ggttaaaaag    5460
gatcgatcct ctagccacgg gtgcgcatga tcgtgctcct gtcgttgagg acccggctag    5520
gctggcgggg ttgccttact ggttagcaga atgaatcacc gatacgcgag cgaacgtgaa    5580
gcgactgctg ctgcaaaacg tctgcgacct gagcaacaac atgaatggtc ttcggtttcc    5640
```

```
gtgtttcgta aagtctggaa acgcggaagt cagcgctctt ccgcttcctc gctcactgac    5700
tcgctgcgct cggtcgttcg gctgcggcga gcggtatcag ctcactcaaa ggcggtaata    5760
cggttatcca cagaatcagg ggataacgca ggaaagaaca tgtgagcaaa aggccagcaa    5820
aaggccagga accgtaaaaa ggccgcgttg ctggcgtttt tccataggct ccgcccccct    5880
gacgagcatc acaaaaatcg acgctcaagt cagaggtggc gaaacccgac aggactataa    5940
agataccagg cgtttccccc tggaagctcc ctcgtgcgct ctcctgttcc gaccctgccg    6000
cttaccggat acctgtccgc ctttctccct tcgggaagcg tggcgctttc tcatagctca    6060
cgctgtaggt atctcagttc ggtgtaggtc gttcgctcca agctgggctg tgtgcacgaa    6120
ccccccgttc agcccgaccg ctgcgcctta tccggtaact atcgtcttga gtccaacccg    6180
gtaagacacg acttatcgcc actggcagca gccactggta acaggattag cagagcgagg    6240
tatgtaggcg gtgctacaga gttcttgaag tggtggccta actacggcta cactagaagg    6300
acagtatttg gtatctgcgc tctgctgaag ccagttacct tcggaaaaag agttggtagc    6360
tcttgatccg gcaaacaaac caccgctggt agcggtggtt tttttgtttg caagcagcag    6420
attacgcgca gaaaaaaagg atctcaagaa gatcctttga tcttttctac ggggtctgac    6480
gctcagtgga acgaaaactc acgttaaggg attttggtca tgagattatc aaaaaggatc    6540
ttcacctaga tccttttaaa ttaaaaatga agttttaaat caatctaaag tatatatgag    6600
taaacttggt ctgacagtta ccaatgctta atcagtgagg cacctatctc agcgatctgt    6660
ctatttcgtt catccatagt tgcctgactc cccgtcgtgt agataactac gatacgggag    6720
ggcttaccat ctggccccag tgctgcaatg ataccgcgag                          6760

<210> SEQ ID NO 2
<211> LENGTH: 7115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gtgtcgatgg tcatcgactt cgccaaacct gccgcctcct gttcgagacg acgcgaacgc      60
tccacggcgg ccgatggcgc gggcagggca gggggagcca gttgcacgct gtcgcgctcg     120
atcttggccg tagcttgctg gaccatcgag ccgacggact ggaaggtttc gcggggcgca     180
cgcatgacgg tgcggcttgc gatggtttcg gcatcctcgg cggaaaaccc cgcgtcgatc     240
agttcttgcc tgtatgcctt ccggtcaaac gtccgattca ttcaccctcc ttgcgggatt     300
gccccgactc acgccggggc aatgtgccct tattcctgat ttgacccgcc tggtgccttg     360
gtgtccagat aatccacctt atcggcaatg aagtcggtcc cgtagaccgt ctggccgtcc     420
ttctcgtact tggtattccg aatcttgccc tgcacgaata ccagctccgc gaagtcgctc     480
ttcttgatgg agcgcatggg gacgtgcttg gcaatcacgc gcaccccccg gccgttttag     540
cggctaaaaa agtcatggct ctgccctcgg gcggaccacg cccatcatga ccttgccaag     600
ctcgtcctgc ttctcttcga tcttcgccag cagggcgagg atcgtggcat caccgaaccg     660
cgccgtgcgc gggtcgtcgg tgagccgaga tttcagcagg ccgcccaggc ggcccaggtc     720
gccattgatg cgggccagct cgcggacgtg ctcatagtcc acgacgcccg tgattttgta     780
gccctggccg acgccagca ggtaggccta caggctcatg ccggccgccg ccgccttttc     840
ctcaatcgct cttcgttcgt ctggaaggca gtacaccttg ataggtgggc tgcccttcct     900
```

```
ggttggcttg gtttcatcag ccatccgctt gccctcatct gttacgccgg cggtagccgg    960
ccagcctcgc agagcaggat tcccgttgag caccgccagg tgcgaataag ggacagtgaa   1020
gaaggaacac ccgctcgcgg gtgggcctac ttcacctatc ctgcccggct gacgccgttg   1080
gatacaccaa ggaaagtcta cacgaaccct ttggcaaaat cctgtatatc gtgcgaaaaa   1140
ggatggatat accgaaaaaa tcgctataat gaccccgaag cagggttatg cagcggaaaa   1200
gatccgtcga ccctttccga cgctcaccgg gctggttgcc ctcgccgctg ggctggcggc   1260
cgtctatggc cctgcaaacg cgccagaaac gccgtcgaag ccgtgtgcga gacaccgcgg   1320
ccgccggcgt tgtggatacc tcgcggaaaa cttggccctc actgacagat gaggggcgga   1380
cgttgacact tgaggggccg actcacccgg cgcggcgttg acagatgagg ggcaggctcg   1440
atttcggccg cgacgtggaa gctggccagc ctcgcaaatc ggcgaaaacg cctgattta    1500
cgcgagtttc ccacagatga tgtggacaag cctggggata agtgccctgc ggtattgaca   1560
cttgaggggc gcgactactg acagatgagg ggcgcgatcc ttgacacttg aggggcagag   1620
tgctgacaga tgagggcgc acctattgac atttgagggg ctgtccacag gcagaaaatc   1680
cagcatttgc aagggtttcc gcccgttttt cggccaccgc taacctgtct tttaacctgc   1740
ttttaaacca atatttataa accttgtttt taaccagggc tgcgccctgt gcgcgtgacc   1800
gcgcacgccg aagggggtg cccccccttc tcgaaccctc ccggcccgct aacgcgggcc    1860
tcccatcccc ccaggggctg cgcccctcgg ccgcgaacgg cctcacccca aaaatggcag   1920
ccaagctgac cacttctgcg ctcggccctt ccggctggct ggtttattgc tgataaatct   1980
ggagccggtg agcgtgggtc tcgcggtatc attgcagcac tggggccaga tggtaagccc   2040
tcccgtatcg tagttatcta cacgacgggg agtcaggcaa ctatggatga acgaaataga   2100
cagatcgctg agataggtgc ctcactgatt aagcattggt aactgtcaga ccaagtttac   2160
tcatatatac tttagattga tttaaaactt cattttaat ttaaaaggat ctaggtgaag    2220
atccttttg ataatctcat gaccaaaatc ccttaacgtg agttttcgtt ccactgagcg    2280
tcagaccccg tagaaaagat caaaggatct tcttgagatc ctttttttct gcgcgtaatc   2340
tgctgcttgc aaacaaaaaa accaccgcta ccagcggtgg tttgtttgcc ggatcaagag   2400
ctaccaactc tttttccgaa ggtaactggc ttcagcagag cgcagatacc aaatactgtt   2460
cttctagtgt agccgtagtt aggccaccac ttcaagaact ctgtagcacc gcctacatac   2520
ctcgctctgc taatcctgtt accagtggct gctgccagtg gcgataagtc gtgtcttacc   2580
gggttggact caagacgata gttaccggat aaggcgcagc ggtcgggctg aacggggggt   2640
tcgtgcacac agcccagctt ggagcgaacg acctacaccg aactgagata cctacagcgt   2700
gagctatgag aaagcgccac gcttcccgaa gggagaaagg cggacaggta tccggtaagc   2760
ggcagggtcg gaacaggaga gcgcacgagg gagcttccag ggggaaacgc ctggtatctt   2820
tatagtcctg tcgggtttcg ccacctctga cttgagcgtc gatttttgtg atgctcgtca   2880
gggggcgga gcctatggaa aaacgccagc aacgcggcct ttttacggtt cctggccttt    2940
tgctggcctt ttgctcacat gttctttcct gcgttatccc ctgattctgt ggataaccgt   3000
attaccgcct ttgagtgagc tgataccgct cgccgcagcc gaacgaccga gcgcagcgag   3060
tcagtgagcg aggaagcgga agagcgccca atacgcaaac cgcctctccc cgcgcgttgg   3120
ccgattcatt aatgcagctg gcacgacagg tttcccgact actagtccaa caacttatac   3180
catgcctac aaaaaggcaa acaatggtac ttgacgactc atcacaacaa ttgtagttgt    3240
agcagggaga gaccccgagg taccgcttcc tagcaggtgg tgccgctggc gacctgcgtt   3300
```

```
tcaccctgcc ataaagaaac tgttacccgt aggtagtcac gcaactcgcc gcacatctga    3360
acttcagcct ccagtacagc gcggctgaaa tcatcattaa agcgagtggc aacatggaaa    3420
tcgctgattt gtgtagtcgg tttatgcagc aacgagacgt cacggaaaat gccgctcatc    3480
cgccacatat cctgatcttc cagataactg ccgtcattcc agcgcagcac catcaccgcg    3540
aggcggtttt ctccggcgcg taaaaatgcg ctcaggtcaa attcagacgg caaacgactg    3600
tcctggccgt aaccgaccca gcgcccgttg caccacagat gaaacgccga gttaacgcca    3660
tcaaaaataa ttcgcgtctg gccttcctgt agccagcttt catcaacatt aaatgtgagc    3720
gagtaacaac ccgtcggatt ctccgtggga acaaacggcg gattgaccgt aatgggatag    3780
gtcacgttgg tgtagatggg cgcatcgtaa ccgtgcatct gccagtttga ggggacgacg    3840
acagtatcgg cctcaggaag atcgcactcc agccagcttt ccggcaccgc ttctggtgcc    3900
ggaaaccagg caaagcgcca ttcgccattc aggctgcgca actgttggga agggcgatcg    3960
gtgcgggcct cttcgctatt acgccagctg gcgaaagggg gatgtgctgc aaggcgatta    4020
agttgggtaa cgccagggtt ttcccagtca cgacgttgta aaacgacggc cagtgaatcc    4080
gtaatcatgg tcatagctgt ttcctgtgta aaattgttat ccgctcacaa ttccacacaa    4140
catacgagcc ggaagcataa agtgtaaagc ctggggtgcc taatgagtga gctaactcac    4200
attaattgcg ttgcgctcac ctgctagggc ctggatccat ggtttaaact caggaattca    4260
cgtgcgcacc tgtgctgggc gcgctgtcgg atcgtttcgg gcggcggcca atcttgctcg    4320
tctcgctggc cggcgccact gtcgactacg ccatcatggc gacagcgcct ttcctttggg    4380
ttctctatat cgggcggatc gtggccggca tcaccggggc gactggggcg gtagccggcg    4440
cttatattgc cgatgacctg cagggggggg ggggcgctga ggtctgcctc gtgaagaagg    4500
tgttgctgac tcataccagg cctgaatcgc cccatcatcc agccagaaag tgagggagcc    4560
acggttgatg agagctttgt tgtaggtgga ccagttggtg attttgaact tttgctttgc    4620
cacggaacgg tctgcgttgt cgggaagatg cgtgatctga tccttcaact cagcaaaagt    4680
tcgatttatt caacaaagcc gccgtcccgt caagtcagcg taatgctctg ccagtgttac    4740
aaccaattaa ccaattctga ttagaaaaac tcatcgagca tcaaatgaaa ctgcaattta    4800
ttcatatcag gattatcaat accatatttt tgaaaagcc gtttctgtaa tgaaggagaa    4860
aactcaccga ggcagttcca taggatggca agatcctggt atcggtctgc gattccgact    4920
cgtccaacat caatacaacc tattaatttc ccctcgtcaa aaataaggtt atcaagtgag    4980
aaatcaccat gagtgacgac tgaatccggt gagaatggca aaagcttatg catttctttc    5040
cagacttgtt caacaggcca gccattacgc tcgtcatcaa aatcactcgc atcaaccaaa    5100
ccgttattca ttcgtgattg cgcctgagcg agacgaaata cgcgatcgct gttaaaagga    5160
caattacaaa caggaatcga atgcaaccgg cgcaggaaca ctgccagcgc atcaacaata    5220
ttttcacctg aatcaggata ttcttctaat acctggaatg ctgttttccc ggggatcgca    5280
gtggtgagta accatgcatc atcaggagta cggataaaat gcttgatggt cggaagaggc    5340
ataaattccg tcagccagtt tagtctgacc atctcatctg taacatcatt ggcaacgcta    5400
cctttgccat gtttcagaaa caactctggc gcatcgggct tcccatacaa tcgatagatt    5460
gtcgcacctg attgcccgac attatcgcga gcccatttat acccatataa atcagcatcc    5520
atgttggaat ttaatcgcgg cctcgagcaa gacgtttccc gttgaatatg gctcataaca    5580
ccccttgtat tactgtttat gtaagcagac agttttattg ttcatgatga tatatttta    5640
```

```
tcttgtgcaa tgtaacatca gagattttga gacacaacgt ggctttcccc cccccccctg    5700
caggtccgac acggggatgg atggcgttcc cgatcatggt cctgcttgct tcgggtggca    5760
tcggaatgcc ggcgctgcaa gcaatgttgt ccaggcacgt ggatgaggaa cgtcaggggc    5820
agctgcaagg ctcactggcg gcgctcacca gcctgacctc gatcgtcgga ccctcctct     5880 tcacggcgat ctatgcggct tctataacaa cgtggaacgg gtgggcatgg attgcaggcg    5940
ctgccctcta cttgctctgc ctgccggcgc tgcgtcgcgg gctttggagc ggcgcagggc    6000
aacgagccga tcgctgatcg tggaaacgat aggcctatgc catgcgggtc aaggcgactt    6060
ccggcaagct atacgcgccc tagaattgtc aattttaatc ctctgtttat cggcagttcg    6120
tagagcgcgc cgtgcgtccc gagcgatact gagcgaagca agtgcgtcga gcagtgcccg    6180
cttgttcctg aaatgccagt aaagcgctgg ctgctgaacc cccagccgga actgacccca    6240
caaggcccta gcgtttgcaa tgcaccaggt catcattgac ccaggcgtgt tccaccaggc    6300
cgctgcctcg caactcttcg caggcttcgc cgacctgctc gcgccacttc ttcacgcggg    6360
tggaatccga tccgcacatg aggcggaagg tttccagctt gagcgggtac ggctcccggt    6420
gcgagctgaa atagtcgaac atccgtcggg ccgtcggcga cagcttgcgg tacttctccc    6480
atatgaattt cgtgtagtgg tcgccagcaa acagcacgac gatttcctcg tcgatcagga    6540
cctggcaacg ggacgttttc ttgccacggt ccaggacgcg gaagcggtgc agcagcgaca    6600
ccgattccag gtgcccaacg cggtcggacg tgaagcccat cgccgtcgcc tgtaggcgcg    6660
acaggcattc ctcggccttc gtgtaatacc ggccattgat cgaccagccc aggtcctggc    6720
aaagctcgta gaacgtgaag gtgatcggct cgccgatagg ggtgcgcttc gcgtactcca    6780
acagctgctg ccacaccagt tcgtcatcgt cggcccgcag ctcgacgccg gtgtaggtga    6840
tcttcacgtc cttgttgacg tggaaaatga ccttgttttg cagcgcctcg cgcgggattt    6900
tcttgttgcg cgtggtgaac agggcagagc gggccgtgtc gtttggcatc gctcgcatcg    6960
tgtccggcca cggcgcaata tcgaacaagg aaagctgcat ttccttgatc tgctgcttcg    7020
tgtgtttcag caacgcggcc tgcttggcct cgctgacctg ttttgccagg tcctcgccgg    7080 cggttttcg cttcttggtc gtcatagttc ctcgc                                7115
```

<210> SEQ ID NO 3
<211> LENGTH: 326
<212> TYPE: DNA
<213> ORGANISM: Methylobacterium extorquens

<400> SEQUENCE: 3

```
gttgacgaca acggtgcgat gggtcccggc cccggtcaag acgatgccaa tacgttgcga     60
cactacgcct tggcactttt agaattgcct tatcgtcctg ataagaaatg tccgaccagc    120
taaagacatc gcgtccaatc aaagcctaga aaatataggc gaaggacgc taataagtct     180 ttcataagac cgcgcaaatc taagaatatc cttagattca cgatgcggca cttcggatga    240
cttccgagcg agcctggaac ctcagaaaaa cgtctgagag ataccgcgag ccgaaaggc    300 gaggcggttc agcgaggaga cgcagg                                         326
```

<210> SEQ ID NO 4
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

| ccaacaactt ataccatggc ctacaaaaag gcaaacaatg gtacttgacg actcatcaca | 60 |
| acaattgtag ttgtagcagg gagagacccc ga | 92 |

<210> SEQ ID NO 5
<211> LENGTH: 503
<212> TYPE: DNA
<213> ORGANISM: Methylobacterium extorquens

<400> SEQUENCE: 5

| caccgcgcgg gacttcatct tgccccggca gatgcgcagg gcctccaccg tgcgctcgat | 60 |
| cgccgcctcg gtgaggcgat tggaattgcc caatccctcg ccgagccgga cgatgcggga | 120 |
| gaaggcgtcg atcacccgga agccgttggg cgtcggctcg cgaccagaa ggcggcaatt | 180 |
| gttggtgccg agatcgagcg cggcataggc gtcgcgtcgg ccgtgccgac cggtttcgta | 240 |
| gcggggaggg aagctctcga tcgggcgtcc gcccgtgacc gtgcgggaac cctcccgcgc | 300 |
| tgtctgcggg tcggcggtgg ggcgggccga cacggcggcg cgctctcat ccctcatcga | 360 |
| cgcgaccgaa cttcctggcg atgcagcccg gcaagacgcc gggccgacgt ggcaccaagg | 420 |
| ctacaggcgt tattcaggaa ctgcaaaggc tggatggccg gccttacacg atttgccgca | 480 |
| tggattgttt cgcgaaaagt ccc | 503 |

<210> SEQ ID NO 6
<211> LENGTH: 500
<212> TYPE: DNA
<213> ORGANISM: Methylobacterium extorquens

<400> SEQUENCE: 6

| cgccccaaga ctcccaacct gatatcgtcg gcgcaatctt ggccggaagc gggcgagggg | 60 |
| caagaggcac ggattgtcgc gtgccgccgg tctcgaccgg ttccggccgc gttcagggcc | 120 |
| gccgccgacg cagcgggagc acggcagcgg cgccgatctg tgggccggtc tcggcgtcga | 180 |
| gatcgggcac ggcgatgatc ggcgcgccgc gcaggtcccg gcgcatgacg atagcgccgc | 240 |
| gctcctccag atagcccagc atgcgccggg cacgccccgc cgaggaggtg ccgtaggcct | 300 |
| ccgcgagcgc cgcgtcggaa gggcagggcg aaccttcgag cgccgtgcgg gcgatgagca | 360 |
| ggaacaaccc ggccagatcc tccggcagac cggcggcgat ctcctgcgcc cgctcccaac | 420 |
| cgggtccctc ggcggtggcg ccctggacgc cggcccgcgc cacggcgagc cgccgcttga | 480 |
| actcgggcag gcccatcgcc | 500 |

<210> SEQ ID NO 7
<211> LENGTH: 178
<212> TYPE: DNA
<213> ORGANISM: Paracoccus zeaxanthinifaciens

<400> SEQUENCE: 7

| gactaggtct ttcccttgcc ggaacaatcg gctaaagcct tccgcagtcg gggcgtagcg | 60 |
| cagcctggta gcgcgacggt tttgggtacc gtaggtcgga ggttcgaatc ctctcgcccc | 120 |
| gaccatcttc gggaaaacat taatatttcc agcgacggaa cgcgtgatgc gcctgccg | 178 |

<210> SEQ ID NO 8
<211> LENGTH: 227
<212> TYPE: DNA
<213> ORGANISM: Paracoccus zeaxanthinifaciens

<400> SEQUENCE: 8

```
ccgcatccgt ctgcatcggc gggggcgagg cgacggccat cgcgctggaa cggctgagct      60
aattcatttg cgcgaatccg cgttttcgt gcacgatggg ggaaccggaa acggccacgc      120
ctgttgtggt tgcgtcgacc tgtcttcggg ccatgcccgt gacgcgatgt ggcaggcgca     180
tggggcgttg ccgatccggt cgcatgactg acgcaacgaa ggcaccg                  227
```

<210> SEQ ID NO 9
<211> LENGTH: 5479
<212> TYPE: DNA
<213> ORGANISM: Paracoccus zeaxanthinifaciens

<400> SEQUENCE: 9

```
gactaggtct ttcccttgcc ggaacaatcg gctaaagcct tccgcagtcg gggcgtagcg      60
cagcctggta gcgcgacggt tttgggtacc gtaggtcgga ggttcgaatc ctctcgcccc     120
gaccatcttc gggaaaacat taatatttcc agcgacggaa cgcgtgatgc gcctgccgcg     180
ttcggcggcg aatgtcacgg atgatccgcc tatgagccct gaacgcagat gtcacgcgat    240
gccctttggt cgcaccccga tgggctggtc atgcaccgcg cggcagcgta gcctgttccc    300
tgtcatatca gcaagggc cggcatgagc acttgggccg caatcctgac cgtcatcctg     360
accgtcgccg cgatggagct gacggcctac tccgtccatc ggtggatcat gcatggcccc    420
ctgggctggg gctggcataa atcgcaccac gacgaggatc acgaccacgc gctcgagaag    480
aacgacctct atggcgtcat cttcgcggta atctcgatcg tgctgttcgc gatcggcgcg    540
atggggtcgg atctggcctg gtggctggcg gtggggtca cctgctacgg gctgatctac     600
tatttcctgc atgacggctt ggtgcatggg cgctggccgt tccgctatgt ccccaagcgc    660
ggctatcttc gtcgcgtcta ccaggcacac aggatgcatc acgcggtcca tggccgcgag    720
aactgcgtca gcttcggttt catctgggcg ccctcggtcg acagcctcaa ggcagagctg    780
aaacgctcgg gcgcgctgct gaaggaccgc gaaggggcgg atcgcaatac atgagccatg    840
atctgctgat cgcgggcgcg ggctgtccg gtgcgctgat cgcgcttgcc gttcgcgacc    900
gcagaccgga tgcgcgcatc gtgatgctcg acgcgcggtc cggcccctcg gaccagcaca    960
cctggtcctg ccacgacacg gatctttcgc ccgaatgggc ggcgcgcctg tcgcccattc   1020
gtcgcggcga atggacggat caggaggtcg cgtttcccga ccattcgcgc cgcctgacga   1080
caggctatgg ctcgatcgag gcgggcgcgc tgatcgggct gctgcagggt gtcgatctgc   1140
ggtggaatac gcatgtcgcg acgctggacg ataccggcgc gacgctgacg gacggctcgc   1200
ggatcgaggc tgcctgcgtg atcgacgccc gtggtgccgt cgagaccccg cacctgaccg   1260 tgggttttcca gaaattcgtg ggcgtcgaga tcgagaccga cgcccccat ggcgtcgagc   1320 gcccgatgat catggacgcg accgttccgc agatggacgg gtaccgcttc atctatctgc   1380
tgcccttcag tcccaccccgc atcctgatcg aggatacgcg ctacagcgac ggcggcgatc   1440
tggacgatgg cgcgctggcg caggcgtcgc tggactatgc cgccaggcgg ggctggaccg   1500
ggcaggagat gcggcgcgaa aggggcatcc tgcccatcgc gctggcccat gacgccatag   1560
gcttctggcg cgaccacgcg cagggggcgg tgccggttgg gctgggggca gggctgttcc   1620
accccgtcac cggatattcg ctgccctatg ccgcgcaggt cgcggatgcc atcgcggcgc   1680
gcgacctgac gaccgcgtcc gcccgtcgcg cggtgcgcgg ctgggccatc gatcgcgcgg   1740
atcgcgaccg cttcctgcgg ctgctgaacc ggatgctgtt ccgcggctgc ccgcccgacc   1800
gtcgctatcg cctgctgcag cggttctacc gcctgccgca gccgctgatc gagcgcttct   1860
```

```
atgccgggcg cctgacattg gccgaccggc ttcgcatcgt caccggacgc ccgcccattc   1920
cgctgtcgca ggccgtgcgc tgcctgcccg aacgcccccct gctgcaggag agagcatgag   1980
ttccgccatc gtcatcggcg caggtttcgg cgggcttgcg cttgccatcc gcctgcaatc   2040
ggccggcatc gcgaccacca tcgtcgaggc ccgcgacaag cccggcggcc gcgcctatgt   2100
ctggaacgat cagggccacg tcttcgatgc aggcccgacg gtcgtgaccg accccgacag   2160
cctgcgagag ctgtgggccc tcagcggcca accgatggag cgtgacgtga cgctgctgcc   2220
ggtctcgccc ttctaccggc tgacatgggc ggacggccgc agcttcgaat acgtgaacga   2280
cgacgacgag ctgatccgcc aggtcgcctc cttcaatccc gccgatgtcg atggctatcg   2340
ccgcttccac gattacgccg aggaggtcta tcgcgagggg tatctgaagc tggggaccac   2400
gcccttcctg aagctgggcc agatgctgaa cgccgcgccc gcgctgatgc gcctgcaggc   2460
ataccgctcg gtccacagca tggtggcgcg cttcatccag acccgcatc tgcggcaggc   2520 cttctcgttc cacacgctgc tggtcggcgg gaacccgttt cgaccagct cgatctatgc   2580 gctgatccat gcgctggaac ggcgcggcgg cgtctggttc gccaagggcg gcaccaacca   2640
gctggtcgcg ggcatggtcg ccctgttcga gcgtcttggc ggcacgctgc tgctgaatgc   2700
ccgcgtcacg cggatcgaca ccgagggcga tcgcgccacg ggcgtcacgc tgctggacgg   2760
gcggcagttg cgcgcggata cggtggccag caacggcgac gtgatgcaca gctatcgcga   2820
cctgctgggc cataccccgcc gcgggcgcac caaggccgcg atcctgaacc ggcagcgctg   2880
gtcgatgtcg ctgttcgtgc tgcatttcgg cctgtccaag cgccccgaga acctggccca   2940
ccacagcgtc atcttcggcc gcgcgctacaa ggggctggtg aacgagatct tcaacgggcc   3000
acgcctgccg gacgatttct cgatgtatct gcattcgccc tgcgtgaccg atcccagcct   3060
ggcccccgag gggatgtcca cgcattacgt ccttgcgccc gttccgcatc tgggccgcgc   3120
cgatgtcgat tgggaagccg aggccccggg ctatgccgag cgcatcttcg aggaactgga   3180
gcgccgcgcc atccccgacc tgcgcaagca cctgaccgtc agccgcatct tcagccccgc   3240
cgatttcagc accgaactgt cggcccatca cggcagcgcc ttctcggtcg agccgatcct   3300
gacgcaatcc gcctggttcc gcccgcataa ccgcgaccgc gcgatcccga acttctacat   3360
cgtgggggcg ggcacgcatc cgggtgcggg catcccgggt gtcgttggca cgccaaggc   3420 cacggcgcag gtcatgctgt cggacctggc cgtcgcatga ccgatctgac ggcgacttcc   3480
gaagcggcca tcgcgcaggg ttcgcaaagc ttcgcgcagg cggccaagct gatgccgccc   3540
ggcatccgcg aggatacggt catgctctat gcctggtgca ggcatgcgga tgacgtgatc   3600
gacgggcagg tcatgggttc tgcccccgag gcgggcggcg acccacaggc gcggctggat   3660
gcgctgcgcg ccgacacgct ggccgcgctg cacgaggacg gcccgatgtc gccgcccttc   3720
gcggcgctgc gccaggtcgc ccggcggcat gatttcccgg acctttggcc gatggacctg   3780
atcgagggtt tcgcgatgga tgtcgcggat cgcgaatacc gcagcctgga tgacgtgctg   3840
gaatattcct accacgtcgc ggggggtcgtg ggcgtgatga tggcgcgggt gatgggcgtg   3900
caggacgatg cggtgctgga tcgcgcctgc gatctgggcc ttgcgttcca gctgacgaac   3960
atcgctcgcg acgtgatcga cgatgccgcc atcgggcgct gctatctgcc tgccgactgg   4020
ctggccgagg cgggggcgac ggttgagggt ccggtgcctt cggacgcgct ctattccgtc   4080
atcatccgcc tgcttgacgc ggccgagccc tattatgcct cggcgcggca ggggcttccg   4140
catctgccgc cgcgctgcgc gtggtcgatc gccgccgcgc tgcgtatcta tcgcgcaatc   4200
gggacgcgca tccggcaggg tggccccgag gcctatcgcc agcggatcag cacgtcgaag   4260
```

```
gctgccaaga tcgggcttct ggcgcgcgga ggcttggacg cggccgcatc gcgcctgcgc    4320
ggcggtgaaa tcagccgcga cggcctgtgg acccgaccgc gcgcctaggc gctgcggcgg    4380
atgtcatgcg gcagcacgcg ggccagcagg tccgcgatct gcccccccgcg gaacagccgg    4440 gtgcgcatca gctcgtccag ttgcgcgcgg ctggcgcggt aatgctgcgc cacgtcgccc    4500
atctgtccga ccgccatcag gccgcgcttt gggccggggg cggcggtgtc gcgccccgta    4560
tccttgccgg tgctggcctt gtcgccgatc acgtccagca ggtcgtcata ggactggaag    4620
acccgaccaa gctgacgccc gaaggccatg agctgctcgg tctcggcctt gtccagaccc    4680
ttaataatgg acagcatctc gaggcccgcg acgaacagca cgccggtctt gaggtcctgt    4740
tcacgttcga tcccggcggc gtccttgggg gcgtgcaggt ccagatcctg ccctgcgcac    4800
agccccaccg gtcccatcgc gcgcgacatg gatgcgacca gccttgcgcg ctgatccggc    4860
gtcgcgccgc gcgcctcgcc caaaatccgc atggcctcgg tgatcagggc gatgcccgca    4920
agcaccgcgc gcccctcgcc atgggcgaca tgggtggcgg gctgaccgcg acgggtcctg    4980
gcatcgtcca tgcagggcat gtcgtcgaag atcagcgatg cggcatggac catctcgacc    5040
gcgcaggcgg catcgaccat cgcatcgcag accccgcccg agctttcggc gaccatcagc    5100
atcagcacgg cgcgaaagcg tttgccgggg gacagggcgg catcgctcat ggccgcgccg    5160
agcggggccg agaccacgcc gaactggccc gagatctgcg ccagcctgat ctcgaccaga    5220
tcgcgtaggg ggaattgctg cttgggcgtc atcggtgcct tcgttgcgtc agtcatgcga    5280
ccggatcggc aacgccccat cgcgcctgcca catcgcgtca cgggcatggc ccgaagacag    5340
gtcgacgcaa ccacaacagg cgtggccgtt tccggttccc ccatcgtgca cgaaaaacgc    5400
ggattcgcgc aaatgaatta gctcagccgt tccagcgcga tggccgtcgc ctcgccccg    5460 ccgatgcaga cggatgcgg                                                5479
```

<210> SEQ ID NO 10
<211> LENGTH: 169
<212> TYPE: PRT
<213> ORGANISM: Paracoccus zeaxanthinifaciens

<400> SEQUENCE: 10

```
Met Ser Thr Trp Ala Ala Ile Leu Thr Val Ile Leu Thr Val Ala Ala
1               5                   10                  15

Met Glu Leu Thr Ala Tyr Ser Val His Arg Trp Ile Met His Gly Pro
                20                  25                  30

Leu Gly Trp Gly Trp His Lys Ser His His Asp Glu Asp His Asp His
            35                  40                  45

Ala Leu Glu Lys Asn Asp Leu Tyr Gly Val Ile Phe Ala Val Ile Ser
        50                  55                  60

Ile Val Leu Phe Ala Ile Gly Ala Met Gly Ser Asp Leu Ala Trp Trp
65                  70                  75                  80

Leu Ala Val Gly Val Thr Cys Tyr Gly Leu Ile Tyr Tyr Phe Leu His
                85                  90                  95

Asp Gly Leu Val His Gly Arg Trp Pro Phe Arg Tyr Val Pro Lys Arg
            100                 105                 110

Gly Tyr Leu Arg Arg Val Tyr Gln Ala His Arg Met His His Ala Val
        115                 120                 125

His Gly Arg Glu Asn Cys Val Ser Phe Gly Phe Ile Trp Ala Pro Ser
    130                 135                 140

Val Asp Ser Leu Lys Ala Glu Leu Lys Arg Ser Gly Ala Leu Leu Lys
```

```
145                 150                 155                 160

Asp Arg Glu Gly Ala Asp Arg Asn Thr
                165

<210> SEQ ID NO 11
<211> LENGTH: 382
<212> TYPE: PRT
<213> ORGANISM: Paracoccus zeaxanthinifaciens

<400> SEQUENCE: 11

Met Ser His Asp Leu Leu Ile Ala Gly Ala Gly Leu Ser Gly Ala Leu
1               5                   10                  15

Ile Ala Leu Ala Val Arg Asp Arg Pro Asp Ala Arg Ile Val Met
            20                  25                  30

Leu Asp Ala Arg Ser Gly Pro Ser Asp Gln His Thr Trp Ser Cys His
        35                  40                  45

Asp Thr Asp Leu Ser Pro Glu Trp Leu Ala Arg Leu Ser Pro Ile Arg
    50                  55                  60

Arg Gly Glu Trp Thr Asp Gln Glu Val Ala Phe Pro Asp His Ser Arg
65                  70                  75                  80

Arg Leu Thr Thr Gly Tyr Gly Ser Ile Glu Ala Gly Ala Leu Ile Gly
                85                  90                  95

Leu Leu Gln Gly Val Asp Leu Arg Trp Asn Thr His Val Ala Thr Leu
            100                 105                 110

Asp Asp Thr Gly Ala Thr Leu Thr Asp Gly Ser Arg Ile Glu Ala Ala
        115                 120                 125

Cys Val Ile Asp Ala Arg Gly Ala Val Glu Thr Pro His Leu Thr Val
    130                 135                 140

Gly Phe Gln Lys Phe Val Gly Val Glu Ile Glu Thr Asp Ala Pro His
145                 150                 155                 160

Gly Val Glu Arg Pro Met Ile Met Asp Ala Thr Val Pro Gln Met Asp
                165                 170                 175

Gly Tyr Arg Phe Ile Tyr Leu Leu Pro Phe Ser Pro Thr Arg Ile Leu
            180                 185                 190

Ile Glu Asp Thr Arg Tyr Ser Asp Gly Gly Asp Leu Asp Gly Ala
        195                 200                 205

Leu Ala Gln Ala Ser Leu Asp Tyr Ala Ala Arg Arg Gly Trp Thr Gly
    210                 215                 220

Gln Glu Met Arg Arg Glu Arg Gly Ile Leu Pro Ile Ala Leu Ala His
225                 230                 235                 240

Asp Ala Ile Gly Phe Trp Arg Asp His Ala Gln Gly Ala Val Pro Val
                245                 250                 255

Gly Leu Gly Ala Gly Leu Phe His Pro Val Thr Gly Tyr Ser Leu Pro
            260                 265                 270

Tyr Ala Ala Gln Val Ala Asp Ala Ile Ala Ala Arg Asp Leu Thr Thr
        275                 280                 285

Ala Ser Ala Arg Arg Ala Val Arg Gly Trp Ala Ile Asp Arg Ala Asp
    290                 295                 300

Arg Asp Arg Phe Leu Arg Leu Leu Asn Arg Met Leu Phe Arg Gly Cys
305                 310                 315                 320

Pro Pro Asp Arg Arg Tyr Arg Leu Leu Gln Arg Phe Tyr Arg Leu Pro
                325                 330                 335

Gln Pro Leu Ile Glu Arg Phe Tyr Ala Gly Arg Leu Thr Leu Ala Asp
            340                 345                 350
```

```
Arg Leu Arg Ile Val Thr Gly Arg Pro Ile Pro Leu Ser Gln Ala
        355                 360                 365

Val Arg Cys Leu Pro Glu Arg Pro Leu Leu Gln Glu Arg Ala
    370                 375                 380

<210> SEQ ID NO 12
<211> LENGTH: 494
<212> TYPE: PRT
<213> ORGANISM: Paracoccus zeaxanthinifaciens

<400> SEQUENCE: 12

Met Ser Ser Ala Ile Val Ile Gly Ala Gly Phe Gly Gly Leu Ala Leu
1               5                   10                  15

Ala Ile Arg Leu Gln Ser Ala Gly Ile Ala Thr Thr Ile Val Glu Ala
            20                  25                  30

Arg Asp Lys Pro Gly Gly Arg Ala Tyr Val Trp Asn Asp Gln Gly His
        35                  40                  45

Val Phe Asp Ala Gly Pro Thr Val Val Thr Asp Pro Asp Ser Leu Arg
    50                  55                  60

Glu Leu Trp Ala Leu Ser Gly Gln Pro Met Glu Arg Asp Val Thr Leu
65                  70                  75                  80

Leu Pro Val Ser Pro Phe Tyr Arg Leu Thr Trp Ala Asp Gly Arg Ser
                85                  90                  95

Phe Glu Tyr Val Asn Asp Asp Glu Leu Ile Arg Gln Val Ala Ser
            100                 105                 110

Phe Asn Pro Ala Asp Val Asp Gly Tyr Arg Arg Phe His Asp Tyr Ala
        115                 120                 125

Glu Glu Val Tyr Arg Glu Gly Tyr Leu Lys Leu Gly Thr Thr Pro Phe
    130                 135                 140

Leu Lys Leu Gly Gln Met Leu Asn Ala Ala Pro Ala Leu Met Arg Leu
145                 150                 155                 160

Gln Ala Tyr Arg Ser Val His Ser Met Val Ala Arg Phe Ile Gln Asp
                165                 170                 175

Pro His Leu Arg Gln Ala Phe Ser Phe His Thr Leu Leu Val Gly Gly
            180                 185                 190

Asn Pro Phe Ser Thr Ser Ser Ile Tyr Ala Leu Ile His Ala Leu Glu
        195                 200                 205

Arg Arg Gly Gly Val Trp Phe Ala Lys Gly Gly Thr Asn Gln Leu Val
    210                 215                 220

Ala Gly Met Val Ala Leu Phe Glu Arg Leu Gly Gly Thr Leu Leu Leu
225                 230                 235                 240

Asn Ala Arg Val Thr Arg Ile Asp Thr Glu Gly Asp Arg Ala Thr Gly
                245                 250                 255

Val Thr Leu Leu Asp Gly Arg Gln Leu Arg Ala Asp Thr Val Ala Ser
            260                 265                 270

Asn Gly Asp Val Met His Ser Tyr Arg Asp Leu Leu Gly His Thr Arg
        275                 280                 285

Arg Gly Arg Thr Lys Ala Ala Ile Leu Asn Arg Gln Arg Trp Ser Met
    290                 295                 300

Ser Leu Phe Val Leu His Phe Gly Leu Ser Lys Arg Pro Glu Asn Leu
305                 310                 315                 320

Ala His His Ser Val Ile Phe Gly Pro Arg Tyr Lys Gly Leu Val Asn
                325                 330                 335

Glu Ile Phe Asn Gly Pro Arg Leu Pro Asp Asp Phe Ser Met Tyr Leu
            340                 345                 350
```

-continued

His Ser Pro Cys Val Thr Asp Pro Ser Leu Ala Pro Glu Gly Met Ser
        355                 360                 365

Thr His Tyr Val Leu Ala Pro Val Pro His Leu Gly Arg Ala Asp Val
    370                 375                 380

Asp Trp Glu Ala Glu Ala Pro Gly Tyr Ala Glu Arg Ile Phe Glu Glu
385                 390                 395                 400

Leu Glu Arg Arg Ala Ile Pro Asp Leu Arg Lys His Leu Thr Val Ser
                405                 410                 415

Arg Ile Phe Ser Pro Ala Asp Phe Ser Thr Glu Leu Ser Ala His His
            420                 425                 430

Gly Ser Ala Phe Ser Val Glu Pro Ile Leu Thr Gln Ser Ala Trp Phe
        435                 440                 445

Arg Pro His Asn Arg Asp Arg Ala Ile Pro Asn Phe Tyr Ile Val Gly
    450                 455                 460

Ala Gly Thr His Pro Gly Ala Gly Ile Pro Gly Val Val Gly Ser Ala
465                 470                 475                 480

Lys Ala Thr Ala Gln Val Met Leu Ser Asp Leu Ala Val Ala
                485                 490

<210> SEQ ID NO 13
<211> LENGTH: 303
<212> TYPE: PRT
<213> ORGANISM: Paracoccus zeaxanthinifaciens

<400> SEQUENCE: 13

Met Thr Asp Leu Thr Ala Thr Ser Glu Ala Ala Ile Ala Gln Gly Ser
1               5                   10                  15

Gln Ser Phe Ala Gln Ala Ala Lys Leu Met Pro Pro Gly Ile Arg Glu
            20                  25                  30

Asp Thr Val Met Leu Tyr Ala Trp Cys Arg His Ala Asp Asp Val Ile
        35                  40                  45

Asp Gly Gln Val Met Gly Ser Ala Pro Glu Ala Gly Gly Asp Pro Gln
    50                  55                  60

Ala Arg Leu Asp Ala Leu Arg Ala Asp Thr Leu Ala Ala Leu His Glu
65                  70                  75                  80

Asp Gly Pro Met Ser Pro Phe Ala Ala Leu Arg Gln Val Ala Arg
                85                  90                  95

Arg His Asp Phe Pro Asp Leu Trp Pro Met Asp Leu Ile Glu Gly Phe
            100                 105                 110

Ala Met Asp Val Ala Asp Arg Glu Tyr Arg Ser Leu Asp Asp Val Leu
        115                 120                 125

Glu Tyr Ser Tyr His Val Ala Gly Val Val Gly Val Met Met Ala Arg
    130                 135                 140

Val Met Gly Val Gln Asp Asp Ala Val Leu Asp Arg Ala Cys Asp Leu
145                 150                 155                 160

Gly Leu Ala Phe Gln Leu Thr Asn Ile Ala Arg Asp Val Ile Asp Asp
                165                 170                 175

Ala Ala Ile Gly Arg Cys Tyr Leu Pro Ala Asp Trp Leu Ala Glu Ala
            180                 185                 190

Gly Ala Thr Val Glu Gly Pro Val Pro Ser Asp Ala Leu Tyr Ser Val
        195                 200                 205

Ile Ile Arg Leu Leu Asp Ala Ala Glu Pro Tyr Tyr Ala Ser Ala Arg
    210                 215                 220

Gln Gly Leu Pro His Leu Pro Pro Arg Cys Ala Trp Ser Ile Ala Ala

```
                225                 230                 235                 240
Ala Leu Arg Ile Tyr Arg Ala Ile Gly Thr Arg Ile Arg Gln Gly Gly
                    245                 250                 255

Pro Glu Ala Tyr Arg Gln Arg Ile Ser Thr Ser Lys Ala Ala Lys Ile
                260                 265                 270

Gly Leu Leu Ala Arg Gly Gly Leu Asp Ala Ala Ala Ser Arg Leu Arg
                275                 280                 285

Gly Gly Glu Ile Ser Arg Asp Gly Leu Trp Thr Arg Pro Arg Ala
            290                 295                 300

<210> SEQ ID NO 14
<211> LENGTH: 295
<212> TYPE: PRT
<213> ORGANISM: Paracoccus zeaxanthinifaciens

<400> SEQUENCE: 14

Met Thr Pro Lys Gln Gln Phe Pro Leu Arg Asp Leu Val Glu Ile Arg
1               5                   10                  15

Leu Ala Gln Ile Ser Gly Gln Phe Gly Val Val Ser Ala Pro Leu Gly
                20                  25                  30

Ala Ala Met Ser Asp Ala Ala Leu Ser Pro Gly Lys Arg Phe Arg Ala
            35                  40                  45

Val Leu Met Leu Met Val Ala Glu Ser Ser Gly Gly Val Cys Asp Ala
50                  55                  60

Met Val Asp Ala Ala Cys Ala Val Glu Met Val His Ala Ala Ser Leu
65                  70                  75                  80

Ile Phe Asp Asp Met Pro Cys Met Asp Asp Ala Arg Thr Arg Arg Gly
                85                  90                  95

Gln Pro Ala Thr His Val Ala His Gly Glu Gly Arg Ala Val Leu Ala
            100                 105                 110

Gly Ile Ala Leu Ile Thr Glu Ala Met Arg Ile Leu Gly Glu Ala Arg
        115                 120                 125

Gly Ala Thr Pro Asp Gln Arg Ala Arg Leu Val Ala Ser Met Ser Arg
    130                 135                 140

Ala Met Gly Pro Val Gly Leu Cys Ala Gly Gln Asp Leu Asp Leu His
145                 150                 155                 160

Ala Pro Lys Asp Ala Ala Gly Ile Glu Arg Glu Gln Asp Leu Lys Thr
                165                 170                 175

Gly Val Leu Phe Val Ala Gly Leu Glu Met Leu Ser Ile Ile Lys Gly
            180                 185                 190

Leu Asp Lys Ala Glu Thr Glu Gln Leu Met Ala Phe Gly Arg Gln Leu
        195                 200                 205

Gly Arg Val Phe Gln Ser Tyr Asp Asp Leu Leu Asp Val Ile Gly Asp
    210                 215                 220

Lys Ala Ser Thr Gly Lys Asp Thr Gly Arg Asp Thr Ala Ala Pro Gly
225                 230                 235                 240

Pro Lys Arg Gly Leu Met Ala Val Gly Gln Met Gly Asp Val Ala Gln
                245                 250                 255

His Tyr Arg Ala Ser Arg Ala Gln Leu Asp Glu Leu Met Arg Thr Arg
            260                 265                 270

Leu Phe Arg Gly Gly Gln Ile Ala Asp Leu Leu Ala Arg Val Leu Pro
        275                 280                 285

His Asp Ile Arg Arg Ser Ala
    290                 295
```

<210> SEQ ID NO 15
<211> LENGTH: 4019
<212> TYPE: DNA
<213> ORGANISM: Sphingomonas astaxanthinifaciens

<400> SEQUENCE: 15

| | | | | | |
|---|---|---|---|---|---|
| atgatgaagc | gcgcggacct | ggtgatcgtc | ggtggaggac | tggccggcgg | cctgtgcgcc | 60 |
| ctcgcccttc | gccgccgccg | ccctgacctc | aggctgctgc | tggtcgagcc | ggggccaagc | 120 |
| atcggcggca | accatctctg | gtccttcttc | gaaagcgacg | tcgccccgc | cgaccgctgg | 180 |
| ctgaccgacc | cgctgatccg | gcatcgctgg | cccgattacg | aggtccgctt | cccggcgcac | 240 |
| cagcgccacc | tcgccgaagc | ctatcagacc | atcgagagcg | aggcgctcga | cgaggccgtg | 300 |
| cgcaaggccc | tttccgccga | ggagatcgtc | cgggccgaag | ccaccgacct | tggcccgacc | 360 |
| cacgtcaccc | tcgcgaccgg | cgagcggatc | gaggcgaagg | cggtgctcga | cgcgcgcggg | 420 |
| ggcaaagccg | aggggctcga | tctcggctgg | cagaaattcc | tcggccagct | gctgaccatc | 480 |
| ccgcaggcc | acggcctcac | ccgtccgatc | gtgatggacg | cgacggtcga | ccagcatgac | 540 |
| ggctatcgct | tcgtctactg | cctgcccttc | agcccgaccg | aactcttcgt | cgaggacact | 600 |
| tattacagcg | acgggcccga | gctcgaccac | gaccgattgc | gtgaccggat | cggcgattat | 660 |
| gccgcggcac | agggctggca | ggtcgcggac | cgcagccgcg | aggagcatgg | cgcgctgcca | 720 |
| gtggtgatcg | gcgcgatttt | cgaccggctg | tggcccgccg | ccgaccatgt | cgcccggggcc | 780 |
| ggcgcgcgcg | gcggttttctt | ccatccgctg | accagctatt | cgctgcccga | cgcggtccgc | 840 |
| ttcgccatct | ggctggcgga | caaggccacg | ttcgacgccc | ggctcggggc | gcgaccccgc | 900 |
| gcgcggggcc | gccgccactg | gaggtcgggt | gccttctacc | ggctgctcac | cgcgctcctg | 960 |
| ttccacgccg | ccgagcccgg | ccagcgctac | ctcgtgctgg | agcgtttcta | ccgcctttcc | 1020 |
| ggccccttga | tcggccgctt | ctacgcgggg | atgagcaccg | gctatgacaa | ggcgcgcgtg | 1080 |
| ctcgcgggca | agccgccggt | gcccttcttc | cgggcactca | gggtattgag | ggacagcttg | 1140 |
| tgaagagtgc | aatcgtgatc | ggtgccggct | tcggcggcct | ggcgctggcc | atccgcctcc | 1200 |
| agtcggccgg | ggtgaagacc | accatcgtcg | aggcccgcga | ccggcccggc | ggccgcgcct | 1260 |
| atgtctggga | aaaggacggc | cacgtgttcg | acgcgggccc | gaccgtgatc | accgatcccg | 1320 |
| actgtctcca | gcggctgtgg | aagctgtcgg | gccacgacat | gtcggaggat | gtcgagctcg | 1380 |
| tcccggtcaa | gcccttctac | cggctctcct | ggcccgacgg | cgtggtgttc | gattacacca | 1440 |
| atgacgacgc | cgagctcaaa | gccgcgatgg | acgcactcaa | tcccgacgac | tgggcgggct | 1500 |
| accagcgctt | cctcgcctat | agcgccgggg | tctataacga | gggctatgtg | aagctcggga | 1560 |
| ccaaggcgtt | tgaaagcctc | ggcgacatgc | tcaaggccgc | gcccgcgctc | gccaaatatc | 1620 |
| aggcttggcg | gtcggtctat | cgatcgtgt | cgagcttcgt | gaaggacgag | cacctgcgcc | 1680 |
| agaccttgtc | cttccacacg | ctgctggtcg | gcggcaatcc | gatgacctgc | tcgtcgatct | 1740 |
| acgcgctgat | ccacaagctc | gagcgcgacg | gcggggtgtg | gttcgccaag | ggcgggacca | 1800 |
| acaagctgat | cgccggcatg | gtccgccagt | tcgagcggat | cggcgggacc | attcgccttg | 1860 |
| gcgatccggt | cactgcgatc | ctggccgaga | cgatcgggt | caccggggtg | cgcaccgcct | 1920 |
| cgggttggag | cgccaccgcc | gacgcggtcg | cctccaatgg | cgacgtggtc | cacagctatg | 1980 |
| gcctgatcga | gggttccgac | cgcggccagc | aacaggtccg | cgccctcaag | cgcaagcgtt | 2040 |
| tctcgcccgg | cctgttcgtg | ctccatttcg | ggctcgaggg | gacgtcggac | ctcgcccacc | 2100 |
| acacgatcct | gttcggcccg | cgctacggcg | gcctcgtcaa | cgacatctac | aagaccgggc | 2160 |

```
ggctcgcgac cgacccgtcg ctctacatcc accaccgac catcaccgac ccgtccatgg    2220
cgccgccggg ctgctcgacc ttctacgcgc ttgccccccgt ccccaatgcc ggcaaggccg   2280
atgtcgactg ggcggtcgag gggccgaaat atcaggaggt cgtgctcgac acgatcgccg    2340
agcggctgat ccccgacgtg cgccagcgga tccggaccat cttccattac accccggccg    2400
atttctcggc cgacctcgcc gcccacctcg gctccgcatt cagcctcgag ccggtgctgt    2460
ggcagtcggc ctggttccgc acccacaatc gcgacgacaa gctcaggaac ctctatttcg    2520
tcggtgccgg cactcaccca ggcgcgggga tcccgggggt ggtcggaagc gccgaggcga    2580
ctgcggggct gatgctggcg tgagcgaagc tgacgaacgg gcacggctgg tccaggccgc    2640
gctggaaagc atttcggcgg gctccaagag tttttcgcttc gccagccagt tgttcgacca   2700
gcagacccga gagcgcagct ggctgctcta cagctggtgc cgcgcctgcg acgacgtgac    2760
cgacggccag accctgggcc atgatgcgga gcgggtcgac gatcccgccg cccgcctcgc    2820
cttcctcaag gcgaagaccg ccgaggcgtt cgcgggccaa ccgacgggac ttgtcccctt    2880
cgacgcactg cgcgtggtcg ccgccgaatg cgcgattccc caggccgtcg ccggcgacca    2940
tctcgccggg ttcgagcgcg acgccggggg gtggcggccg accacgaccg acgacctcct    3000
ctcttattgc taccaggttg ctggcgcggt gggcgtgatg atggcgcacg tcatgggcgt    3060
gccgcccgag gacgaggaca cgctcaaccg cgcagccgac ttggggatcg ccttccagct    3120
cgccaatatc gcccgcgaca tcgtcgacga tgccaaggtc gggcgggtct atctgcccgc    3180
cgaatggctt gccgccgagg ggctggccgg ggccgacctc gccgatcccg cgcatcgccc    3240
ggccctcgcg cgcctcgccc accgcctcgc cgacatggcc gacgcctatc gccgctcggc    3300
ccgggtcggc gcggcccgcc tgcccttccg cagccgctgg gcggtgctcg cggccagcgg    3360
catctacggc gagatcgcga cccgcgccgc cgcgctcggg ccccgcgcct gggacgagcg    3420
gatcaccacc tcgaaggcgg aaaaggccgc gctggtgatg gaggccttct gggaagcctt    3480
gtggcgggtc aggcccgctc ctcgtgacgg gctgtggacc cgccccgcgc acgcctgagc    3540
tgcgcctcgc ggctggcctg gagcgcctgc ttcagccgct cgaccggcgg ggcgtaaagg    3600
aagccgaagc tcaccgcccc gtcgcggctc tcgaccgcat ggtgcagctt gtgcgcctgg    3660
acgatccgct tgaaataggt cgaacgcggc acgatccggt gcggcagccg ccgtggacg     3720 atgacgtcgt gaaagccgaa atagatcacc ccgtagaagg ccaccccggc ccccatccac    3780
gtcgcccagt cgcccccagcc gccattgagc ccgccccaga tcagcaggat cgagggcaaa   3840
gcgaagacca cggcatagag gtcgttccgc tcgaaccagc cggtccgcgc gcgatgatgg    3900
ctttcgtgcc agttccagcc gagccgcgag tgcatcacga agcggtggag gacataggcg    3960
aagccctcca tcagaaggac cgtcgatacg aacagggcga gaccggcagg ccaggacat    4019
```

<210> SEQ ID NO 16
<211> LENGTH: 176
<212> TYPE: PRT
<213> ORGANISM: Sphingomonas astaxanthinifaciens

<400> SEQUENCE: 16

Met Ser Trp Pro Ala Gly Leu Ala Leu Phe Val Ser Thr Val Leu Leu
1               5                   10                  15

Met Glu Gly Phe Ala Tyr Val Leu His Arg Phe Val Met His Ser Arg
                20                  25                  30

Leu Gly Trp Asn Trp His Glu Ser His His Arg Ala Arg Thr Gly Trp
            35                  40                  45

```
Phe Glu Arg Asn Asp Leu Tyr Ala Val Val Phe Ala Leu Pro Ser Ile
    50                  55                  60

Leu Leu Ile Trp Gly Gly Leu Asn Gly Gly Trp Gly Asp Trp Ala Thr
65                  70                  75                  80

Trp Met Gly Ala Gly Val Ala Phe Tyr Gly Val Ile Tyr Phe Gly Phe
                85                  90                  95

His Asp Val Ile Val His Gly Arg Leu Pro His Arg Ile Val Pro Arg
                100                 105                 110

Ser Thr Tyr Phe Lys Arg Ile Val Gln Ala His Lys Leu His His Ala
            115                 120                 125

Val Glu Ser Arg Asp Gly Ala Val Ser Phe Gly Phe Leu Tyr Ala Pro
    130                 135                 140

Pro Val Glu Arg Leu Lys Gln Ala Leu Gln Ala Ser Arg Glu Ala Gln
145                 150                 155                 160

Leu Arg Arg Ala Arg Gly Gly Ser Thr Ala Arg His Glu Glu Arg Ala
                165                 170                 175

<210> SEQ ID NO 17
<211> LENGTH: 380
<212> TYPE: PRT
<213> ORGANISM: Sphingomonas astaxanthinifaciens

<400> SEQUENCE: 17

Met Met Lys Arg Ala Asp Leu Val Ile Val Gly Gly Gly Leu Ala Gly
1               5                   10                  15

Gly Leu Cys Ala Leu Ala Leu Arg Arg Arg Pro Asp Leu Arg Leu
            20                  25                  30

Leu Leu Val Glu Pro Gly Pro Ser Ile Gly Gly Asn His Leu Trp Ser
            35                  40                  45

Phe Phe Glu Ser Asp Val Ala Pro Ala Asp Arg Trp Leu Thr Asp Pro
    50                  55                  60

Leu Ile Arg His Arg Trp Pro Asp Tyr Glu Val Arg Phe Pro Ala His
65                  70                  75                  80

Gln Arg His Leu Ala Glu Ala Tyr Gln Thr Ile Glu Ser Glu Ala Leu
                85                  90                  95

Asp Glu Ala Val Arg Lys Ala Leu Ser Ala Glu Glu Ile Val Arg Ala
                100                 105                 110

Glu Ala Thr Asp Leu Gly Pro Thr His Val Thr Leu Ala Thr Gly Glu
            115                 120                 125

Arg Ile Glu Ala Lys Ala Val Leu Asp Ala Arg Gly Gly Lys Ala Glu
    130                 135                 140

Gly Leu Asp Leu Gly Trp Gln Lys Phe Leu Gly Gln Leu Leu Thr Ile
145                 150                 155                 160

Pro Gln Gly His Gly Leu Thr Arg Pro Ile Val Met Asp Ala Thr Val
                165                 170                 175

Asp Gln His Asp Gly Tyr Arg Phe Val Tyr Cys Leu Pro Phe Ser Pro
                180                 185                 190

Thr Glu Leu Phe Val Glu Asp Thr Tyr Tyr Ser Asp Gly Pro Glu Leu
            195                 200                 205

Asp His Asp Arg Leu Arg Asp Arg Ile Gly Asp Tyr Ala Ala Ala Gln
    210                 215                 220

Gly Trp Gln Val Ala Asp Arg Ser Arg Glu Glu His Gly Ala Leu Pro
225                 230                 235                 240

Val Val Ile Gly Gly Asp Phe Asp Arg Leu Trp Pro Ala Ala Asp His
```

|     |     |     |     |     | 245 |     |     |     | 250 |     |     |     |     | 255 |
| --- | --- | --- | --- | --- | --- | --- | --- | --- | --- | --- | --- | --- | --- | --- |
| Val | Ala | Arg | Ala | Gly | Ala | Arg | Gly | Gly | Phe | Phe | His | Pro | Leu | Thr | Ser |
|     |     |     |     | 260 |     |     |     |     | 265 |     |     |     | 270 |     |     |

Tyr Ser Leu Pro Asp Ala Val Arg Phe Ala Ile Trp Leu Ala Asp Lys
      275                 280                 285

Ala Thr Phe Asp Ala Arg Leu Gly Ala Ala Thr Arg Ala Arg Gly Arg
      290                 295                 300

Arg His Trp Arg Ser Gly Ala Phe Tyr Arg Leu Leu Thr Ala Leu Leu
305                 310                 315                 320

Phe His Ala Ala Glu Pro Gly Gln Arg Tyr Leu Val Leu Glu Arg Phe
                  325                 330                 335

Tyr Arg Leu Ser Gly Pro Leu Ile Gly Arg Phe Tyr Ala Gly Met Ser
                  340                 345                 350

Thr Gly Tyr Asp Lys Ala Arg Val Leu Ala Gly Lys Pro Pro Val Pro
                  355                 360                 365

Phe Phe Arg Ala Leu Arg Val Leu Arg Asp Ser Leu
            370                 375                 380

<210> SEQ ID NO 18
<211> LENGTH: 487
<212> TYPE: PRT
<213> ORGANISM: Sphingomonas astaxanthinifaciens

<400> SEQUENCE: 18

Val Lys Ser Ala Ile Val Ile Gly Ala Gly Phe Gly Gly Leu Ala Leu
1               5                   10                  15

Ala Ile Arg Leu Gln Ser Ala Gly Val Lys Thr Thr Ile Val Glu Ala
                  20                  25                  30

Arg Asp Arg Pro Gly Gly Arg Ala Tyr Val Trp Glu Lys Asp Gly His
                  35                  40                  45

Val Phe Asp Ala Gly Pro Thr Val Ile Thr Asp Pro Asp Cys Leu Gln
      50                  55                  60

Arg Leu Trp Lys Leu Ser Gly His Asp Met Ser Glu Asp Val Glu Leu
65                  70                  75                  80

Val Pro Val Lys Pro Phe Tyr Arg Leu Ser Trp Pro Asp Gly Val Val
                  85                  90                  95

Phe Asp Tyr Thr Asn Asp Ala Glu Leu Lys Ala Ala Met Asp Ala
                  100                 105                 110

Leu Asn Pro Asp Asp Trp Ala Gly Tyr Gln Arg Phe Leu Ala Tyr Ser
            115                 120                 125

Ala Gly Val Tyr Asn Glu Gly Tyr Val Lys Leu Gly Thr Lys Ala Phe
      130                 135                 140

Glu Ser Leu Gly Asp Met Leu Lys Ala Ala Pro Ala Leu Ala Lys Tyr
145                 150                 155                 160

Gln Ala Trp Arg Ser Val Tyr Ser Ile Val Ser Ser Phe Val Lys Asp
                  165                 170                 175

Glu His Leu Arg Gln Thr Leu Ser Phe His Thr Leu Leu Val Gly Gly
                  180                 185                 190

Asn Pro Met Thr Cys Ser Ser Ile Tyr Ala Leu Ile His Lys Leu Glu
            195                 200                 205

Arg Asp Gly Gly Val Trp Phe Ala Lys Gly Gly Thr Asn Lys Leu Ile
      210                 215                 220

Ala Gly Met Val Arg Gln Phe Glu Arg Ile Gly Gly Thr Ile Arg Leu
225                 230                 235                 240

```
Gly Asp Pro Val Thr Ala Ile Leu Ala Glu Asn Asp Arg Val Thr Gly
            245                 250                 255

Val Arg Thr Ala Ser Gly Trp Ser Ala Thr Asp Ala Val Ala Ser
        260                 265                 270

Asn Gly Asp Val Val His Ser Tyr Gly Leu Ile Glu Gly Ser Asp Arg
            275                 280                 285

Gly Gln Gln Gln Val Arg Ala Leu Lys Arg Lys Arg Phe Ser Pro Gly
        290                 295                 300

Leu Phe Val Leu His Phe Gly Leu Glu Gly Thr Ser Asp Leu Ala His
305                 310                 315                 320

His Thr Ile Leu Phe Gly Pro Arg Tyr Gly Gly Leu Val Asn Asp Ile
                325                 330                 335

Tyr Lys Thr Gly Arg Leu Ala Thr Asp Pro Ser Leu Tyr Ile His His
            340                 345                 350

Pro Thr Ile Thr Asp Pro Ser Met Ala Pro Pro Gly Cys Ser Thr Phe
                355                 360                 365

Tyr Ala Leu Ala Pro Val Pro Asn Ala Gly Lys Ala Asp Val Asp Trp
            370                 375                 380

Ala Val Glu Gly Pro Lys Tyr Gln Glu Val Val Leu Asp Thr Ile Ala
385                 390                 395                 400

Glu Arg Leu Ile Pro Asp Val Arg Gln Arg Ile Arg Thr Ile Phe His
                405                 410                 415

Tyr Thr Pro Ala Asp Phe Ser Ala Asp Leu Ala Ala His Leu Gly Ser
            420                 425                 430

Ala Phe Ser Leu Glu Pro Val Leu Trp Gln Ser Ala Trp Phe Arg Thr
            435                 440                 445

His Asn Arg Asp Asp Lys Leu Arg Asn Leu Tyr Phe Val Gly Ala Gly
    450                 455                 460

Thr His Pro Gly Ala Gly Ile Pro Gly Val Val Gly Ser Ala Glu Ala
465                 470                 475                 480

Thr Ala Gly Leu Met Leu Ala
            485

<210> SEQ ID NO 19
<211> LENGTH: 312
<212> TYPE: PRT
<213> ORGANISM: Sphingomonas astaxanthinifaciens

<400> SEQUENCE: 19

Val Ser Glu Ala Asp Glu Arg Ala Arg Leu Val Gln Ala Ala Leu Glu
1               5                   10                  15

Ser Ile Ser Ala Gly Ser Lys Ser Phe Arg Phe Ala Ser Gln Leu Phe
            20                  25                  30

Asp Gln Gln Thr Arg Glu Arg Ser Trp Leu Leu Tyr Ser Trp Cys Arg
        35                  40                  45

Ala Cys Asp Asp Val Thr Asp Gly Gln Thr Leu Gly His Asp Ala Glu
    50                  55                  60

Arg Val Asp Asp Pro Ala Ala Arg Leu Ala Phe Leu Lys Ala Lys Thr
65                  70                  75                  80

Ala Glu Ala Phe Ala Gly Gln Pro Thr Gly Leu Val Pro Phe Asp Ala
                85                  90                  95

Leu Arg Val Val Ala Glu Cys Ala Ile Pro Gln Ala Val Ala Gly
            100                 105                 110

Asp His Leu Ala Gly Phe Glu Arg Asp Ala Gly Gly Trp Arg Pro Thr
        115                 120                 125
```

```
Thr Thr Asp Asp Leu Leu Ser Tyr Cys Tyr Gln Val Ala Gly Ala Val
            130                 135                 140

Gly Val Met Met Ala His Val Met Gly Val Pro Pro Glu Asp Glu Asp
145                 150                 155                 160

Thr Leu Asn Arg Ala Ala Asp Leu Gly Ile Ala Phe Gln Leu Ala Asn
                165                 170                 175

Ile Ala Arg Asp Ile Val Asp Ala Lys Val Gly Arg Val Tyr Leu
            180                 185                 190

Pro Ala Glu Trp Leu Ala Ala Glu Gly Leu Ala Gly Ala Asp Leu Ala
                195                 200                 205

Asp Pro Ala His Arg Pro Ala Leu Ala Arg Leu Ala His Arg Leu Ala
            210                 215                 220

Asp Met Ala Asp Ala Tyr Arg Arg Ser Ala Arg Val Gly Ala Ala Arg
225                 230                 235                 240

Leu Pro Phe Arg Ser Arg Trp Ala Val Leu Ala Ala Ser Gly Ile Tyr
                245                 250                 255

Gly Glu Ile Ala Thr Arg Ala Ala Ala Leu Gly Pro Arg Ala Trp Asp
                260                 265                 270

Glu Arg Ile Thr Thr Ser Lys Ala Glu Lys Ala Ala Leu Val Met Glu
                275                 280                 285

Ala Phe Trp Glu Ala Leu Trp Arg Val Arg Pro Ala Pro Arg Asp Gly
290                 295                 300

Leu Trp Thr Arg Pro Ala His Ala
305                 310

<210> SEQ ID NO 20
<211> LENGTH: 249
<212> TYPE: PRT
<213> ORGANISM: Sphingomonas astaxanthinifaciens

<400> SEQUENCE: 20

Met Ala Pro Met Leu Ser Asp Ala Gln Arg Arg Gln Ala Met Ile
1               5                   10                  15

Gly Leu Gly Leu Ala Ala Ala Ile Thr Ala Ala Phe Val Ala Leu His
                20                  25                  30

Val Trp Ser Val Phe Phe Leu Pro Leu Glu Gly Ala Gly Trp Trp Leu
            35                  40                  45

Ala Leu Pro Ile Val Ala Val Gln Thr Trp Leu Ser Val Gly Leu Phe
50                  55                  60

Ile Val Ala His Asp Ala Met His Gly Ser Leu Ala Pro Gly Arg Pro
65                  70                  75                  80

Ala Thr Asn Leu Phe Trp Gly Arg Leu Thr Leu Leu Tyr Ala Gly
                85                  90                  95

Phe Trp Leu Asp Arg Leu Ser Pro Lys His Phe Asp His His Arg His
            100                 105                 110

Val Gly Thr Glu Arg Asp Pro Asp Phe Ser Val Asp His Pro Thr Arg
            115                 120                 125

Phe Trp Pro Trp Tyr Tyr Ala Phe Met Arg Arg Tyr Phe Gly Leu Arg
            130                 135                 140

Glu Tyr Leu Val Leu Asn Ala Leu Val Leu Ala Tyr Val Leu Val Leu
145                 150                 155                 160

Lys Ala Pro Leu Gly Asn Leu Leu Leu Phe Trp Ala Leu Pro Ser Ile
                165                 170                 175

Leu Ser Ser Ile Gln Leu Phe Tyr Phe Gly Thr Tyr Leu Pro His Arg
```

```
                 180                 185                 190
His Glu Asp Ala Pro Phe Ala Asp Gln His Asn Ala Arg Ser Asn Asp
                195                 200                 205

Phe Pro Val Trp Leu Ser Leu Leu Thr Cys Phe His Phe Gly Tyr His
        210                 215                 220

Arg Glu His His Leu Ser Pro Gly Thr Pro Trp Gln Leu Pro Arg
225                 230                 235                 240

Arg Arg Arg Glu Leu Ala Leu Pro Ala
                245

<210> SEQ ID NO 21
<211> LENGTH: 3935
<212> TYPE: DNA
<213> ORGANISM: Siansivirga zeaxanthinifaciens

<400> SEQUENCE: 21
atgaaaaaag aaataataat tatcggttca ggttttttcgt ctctagcagc atcctgctat      60
ttggcgaaag caggttataa tgtaacttta ttagaaaaaa acaacactat tggaggcaga     120
gctcgacaat tagttaaaga cggttttact ttcgatatag gtccaacttg tattggatg     180 cccgatgtat ttgaacgctt cttcaatgat tttgataaaa accttcaga ttactatagt     240 cttgaaaaac tgaatcccgc atacagtgtt tattttggaa aaacgacta cattaccatt     300 gaagatacat tagcgaaaat ttctgaagca tttgaaaaag aagaacctgg aagttcaaaa     360
aaactaaaca cctttattga aaagctaaa agcaactacg atatagcaat taagatttg      420 gtttataacc ctggcgtatc gcctctagaa ttggttacta ttgctactat aaaaaaatta     480
gaccaattct ttagtaacat aaaaagagat gttagaaaag aattttaaaaa tgaaaggtta     540 gtaaaaattc ttgaatttcc tgttttattt ttaggagcaa aaccaagcga tacaccttcg     600
ttttatagtt ttatgaatta tgcagatttt ggccttggga cgtttcatcc aaaaaaaggc     660
atgtatcaag ttatcctagc gcttgaaaat ctggcaaaat ctcttggtgt tattataaaa     720
acaaatgctc ccatagaaaa aattatcatt gaaaacaacg aagtaaaagg tgttatttca     780
aatggaaaaa caataaatac caacattgtt gttagtggag ccgattacca tcataccgaa     840
acgttattag ataaaacata cagacaatat agtgagtctt actggagtaa aaagactttt     900
gcaccgtcat cactactatt ttatgtaggt ttcgataaaa agattcaaaa tgtaaatcat     960
cacacattat tttttgatgt agattttgat gtacatgcag aagccatata cgatactcca    1020
aaatggcccg aagaaccact ttttttacgca agttttccta gtataacgga tgctaacagc    1080
gccccagaag gtaaagaagc tggcatattt ttaatacct tagcgccagg attagaagat     1140
acagaagcgt taagagaagc ctattttgaa aaaattatga cacgttttga ggccttaact    1200
agtcaaaata ttaaaaaaca tgttatattt aaagagagtt tttgtatcaa tgattttata    1260
aaagattata attcttacaa aggaaacgct tacggaatgg ctaatacaat tacccaaacc    1320
gcatttttaa gacccaaatt aaaaagtaaa aaagttaaag gttatttttt tacaggtcaa    1380
ttaacagttc ctggtcccgg tgtaccacca tcattaattt caggaaagtt agtagcagat    1440
ttagtaacca acaccattc tttatgaaag cattatttga taccgtttca tacaattgca    1500
gcaaattagt aacaaaatct tatagcactt catttttcgct tgctactaaa atgctataca    1560
aatctataag acccgatatt tacaacattt acggatttgt tagatttgct gatgagattg    1620
tagattcgtt tcatgatttt aataagaag aactacttaa caaatttgaa gccgatttag    1680
agcatgctct cgaacatagg gtaagtttaa acccctatttt aaatgccttc cagtacacat    1740
```

-continued

```
accataagaa taaaatagag aaaagcatgg tcgatgcttt tatgaaaagt atgcgacttg   1800
atttacataa aactcaatac ctaacaaacg aagagtacaa agaatacatt tacggttctg   1860
cagatgttgt aggacttatg tgtttaaagg ttttttgtgaa tggtgataac gaaaaatttg   1920
aagctttaaa agatacagcc atggcacttg gttctgcttt tcaaaaagtt aacttttaa    1980 gagatttaaa agatgattac gaaggtttaa acagaacata tttcccgaat accgatttaa   2040
ataaccttga tgaacaatcg aaactagata ttattcaaga tattgaaaaa gattttgaaa   2100
aaggcttaac aggaattaaa aaattaccaa ttgaggctaa atttggtgtt tttatggctt   2160
acagatatta tcatcaattg cttaaaaaac ttaaaaaaac acctgctttt aatattaaaa   2220
acaccagaat acgcgtttca atcctaaaa aaatagaatt attaatgcgt agttatgtaa    2280
aatatcaatt aaaattaatg taaatttata gtatgcaaac actattatgg ataatcattt   2340
ttttagcaac gtattgtatc atggaattta tggcgtggtt tacgcataaa tacattatgc   2400 atggctttt atggagttta cacaaagacc atcacaagaa agatcacgat agttggttcg    2460
aaagaaacga tgcttttttt tatttatg ctattgttag cataggttgt ttttttactt      2520
ggaaatacga catattttgg gctggtttac ccattggcgt tggtattttt gcttatggat   2580
tatcatactt tttggtacac gatatattta ttcatcaacg ttttaaatta tttagaaatg   2640
ccaataactg gtatgctaaa ggtgtaagac gtgctcacaa aatgcaccac aaacatattg   2700 gaaagaaga tggcgaatgc tttggtatgt tgtttgttcc ttttaaatac ttcaagaaat     2760
aattttctat taattacatg atatctaaca cccatttcga ttatatcatt attggaaatg   2820
gattagcagg gcttcagttg gcattaaaaa tgagtgctga tgtttatttt aaagataaac   2880
gcatcgcttt aatagatggt tctaacaaaa acacaaacga taaaacctgg agtttttggg   2940
aagaaaactc atctcaatgg gatgccatta caactaaaag ttggaatatt gccaacattt   3000
acacttccaa aaaacatatt tcattagcac tttgccccta taaatataaa tctatacgtt   3060
ctatagattt atataattat gcgaaattcg agcttcaaaa acattctaat ttttcattta   3120
taattgattt tgtatgtact accacagaaa cagaagataa aaaggtatta gtagaaactt   3180
cctctaataa attcactgcc tcacatgttt ttgatagtag aattccagaa gattttttc    3240 aaaaaaataa aaattacaca cacataattc aacactttaa aggctatgta attaaaacag   3300
aagaagccta ttttaatgac gacaccttca cgatgatgga ttatcgattg aaagatggtg   3360
aacaaaccac atttacctat gtactgcctt tttcaaaaac agaagcttta atagaattta   3420 cctatttttac agaaaattta gttaatgaag ccgtttatga tgcattcatt gaaaaataca   3480
taaaaaacta tcttaaaatt gactcgtatt taattatgga aacagaaata ggtcaaattc   3540
ctatgactaa tttcccatt gcaaggttca atacaaaaaa tataacgaaa ataggcactg    3600
gtggtggatg ggtaaagggg tctacggggtt attcttttaa acataccgaa aaaaaatat   3660 ctaaaatcat cgaaaatatt aaagctaaca acataccaag cgctcactta tttaagaaaa   3720
ggtatcgttt ttatgacaaa atatttttaa aggttttaaa agataacaac cacaaaggcg   3780
aatggatttt tgagcaattt tacaacaaaa attctcctca aaatatgttt aaatttcttg   3840
atgaagaatc tactttttt gatgaattaa aaattatgta ttcattattc tctttgcctt     3900
ttattaaagc atttttcaag accctttcca aataa                              3935
```

<210> SEQ ID NO 22
<211> LENGTH: 149
<212> TYPE: PRT

<213> ORGANISM: Siansivirga zeaxanthinifaciens

<400> SEQUENCE: 22

| | | | | | | | | | | | | | | | |
|---|---|---|---|---|---|---|---|---|---|---|---|---|---|---|---|
| Met | Gln | Thr | Leu | Leu | Trp | Ile | Ile | Ile | Phe | Leu | Ala | Thr | Tyr | Cys | Ile |
| 1 | | | | 5 | | | | | 10 | | | | | 15 | |
| Met | Glu | Phe | Met | Ala | Trp | Phe | Thr | His | Lys | Tyr | Ile | Met | His | Gly | Phe |
| | | | 20 | | | | | 25 | | | | | 30 | | |
| Leu | Trp | Ser | Leu | His | Lys | Asp | His | Lys | Lys | Asp | His | Asp | Ser | Trp | |
| | | 35 | | | | | 40 | | | | | 45 | | | |
| Phe | Glu | Arg | Asn | Asp | Ala | Phe | Phe | Ile | Phe | Tyr | Ala | Ile | Val | Ser | Ile |
| | 50 | | | | | 55 | | | | | 60 | | | | |
| Gly | Cys | Phe | Leu | Leu | Trp | Lys | Tyr | Asp | Ile | Phe | Trp | Ala | Gly | Leu | Pro |
| 65 | | | | | 70 | | | | | 75 | | | | | 80 |
| Ile | Gly | Val | Gly | Ile | Phe | Ala | Tyr | Gly | Leu | Ser | Tyr | Phe | Leu | Val | His |
| | | | | 85 | | | | | 90 | | | | | 95 | |
| Asp | Ile | Phe | Ile | His | Gln | Arg | Phe | Lys | Leu | Phe | Arg | Asn | Ala | Asn | Asn |
| | | | 100 | | | | | 105 | | | | | 110 | | |
| Trp | Tyr | Ala | Lys | Gly | Val | Arg | Arg | Ala | His | Lys | Met | His | His | Lys | His |
| | | | 115 | | | | | 120 | | | | | 125 | | |
| Ile | Gly | Lys | Glu | Asp | Gly | Glu | Cys | Phe | Gly | Met | Leu | Phe | Val | Pro | Phe |
| | | | 130 | | | | | 135 | | | | | 140 | | |
| Lys | Tyr | Phe | Lys | Lys | | | | | | | | | | | |
| 145 | | | | | | | | | | | | | | | |

<210> SEQ ID NO 23
<211> LENGTH: 385
<212> TYPE: PRT
<213> ORGANISM: Siansivirga zeaxanthinifaciens

<400> SEQUENCE: 23

| | | | | | | | | | | | | | | | |
|---|---|---|---|---|---|---|---|---|---|---|---|---|---|---|---|
| Met | Ile | Ser | Asn | Thr | His | Phe | Asp | Tyr | Ile | Ile | Ile | Gly | Asn | Gly | Leu |
| 1 | | | | 5 | | | | | 10 | | | | | 15 | |
| Ala | Gly | Leu | Gln | Leu | Ala | Leu | Lys | Met | Ser | Ala | Asp | Val | Tyr | Phe | Lys |
| | | | 20 | | | | | 25 | | | | | 30 | | |
| Asp | Lys | Arg | Ile | Ala | Leu | Ile | Asp | Gly | Ser | Asn | Lys | Asn | Thr | Asn | Asp |
| | | | 35 | | | | | 40 | | | | | 45 | | |
| Lys | Thr | Trp | Ser | Phe | Trp | Glu | Glu | Asn | Ser | Ser | Gln | Trp | Asp | Ala | Ile |
| | 50 | | | | | 55 | | | | | 60 | | | | |
| Thr | Thr | Lys | Ser | Trp | Asn | Ile | Ala | Asn | Ile | Tyr | Thr | Ser | Lys | Lys | His |
| 65 | | | | | 70 | | | | | 75 | | | | | 80 |
| Ile | Ser | Leu | Ala | Leu | Cys | Pro | Tyr | Lys | Tyr | Lys | Ser | Ile | Arg | Ser | Ile |
| | | | | 85 | | | | | 90 | | | | | 95 | |
| Asp | Leu | Tyr | Asn | Tyr | Ala | Lys | Phe | Glu | Leu | Gln | Lys | His | Ser | Asn | Phe |
| | | | 100 | | | | | 105 | | | | | 110 | | |
| Ser | Phe | Ile | Ile | Asp | Phe | Val | Cys | Thr | Thr | Glu | Thr | Glu | Asp | Lys | |
| | | | 115 | | | | | 120 | | | | | 125 | | |
| Lys | Val | Leu | Val | Glu | Thr | Ser | Ser | Asn | Lys | Phe | Thr | Ala | Ser | His | Val |
| | | | 130 | | | | | 135 | | | | | 140 | | |
| Phe | Asp | Ser | Arg | Ile | Pro | Glu | Asp | Phe | Phe | Gln | Lys | Asn | Lys | Asn | Tyr |
| 145 | | | | | 150 | | | | | 155 | | | | | 160 |
| Thr | His | Ile | Ile | Gln | His | Phe | Lys | Gly | Tyr | Val | Ile | Lys | Thr | Glu | Glu |
| | | | | 165 | | | | | 170 | | | | | 175 | |
| Ala | Tyr | Phe | Asn | Asp | Asp | Thr | Phe | Thr | Met | Met | Asp | Tyr | Arg | Leu | Lys |
| | | | 180 | | | | | 185 | | | | | 190 | | |
| Asp | Gly | Glu | Gln | Thr | Thr | Phe | Thr | Tyr | Val | Leu | Pro | Phe | Ser | Lys | Thr |

```
                195                 200                 205
Glu Ala Leu Ile Glu Phe Thr Tyr Phe Thr Glu Asn Leu Val Asn Glu
210                 215                 220

Ala Val Tyr Asp Ala Phe Ile Glu Lys Tyr Ile Lys Asn Tyr Leu Lys
225                 230                 235                 240

Ile Asp Ser Tyr Leu Ile Met Glu Thr Glu Ile Gly Gln Ile Pro Met
                245                 250                 255

Thr Asn Phe Pro Phe Ala Arg Phe Asn Thr Lys Asn Ile Thr Lys Ile
                260                 265                 270

Gly Thr Gly Gly Gly Trp Val Lys Gly Ser Thr Gly Tyr Ser Phe Lys
                275                 280                 285

His Thr Glu Lys Lys Ile Ser Lys Ile Ile Glu Asn Ile Lys Ala Asn
290                 295                 300

Asn Ile Pro Ser Ala His Leu Phe Lys Lys Arg Tyr Arg Phe Tyr Asp
305                 310                 315                 320

Lys Ile Phe Leu Lys Val Leu Lys Asp Asn Asn His Lys Gly Glu Trp
                325                 330                 335

Ile Phe Glu Gln Phe Tyr Asn Lys Asn Ser Pro Gln Asn Met Phe Lys
                340                 345                 350

Phe Leu Asp Glu Glu Ser Thr Phe Asp Glu Leu Lys Ile Met Tyr
                355                 360                 365

Ser Leu Phe Ser Leu Pro Phe Ile Lys Ala Phe Phe Lys Thr Leu Phe
                370                 375                 380

Lys
385

<210> SEQ ID NO 24
<211> LENGTH: 488
<212> TYPE: PRT
<213> ORGANISM: Siansivirga zeaxanthinifaciens

<400> SEQUENCE: 24

Met Lys Lys Glu Ile Ile Ile Gly Ser Gly Phe Ser Ser Leu Ala
1               5                   10                  15

Ala Ser Cys Tyr Leu Ala Lys Ala Gly Tyr Asn Val Thr Leu Leu Glu
                20                  25                  30

Lys Asn Asn Thr Ile Gly Gly Arg Ala Arg Gln Leu Val Lys Asp Gly
                35                  40                  45

Phe Thr Phe Asp Ile Gly Pro Thr Trp Tyr Trp Met Pro Asp Val Phe
    50                  55                  60

Glu Arg Phe Phe Asn Asp Phe Asp Lys Lys Pro Ser Asp Tyr Tyr Ser
65                  70                  75                  80

Leu Glu Lys Leu Asn Pro Ala Tyr Ser Val Tyr Phe Gly Lys Asn Asp
                85                  90                  95

Tyr Ile Thr Ile Glu Asp Thr Leu Ala Lys Ile Ser Glu Ala Phe Glu
                100                 105                 110

Lys Glu Glu Pro Gly Ser Ser Lys Leu Asn Thr Phe Ile Glu Lys
            115                 120                 125

Ala Lys Ser Asn Tyr Asp Ile Ala Ile Lys Asp Leu Val Tyr Asn Pro
130                 135                 140

Gly Val Ser Pro Leu Glu Leu Val Thr Ile Ala Thr Ile Lys Lys Leu
145                 150                 155                 160

Asp Gln Phe Phe Ser Asn Ile Lys Arg Asp Val Arg Lys Glu Phe Lys
                165                 170                 175
```

```
Asn Glu Arg Leu Val Lys Ile Leu Glu Phe Pro Val Leu Phe Leu Gly
            180                 185                 190

Ala Lys Pro Ser Asp Thr Pro Ser Phe Tyr Ser Phe Met Asn Tyr Ala
        195                 200                 205

Asp Phe Gly Leu Gly Thr Phe His Pro Lys Lys Gly Met Tyr Gln Val
    210                 215                 220

Ile Leu Ala Leu Glu Asn Leu Ala Lys Ser Leu Gly Val Ile Ile Lys
225                 230                 235                 240

Thr Asn Ala Pro Ile Glu Lys Ile Ile Glu Asn Asn Glu Val Lys
                245                 250                 255

Gly Val Ile Ser Asn Gly Lys Thr Ile Asn Thr Asn Ile Val Val Ser
            260                 265                 270

Gly Ala Asp Tyr His His Thr Glu Thr Leu Leu Asp Lys Thr Tyr Arg
        275                 280                 285

Gln Tyr Ser Glu Ser Tyr Trp Ser Lys Lys Thr Phe Ala Pro Ser Ser
    290                 295                 300

Leu Leu Phe Tyr Val Gly Phe Asp Lys Lys Ile Gln Asn Val Asn His
305                 310                 315                 320

His Thr Leu Phe Phe Asp Val Asp Phe Asp Val His Ala Glu Ala Ile
                325                 330                 335

Tyr Asp Thr Pro Lys Trp Pro Glu Glu Pro Leu Phe Tyr Ala Ser Phe
            340                 345                 350

Pro Ser Ile Thr Asp Ala Asn Ser Ala Pro Glu Gly Lys Glu Ala Gly
        355                 360                 365

Ile Phe Leu Ile Pro Leu Ala Pro Gly Leu Glu Asp Thr Glu Ala Leu
    370                 375                 380

Arg Glu Ala Tyr Phe Glu Lys Ile Met Thr Arg Phe Glu Ala Leu Thr
385                 390                 395                 400

Ser Gln Asn Ile Lys Lys His Val Ile Phe Lys Glu Ser Phe Cys Ile
                405                 410                 415

Asn Asp Phe Ile Lys Asp Tyr Asn Ser Tyr Lys Gly Asn Ala Tyr Gly
            420                 425                 430

Met Ala Asn Thr Ile Thr Gln Thr Ala Phe Leu Arg Pro Lys Leu Lys
        435                 440                 445

Ser Lys Lys Val Lys Gly Leu Phe Phe Thr Gly Gln Leu Thr Val Pro
    450                 455                 460

Gly Pro Gly Val Pro Pro Ser Leu Ile Ser Gly Lys Leu Val Ala Asp
465                 470                 475                 480

Leu Val Thr Lys His His Ser Leu
                485

<210> SEQ ID NO 25
<211> LENGTH: 279
<212> TYPE: PRT
<213> ORGANISM: Siansivirga zeaxanthinifaciens

<400> SEQUENCE: 25

Met Lys Ala Leu Phe Asp Thr Val Ser Tyr Asn Cys Ser Lys Leu Val
1               5                   10                  15

Thr Lys Ser Tyr Ser Thr Ser Phe Ser Leu Ala Thr Lys Met Leu Tyr
            20                  25                  30

Lys Ser Ile Arg Pro Asp Ile Tyr Asn Ile Tyr Gly Phe Val Arg Phe
        35                  40                  45

Ala Asp Glu Ile Val Asp Ser Phe His Asp Phe Asn Lys Glu Glu Leu
    50                  55                  60
```

Leu Asn Lys Phe Glu Ala Asp Leu Glu His Ala Leu His Arg Val
65                  70                  75                  80

Ser Leu Asn Pro Ile Leu Asn Ala Phe Gln Tyr Thr Tyr His Lys Asn
            85                  90                  95

Lys Ile Glu Lys Ser Met Val Asp Ala Phe Met Lys Ser Met Arg Leu
        100                 105                 110

Asp Leu His Lys Thr Gln Tyr Leu Thr Asn Glu Glu Tyr Lys Glu Tyr
    115                 120                 125

Ile Tyr Gly Ser Ala Asp Val Val Gly Leu Met Cys Leu Lys Val Phe
130                 135                 140

Val Asn Gly Asp Asn Glu Lys Phe Glu Ala Leu Lys Asp Thr Ala Met
145                 150                 155                 160

Ala Leu Gly Ser Ala Phe Gln Lys Val Asn Phe Leu Arg Asp Leu Lys
                165                 170                 175

Asp Asp Tyr Glu Gly Leu Asn Arg Thr Tyr Phe Pro Asn Thr Asp Leu
            180                 185                 190

Asn Asn Leu Asp Glu Gln Ser Lys Leu Asp Ile Ile Gln Asp Ile Glu
        195                 200                 205

Lys Asp Phe Glu Lys Gly Leu Thr Gly Ile Lys Lys Leu Pro Ile Glu
210                 215                 220

Ala Lys Phe Gly Val Phe Met Ala Tyr Arg Tyr Tyr His Gln Leu Leu
225                 230                 235                 240

Lys Lys Leu Lys Lys Thr Pro Ala Phe Asn Ile Lys Asn Thr Arg Ile
                245                 250                 255

Arg Val Ser Asn Pro Lys Lys Ile Glu Leu Leu Met Arg Ser Tyr Val
            260                 265                 270

Lys Tyr Gln Leu Lys Leu Met
            275

<210> SEQ ID NO 26
<211> LENGTH: 3904
<212> TYPE: DNA
<213> ORGANISM: Mesoflavibacter zeaxanthinifaciens

<400> SEQUENCE: 26
atgaaaaata aaatagcaat aataggttct gggttttctg ctttatctgc tgcatgttat      60
cttgctaagg atggatttaa tgtttcagtt tttgaaaaaa atgatactgt aggaggacgt    120
tgtagacagt ttaaaaaaga tggatttact tttgatatgg gaccaagctg gtattggatg    180
cctgatatat ttgataagtt ttttaatgat tttgataaaa aaacttcaga tttttatcag    240
ctagacaagc tttctcctgc gtataaaatt ttctttaatg atgaagttat caccatagga    300
gatacaatgg agaaaatttg cgaagaattt gaacgcatag aaaaaggaag ttcaattcct    360
cttaaaaaat ttataaataa agctgcagat aattataaca ttgccataaa caaaattgta    420
ttaaaaccag gtgtttcacc cttagaattg gttactaaag atactgttac tagactagat    480 caattttta aaacaataag cagtgatgtt agacgccagt ttaaaaaccc taaactaata    540
tctactttag agtttcctgt tttgtttttg ggtgcaaaac caagcaatac accttctttt    600
tatagtttta tgaattacgc cgattttggc ttaggtactt ggcatcctaa aggcggaatg    660
tatcaaataa ttcttgcaat gagacaactt gcagaagaat taggtgtttc aataaatgta    720
aactctaatg ttactaatat taatgttgaa ataatacat caacatcaat tactgttaac    780
ggtaaaactt taagtttga tgttgtttta agcggtgcag attatcatca ctcagaaacg    840

```
ttgttagata gaaaatatag acagtattca gaaaaatatt ggaacaataa aacctttgct    900
ccttcttctc tcctatttta cgtaggtttt gataagaaat tgaaaaatgt aaaccatcat    960
aacttatttt ttgataccaa cttttgaaacg catgcagaag atatttacga taatccaaaa   1020
tggcctaaag aacctctatt ttatgccaat ttcccatctg taacagataa cagcatggcg   1080
cctaatggta agaaaatgg ttttttctta ataccaattg ctcctaactt agaagataca    1140
cctcaattaa gagaacaata ttttgatata atcatgtctc gttttgaaaa attaactcaa    1200
caagatgtta aaaatagtat tatctttaaa gaaagctttt gtgttaaaga tttttattgaa   1260
gcatataatt cctacaaagg aaacgcatac ggaatggcta atacgctaac gcaaaccgct    1320
tttttaagac caaatttaaa gagtaaaaaa gttaacaacc tctactttac aggacaatta    1380
actgttcctg gtccaggtgt gccgccagca cttatatctg gaaaattagt agcagaatta    1440
atccaaaaac accaccaaaa actatgaaag caatatttga ttctgtgtcg tacaattgta    1500
gtaaagttgt tactacatct tacagcactt cgttttcttt agctacaaaa atgcttgcaa    1560
agtctatcag acaggatatt tataatattt atggttttgt gaggtttgca gatgagattg    1620
tagacacttt tcatgattat gataaagaaa cttatttaa caattttgaa aatgatttag     1680
aattagctct aaaaaacaaa attagcctaa atccaatatt aaatgcgttt caacatacat    1740
atcacaagta taacatcgaa aaacatatgg ttgatgcttt tatgaaaagt atgcgactag    1800
atttatctaa aactaaatac actacagacc aagagtataa agattatatt tatggttctg    1860
cagacgtagt tggactaatg tgtttaaaag tctttgttaa aggagataat gatcaatacg    1920
aaaaacttaa agacacagca atgtcattag gttctgcttt tcaaaaggtg aattttttac    1980
gagacttaaa agctgatcac gaattacttg atagaactta tttcccaaat acagatttaa    2040
ataatcaac tgaagaagat aaactattca tcattaatga tattgaaaac gattttaaaa     2100
aaggcttaga aggtataaaa caattaccta tggaggctaa atttggagta tttatggctt    2160
atagatacta tcaccagtta ctggcaaagc ttaaaaaaac accagcatta gaaattaaaa    2220
atactagaat aagagtacca aactacaaaa aggcagaact tttaactaga agctacgtaa    2280
agtatcagtt aaatttatta taattagaca tgaaaacatt gtattggata ttaatatttt    2340
taggcacatt ttctatcatg gaatttatgg catggtttac acataaatac atcatgcacg    2400
gatttttatg gtcactacat aaagaccatc atctaaaaga tcacgatagc tggtttgagc    2460
gtaatgatgc cttttttatc ttttatgcaa ttgtaagtat gacttgcttt tacttatgga    2520
gttacgaaga tatatggtat acattaccaa taggcttagg cattatggct tatggtgcag    2580
cttacttctt agtacacgat atttttatcc atcaacgctt taaaatgttt agaaatgcta    2640
ataattggta cgcacgtggt gttagacgtg cacacaaaat acatcacaag catataggca    2700
aagaagatgg agaaaacttt ggcatgttag tcgtaccatt taagtacttc aaaaaataga    2760
ctaaatgtct caaaaacatt atgattatat catagttggc aatggtttag ctggacttca    2820
attagcctta gcttttgcca aggattcata ttttaataat aaatccattg ctttaataga    2880
cgcttctact aaaactgaaa atgataaaac ttggagtttt tgggaacaaa acaatagcac    2940
ttttagtcat ttaacttacc aatcctggca acatgcaact atctacgcag aagaccaaaa    3000
aataagctta aatctaaaac cttatactta taaatctata cgtgcaatag acttttatac    3060
ggaagctaaa gcacaactca atcagcaaga caatattaca ttttggtgg aaaccgtgac    3120
ttcggttaaa gaaaaagaaa tagttgaagt cacaaccaaa acaaacaact atacgacaaa    3180
tcatgttttt gatagtcgga ttccagacgc gttttttaaa gatgaaaaag ccacaacttt    3240
```

```
aatacaacat ttaaaggct ggattataga agctgaaaac gatgttttta atgaaaacag    3300
cttaacaatg atggattatc gattaaaaga taataatcaa acaaccttta tgtatgtgtt    3360
accgcataca aaaataaag cgttagtaga atttacatat tttacggaaa acactgttaa    3420
aagtgaccat tacgacaact atttaaagca atatatttca gaatatttaa acattaataa    3480
ttataatatt gtcgaaactg aagttggtca ataccaatg acaacttttta attttcaatt    3540 gtttaactct tccaaaatca ctaaaattgg tacagctggc ggttgggtaa aaccttctac    3600
gggatattct tttaaactca cagaaaaag agttgcaaaa attattgaga atataaaaac    3660
caatcaacca accacaaacg gatttttta aaacaagtat aaattttacg acaaagtatt    3720
tttacaagtt ttaaagata ataatgaaaa aggcgaatgg gtttttaatc aattttacag    3780
taaaaatagc acaccaacca tgtttaaatt tttagatgaa gagtcttcac tttttgaaga    3840
cattaaaatt atgtggtcgt tatttagttt cagtttttatt aaagcttttt ttaaaacgct    3900
ttaa                                                                 3904
```

<210> SEQ ID NO 27
<211> LENGTH: 149
<212> TYPE: PRT
<213> ORGANISM: Mesoflavibacter zeaxanthinifaciens

<400> SEQUENCE: 27

```
Met Lys Thr Leu Tyr Trp Ile Leu Ile Phe Leu Gly Thr Phe Ser Ile
1               5                   10                  15

Met Glu Phe Met Ala Trp Phe Thr His Lys Tyr Ile Met His Gly Phe
            20                  25                  30

Leu Trp Ser Leu His Lys Asp His Leu Lys Asp His Asp Ser Trp
        35                  40                  45

Phe Glu Arg Asn Asp Ala Phe Phe Ile Phe Tyr Ala Ile Val Ser Met
    50                  55                  60

Thr Cys Phe Tyr Leu Trp Ser Tyr Glu Asp Ile Trp Tyr Thr Leu Pro
65                  70                  75                  80

Ile Gly Leu Gly Ile Met Ala Tyr Gly Ala Ala Tyr Phe Leu Val His
                85                  90                  95

Asp Ile Phe Ile His Gln Arg Phe Lys Met Phe Arg Asn Ala Asn Asn
            100                 105                 110

Trp Tyr Ala Arg Gly Val Arg Arg Ala His Lys Ile His His Lys His
        115                 120                 125

Ile Gly Lys Glu Asp Gly Glu Asn Phe Gly Met Leu Val Val Pro Phe
    130                 135                 140

Lys Tyr Phe Lys Lys
145
```

<210> SEQ ID NO 28
<211> LENGTH: 379
<212> TYPE: PRT
<213> ORGANISM: Mesoflavibacter zeaxanthinifaciens

<400> SEQUENCE: 28

```
Met Ser Gln Lys His Tyr Asp Tyr Ile Ile Val Gly Asn Gly Leu Ala
1               5                   10                  15

Gly Leu Gln Leu Ala Leu Ala Phe Ala Lys Asp Ser Tyr Phe Asn Asn
            20                  25                  30

Lys Ser Ile Ala Leu Ile Asp Ala Ser Thr Lys Thr Glu Asn Asp Lys
        35                  40                  45
```

Thr Trp Ser Phe Trp Glu Gln Asn Asn Ser Phe Ser His Leu Thr
    50                  55                  60

Tyr Gln Ser Trp Gln His Ala Thr Ile Tyr Ala Glu Asp Gln Lys Ile
65                  70                  75                  80

Ser Leu Asn Leu Lys Pro Tyr Thr Tyr Lys Ser Ile Arg Ala Ile Asp
                85                  90                  95

Phe Tyr Thr Glu Ala Lys Ala Gln Leu Asn Gln Gln Asp Asn Ile Thr
            100                 105                 110

Phe Leu Val Glu Thr Val Thr Ser Val Lys Glu Lys Glu Ile Val Glu
        115                 120                 125

Val Thr Thr Lys Thr Asn Asn Tyr Thr Thr Asn His Val Phe Asp Ser
    130                 135                 140

Arg Ile Pro Asp Ala Phe Phe Lys Asp Glu Lys Ala Thr Thr Leu Ile
145                 150                 155                 160

Gln His Phe Lys Gly Trp Ile Ile Glu Ala Glu Asn Asp Val Phe Asn
                165                 170                 175

Glu Asn Ser Leu Thr Met Met Asp Tyr Arg Leu Lys Asp Asn Asn Gln
            180                 185                 190

Thr Thr Phe Met Tyr Val Leu Pro His Thr Lys Asn Lys Ala Leu Val
        195                 200                 205

Glu Phe Thr Tyr Phe Thr Glu Asn Thr Val Lys Ser Asp His Tyr Asp
    210                 215                 220

Asn Tyr Leu Lys Gln Tyr Ile Ser Glu Tyr Leu Asn Ile Asn Asn Tyr
225                 230                 235                 240

Asn Ile Val Glu Thr Glu Val Gly Gln Ile Pro Met Thr Thr Phe Asn
                245                 250                 255

Phe Gln Leu Phe Asn Ser Ser Lys Ile Thr Lys Ile Gly Thr Ala Gly
            260                 265                 270

Gly Trp Val Lys Pro Ser Thr Gly Tyr Ser Phe Lys Leu Thr Glu Lys
        275                 280                 285

Arg Val Ala Lys Ile Ile Glu Asn Ile Lys Thr Asn Gln Pro Thr Thr
    290                 295                 300

Asn Gly Phe Phe Lys Asn Lys Tyr Lys Phe Tyr Asp Lys Val Phe Leu
305                 310                 315                 320

Gln Val Leu Lys Asp Asn Asn Glu Lys Gly Glu Trp Val Phe Asn Gln
                325                 330                 335

Phe Tyr Ser Lys Asn Ser Thr Pro Thr Met Phe Lys Phe Leu Asp Glu
            340                 345                 350

Glu Ser Ser Leu Phe Glu Asp Ile Lys Ile Met Trp Ser Leu Phe Ser
        355                 360                 365

Phe Ser Phe Ile Lys Ala Phe Phe Lys Thr Leu
    370                 375

<210> SEQ ID NO 29
<211> LENGTH: 488
<212> TYPE: PRT
<213> ORGANISM: Mesoflavibacter zeaxanthinifaciens

<400> SEQUENCE: 29

Met Lys Asn Lys Ile Ala Ile Ile Gly Ser Gly Phe Ser Ala Leu Ser
1               5                   10                  15

Ala Ala Cys Tyr Leu Ala Lys Asp Gly Phe Asn Val Ser Val Phe Glu
            20                  25                  30

Lys Asn Asp Thr Val Gly Gly Arg Cys Arg Gln Phe Lys Lys Asp Gly

```
                35                  40                  45
Phe Thr Phe Asp Met Gly Pro Ser Trp Tyr Trp Met Pro Asp Ile Phe
 50                  55                  60

Asp Lys Phe Asn Asp Phe Asp Lys Lys Thr Ser Asp Phe Tyr Gln
 65                  70                  75                  80

Leu Asp Lys Leu Ser Pro Ala Tyr Lys Ile Phe Phe Asn Asp Glu Val
                     85                  90                  95

Ile Thr Ile Gly Asp Thr Met Glu Lys Ile Cys Glu Glu Phe Glu Arg
                100                 105                 110

Ile Glu Lys Gly Ser Ser Ile Pro Leu Lys Lys Phe Ile Asn Lys Ala
                115                 120                 125

Ala Asp Asn Tyr Asn Ile Ala Ile Asn Lys Ile Val Leu Lys Pro Gly
                130                 135                 140

Val Ser Pro Leu Glu Leu Val Thr Lys Asp Thr Val Thr Arg Leu Asp
145                 150                 155                 160

Gln Phe Phe Lys Thr Ile Ser Ser Asp Val Arg Arg Gln Phe Lys Asn
                     165                 170                 175

Pro Lys Leu Ile Ser Thr Leu Glu Phe Pro Val Leu Phe Leu Gly Ala
                180                 185                 190

Lys Pro Ser Asn Thr Pro Ser Phe Tyr Ser Phe Met Asn Tyr Ala Asp
                195                 200                 205

Phe Gly Leu Gly Thr Trp His Pro Lys Gly Gly Met Tyr Gln Ile Ile
                210                 215                 220

Leu Ala Met Arg Gln Leu Ala Glu Glu Leu Gly Val Ser Ile Asn Val
225                 230                 235                 240

Asn Ser Asn Val Thr Asn Ile Asn Val Glu Asn Asn Thr Ser Thr Ser
                     245                 250                 255

Ile Thr Val Asn Gly Lys Thr Leu Lys Phe Asp Val Val Leu Ser Gly
                260                 265                 270

Ala Asp Tyr His His Ser Glu Thr Leu Leu Asp Arg Lys Tyr Arg Gln
                275                 280                 285

Tyr Ser Glu Lys Tyr Trp Asn Asn Lys Thr Phe Ala Pro Ser Ser Leu
290                 295                 300

Leu Phe Tyr Val Gly Phe Asp Lys Lys Leu Lys Asn Val Asn His His
305                 310                 315                 320

Asn Leu Phe Phe Asp Thr Asn Phe Glu Thr His Ala Glu Asp Ile Tyr
                     325                 330                 335

Asp Asn Pro Lys Trp Pro Lys Glu Pro Leu Phe Tyr Ala Asn Phe Pro
                340                 345                 350

Ser Val Thr Asp Asn Ser Met Ala Pro Asn Gly Lys Glu Asn Gly Phe
                355                 360                 365

Phe Leu Ile Pro Ile Ala Pro Asn Leu Glu Asp Thr Pro Gln Leu Arg
                370                 375                 380

Glu Gln Tyr Phe Asp Ile Ile Met Ser Arg Phe Glu Lys Leu Thr Gln
385                 390                 395                 400

Gln Asp Val Lys Asn Ser Ile Ile Phe Lys Glu Ser Phe Cys Val Lys
                     405                 410                 415

Asp Phe Ile Glu Ala Tyr Asn Ser Tyr Lys Gly Asn Ala Tyr Gly Met
                420                 425                 430

Ala Asn Thr Leu Thr Gln Thr Ala Phe Leu Arg Pro Asn Leu Lys Ser
                435                 440                 445

Lys Lys Val Asn Asn Leu Tyr Phe Thr Gly Gln Leu Thr Val Pro Gly
450                 455                 460
```

Pro Gly Val Pro Pro Ala Leu Ile Ser Gly Lys Leu Val Ala Glu Leu
465                 470                 475                 480

Ile Gln Lys His His Gln Lys Leu
                485

<210> SEQ ID NO 30
<211> LENGTH: 279
<212> TYPE: PRT
<213> ORGANISM: Mesoflavibacter zeaxanthinifaciens

<400> SEQUENCE: 30

Met Lys Ala Ile Phe Asp Ser Val Ser Tyr Asn Cys Ser Lys Val Val
1               5                   10                  15

Thr Thr Ser Tyr Ser Thr Ser Phe Ser Leu Ala Thr Lys Met Leu Ala
            20                  25                  30

Lys Ser Ile Arg Gln Asp Ile Tyr Asn Ile Tyr Gly Phe Val Arg Phe
        35                  40                  45

Ala Asp Glu Ile Val Asp Thr Phe His Asp Tyr Asp Lys Glu Thr Leu
    50                  55                  60

Phe Asn Asn Phe Glu Asn Asp Leu Glu Leu Ala Leu Lys Asn Lys Ile
65                  70                  75                  80

Ser Leu Asn Pro Ile Leu Asn Ala Phe Gln His Thr Tyr His Lys Tyr
                85                  90                  95

Asn Ile Glu Lys His Met Val Asp Ala Phe Met Lys Ser Met Arg Leu
            100                 105                 110

Asp Leu Ser Lys Thr Lys Tyr Thr Thr Asp Gln Glu Tyr Lys Asp Tyr
        115                 120                 125

Ile Tyr Gly Ser Ala Asp Val Val Gly Leu Met Cys Leu Lys Val Phe
    130                 135                 140

Val Lys Gly Asp Asn Asp Gln Tyr Glu Lys Leu Lys Asp Thr Ala Met
145                 150                 155                 160

Ser Leu Gly Ser Ala Phe Gln Lys Val Asn Phe Leu Arg Asp Leu Lys
                165                 170                 175

Ala Asp His Glu Leu Leu Asp Arg Thr Tyr Phe Pro Asn Thr Asp Leu
            180                 185                 190

Asn Asn Leu Thr Glu Glu Asp Lys Leu Phe Ile Ile Asn Asp Ile Glu
        195                 200                 205

Asn Asp Phe Lys Lys Gly Leu Glu Gly Ile Lys Gln Leu Pro Met Glu
    210                 215                 220

Ala Lys Phe Gly Val Phe Met Ala Tyr Arg Tyr Tyr His Gln Leu Leu
225                 230                 235                 240

Ala Lys Leu Lys Lys Thr Pro Ala Leu Glu Ile Lys Asn Thr Arg Ile
                245                 250                 255

Arg Val Pro Asn Tyr Lys Lys Ala Glu Leu Leu Thr Arg Ser Tyr Val
            260                 265                 270

Lys Tyr Gln Leu Asn Leu Leu
        275

<210> SEQ ID NO 31
<211> LENGTH: 7292
<212> TYPE: DNA
<213> ORGANISM: Escherichia vulneris

<400> SEQUENCE: 31
atggtgagtg gcagtaaagc gggcgttttcg cctcatcgcg aaatagaagt aatgagacaa    60

```
tccattgacg atcacctggc tggcctgtta cctgaaaccg acagccagga tatcgtcagc      120
cttgcgatgc gtgaaggcgt catggcaccc ggtaaacgga tccgtccgct gctgatgctg      180
ctggccgccc gcgacctccg ctaccagggc agtatgccta cgctgctcga tctcgcctgc      240
gccgttgaac tgacccatac cgcgtcgctg atgctcgacg acatgccctg catggacaac      300
gccgagctgc gccgcggtca gcccactacc cacaaaaaat tggtgagag cgtggcgatc       360 cttgcctccg ttgggctgct ctctaaagcc tttggtctga tcgccgccac cggcgatctg      420
ccgggggaga ggcgtgccca ggcggtcaac gagctctcta ccgccgtggg cgtgcagggc      480
ctggtactgg ggcagtttcg cgatcttaac gatgccgccc tcgaccgtac ccctgacgct      540
atcctcagca ccaaccacct caagaccggc attctgttca gcgcgatgct gcagatcgtc      600
gccattgctt ccgcctcgtc gccgagcacg cgagagacgc tgcacgcctt cgccctcgac      660
ttcggccagg cgtttcaact gctggacgat ctgcgtgacg atcacccgga aaccggtaaa      720
gatcgcaata aggacgcggg aaaatcgacg ctggtcaacc ggctgggcgc agacgcggcc      780
cggcaaaagc tgcgcgagca tattgattcc gccgacaaac acctcacttt tgcctgtccg      840
cagggcggcg ccatccgaca gtttatgcat ctgtggtttg gccatcacct tgccgactgg      900
tcaccggtca tgaaaatcgc ctgataccgc ccttttgggt tcaagcagta cataacgatg      960
gaaccacatt acaggagtag tgatgaatga aggacgagcg ccttgttcag cgtaagaacg     1020
atcatctgga tatcgttctc gaccccgtc gcgccgtaac tcaggctagc gcaggttttg      1080
agcgctggcg ctttacccac tgcgccctgc cagagctgaa ttttagcgac atcacgctgg     1140
aaaccacctt cctgaatcgg cagctacagg ctccgctgct gatcagctcc atgaccggcg     1200
gcgttgagcg ctcgcgccat atcaaccgcc acctcgccga ggcggcgcag gtgctaaaaa     1260
ttgcgatggg ggtgggctcc cagcgcgtcg ccattgagag cgacgcgggc ttagggctgg     1320
ataaaaccct gcggcagctg gctccggacg tgccgctgct ggcgaacctc ggcgcggcgc     1380
agctgaccgg cagaaaaggt attgattacg cccgacgggc cgtggagatg atcgaggcgg     1440
atgcgctgat tgtgcaccta aaccgctgc aggaggcgct acagcccggc ggcgatcgcg      1500
actggcgcgg acggctggcg gctattgaaa tctctggtccg cgagctgccc gttccgctgg     1560
tggtgaaaga ggtgggagcc ggtatctccc gaaccgtggc cgggcagctg atcgatgccg     1620
gcgttaccgt gattgacgtc gcgggcgcgg cggcaccag ctgggccgcc gttgaaggcg      1680
agcgggcggc caccgagcag cagcgcagcg tggccaacgt cttttgccgac tgggggatcc     1740 ccaccgctga ggcgctggtt gacattgccg aggcctggcc gcagatgccc cttattgcct     1800
cgggcgggat taaaaacggc gtcgacgcgg cgaaagcgct gcggctcggc gcgtgcatgg     1860
tagggcaggc cgccgccgtg ctcggcagcg caggcgtctc cacggagaag gtgatcgatc     1920
acttcaacgt gattattgag cagctgcggg tggcctgctt ctgcaccggc agccgcagcc     1980
tgagcgatct aaagcaggct gatatccgct atgtgcggga tacgccatga gccattttgc     2040
cattgtggca ccgccgctct acagtcatgc ggtggcgctg catgccctgg cgctggagat     2100
ggcccaacgc ggccaccggg tgaccttttct caccggcaac gtcgcctcgc tggcagagca     2160
ggaaacggag cgggtggcgt tctatccact tcccgccagc gtgcaacagg cccagcgcaa     2220
cgtccagcag cagagtaacg gcaacctgct gcggctgatt gcggccatgt catccctgac     2280
cgatgtgctc tgccagcagt tgcccgctat tctacagcgg ctggcggtgg acgcgctgat     2340
tgtcgatgag atggagcccg ccggaagcct ggtcgccgag gcgctgggac taccattat      2400 ctctattgcc tgcgcgctgc cggtcaaccg cgagccgggt ctgccgctgc cggtgatgcc     2460
```

| | |
|---|---|
| gtttcactac gccgaggata agagagccct gcggcgtttt caggtcagcg aacggatcta | 2520 |
| cgatgcgctg atgtaccgc acgggcagac gatcctgcgc cacgcccagc gctttggttt | 2580 |
| gccggagcgc aggcgtctcg acgagtgtct ctcgccgctg gcgcagatta gccagtccgt | 2640 |
| tccggccctc gacttccac gccgggcgct gccgaactgt tttcactacg tgggagcact | 2700 |
| gcgctatcag ccgccgccgc aggtagaacg ctcgccacgc agcacgccgc ggatctttgc | 2760 |
| ctcgctgggc accctccagg gccaccgtct acgcctgttt cagaagatcg cccgcgcctg | 2820 |
| tgccagcgtg ggggcggagg tgaccattgc ccactgcgat ggcctgacgc ccgcccaggc | 2880 |
| cgactcgctc tacgcctgcg gcgcgacgga ggtggtcagc tttgtcgacc agccgcgcta | 2940 |
| cgttgccgag gctaatctgg tgatcaccca cggcggtctc aataccgtac tggatgcgct | 3000 |
| ggctgccgcg acgccggtgc tggcggtgcc actctctttc gaccagcccg ccgtggctgc | 3060 |
| ccggctggtc tataacgggc tgggtcgccg ggtatcgcgc tttgccagac agcagacgct | 3120 |
| ggcggatgag attgcccaac tgctgggga tgagacgctg catcagcgtc tggcgacggc | 3180 |
| ccgccagcag cttaacgacg ccgggggcac gccccgtgcg gcgaccctga ttgaacaggc | 3240 |
| catagcagg agtgagagcg tatcgtgagg gatctgattt tagtcggcgg cggcctggcc | 3300 |
| aacgggctga tcgcctggcg tctgcgccag cgctacccgc agcttaacct gctgctgatc | 3360 |
| gaggccgggg agcagcccgg cgggaaccat acctggtcat ccatgaaga cgatctgact | 3420 |
| cccgggcagc acgcctggct ggccccgctg gtggcccacg cctggccggg ctatgaggtg | 3480 |
| cagtttcccg atcttcgccg tcgcctcgcg cgcggctact actccattac ctcagagcgc | 3540 |
| tttgccgagg ccctgcatca ggcgctgggg gagaacatct ggctaaactg ttcggtgagc | 3600 |
| gaggtgttac ccaatagcgt gcgccttgcc aacggtgagg cgctgcttgc cggagcggtg | 3660 |
| attgacggac gcggcgtgac cgccagttcg gcgatgcaaa ccggctatca gctctttctt | 3720 |
| ggtcagcagt ggcggctgac acagcccac ggcctgaccg taccgatcct gatggatgcc | 3780 |
| acggtggcgc agcagcaggg ctatcgcttt gtctacacgc tgccgctctc cgccgacacg | 3840 |
| ctgctgatcg aggatacgcg ctacgccaat gtcccgcagc gtgatgataa tgccctacgc | 3900 |
| cagacggtta ccgactatgc tcacagcaaa gggtggcagc tggcccagct tgaacgcgag | 3960 |
| gagaccggct gtctgccgat taccctggcg ggtgacatcc aggctctgtg gccgatgcg | 4020 |
| ccgggcgtgc cgcgctcggg aatgcgggct gggctatttc accctaccac tggctattcg | 4080 |
| ctgccgctgg cggtggccct tgccgacgcg attgccgaca gcccgcggct gggcagcgtt | 4140 |
| ccgctctatc agctcacccg gcagtttgcc gaacgccact ggcgcaggca gggattcttc | 4200 |
| cgcctgctga accggatgct tttcctggcc gggcgcgagg agaaccgctg gcgggtgatg | 4260 |
| cagcgctttt atgggctgcc ggagcccacc gtagagcgct tttacgccgg tcggctctct | 4320 |
| ctctttgata aggcccgcat tttgacgggc aagccaccgg ttccgctggg cgaagcctgg | 4380 |
| cgggcggcgc tgaaccattt tcctgacaga cgagataaag gatgaaaaaa accgttgtga | 4440 |
| ttggcgcagg ctttggtggc ctggcgctgg cgattcgcct gcaggcggca gggatcccaa | 4500 |
| ccgtactgct ggagcagcgg gacaagcccg gcggtcgggc ctacgtctgg catgaccagg | 4560 |
| gctttacctt tgacgccggg ccgacggtga tcaccgatcc taccgcgctt gaggcgctgt | 4620 |
| tcacccctggc cggcaggcgc atggaggatt acgtcaggct gctgccggta aaacccttct | 4680 |
| accgactctg ctgggagtcc gggaagaccc tcgactatgc taacgacagc gccgagcttg | 4740 |
| aggcgcagat tacccagttc aaccccgcg acgtcgaggg ctaccggcgc tttctggctt | 4800 |

```
actcccaggc ggtattccag gagggatatt tgcgcctcgg cagcgtgccg ttcctctctt    4860
ttcgcgacat gctgcgcgcc gggccgcagc tgcttaagct ccaggcgtgg cagagcgtct    4920
accagtcggt ttcgcgcttt attgaggatg agcatctgcg gcaggccttc tcgttccact    4980
ccctgctggt aggcggcaac cccttcacca cctcgtccat ctacaccctg atccacgccc    5040
ttgagcggga gtggggggtc tggttccctg agggcggcac cggggcgctg gtgaacggca    5100
tggtgaagct gtttaccgat ctgggcgggg agatcgaact caacgcccgg gtcgaagagc    5160
tggtggtggc cgataaccgc gtaagccagg tccggctggc ggatggtcgg atctttgaca    5220
ccgacgccgt agcctcgaac gctgacgtgg tgaacaccta taaaaagctg ctcggccacc    5280
atccggtggg gcagaagcgg gcggcagcgc tggagcgcaa gagcatgagc aactcgctgt    5340
ttgtgctcta cttcggcctg aaccagcctc attcccagct ggcgcaccat accatctgtt    5400
ttggtccccg ctaccgggag ctgatcgacg agatctttac cggcagcgcg ctggcggatg    5460
acttctcgct ctacctgcac tcgccctgcg tgaccgatcc ctcgctcgcg cctcccggct    5520
gcgccagctt ctacgtgctg gccccggtgc cgcatcttgg caacgcgccg ctggactggg    5580
cgcaggaggg gccgaagctg cgcgaccgca tctttgacta ccttgaagag cgctatatgc    5640
ccggcctgcg tagccagctg gtgacccagc ggatctttac cccggcagac ttccacgaca    5700
cgctggatgc gcatctggga tcggccttct ccatcgagcc gctgctgacc caaagcgcct    5760
ggttccgccc gcacaaccgc gacagcgaca ttgccaacct ctacctggtg ggcgcaggta    5820
ctcaccctgg ggcgggcatt cctggcgtag tggcctcggc gaaagccacc gccagcctga    5880
tgattgagga tctgcaatga gccaaccgcc gctgcttgac cacgccacgc agaccatggc    5940
caacggctcg aaaagttttg ccaccgctgc gaagctgttc gacccggcca cccgccgtag    6000
cgtgctgatg ctctacacct ggtgccgcca ctgcgatgac gtcattgacg accagaccca    6060
cggcttcgcc agcgaggccg cggcggagga ggaggccacc cagcgcctgg cccggctgcg    6120
cacgctgacc ctggcggcgt ttgaaggggc cgagatgcag gatccggcct tcgctgcctt    6180
tcaggaggtg gcgctgaccc acggtattac gccccgcatg gcgctcgatc acctcgacgg    6240
ctttgcgatg gacgtggctc agacccgcta tgtcaccttt gaggatacgc tgcgctactg    6300
ctatcacgtg gcgggcgtgg tgggtctgat gatggccagg gtgatgggcg tgcgggatga    6360
gcgggtgctg gatcgcgcct gcgatctggg gctggccttc cagctgacga atatcgcccg    6420
ggatattatt gacgatgcgg ctattgaccg ctgctatctg cccgccgagt ggctgcagga    6480
tgccgggctg accccggaga actatgccgc gcgggagaat cgggccgcgc tggcgcgggt    6540
ggcggagcgg cttattgatg ccgcagagcc gtactacatc tcctcccagg ccgggctaca    6600
cgatctgccg ccgcgctgcg cctggcgat cgccaccgcc cgcagcgtct accgggagat    6660
cggtattaag gtaaaagcgg cgggaggcag cgcctgggat cgccgccagc acaccagcaa    6720
aggtgaaaaa attgccatgc tgatggcggc accggggcag gttattcggg cgaagacgac    6780
gagggtgacg ccgcgtccgg ccggtctttg gcagcgtccc gtttaggcgg gcggccatga    6840
cgttcacgca ggatcgcctg taggtcggca ggcttgcggg cgtaaataaa accgaaggag    6900
acgcagccct cccggccgcg caccgcgtgg tgcaggcggg gggcgacgta gagccgcttc    6960
aggtagcccc ggcgcgggat ccagtggaag ggccagcgct gatgcaccag accgtcgtgc    7020
accaggaagt agagcaggcc atagaccgtc atgccgcagc caatccactg caggggccaa    7080
acgcccgccg tgcccacggc aatcagcgcg atagccaccc cggcaaacac caccgcaaag    7140
agatcgttta gctcaaatac gcccttgcgc ggggtatggt gtgactcatg ccagcgccat    7200
```

```
cccagccgt gcataatgta gcggtgggta aacgcggcga tgccctccat cgcaataacg    7260
ctcaagatga cgattaaact atttactagc at                                 7292
```

<210> SEQ ID NO 32
<211> LENGTH: 176
<212> TYPE: PRT
<213> ORGANISM: Escherichia vulneris

<400> SEQUENCE: 32

Met Leu Val Asn Ser Leu Ile Val Ile Leu Ser Val Ile Ala Met Glu
1               5                   10                  15

Gly Ile Ala Ala Phe Thr His Arg Tyr Ile Met His Gly Trp Gly Trp
            20                  25                  30

Arg Trp His Glu Ser His His Thr Pro Arg Lys Gly Val Phe Glu Leu
        35                  40                  45

Asn Asp Leu Phe Ala Val Val Phe Ala Gly Val Ala Ile Ala Leu Ile
    50                  55                  60

Ala Val Gly Thr Ala Gly Val Trp Pro Leu Gln Trp Ile Gly Cys Gly
65                  70                  75                  80

Met Thr Val Tyr Gly Leu Leu Tyr Phe Leu Val His Asp Gly Leu Val
                85                  90                  95

His Gln Arg Trp Pro Phe His Trp Ile Pro Arg Arg Gly Tyr Leu Lys
            100                 105                 110

Arg Leu Tyr Val Ala His Arg Leu His His Ala Val Arg Gly Arg Glu
        115                 120                 125

Gly Cys Val Ser Phe Gly Phe Ile Tyr Ala Arg Lys Pro Ala Asp Leu
    130                 135                 140

Gln Ala Ile Leu Arg Glu Arg His Gly Arg Pro Pro Lys Arg Asp Ala
145                 150                 155                 160

Ala Lys Asp Arg Pro Asp Ala Ala Ser Pro Ser Ser Ser Pro Glu
                165                 170                 175

<210> SEQ ID NO 33
<211> LENGTH: 386
<212> TYPE: PRT
<213> ORGANISM: Escherichia vulneris

<400> SEQUENCE: 33

Val Arg Asp Leu Ile Leu Val Gly Gly Gly Leu Ala Asn Gly Leu Ile
1               5                   10                  15

Ala Trp Arg Leu Arg Gln Arg Tyr Pro Gln Leu Asn Leu Leu Leu Ile
            20                  25                  30

Glu Ala Gly Glu Gln Pro Gly Gly Asn His Thr Trp Ser Phe His Glu
        35                  40                  45

Asp Asp Leu Thr Pro Gly Gln His Ala Trp Leu Ala Pro Leu Val Ala
    50                  55                  60

His Ala Trp Pro Gly Tyr Glu Val Gln Phe Pro Asp Leu Arg Arg Arg
65                  70                  75                  80

Leu Ala Arg Gly Tyr Tyr Ser Ile Thr Ser Glu Arg Phe Ala Glu Ala
                85                  90                  95

Leu His Gln Ala Leu Gly Glu Asn Ile Trp Leu Asn Cys Ser Val Ser
            100                 105                 110

Glu Val Leu Pro Asn Ser Val Arg Leu Ala Asn Gly Glu Ala Leu Leu
        115                 120                 125

Ala Gly Ala Val Ile Asp Gly Arg Gly Val Thr Ala Ser Ser Ala Met

```
            130                 135                 140
Gln Thr Gly Tyr Gln Leu Phe Leu Gly Gln Gln Trp Arg Leu Thr Gln
145                 150                 155                 160

Pro His Gly Leu Thr Val Pro Ile Leu Met Asp Ala Thr Val Ala Gln
                165                 170                 175

Gln Gln Gly Tyr Arg Phe Val Tyr Thr Leu Pro Leu Ser Ala Asp Thr
            180                 185                 190

Leu Leu Ile Glu Asp Thr Arg Tyr Ala Asn Val Pro Gln Arg Asp Asp
        195                 200                 205

Asn Ala Leu Arg Gln Thr Val Thr Asp Tyr Ala His Ser Lys Gly Trp
    210                 215                 220

Gln Leu Ala Gln Leu Glu Arg Glu Thr Gly Cys Leu Pro Ile Thr
225                 230                 235                 240

Leu Ala Gly Asp Ile Gln Ala Leu Trp Ala Asp Ala Pro Gly Val Pro
                245                 250                 255

Arg Ser Gly Met Arg Ala Gly Leu Phe His Pro Thr Thr Gly Tyr Ser
            260                 265                 270

Leu Pro Leu Ala Val Ala Leu Ala Asp Ala Ile Ala Asp Ser Pro Arg
        275                 280                 285

Leu Gly Ser Val Pro Leu Tyr Gln Leu Thr Arg Gln Phe Ala Glu Arg
    290                 295                 300

His Trp Arg Arg Gln Gly Phe Phe Arg Leu Leu Asn Arg Met Leu Phe
305                 310                 315                 320

Leu Ala Gly Arg Glu Glu Asn Arg Trp Arg Val Met Gln Arg Phe Tyr
                325                 330                 335

Gly Leu Pro Glu Pro Thr Val Glu Arg Phe Tyr Ala Gly Arg Leu Ser
            340                 345                 350

Leu Phe Asp Lys Ala Arg Ile Leu Thr Gly Lys Pro Pro Val Pro Leu
        355                 360                 365

Gly Glu Ala Trp Arg Ala Ala Leu Asn His Phe Pro Asp Arg Arg Asp
    370                 375                 380

Lys Gly
385

<210> SEQ ID NO 34
<211> LENGTH: 486
<212> TYPE: PRT
<213> ORGANISM: Escherichia vulneris

<400> SEQUENCE: 34

Met Lys Lys Thr Val Val Ile Gly Ala Gly Phe Gly Gly Leu Ala Leu
1               5                   10                  15

Ala Ile Arg Leu Gln Ala Ala Gly Ile Pro Thr Val Leu Leu Glu Gln
            20                  25                  30

Arg Asp Lys Pro Gly Gly Arg Ala Tyr Val Trp His Asp Gln Gly Phe
        35                  40                  45

Thr Phe Asp Ala Gly Pro Thr Val Ile Thr Asp Pro Thr Ala Leu Glu
    50                  55                  60

Ala Leu Phe Thr Leu Ala Gly Arg Arg Met Glu Asp Tyr Val Arg Leu
65                  70                  75                  80

Leu Pro Val Lys Pro Phe Tyr Arg Leu Cys Trp Glu Ser Gly Lys Thr
                85                  90                  95

Leu Asp Tyr Ala Asn Asp Ser Ala Glu Leu Glu Ala Gln Ile Thr Gln
            100                 105                 110
```

-continued

Phe Asn Pro Arg Asp Val Glu Gly Tyr Arg Arg Phe Leu Ala Tyr Ser
115                 120                 125

Gln Ala Val Phe Gln Glu Gly Tyr Leu Arg Leu Gly Ser Val Pro Phe
130                 135                 140

Leu Ser Phe Arg Asp Met Leu Arg Ala Gly Pro Gln Leu Leu Lys Leu
145                 150                 155                 160

Gln Ala Trp Gln Ser Val Tyr Gln Ser Val Ser Arg Phe Ile Glu Asp
            165                 170                 175

Glu His Leu Arg Gln Ala Phe Ser His Ser Leu Leu Val Gly Gly
        180                 185                 190

Asn Pro Phe Thr Thr Ser Ser Ile Tyr Thr Leu Ile His Ala Leu Glu
            195                 200                 205

Arg Glu Trp Gly Val Trp Phe Pro Glu Gly Gly Thr Gly Ala Leu Val
210                 215                 220

Asn Gly Met Val Lys Leu Phe Thr Asp Leu Gly Gly Glu Ile Glu Leu
225                 230                 235                 240

Asn Ala Arg Val Glu Glu Leu Val Val Ala Asp Asn Arg Val Ser Gln
                245                 250                 255

Val Arg Leu Ala Asp Gly Arg Ile Phe Asp Thr Asp Ala Val Ala Ser
            260                 265                 270

Asn Ala Asp Val Val Asn Thr Tyr Lys Lys Leu Leu Gly His His Pro
275                 280                 285

Val Gly Gln Lys Arg Ala Ala Leu Glu Arg Lys Ser Met Ser Asn
        290                 295                 300

Ser Leu Phe Val Leu Tyr Phe Gly Leu Asn Gln Pro His Ser Gln Leu
305                 310                 315                 320

Ala His His Thr Ile Cys Phe Gly Pro Arg Tyr Arg Glu Leu Ile Asp
                325                 330                 335

Glu Ile Phe Thr Gly Ser Ala Leu Ala Asp Asp Phe Ser Leu Tyr Leu
            340                 345                 350

His Ser Pro Cys Val Thr Asp Pro Ser Leu Ala Pro Pro Gly Cys Ala
355                 360                 365

Ser Phe Tyr Val Leu Ala Pro Val Pro His Leu Gly Asn Ala Pro Leu
370                 375                 380

Asp Trp Ala Gln Glu Gly Pro Lys Leu Arg Asp Arg Ile Phe Asp Tyr
385                 390                 395                 400

Leu Glu Glu Arg Tyr Met Pro Gly Leu Arg Ser Gln Leu Val Thr Gln
                405                 410                 415

Arg Ile Phe Thr Pro Ala Asp Phe His Asp Thr Leu Asp Ala His Leu
            420                 425                 430

Gly Ser Ala Phe Ser Ile Glu Pro Leu Leu Thr Gln Ser Ala Trp Phe
        435                 440                 445

Arg Pro His Asn Arg Asp Ser Asp Ile Ala Asn Leu Tyr Leu Val Gly
450                 455                 460

Ala Gly Thr His Pro Gly Ala Gly Ile Pro Gly Val Val Ala Ser Ala
465                 470                 475                 480

Lys Ala Thr Ala Ser Leu
            485

<210> SEQ ID NO 35
<211> LENGTH: 309
<212> TYPE: PRT
<213> ORGANISM: Escherichia vulneris

<400> SEQUENCE: 35

Met Ser Gln Pro Pro Leu Leu Asp His Ala Thr Gln Thr Met Ala Asn
1               5                   10                  15

Gly Ser Lys Ser Phe Ala Thr Ala Ala Lys Leu Phe Asp Pro Ala Thr
            20                  25                  30

Arg Arg Ser Val Leu Met Leu Tyr Thr Trp Cys Arg His Cys Asp Asp
            35                  40                  45

Val Ile Asp Asp Gln Thr His Gly Phe Ala Ser Glu Ala Ala Ala Glu
    50                  55                  60

Glu Glu Ala Thr Gln Arg Leu Ala Arg Leu Arg Thr Leu Thr Leu Ala
65                  70                  75                  80

Ala Phe Glu Gly Ala Glu Met Gln Asp Pro Ala Phe Ala Ala Phe Gln
                85                  90                  95

Glu Val Ala Leu Thr His Gly Ile Thr Pro Arg Met Ala Leu Asp His
                100                 105                 110

Leu Asp Gly Phe Ala Met Asp Val Ala Gln Thr Arg Tyr Val Thr Phe
            115                 120                 125

Glu Asp Thr Leu Arg Tyr Cys Tyr His Val Ala Gly Val Val Gly Leu
130                 135                 140

Met Met Ala Arg Val Met Gly Val Arg Asp Glu Arg Val Leu Asp Arg
145                 150                 155                 160

Ala Cys Asp Leu Gly Leu Ala Phe Gln Leu Thr Asn Ile Ala Arg Asp
                165                 170                 175

Ile Ile Asp Asp Ala Ala Ile Asp Arg Cys Tyr Leu Pro Ala Glu Trp
                180                 185                 190

Leu Gln Asp Ala Gly Leu Thr Pro Glu Asn Tyr Ala Ala Arg Glu Asn
            195                 200                 205

Arg Ala Ala Leu Ala Arg Val Ala Glu Arg Leu Ile Asp Ala Ala Glu
210                 215                 220

Pro Tyr Tyr Ile Ser Ser Gln Ala Gly Leu His Asp Leu Pro Pro Arg
225                 230                 235                 240

Cys Ala Trp Ala Ile Ala Thr Ala Arg Ser Val Tyr Arg Glu Ile Gly
                245                 250                 255

Ile Lys Val Lys Ala Ala Gly Gly Ser Ala Trp Asp Arg Arg Gln His
                260                 265                 270

Thr Ser Lys Gly Glu Lys Ile Ala Met Leu Met Ala Ala Pro Gly Gln
            275                 280                 285

Val Ile Arg Ala Lys Thr Thr Arg Val Thr Pro Arg Pro Ala Gly Leu
            290                 295                 300

Trp Gln Arg Pro Val
305

<210> SEQ ID NO 36
<211> LENGTH: 307
<212> TYPE: PRT
<213> ORGANISM: Escherichia vulneris

<400> SEQUENCE: 36

Met Val Ser Gly Ser Lys Ala Gly Val Ser Pro His Arg Glu Ile Glu
1               5                   10                  15

Val Met Arg Gln Ser Ile Asp Asp His Leu Ala Gly Leu Leu Pro Glu
            20                  25                  30

Thr Asp Ser Gln Asp Ile Val Ser Leu Ala Met Arg Glu Gly Val Met
            35                  40                  45

Ala Pro Gly Lys Arg Ile Arg Pro Leu Leu Met Leu Leu Ala Ala Arg

```
                50                  55                  60
Asp Leu Arg Tyr Gln Gly Ser Met Pro Thr Leu Leu Asp Leu Ala Cys
 65                  70                  75                  80

Ala Val Glu Leu Thr His Thr Ala Ser Leu Met Leu Asp Asp Met Pro
                 85                  90                  95

Cys Met Asp Asn Ala Glu Leu Arg Arg Gly Gln Pro Thr Thr His Lys
                100                 105                 110

Lys Phe Gly Glu Ser Val Ala Ile Leu Ala Ser Val Gly Leu Leu Ser
                115                 120                 125

Lys Ala Phe Gly Leu Ile Ala Ala Thr Gly Asp Leu Pro Gly Glu Arg
                130                 135                 140

Arg Ala Gln Ala Val Asn Glu Leu Ser Thr Ala Val Gly Val Gln Gly
145                 150                 155                 160

Leu Val Leu Gly Gln Phe Arg Asp Leu Asn Asp Ala Ala Leu Asp Arg
                165                 170                 175

Thr Pro Asp Ala Ile Leu Ser Thr Asn His Leu Lys Thr Gly Ile Leu
                180                 185                 190

Phe Ser Ala Met Leu Gln Ile Val Ala Ile Ala Ser Ala Ser Ser Pro
                195                 200                 205

Ser Thr Arg Glu Thr Leu His Ala Phe Ala Leu Asp Phe Gly Gln Ala
210                 215                 220

Phe Gln Leu Leu Asp Asp Leu Arg Asp Asp His Pro Glu Thr Gly Lys
225                 230                 235                 240

Asp Arg Asn Lys Asp Ala Gly Lys Ser Thr Leu Val Asn Arg Leu Gly
                245                 250                 255

Ala Asp Ala Ala Arg Gln Lys Leu Arg Glu His Ile Asp Ser Ala Asp
                260                 265                 270

Lys His Leu Thr Phe Ala Cys Pro Gln Gly Gly Ala Ile Arg Gln Phe
                275                 280                 285

Met His Leu Trp Phe Gly His His Leu Ala Asp Trp Ser Pro Val Met
                290                 295                 300

Lys Ile Ala
305

<210> SEQ ID NO 37
<211> LENGTH: 347
<212> TYPE: PRT
<213> ORGANISM: Escherichia vulneris

<400> SEQUENCE: 37

Met Lys Asp Glu Arg Leu Val Gln Arg Lys Asn Asp His Leu Asp Ile
  1                   5                  10                  15

Val Leu Asp Pro Arg Arg Ala Val Thr Gln Ala Ser Ala Gly Phe Glu
                 20                  25                  30

Arg Trp Arg Phe Thr His Cys Ala Leu Pro Glu Leu Asn Phe Ser Asp
                 35                  40                  45

Ile Thr Leu Glu Thr Thr Phe Leu Asn Arg Gln Leu Gln Ala Pro Leu
 50                  55                  60

Leu Ile Ser Ser Met Thr Gly Gly Val Glu Arg Ser Arg His Ile Asn
 65                  70                  75                  80

Arg His Leu Ala Glu Ala Ala Gln Val Leu Lys Ile Ala Met Gly Val
                 85                  90                  95

Gly Ser Gln Arg Val Ala Ile Glu Ser Asp Ala Gly Leu Gly Leu Asp
                100                 105                 110
```

Lys Thr Leu Arg Gln Leu Ala Pro Asp Val Pro Leu Leu Ala Asn Leu
            115                 120                 125

Gly Ala Ala Gln Leu Thr Gly Arg Lys Gly Ile Asp Tyr Ala Arg Arg
        130                 135                 140

Ala Val Glu Met Ile Glu Ala Asp Ala Leu Ile Val His Leu Asn Pro
145                 150                 155                 160

Leu Gln Glu Ala Leu Gln Pro Gly Gly Asp Arg Asp Trp Arg Gly Arg
                165                 170                 175

Leu Ala Ala Ile Glu Thr Leu Val Arg Glu Leu Pro Val Pro Leu Val
            180                 185                 190

Val Lys Glu Val Gly Ala Gly Ile Ser Arg Thr Val Ala Gly Gln Leu
        195                 200                 205

Ile Asp Ala Gly Val Thr Val Ile Asp Val Ala Gly Ala Gly Gly Thr
    210                 215                 220

Ser Trp Ala Ala Val Glu Gly Glu Arg Ala Ala Thr Glu Gln Gln Arg
225                 230                 235                 240

Ser Val Ala Asn Val Phe Ala Asp Trp Gly Ile Pro Thr Ala Glu Ala
                245                 250                 255

Leu Val Asp Ile Ala Glu Ala Trp Pro Gln Met Pro Leu Ile Ala Ser
            260                 265                 270

Gly Gly Ile Lys Asn Gly Val Asp Ala Ala Lys Ala Leu Arg Leu Gly
        275                 280                 285

Ala Cys Met Val Gly Gln Ala Ala Val Leu Gly Ser Ala Gly Val
    290                 295                 300

Ser Thr Glu Lys Val Ile Asp His Phe Asn Val Ile Ile Glu Gln Leu
305                 310                 315                 320

Arg Val Ala Cys Phe Cys Thr Gly Ser Arg Ser Leu Ser Asp Leu Lys
                325                 330                 335

Gln Ala Asp Ile Arg Tyr Val Arg Asp Thr Pro
            340                 345

<210> SEQ ID NO 38
<211> LENGTH: 6228
<212> TYPE: DNA
<213> ORGANISM: Pantoea ananatis

<400> SEQUENCE: 38
atgacggtct cgcaaaaaaa acacgttcat ctcactcgcg atgctgcgga gcagttactg      60
gctgatattg atcgacgcct tgatcagtta ttgcccgtgg agggagaacg ggatgttgtg     120
ggtgccgcga tgcgtgaagg tgcgctggca ccgggaaaac gtattcgccc catgttgctg     180
ttgctgaccg cccgcgatct gggttgcgct gtcagccatg acggattact ggatttggcc     240
tgtgcggtgg aaatggtcca cgcggcttcg ctgatccttg acgatatgcc ctgcatggac     300
gatgcgaagc tgcggcgcgg acgccctacc attcattctc attacggaga gcatgtggca     360
atactggcgc ggttgccttg ctgagtaaa gcctttggcg taattgccga tgcagatggc     420
ctcacgccgc tggcaaaaaa tcgggcggtt tctgaactgt caaacgccat cggcatgcaa     480
ggattggttc agggtcagtt caaggatctg tctgaagggg ataagccgcg cagcgctgaa     540
gctattttga tgacgaatca ctttaaaacc agcacgctgt tttgtgcctc catgcagatg     600
gcctcgattg ttgcgaatgc ctccagcgaa gcgcgtgatt gcctgcatcg tttttcactt     660
gatcttggtc aggcatttca actgctggac gatttgaccg atggcatgac cgacaccggt     720
aaggatagca atcaggacgc cggtaaatcg acgctggtca atctgttagg cccgagggcg     780

```
gttgaagaac gtctgagaca acatcttcag cttgccagtg agcatctctc tgcggcctgc      840
caacacgggc acgccactca acattttatt caggcctggt ttgacaaaaa actcgctgcc      900
gtcagttaag gatgctgcat gagccatttc gcggcgatcg caccgccttt ttacagccat      960
gttcgcgcat tacagaatct cgctcaggaa ctggtcgcgc gcggtcatcg ggtgaccttt     1020
attcagcaat acgatattaa acacttgatc gatagcgaaa ccattggatt tcattccgtc     1080
gggacagaca gccatccccc cggcgcgtta acgcgcgtgc tacacctggc ggctcatcct     1140
ctggggccgt caatgctgaa gctcatcaat gaaatggcgc gcaccaccga tatgctgtgc     1200
cgcgaactcc cccaggcatt taacgatctg gccgtcgatg gcgtcattgt tgatcaaatg     1260
gaaccggcag gcgcgctcgt tgctgaagca ctgggactgc cgtttatctc tgtcgcctgc     1320
gcgctgcctc tcaatcgtga accggatatg cccctggcgg ttatgccttt cgaatacggg     1380
accagcgacg cggctcgcga acgttatgcc gccagtgaaa aaatttatga ctggctaatg     1440
cgtcgtcatg accgtgtcat tgccgaacac agccacagaa tgggcttagc cccccggcaa     1500
aagcttcacc agtgttttc gccactggcg caaatcagcc agcttgttcc tgaactggat      1560
tttccccgca aagcgttacc ggcttgtttt catgccgtcg ggcctctgcg cgaaacgcac     1620
gcaccgtcaa cgtcttcatc ccgttatttt acatcctcag aaaaacccg gattttcgcc      1680 tcgctgggca cgcttcaggg acaccgttat gggctgttta aaacgatagt gaaagcctgt     1740
gaagaaattg acggtcagct cctgttagcc cactgtggtc gtcttacgga ctctcagtgt     1800
gaagagctgg cgcgaagccg tcatacacag gtggtggatt ttgccgatca gtcagccgcg     1860
ctgtctcagg cgcagctggc gatcacccac ggcggcatga atacggtact ggacgcgatt     1920
aattaccgga cgccccttt agcgcttccg ctggcctttg atcagcccgg cgtcgcgtca      1980
cgcatcgttt atcacggcat cggcaagcgt gcttcccgct ttaccaccag ccatgctttg     2040
gctcgtcaga tgcgttcatt gctgaccaac gtcgactttc agcagcgcat ggcgaaaatc     2100
cagacagccc ttcgtttggc aggggggcacc atggccgctg ccgatatcat tgagcaggtt   2160
atgtgcaccg gtcagcctgt cttaagtggg agcggctatg caaccgcatt atgatctgat     2220
tctcgtgggg gctggactcg cgaatggcct tatcgccctg cgtcttcagc agcagcaacc     2280
tgatatgcgt attttgctta tcgacgccgc accccaggcg ggcgggaatc atacgtggtc    2340
atttcaccac gatgatttga ctgagagcca acatcgttgg atagctccgc tggtggttca     2400
tcactggccc gactatcagg tacgctttcc cacacgccgt cgtaagctga acagcggcta     2460
cttttgtatt acttctcagc gtttcgctga ggttttacag cgacagtttg gcccgcactt     2520
gtggatggat accgcggtcg cagaggttaa tgcggaatct gttcggttga aaaagggtca     2580
ggttatcggt gcccgcgcgg tgattgacgg gcggggttat gcggcaaatt cagcactgag     2640
cgtgggcttc caggcgttta ttggccagga atggcgattg agccaccgc atggtttatc      2700 gtctcccatt atcatggatg ccacggtcga tcagcaaaat ggttatcgct tcgtgtacag     2760
cctgccgctc tcgccgacca gattgttaat tgaagacacg cactatattg ataatgcgac     2820
attagatcct gaatgcgcgc ggcaaaatat ttgcgactat gccgcgcaac agggttggca    2880
gcttcagaca ctgctgcgag aagaacaggg cgccttaccc attactctgt cgggcaatgc     2940
cgacgcattc tggcagcagc gccccctggc ctgtagtgga ttacgtgccg gtctgttcca    3000
tcctaccacc ggctattcac tgccgctggc ggttgccgtg gccgaccgcc tgagtgcact    3060
tgatgtcttt acgtcggcct caattcacca tgccattacg catttgcccg cgagcgctg      3120 gcagcagcag ggcttttttcc gcatgctgaa tcgcatgctg tttttagccg gacccgccga   3180
```

```
ttcacgctgg cgggttatgc agcgttttta tggtttacct gaagatttaa ttgcccgttt    3240
ttatgcggga aaactcacgc tgaccgatcg gctacgtatt ctgagcggca agccgcctgt    3300
tccggtatta gcagcattgc aagccattat gacgactcat cgttaaagag cgactacatg    3360
aaaccaacta cggtaattgg tgcaggcttc ggtggcctgg cactggcaat tcgtctacaa    3420
gctgcgggga tccccgtctt actgcttgaa caacgtgata acccggcgg tcgggcttat     3480 gtctacgagg atcaggggtt tacctttgat gcaggcccga cggttatcac cgatcccagt    3540
gccattgaag aactgtttgc actggcagga aaacagttaa aagagtatgt cgaactgctg    3600
ccggttacgc cgttttaccg cctgtgttgg gagtcaggga aggtctttaa ttacgataac    3660
gatcaaaccc ggctcgaagc gcagattcag cagtttaatc cccgcgatgt cgaaggttat    3720
cgtcagtttc tggactattc acgcgcggtg tttaaagaag gctatctaaa gctcggtact    3780
gtcccttttt tatcgttcag agacatgctt cgcgccgcac ctcaactggc gaaactgcag    3840
gcatggagaa gcgtttacag taaggttgcc agttacatcg aagatgaaca tctgcgccag    3900
gcgttttctt tccactcgct gttggtgggc ggcaatccct tcgccacctc atccatttat    3960
acgttgatac acgcgctgga gcgtgagtgg ggcgtctggt ttccgcgtgg cggcaccggc    4020
gcattagttc aggggatgat aaagctgttt caggatctgg tggcgaagt cgtgttaaac     4080 gccagagtca gccatatgga aacgacagga aacaagattg aagccgtgca tttagaggac    4140
ggtcgcaggt tcctgacgca agccgtcgcg tcaaatgcag atgtggttca tacctatcgc    4200
gacctgttaa gccagcaccc tgccgcggtt aagcagtcca acaaactgca gactaagcgc    4260
atgagtaact ctctgtttgt gctctatttt ggtttgaatc accatcatga tcagctcgcg    4320
catcacacgg tttgtttcgg cccgcgttac cgcgagctga ttgacgaaat ttttaatcat    4380
gatggcctcg cagaggactt ctcactttat ctgcacgcgc cctgtgtcac ggattcgtca    4440
ctggcgcctg aaggttgcgg cagttactat gtgttggcgc cggtgccgca tttaggcacc    4500
gcgaacctcg actggacggt tgaggggcca aaactacgcg accgtatttt tgcgtacctt    4560
gagcagcatt acatgcctgg cttacggagt cagctggtca cgcaccggat gtttacgccg    4620
tttgattttc gcgaccagct taatgcctat catggctcag ccttttctgt ggagcccgtt    4680
cttacccaga gcgcctggtt tcggccgcat aaccgcgata aaaccattac taatctctac    4740
ctggtcggcg caggcacgca tcccggcgca ggcattcctg gcgtcatcgg ctcggcaaaa    4800
gcgacagcag gtttgatgct ggaggatctg atatgaataa tccgtcgtta ctcaatcatg    4860
cggtcgaaac gatggcagtt ggctcgaaaa gttttgcgac agcctcaaag ttatttgatg    4920
caaaaacccg gcgcagcgta ctgatgctct acgcctggtg ccgccattgt gacgatgtta    4980
ttgacgatca gacgctgggc tttcaggccc ggcagcctgc cttacaaacg cccgaacaac    5040
gtctgatgca acttgagatg aaaacgcgcc aggcctatgc aggatcgcag atgcacgaac    5100
cggcgtttgc ggcttttcag gaagtggcta tggctcatga tatcgcccg gcttacgcgt      5160 ttgatcatct ggaaggcttc gccatggatg tacgcgaagc gcaatacagc caactggatg    5220
atacgctgcg ctattgctat cacgttgcag gcgttgtcgg cttgatgatg gcgcaaatca    5280
tgggcgtgcg ggataacgcc acgctggacc gcgcctgtga ccttgggctg gcatttcagt    5340
tgaccaatat tgctcgcgat attgtggacg atgcgcatgc gggccgctgt tatctgccgg    5400
caagctggct ggagcatgaa ggtctgaaca aagagaatta tgcggcacct gaaaaccgtc    5460
aggcgctgag ccgtatcgcc cgtcgtttgg tgcaggaagc agaaccttac tatttgtctg    5520
```

-continued

```
ccacagccgg cctggcaggg ttgccnctgc gttccgcctg ggcaatcgct acggcgaagc    5580
aggtttaccg gaaaataggt gtcaaagttg aacaggccgg tcagcaagcc tgggatcagc    5640
ggcagtcaac gaccacgccc gaaaaattaa cgctgctgct ggccgcctct ggtcaggccc    5700
ttacttcccg gatgcgggct catcctcccc gccctgcgca tctctggcag cgcccgctct    5760
agcgccatgt ctttcccgga gcgtcgcctg aagttttgac aggggcggcg catagaggaa    5820
gccaaaagaa acacaacctt ctttgcccct gacggcgtga tgcataccggt gcgccatata   5880 caaccgtttg aggtagccct tgcgtggaat atagcggaat ggccaacgtt gatgcaccag    5940
cccgtcgtgc accataaaat agagtaatcc atacgccgtc atacctgcgc caatccactg    6000
gagcggccac attcctgtac tgcccagata atcagcagg atcgataatg cagcaaaaac     6060
cacggcataa agatcgttaa cttcaaacgc acctttacgc ggttcatgat gtgaaagatg    6120 ccatcccaa ccccagccgt gcatgatgta tttgtgtgcc agtgcagcaa tcacttccat     6180
gccaatcacg gtaacgaaaa cgatcagggc attccaaatc cacaacat                 6228
```

```
<210> SEQ ID NO 39
<211> LENGTH: 175
<212> TYPE: PRT
<213> ORGANISM: Pantoea ananatis

<400> SEQUENCE: 39

Met Leu Trp Ile Trp Asn Ala Leu Ile Val Phe Val Thr Val Ile Gly
1               5                   10                  15

Met Glu Val Ile Ala Ala Leu Ala His Lys Tyr Ile Met His Gly Trp
                20                  25                  30

Gly Trp Gly Trp His Leu Ser His His Glu Pro Arg Lys Gly Ala Phe
            35                  40                  45

Glu Val Asn Asp Leu Tyr Ala Val Val Phe Ala Ala Leu Ser Ile Leu
        50                  55                  60

Leu Ile Tyr Leu Gly Ser Thr Gly Met Trp Pro Leu Gln Trp Ile Gly
65                  70                  75                  80

Ala Gly Met Thr Ala Tyr Gly Leu Leu Tyr Phe Met Val His Asp Gly
                85                  90                  95

Leu Val His Gln Arg Trp Pro Phe Arg Tyr Ile Pro Arg Lys Gly Tyr
            100                 105                 110

Leu Lys Arg Leu Tyr Met Ala His Arg Met His Ala Val Arg Gly
        115                 120                 125

Lys Glu Gly Cys Val Ser Phe Gly Phe Leu Tyr Ala Pro Pro Leu Ser
    130                 135                 140

Lys Leu Gln Ala Thr Leu Arg Glu Arg His Gly Ala Arg Ala Gly Ala
145                 150                 155                 160

Ala Arg Asp Ala Gln Gly Gly Glu Asp Glu Pro Ala Ser Gly Lys
                165                 170                 175

<210> SEQ ID NO 40
<211> LENGTH: 382
<212> TYPE: PRT
<213> ORGANISM: Pantoea ananatis

<400> SEQUENCE: 40

Met Gln Pro His Tyr Asp Leu Ile Leu Val Gly Ala Gly Leu Ala Asn
1               5                   10                  15

Gly Leu Ile Ala Leu Arg Leu Gln Gln Gln Pro Asp Met Arg Ile
                20                  25                  30
```

```
Leu Leu Ile Asp Ala Ala Pro Gln Ala Gly Gly Asn His Thr Trp Ser
             35                  40                  45

Phe His His Asp Asp Leu Thr Glu Ser Gln His Arg Trp Ile Ala Pro
 50                  55                  60

Leu Val Val His His Trp Pro Asp Tyr Gln Val Arg Phe Pro Thr Arg
 65                  70                  75                  80

Arg Arg Lys Leu Asn Ser Gly Tyr Phe Cys Ile Thr Ser Gln Arg Phe
                 85                  90                  95

Ala Glu Val Leu Gln Arg Gln Phe Gly Pro His Leu Trp Met Asp Thr
            100                 105                 110

Ala Val Ala Glu Val Asn Ala Glu Ser Val Arg Leu Lys Lys Gly Gln
            115                 120                 125

Val Ile Gly Ala Arg Ala Val Ile Asp Gly Arg Gly Tyr Ala Ala Asn
130                 135                 140

Ser Ala Leu Ser Val Gly Phe Gln Ala Phe Ile Gly Gln Glu Trp Arg
145                 150                 155                 160

Leu Ser His Pro His Gly Leu Ser Ser Pro Ile Ile Met Asp Ala Thr
                165                 170                 175

Val Asp Gln Gln Asn Gly Tyr Arg Phe Val Tyr Ser Leu Pro Leu Ser
            180                 185                 190

Pro Thr Arg Leu Leu Ile Glu Asp Thr His Tyr Ile Asp Asn Ala Thr
            195                 200                 205

Leu Asp Pro Glu Cys Ala Arg Gln Asn Ile Cys Asp Tyr Ala Ala Gln
210                 215                 220

Gln Gly Trp Gln Leu Gln Thr Leu Leu Arg Glu Glu Gln Gly Ala Leu
225                 230                 235                 240

Pro Ile Thr Leu Ser Gly Asn Ala Asp Ala Phe Trp Gln Gln Arg Pro
                245                 250                 255

Leu Ala Cys Ser Gly Leu Arg Ala Gly Leu Phe His Pro Thr Thr Gly
            260                 265                 270

Tyr Ser Leu Pro Leu Ala Val Ala Val Ala Asp Arg Leu Ser Ala Leu
            275                 280                 285

Asp Val Phe Thr Ser Ala Ser Ile His His Ala Ile Thr His Phe Ala
290                 295                 300

Arg Glu Arg Trp Gln Gln Gln Gly Phe Phe Arg Met Leu Asn Arg Met
305                 310                 315                 320

Leu Phe Leu Ala Gly Pro Ala Asp Ser Arg Trp Arg Val Met Gln Arg
                325                 330                 335

Phe Tyr Gly Leu Pro Glu Asp Leu Ile Ala Arg Phe Tyr Ala Gly Lys
            340                 345                 350

Leu Thr Leu Thr Asp Arg Leu Arg Ile Leu Ser Gly Lys Pro Pro Val
            355                 360                 365

Pro Val Leu Ala Ala Leu Gln Ala Ile Met Thr Thr His Arg
370                 375                 380

<210> SEQ ID NO 41
<211> LENGTH: 492
<212> TYPE: PRT
<213> ORGANISM: Pantoea ananatis

<400> SEQUENCE: 41

Met Lys Pro Thr Thr Val Ile Gly Ala Gly Phe Gly Gly Leu Ala Leu
  1               5                  10                  15

Ala Ile Arg Leu Gln Ala Ala Gly Ile Pro Val Leu Leu Leu Glu Gln
                 20                  25                  30
```

```
Arg Asp Lys Pro Gly Gly Arg Ala Tyr Val Tyr Glu Asp Gln Gly Phe
         35                  40                  45

Thr Phe Asp Ala Gly Pro Thr Val Ile Thr Asp Pro Ser Ala Ile Glu
 50                  55                  60

Glu Leu Phe Ala Leu Ala Gly Lys Gln Leu Lys Glu Tyr Val Glu Leu
 65                  70                  75                  80

Leu Pro Val Thr Pro Phe Tyr Arg Leu Cys Trp Glu Ser Gly Lys Val
                 85                  90                  95

Phe Asn Tyr Asp Asn Asp Gln Thr Arg Leu Glu Ala Gln Ile Gln Gln
                100                 105                 110

Phe Asn Pro Arg Asp Val Glu Gly Tyr Arg Gln Phe Leu Asp Tyr Ser
                115                 120                 125

Arg Ala Val Phe Lys Glu Gly Tyr Leu Lys Leu Gly Thr Val Pro Phe
        130                 135                 140

Leu Ser Phe Arg Asp Met Leu Arg Ala Ala Pro Gln Leu Ala Lys Leu
145                 150                 155                 160

Gln Ala Trp Arg Ser Val Tyr Ser Lys Val Ala Ser Tyr Ile Glu Asp
                165                 170                 175

Glu His Leu Arg Gln Ala Phe Ser Phe His Ser Leu Val Gly Gly
                180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
        210                 215                 220

Gln Gly Met Ile Lys Leu Phe Gln Asp Leu Gly Glu Val Val Leu
225                 230                 235                 240

Asn Ala Arg Val Ser His Met Glu Thr Thr Gly Asn Lys Ile Glu Ala
                245                 250                 255

Val His Leu Glu Asp Gly Arg Arg Phe Leu Thr Gln Ala Val Ala Ser
                260                 265                 270

Asn Ala Asp Val Val His Thr Tyr Arg Asp Leu Leu Ser Gln His Pro
        275                 280                 285

Ala Ala Val Lys Gln Ser Asn Lys Leu Gln Thr Lys Arg Met Ser Asn
        290                 295                 300

Ser Leu Phe Val Leu Tyr Phe Gly Leu Asn His His Asp Gln Leu
305                 310                 315                 320

Ala His His Thr Val Cys Phe Gly Pro Arg Tyr Arg Glu Leu Ile Asp
                325                 330                 335

Glu Ile Phe Asn His Asp Gly Leu Ala Glu Asp Phe Ser Leu Tyr Leu
                340                 345                 350

His Ala Pro Cys Val Thr Asp Ser Ser Leu Ala Pro Glu Gly Cys Gly
        355                 360                 365

Ser Tyr Tyr Val Leu Ala Pro Val Pro His Leu Gly Thr Ala Asn Leu
    370                 375                 380

Asp Trp Thr Val Glu Gly Pro Lys Leu Arg Asp Arg Ile Phe Ala Tyr
385                 390                 395                 400

Leu Glu Gln His Tyr Met Pro Gly Leu Arg Ser Gln Leu Val Thr His
                405                 410                 415

Arg Met Phe Thr Pro Phe Asp Phe Arg Asp Gln Leu Asn Ala Tyr His
                420                 425                 430

Gly Ser Ala Phe Ser Val Glu Pro Val Leu Thr Gln Ser Ala Trp Phe
        435                 440                 445
```

```
Arg Pro His Asn Arg Asp Lys Thr Ile Thr Asn Leu Tyr Leu Val Gly
    450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
                485                 490

<210> SEQ ID NO 42
<211> LENGTH: 309
<212> TYPE: PRT
<213> ORGANISM: Pantoea ananatis

<400> SEQUENCE: 42

Met Asn Asn Pro Ser Leu Leu Asn His Ala Val Glu Thr Met Ala Val
1               5                   10                  15

Gly Ser Lys Ser Phe Ala Thr Ala Ser Lys Leu Phe Asp Ala Lys Thr
                20                  25                  30

Arg Arg Ser Val Leu Met Leu Tyr Ala Trp Cys Arg His Cys Asp Asp
            35                  40                  45

Val Ile Asp Asp Gln Thr Leu Gly Phe Gln Ala Arg Gln Pro Ala Leu
50                  55                  60

Gln Thr Pro Glu Gln Arg Leu Met Gln Leu Glu Met Lys Thr Arg Gln
65                  70                  75                  80

Ala Tyr Ala Gly Ser Gln Met His Glu Pro Ala Phe Ala Ala Phe Gln
                85                  90                  95

Glu Val Ala Met Ala His Asp Ile Ala Pro Ala Tyr Ala Phe Asp His
            100                 105                 110

Leu Glu Gly Phe Ala Met Asp Val Arg Glu Ala Gln Tyr Ser Gln Leu
        115                 120                 125

Asp Asp Thr Leu Arg Tyr Cys Tyr His Val Ala Gly Val Val Gly Leu
130                 135                 140

Met Met Ala Gln Ile Met Gly Val Arg Asp Asn Ala Thr Leu Asp Arg
145                 150                 155                 160

Ala Cys Asp Leu Gly Leu Ala Phe Gln Leu Thr Asn Ile Ala Arg Asp
                165                 170                 175

Ile Val Asp Asp Ala His Ala Gly Arg Cys Tyr Leu Pro Ala Ser Trp
            180                 185                 190

Leu Glu His Glu Gly Leu Asn Lys Glu Asn Tyr Ala Ala Pro Glu Asn
        195                 200                 205

Arg Gln Ala Leu Ser Arg Ile Ala Arg Arg Leu Val Gln Glu Ala Glu
210                 215                 220

Pro Tyr Tyr Leu Ser Ala Thr Ala Gly Leu Ala Gly Leu Pro Leu Arg
225                 230                 235                 240

Ser Ala Trp Ala Ile Ala Thr Ala Lys Gln Val Tyr Arg Lys Ile Gly
                245                 250                 255

Val Lys Val Glu Gln Ala Gly Gln Gln Ala Trp Asp Gln Arg Gln Ser
            260                 265                 270

Thr Thr Thr Pro Glu Lys Leu Thr Leu Leu Ala Ala Ser Gly Gln
        275                 280                 285

Ala Leu Thr Ser Arg Met Arg Ala His Pro Arg Pro Ala His Leu
290                 295                 300

Trp Gln Arg Pro Leu
305

<210> SEQ ID NO 43
```

<211> LENGTH: 302
<212> TYPE: PRT
<213> ORGANISM: Pantoea ananatis

<400> SEQUENCE: 43

```
Met Thr Val Cys Ala Lys Lys His Val His Leu Thr Arg Asp Ala Ala
1               5                   10                  15
Glu Gln Leu Leu Ala Asp Ile Asp Arg Arg Leu Asp Gln Leu Leu Pro
            20                  25                  30
Val Glu Gly Glu Arg Asp Val Gly Ala Ala Met Arg Glu Gly Ala
        35                  40                  45
Leu Ala Pro Gly Lys Arg Ile Arg Pro Met Leu Leu Leu Leu Thr Ala
    50                  55                  60
Arg Asp Leu Gly Cys Ala Val Ser His Asp Gly Leu Leu Asp Leu Ala
65                  70                  75                  80
Cys Ala Val Glu Met Val His Ala Ala Ser Leu Ile Leu Asp Asp Met
                85                  90                  95
Pro Cys Met Asp Asp Ala Lys Leu Arg Arg Gly Arg Pro Thr Ile His
            100                 105                 110
Ser His Tyr Gly Glu His Val Ala Ile Leu Ala Ala Val Ala Leu Leu
        115                 120                 125
Ser Lys Ala Phe Gly Val Ile Ala Asp Ala Asp Gly Leu Thr Pro Leu
    130                 135                 140
Ala Lys Asn Arg Ala Val Ser Glu Leu Ser Asn Ala Ile Gly Met Gln
145                 150                 155                 160
Gly Leu Val Gln Gly Gln Phe Lys Asp Leu Ser Glu Gly Asp Lys Pro
                165                 170                 175
Arg Ser Ala Glu Ala Ile Leu Met Thr Asn His Phe Lys Thr Ser Thr
            180                 185                 190
Leu Phe Cys Ala Ser Met Gln Met Ala Ser Ile Val Ala Asn Ala Ser
        195                 200                 205
Ser Glu Ala Arg Asp Cys Leu His Arg Phe Ser Leu Asp Leu Gly Gln
    210                 215                 220
Ala Phe Gln Leu Leu Asp Asp Leu Thr Asp Gly Met Thr Asp Thr Gly
225                 230                 235                 240
Lys Asp Ser Asn Gln Asp Ala Gly Lys Ser Thr Leu Val Asn Leu Leu
                245                 250                 255
Gly Pro Arg Ala Val Glu Glu Arg Leu Arg Gln His Leu Gln Leu Ala
            260                 265                 270
Ser Glu His Leu Ser Ala Ala Cys Gln His Gly His Ala Thr Gln His
        275                 280                 285
Phe Ile Gln Ala Trp Phe Asp Lys Lys Leu Ala Ala Val Ser
    290                 295                 300
```

<210> SEQ ID NO 44
<211> LENGTH: 3760
<212> TYPE: DNA
<213> ORGANISM: Fulvimarina pelagi

<400> SEQUENCE: 44

```
ttgacgtctt ctgcgaaaca gaaggtcgac attgctcttg tgggcggtgg acttgccaat      60
gggctgatcg cctggcggct tgccgaattg cggccggatc tcagcatcgt cgtcctcgaa     120
gccggtgagg cgcctggcgg caaccacaca tggtcgtttc acgaaacgga ccttacaccc     180
gccgctcatc ggtggatcgc gcctttcgtc gctcatcgct ggaccaccaa cgaggtgcaa     240
```

```
ttccccgacc gccatcgtca tctctcgacg gggtatttga gcgcgtcctc ggatctattt    300
cgcgaaaggc tgacgacgcg tctcggcttg cgtatccgca ccggctgtcc ggccgtttct    360
gtcacggcgc gcaaggtgcg actcgaaaac ggcgaagtga tcgaggccgg ctcggtgatt    420
gacgggcgcg gctaccgatc gagcgaacac ctcacgctcg gctttcagaa gtttctcggt    480
caggagatcg aattcgaggc accgcacggc gttgcccgac cggtcatcat ggatgctacc    540
gtcccccagg cggacggcta tcggttcgtc tatcttcttc ccatgacgcc gacgcgttg     600
ctggtcgagg acacctacta tgccgatggc gacgccctcg atcgcggaac gatccggcgc    660
aacatcgcgg cttaccgggc ggcgaagggc tggcctgcgg ggaaagtcgt tcgcgaagaa    720
gatggtgtcc tgccgatcgc gctcgccggc gatatcgagg ccttctggga ggagaagcag    780
ggcgtcccat ccagcggcct caacgctgcg cttttccacc cgacgactgg gtattccttg    840
ccggacgccg tgtatctcgc cgatctgatt gcaggcctgc cggactattc ggccgcaacc    900
ctttatgctg cgacacgccg ccactcggtc gcaacgtgga agcggcgcgg cttcttccgt    960
atgctgaacc gccttctcta tctcgccggt gatccgttga acgttatgt catcctccag     1020
cattttatc gcctgcccga accattggtg tcgcggttct acgctgcgcg gctgacccga     1080
ggtgacaagg tgcggatcct caccggcaag ccgccggtca gtgttatcag cgcgctcaaa    1140
gttctttccc cgagttctgt cgagggagcg cccgcatgaa ccagatgccg cgcgaccttc    1200
ctaacaagac aaagaccgca gtcgttatcg gagcaggctt cggcggactg gcgcttgcga    1260
ttcgacttca ggcggccggt atccaaacga cgcttctcga aaagcgcgac aagcccggcg    1320
gacgggctta cgtctacgag gatcagggct tcaccttcga tgccggccca accgtgatca    1380
ccgacccctc cgcgctcgaa gagctgttcg agacggcgaa cgccaagctt tcggactatg    1440
tcgaactgct tcccgtcaag cctttctacc gtctcgcctg gaagacggc ttcgtcttcg      1500
actatgcaga cgatcaggag gatctcgacc gccagatcgg cgcgaagaac ccgaaggatg    1560
tcgagggcta tcgccgcttc ctcgcttatt cgcgggacgt gttccacgag ggttacgaaa    1620
agctcggcac cgtccctttc ctgaatttca aggatatgat gcgggcagcg ccccagctcg    1680
ttcggctcga ggcctatcgc tcggtctatt cgaaggtcgc ccagttcatc gaggacgacc    1740
agttacggca ggcctttttcc ttccactcgc tcctcgtcgg cggcaatccg ttcgccactt   1800
cttcgatcta cgcgctcatc cacgcgttgg agcgcaaatg gggcgtcttc ttcccgcgcg    1860
gcggcaccgg cgcgctggtc cgcggcatgg ccaagctctt caccgacatt ggcgggagga    1920
tcgaggtgaa tgccgaggtc gagaaatatc cgatcgagaa cgggcgcgcg aagtccgtga    1980
cgactaaggg cggtcaaacc tttcccgcag acttcgtcgc ctcgaatgcc gacgtcgtcc    2040
acacctatgc caagctgatg ggtcgcagcg agcgcggcaa aaagcacggc aattcgctga    2100
agaagaagcg ctttttccatg tcgctcttcg tcatctattt cggcctgaag acccaccggc    2160
cggacattgc ccatcacacg gtctgtttcg gtccgcgcta tcgcccgctg atcgacgaga    2220
ttttcaaggg caaagagctc gcgggcgact tctcgctcta tctccataac ccgtgcgtca    2280
ccgatccctc gctcgcgccg gagggcatgg gctccttcta cgttctgtcc cctgtccccc    2340
atctcggtaa cgccgatata gattgggcgg ttgaggggcc gaaatatcgc gacaggatcc    2400
tcgactatct ggaagagctg tacatccccg gcctgaagga cgatctcgtc accagccgca    2460
tcttcacccc ggctgatttc aagaccgaac tgaacgccca tctcggctcg gccttctcgc    2520
tcgatccggt actgacgcag agcgcttggt tccgccctca caatcgcgac gatcagattc    2580
ccaacctcta cgtcgtcggg gctggtacgc atccaggtgc cggcgttccg ggcgtcgtcg    2640
```

```
gttcggccaa ggcgactgcc ggcctgatga tcgaggacgc gggtctcgcg tgcgtgcctg    2700
catgagtttc gccgaccgcc tcgacgtacc gatcgtcggc ggccttccgt tcgaaaagcg    2760
cgagcgcgcc gcgctggccg ccgaagccga agcgacgatc gcgcaaggct cgaagagttt    2820
cgctgccgcc gcccgcctgt ttgatccgga gatgcgggtc agcgcgctta tgctctatgc    2880
ctggtgccgg cattgcgacg atgtggtcga tgaccagatc cttggttttc gccagccagg    2940
ccgccgggac cgagccggcg atcgcgcacg tctcgatgaa ctcgaggcca agacccttgc    3000
ggcggttcga ggccgatcca cgggcgaagc accattcgac gcgatcggcg atgtcgccct    3060
gcggcatgag ctgccggaat cgctcttgac cgcgcacctc gaaggcttcc ggatggatgt    3120
cgacggccgg gtctacgagg tgattgagga tacgctcgat tattgctacc gggtcgcagg    3180
tgtcgtcggc gtgatgatgg cgcgggtcat gggcatcagg gtcgaaaacg gttcgaaatt    3240
cgacctgacg ctgacccctcg atcgagcctg cgacctcggc atggcctttc agctcaccaa    3300
tatcgcacgt gacatagtcg acgacggcga ggccggacgg gtctacgtgc gaagacatg    3360 gctcgatgcg gctggcgtcc cgggcagcgc catccaccac ccgcgcaatc gggaggcggc    3420
agcggtgttc gctctgcgtc tcctcgatct ggccgagcca tactacgcgt cggcctcgaa    3480
ggggctagcc gcgctgccgc ctcgtgccgc atgggccgtc gcgactgcgc ttggcgtcta    3540
ccgtgagatc gggaccgtca tccgccggcg tggaagtcaa gcctgggacg atcgttcatc    3600
gacaagcgcg gcgaccaagt tcctgcacgc cttcaagggt gtcggttgga cgatgggatc    3660
acgtgtctca gcaggcgcg gcgttcggcc gccggagctc tggacgcgtc ctcgactgct    3720
tgagctcggt gatgcgccca caacaggtct atcggcctga                          3760

<210> SEQ ID NO 45
<211> LENGTH: 3581
<212> TYPE: DNA
<213> ORGANISM: Fulvimarina pelagi

<400> SEQUENCE: 45
ttaggactgg cgagtatgcg gcagagccca ccaaggcgtc catggcgcca aatggtgctc      60
atggtggtag ccaaaatgga agcaggagaa tagcgaggcc acgtaaccga attcgctcga    120
acgtgtgtta tgcgcgtcgg caaaggtgcc cgattcttcg tgtcgatgcg ggcggtaggt    180
tccgaagtag aagagctgca atgacgaaag cagtgacggc aagccgtaaa atagaaccac    240
gttcgtcaca gatgcatcca gtatgacgag ataaaacgtc acgacggtcg agacgaatgc    300
gaccgatctc catccgaaat aacgtgagaa gaaggtgccg aaccaaggcc agaaattctc    360
cggatcatct gcgtagaaat ccgggtcggc cggtgtaccg ggtgcgtcgt ggtgtgcgaa    420
gtgagcatct ctgatctttt tccacgcaaa tcccgcgtag acgaacagga tgaacccgcc    480
gattacggca ttcaaacgcg ttcgacccgg cgccagcgaa ccatgcatgg cgtcgtgagc    540
caggatgaaa agccccaccg tcaaccagca ctggaacacc gtgatcaatg gtgcgagagg    600
caacgtgctg aaattgatgt cgaggaagaa tatcgctgag acgtgtattg cgaaccacga    660
tgccagcagc acggcacaga gcgtcaggcc aatcgtcgtt tggtagggtc tgattttggg    720
tgagtcggcg ggtgtggatc gcggtaacgc acttgccggg atcaggcgtg aggttgggct    780
gagggtcatg acctcgcaaa taagccgaac cgtccgggtg caaaatcgtt tgccgcctcg    840
tttggcgcgg cataacgtcg tccatcctcg ctctgtgcgc tcgcgagaac acgatcgacg    900
gcttctgcag cagcacgcgc accgcctgcg ttggcgattt ccgcctggat cggagcgatc    960
```

-continued

```
cggttcacga aggctgctcg gtttgcaatc aaatcggaaa gtgcattcgc aatggttcgc    1020
ggcttggccc gcttggcggc gatagcctta cccacgccgt gatggagtat acgggcaccg    1080
acacccggct gatcgtagcc aattggcagc gccaacatag gcgtaccgac cgccagacag    1140
tcgagaacgg tgttgagccc cccgtgagtc acgcagacat ctgcgcgtgc gagcatcgcg    1200
cgttgatcga cgaaactgac tacccacttg gccggaagcc tcgaagcttg tcgtggcgag    1260 agcccccgc aatgcgcgat catcaattgc acatcgagcg tctcgcaggc ggatgcgatc     1320
tttttgaata aactgtaacg atgaccttgc accgtgccga gagacgcgaa cacgaagggg    1380
cgcgtcgggt cgatcgtgag acatgtttcc ttcgtcagtc ttgcgactga ggcactgcgg    1440
atgggtccaa ccggcttcag tttcgtcccc ctcggtctcg gaaagtcgaa aacgctgacg    1500
gtctgcgaca aacgcaacac tggcgagaga caggcaacgt cgtcctcccg cggccccagt    1560
ccgaagcgcg tcgcccaggc ttggatcacc ttccgttgct tgcgcatgaa gaatttgccg    1620
acacgctccc cgccgcgatt gcgagcaagt ccctcttcgg tgggatcgta gggccaatcg    1680
agaaacggca gaggcatcgc cacatcccgt tcgattggta gggccgacgc caaggagatg    1740
tgtggcaggc cgagataagc tgcgaccaga ccggcgcctg gctcgaattc atctgcgatg    1800
attgcatcga tttgcatcga acgcatgatg tcccgagcga tgcgacaaaa ctgatctgtt    1860
tctcttgctc gatcggcaac tgcccgcaag ataccgagaa tcccggcgcc gccgccgtca    1920
cgccgacgat gccgaacacc agacatgatt gaagcagaag ccgctagcgt aacaatctcg    1980
atgtcagact ggcagaccat cgtctccgcc tctttcggca gtatgaagac gacgtcgtgg    2040
ccgcgaacct tgagcgcttg ccccagaact tcgaacgcct tgatatggct gtagaacgcc    2100
ggacagacca aagctatgcg tgccaattac atcaatccct cagccgaaac gaatcgacgc    2160
agacaagcac cgcccctatcg atagcaaccg accttaacat agttccgggt gacgatagtc    2220
gaggtagggt atgatcagga cattcctgaa cggcgatgga agcgttcggg tcgatcgaga    2280
aacggctttt aacgtgacga aagaggattg atgtcggccg cgcgcggttc atgctcccta    2340
agcgagatcg ctagccgctc ggctcggttg cgccgacctc gctcgatcgc gaaagtctgg    2400
cccgtcgctt cgacacttgc atgcctgttg ctgacaaacg gcctcgtcgt actctacctc    2460
tgggcgatcg gtagaccgtt catcgcgccg accgaacctc tcaagctgtt tagcgacaac    2520
ctcgccgctg cgaattcgct ttatctctcc gatccctact cgcttctgca cgtcatcttc    2580
ggaatcggtc tcttcctgta tctcgactgg atgaaacctt tctggccgac gagggaaaaa    2640
ctgattgtcg cggtcttggg gagcgcaatc tgggaagtcg tcgagaacac gccatatgtt    2700
gtgggtctgt tcaacgacac gagtgacacg gcagcttaca acggggacag tgtcgcgaat    2760
tcgattggcg atacgatctc tgcggtaatt ggtttttttgt tcgcgaatcg gacagggcgc    2820
cgagtttccc tgttcgttgc attcgcgctt gaatcaatcg ttacagtatg gattggcgat    2880
ggaatcgtta ttggcacgct cagacttctg ggtctgtacc cgatctgatc gacgcgactc    2940
ttgcgcccat cgtcacggcc atgtgtgtgt gccaagatcg agttatatat gtacctcggc    3000
ctgaacgact gaaccaaaac tagaaacgtc gataagaaac gatgacgatc tggactctct    3060
actacgtctg tctcaccctc gtcacgatcg gtttgatgga ggtttatgca tggtgggcgc    3120
acaagttcat catgcatggc aaattcggtt ggggctggca taagtcccac cacgaggaaa    3180
ccgaagggtg gttcgagaag aacgatctct acgctgtcgt tttcgccggc ttcgcgatag    3240
cgctgttcat ggtcggacat ttcctttctc gacccgtgct cgccatcgcc tggggcatca    3300
cgctttacgg attactctac ttcgttgccc atgatggact tgtccatcag cgctggccgt    3360
```

-continued

```
tcaactacgt gccgcatcga ggttatgcaa aacgcctggt tcaagctcat cgtctgcacc    3420
atgcggtgga aggccgcgag cactgcgtct cgttcggctt tctctatgcg ccgccgattg    3480
aaaagctgaa gcgcgatttg cgtgagtccg gaattctcga acgggagcgc atcgagcggt    3540
ctctggacca gcaaggctcc gcccacgcgc cggttcggtg a                       3581
```

<210> SEQ ID NO 46
<211> LENGTH: 392
<212> TYPE: PRT
<213> ORGANISM: Fulvimarina pelagi

<400> SEQUENCE: 46

```
Leu Thr Ser Ser Ala Lys Gln Lys Val Asp Ile Ala Leu Val Gly Gly
1               5                   10                  15

Gly Leu Ala Asn Gly Leu Ile Ala Trp Arg Leu Ala Glu Leu Arg Pro
            20                  25                  30

Asp Leu Ser Ile Val Leu Glu Ala Gly Glu Ala Pro Gly Gly Asn
        35                  40                  45

His Thr Trp Ser Phe His Glu His Asp Leu Thr Pro Ala Ala His Arg
    50                  55                  60

Trp Ile Ala Pro Phe Val Ala His Arg Trp Thr Thr Asn Glu Val Gln
65                  70                  75                  80

Phe Pro Asp Arg His Arg His Leu Ser Thr Gly Tyr Leu Ser Ala Ser
                85                  90                  95

Ser Asp Leu Phe Arg Glu Arg Leu Thr Thr Arg Leu Gly Leu Arg Ile
            100                 105                 110

Arg Thr Gly Cys Pro Ala Val Ser Val Thr Ala Arg Lys Val Arg Leu
        115                 120                 125

Glu Asn Gly Glu Val Ile Glu Ala Gly Ser Val Ile Asp Gly Arg Gly
    130                 135                 140

Tyr Arg Ser Ser Glu His Leu Thr Leu Gly Phe Gln Lys Phe Leu Gly
145                 150                 155                 160

Gln Glu Ile Glu Phe Glu Ala Pro His Gly Val Ala Arg Pro Val Ile
                165                 170                 175

Met Asp Ala Thr Val Pro Gln Ala Asp Gly Tyr Arg Phe Val Tyr Leu
            180                 185                 190

Leu Pro Met Thr Pro Thr Arg Leu Leu Val Glu Asp Thr Tyr Tyr Ala
        195                 200                 205

Asp Gly Asp Ala Leu Asp Arg Gly Thr Ile Arg Arg Asn Ile Ala Ala
    210                 215                 220

Tyr Arg Ala Ala Lys Gly Trp Pro Ala Gly Lys Val Val Arg Glu Glu
225                 230                 235                 240

Asp Gly Val Leu Pro Ile Ala Leu Ala Gly Asp Ile Glu Ala Phe Trp
                245                 250                 255

Glu Glu Lys Gln Gly Val Pro Ser Ser Gly Leu Asn Ala Ala Leu Phe
            260                 265                 270

His Pro Thr Thr Gly Tyr Ser Leu Pro Asp Ala Val Tyr Leu Ala Asp
        275                 280                 285

Leu Ile Ala Gly Leu Pro Asp Tyr Ser Ala Ala Thr Leu Tyr Ala Ala
    290                 295                 300

Thr Arg Arg His Ser Val Ala Thr Trp Lys Arg Arg Gly Phe Phe Arg
305                 310                 315                 320

Met Leu Asn Arg Leu Leu Tyr Leu Ala Gly Asp Pro Leu Lys Arg Tyr
                325                 330                 335
```

```
Val Ile Leu Gln His Phe Tyr Arg Leu Pro Glu Pro Leu Val Ser Arg
                340                 345                 350

Phe Tyr Ala Ala Arg Leu Thr Arg Gly Asp Lys Val Arg Ile Leu Thr
            355                 360                 365

Gly Lys Pro Pro Val Ser Val Ile Ser Ala Leu Lys Val Leu Ser Pro
370                 375                 380

Ser Ser Val Glu Gly Ala Pro Ala
385                 390

<210> SEQ ID NO 47
<211> LENGTH: 509
<212> TYPE: PRT
<213> ORGANISM: Fulvimarina pelagi

<400> SEQUENCE: 47

Met Asn Gln Met Pro Arg Asp Leu Pro Asn Lys Thr Lys Thr Ala Val
1               5                   10                  15

Val Ile Gly Ala Gly Phe Gly Gly Leu Ala Leu Ala Ile Arg Leu Gln
            20                  25                  30

Ala Ala Gly Ile Gln Thr Thr Leu Leu Glu Lys Arg Asp Lys Pro Gly
        35                  40                  45

Gly Arg Ala Tyr Val Tyr Glu Asp Gln Gly Phe Thr Phe Asp Ala Gly
    50                  55                  60

Pro Thr Val Ile Thr Asp Pro Ser Ala Leu Glu Glu Leu Phe Glu Thr
65                  70                  75                  80

Ala Asn Ala Lys Leu Ser Asp Tyr Val Glu Leu Leu Pro Val Lys Pro
                85                  90                  95

Phe Tyr Arg Leu Ala Trp Glu Asp Gly Phe Val Phe Asp Tyr Ala Asp
            100                 105                 110

Asp Gln Glu Asp Leu Asp Arg Gln Ile Gly Ala Lys Asn Pro Lys Asp
        115                 120                 125

Val Glu Gly Tyr Arg Arg Phe Leu Ala Tyr Ser Arg Asp Val Phe His
    130                 135                 140

Glu Gly Tyr Glu Lys Leu Gly Thr Val Pro Phe Leu Asn Phe Lys Asp
145                 150                 155                 160

Met Met Arg Ala Ala Pro Gln Leu Val Arg Leu Glu Ala Tyr Arg Ser
                165                 170                 175

Val Tyr Ser Lys Val Ala Gln Phe Ile Glu Asp Asp Gln Leu Arg Gln
            180                 185                 190

Ala Phe Ser Phe His Ser Leu Leu Val Gly Gly Asn Pro Phe Ala Thr
        195                 200                 205

Ser Ser Ile Tyr Ala Leu Ile His Ala Leu Glu Arg Lys Trp Gly Val
    210                 215                 220

Phe Phe Pro Arg Gly Gly Thr Gly Ala Leu Val Arg Gly Met Ala Lys
225                 230                 235                 240

Leu Phe Thr Asp Ile Gly Gly Arg Ile Glu Val Asn Ala Glu Val Glu
                245                 250                 255

Asn Ile Ala Ile Glu Asn Gly Arg Ala Lys Ser Val Thr Thr Lys Gly
            260                 265                 270

Gly Gln Thr Phe Pro Ala Asp Phe Val Ala Ser Asn Ala Asp Val Val
        275                 280                 285

His Thr Tyr Ala Lys Leu Met Gly Arg Ser Glu Arg Gly Lys Lys His
    290                 295                 300

Gly Asn Ser Leu Lys Lys Lys Arg Phe Ser Met Ser Leu Phe Val Ile
```

```
305                 310                 315                 320

Tyr Phe Gly Leu Lys Thr His Arg Pro Asp Ile Ala His His Thr Val
                325                 330                 335

Cys Phe Gly Pro Arg Tyr Arg Pro Leu Ile Asp Glu Ile Phe Lys Gly
                340                 345                 350

Lys Glu Leu Ala Gly Asp Phe Ser Leu Tyr Leu His Asn Pro Cys Val
                355                 360                 365

Thr Asp Pro Ser Leu Ala Pro Glu Gly Met Gly Ser Phe Tyr Val Leu
            370                 375                 380

Ser Pro Val Pro His Leu Gly Asn Ala Asp Ile Asp Trp Ala Val Glu
385                 390                 395                 400

Gly Pro Lys Tyr Arg Asp Arg Ile Leu Asp Tyr Leu Glu Glu Leu Tyr
                405                 410                 415

Ile Pro Gly Leu Lys Asp Asp Leu Val Thr Ser Arg Ile Phe Thr Pro
                420                 425                 430

Ala Asp Phe Lys Thr Glu Leu Asn Ala His Leu Gly Ser Ala Phe Ser
                435                 440                 445

Leu Asp Pro Val Leu Thr Gln Ser Ala Trp Phe Arg Pro His Asn Arg
        450                 455                 460

Asp Asp Gln Ile Pro Asn Leu Tyr Val Val Gly Ala Gly Thr His Pro
465                 470                 475                 480

Gly Ala Gly Val Pro Gly Val Gly Ser Ala Lys Ala Thr Ala Gly
                485                 490                 495

Leu Met Ile Glu Asp Ala Gly Leu Ala Cys Val Pro Ala
                500                 505

<210> SEQ ID NO 48
<211> LENGTH: 352
<212> TYPE: PRT
<213> ORGANISM: Fulvimarina pelagi

<400> SEQUENCE: 48

Met Ser Phe Ala Asp Arg Leu Asp Val Pro Ile Val Gly Gly Leu Pro
1               5                   10                  15

Phe Glu Lys Arg Glu Arg Ala Ala Leu Ala Ala Glu Ala Glu Ala Thr
                20                  25                  30

Ile Ala Gln Gly Ser Lys Ser Phe Ala Ala Ala Arg Leu Phe Asp
            35                  40                  45

Pro Glu Met Arg Val Ser Ala Leu Met Leu Tyr Ala Trp Cys Arg His
        50                  55                  60

Cys Asp Asp Val Val Asp Gln Ile Leu Gly Phe Arg Gln Pro Gly
65                  70                  75                  80

Arg Arg Asp Arg Ala Gly Asp Arg Ala Arg Leu Asp Glu Leu Glu Ala
                85                  90                  95

Lys Thr Leu Ala Ala Val Arg Gly Arg Ser Thr Gly Glu Ala Pro Phe
                100                 105                 110

Asp Ala Ile Gly Asp Val Ala Leu Arg His Glu Leu Pro Glu Ser Leu
            115                 120                 125

Leu Thr Ala His Leu Glu Gly Phe Arg Met Asp Val Asp Gly Arg Val
        130                 135                 140

Tyr Glu Val Ile Glu Asp Thr Leu Asp Tyr Cys Tyr Arg Val Ala Gly
145                 150                 155                 160

Val Val Gly Val Met Met Ala Arg Val Met Gly Ile Arg Val Glu Asn
                165                 170                 175
```

```
Gly Ser Lys Phe Asp Leu Thr Leu Thr Leu Asp Arg Ala Cys Asp Leu
            180                 185                 190

Gly Met Ala Phe Gln Leu Thr Asn Ile Ala Arg Asp Ile Val Asp Asp
        195                 200                 205

Gly Glu Ala Gly Arg Val Tyr Val Pro Lys Thr Trp Leu Asp Ala Ala
    210                 215                 220

Gly Val Pro Gly Ser Ala Ile His His Pro Arg Asn Arg Glu Ala Ala
225                 230                 235                 240

Ala Val Phe Ala Leu Arg Leu Leu Asp Leu Ala Glu Pro Tyr Tyr Ala
                245                 250                 255

Ser Ala Ser Lys Gly Leu Ala Ala Leu Pro Pro Arg Ala Ala Trp Ala
            260                 265                 270

Val Ala Thr Ala Leu Gly Val Tyr Arg Glu Ile Gly Thr Val Ile Arg
        275                 280                 285

Arg Arg Gly Ser Gln Ala Trp Asp Asp Arg Ser Ser Thr Ser Ala Ala
    290                 295                 300

Thr Lys Phe Leu His Ala Phe Lys Gly Val Gly Trp Thr Met Gly Ser
305                 310                 315                 320

Arg Val Ser Ser Arg Arg Gly Val Arg Pro Pro Glu Leu Trp Thr Arg
                325                 330                 335

Pro Arg Leu Leu Glu Leu Gly Asp Ala Pro Thr Thr Gly Leu Ser Ala
            340                 345                 350

<210> SEQ ID NO 49
<211> LENGTH: 262
<212> TYPE: PRT
<213> ORGANISM: Fulvimarina pelagi

<400> SEQUENCE: 49

Met Thr Leu Ser Pro Thr Ser Arg Leu Ile Pro Ala Ser Ala Leu Pro
1               5                   10                  15

Arg Ser Thr Pro Ala Asp Ser Pro Lys Ile Arg Pro Tyr Gln Thr Thr
            20                  25                  30

Ile Gly Leu Thr Leu Cys Ala Val Leu Leu Ala Ser Trp Phe Ala Ile
        35                  40                  45

His Val Ser Ala Ile Phe Phe Leu Asp Ile Asn Phe Ser Thr Leu Pro
    50                  55                  60

Leu Ala Pro Leu Ile Thr Val Phe Gln Cys Trp Leu Thr Val Gly Leu
65                  70                  75                  80

Phe Ile Leu Ala His Asp Ala Met His Gly Ser Leu Ala Pro Gly Arg
                85                  90                  95

Thr Arg Leu Asn Ala Val Ile Gly Gly Phe Ile Leu Phe Val Tyr Ala
            100                 105                 110

Gly Phe Ala Trp Lys Lys Ile Arg Asp Ala His Phe Ala His His Asp
        115                 120                 125

Ala Pro Gly Thr Pro Ala Asp Pro Asp Phe Tyr Ala Asp Asp Pro Glu
    130                 135                 140

Asn Phe Trp Pro Trp Phe Gly Thr Phe Phe Ser Arg Tyr Phe Gly Trp
145                 150                 155                 160

Arg Ser Val Ala Phe Val Ser Thr Val Thr Phe Tyr Leu Val Ile
                165                 170                 175

Leu Asp Ala Ser Val Thr Asn Val Val Leu Phe Tyr Gly Leu Pro Ser
            180                 185                 190

Leu Leu Ser Ser Leu Gln Leu Phe Tyr Phe Gly Thr Tyr Arg Pro His
        195                 200                 205
```

Arg His Glu Glu Ser Gly Thr Phe Ala Asp Ala His Asn Thr Arg Ser
    210                 215                 220

Ser Glu Phe Gly Tyr Val Ala Ser Leu Phe Ser Cys Phe His Phe Gly
225                 230                 235                 240

Tyr His His Glu His His Leu Ala Pro Trp Thr Pro Trp Trp Ala Leu
                245                 250                 255

Pro His Thr Arg Gln Ser
            260

<210> SEQ ID NO 50
<211> LENGTH: 179
<212> TYPE: PRT
<213> ORGANISM: Fulvimarina pelagi

<400> SEQUENCE: 50

Met Thr Ile Trp Thr Leu Tyr Tyr Val Cys Leu Thr Leu Val Thr Ile
1               5                   10                  15

Gly Leu Met Glu Val Tyr Ala Trp Trp Ala His Lys Phe Ile Met His
            20                  25                  30

Gly Lys Phe Gly Trp Gly Trp His Lys Ser His His Glu Glu Thr Glu
        35                  40                  45

Gly Trp Phe Glu Lys Asn Asp Leu Tyr Ala Val Val Phe Ala Gly Phe
    50                  55                  60

Ala Ile Ala Leu Phe Met Val Gly His Phe Leu Ser Pro Thr Leu Leu
65                  70                  75                  80

Ala Ile Ala Trp Gly Ile Thr Leu Tyr Gly Leu Leu Tyr Phe Val Ala
                85                  90                  95

His Asp Gly Leu Val His Gln Arg Trp Pro Phe Asn Tyr Val Pro His
            100                 105                 110

Arg Gly Tyr Ala Lys Arg Leu Val Gln Ala His Arg Leu His His Ala
        115                 120                 125

Val Glu Gly Arg Glu His Cys Val Ser Phe Gly Phe Leu Tyr Ala Pro
    130                 135                 140

Pro Ile Glu Lys Leu Lys Arg Asp Leu Arg Glu Ser Gly Ile Leu Glu
145                 150                 155                 160

Arg Glu Arg Ile Glu Arg Ser Leu Asp Gln Gln Gly Ser Ala His Ala
                165                 170                 175

Pro Val Arg

<210> SEQ ID NO 51
<211> LENGTH: 496
<212> TYPE: DNA
<213> ORGANISM: Methylobacterium extorquens

<400> SEQUENCE: 51
gtgtcgccag cttcctcttc cccggcatcg cccggatgct gttcctgaac cccgtgacgc    60
ccaaagtttt cgcctggagc gccgaccggg cggcggtgcg tcgcctcatc gacggcaccg   120
gctcgcgcct cgacccgcag gggctcgacc tctaccggcg gctgttcacc cgccccggcc   180
atgtcgcggg cgccctcggc atgatggcga actgggatct tccggcactc gcccgcgacc   240
tgccggggct cgaaacccgt acgctgctgg tcgtcggcgg ggacgacaag gcgatcaagc   300
ccgacgattc cttcgccttg cgcgagcggt tgcggagcgc acgcgtagaa ttgctgcgtg   360
ggctcggcca cctcgcgcac gaggaggcgc cggagcgggt ggcggagatc attctggcag   420
aagcggacgc ccttggcgcc tcggtatcct gagacgcctc ttgcgctgac gaaaatccca   480
gccatagtgt caacct 496

<210> SEQ ID NO 52
<211> LENGTH: 2573
<212> TYPE: DNA
<213> ORGANISM: Methylobacterium extorquens

<400> SEQUENCE: 52

| | | | | | |
|---|---|---|---|---|---|
| atgttgacac | tggccgtcaa | accgactgtc | acgtccgact | ccgatgcccg | gccgcatgcg | 60 |
| gtcgtgatcg | gggccggctt | cggcgggctg | gccgcggcgg | ttcggctcgg | cgcccgcggc | 120 |
| tatcgcgtca | ccgttctgga | acggctcgac | cagcccggcg | gccgcgcccg | cgtccaccgc | 180 |
| caggacggct | tcaccttcga | tgcggggccc | accatcgtca | ccgcgccgtt | cctgttcgag | 240 |
| gagctgtggc | ggttgtgcgg | gcgggagatg | cgcgaggacg | tgactctcgt | gccgatgcag | 300 |
| ccattctacc | gcattcgctt | cgaggatggg | cagagcttcg | cctatagcgg | cgaccgcgcg | 360 |
| gcgatgcggg | ccgaggtcgc | ccgcttctcg | cccgacgacg | tgtccggcta | cgaacgcttc | 420 |
| atggcccata | gcgaggcggt | gtgccggatg | ggcttcgagg | aactcggcca | cgtcccgttc | 480 |
| ggcagcctcg | gctcgatgct | gcggatcgcg | cccgatctgc | tgcgcttgtc | gggccaccgc | 540 |
| agcgtctacg | acgtggtgtc | ccgcttcatc | cgcgacgagc | ggctgcgcac | catcttcagc | 600 |
| ttccatcccc | tgctcatcgg | cggcaacccg | tttcgcgcca | gcggcatcta | ctgcctgatc | 660 |
| gcccatctgg | agcggcaatg | gggcgtccat | ttcgccatgg | gcggtaccgg | acgactggtg | 720 |
| gacgggctct | gcggcttgat | ccgggggcag | ggaggccgcg | tccgctgcgg | cgaggacgtt | 780 |
| tcgcgcatcc | gcgtcgagga | tgcgcgggcg | acgggtgtgg | tgctggcggg | cggcgaggtc | 840 |
| atccccgccg | acaccgtcgt | ctcgaacgcc | gattccgcct | tcacctacgg | cacgctgctc | 900 |
| ggcggccgga | cccggcgctg | gagcgcgcgg | cgcctggcgc | gcgcctcgtc | ctccatgggg | 960 |
| ctgttcgtct | ggtatttcgg | tacccggaag | aagtacccgg | aggtcgatca | ccacatgatc | 1020 |
| ctgatgggcc | cgcgctatcg | cggcctgttg | caggacatct | tcgaccgcaa | gcacttggcg | 1080 |
| aacgatttca | gcctctatct | ccaccgcccc | accgcgaccg | accgctgctc | gcgccgcccc | 1140 |
| ggctgcgacg | cgttctacgt | gctcgccccg | gtgccgaacc | tcgacggcgg | ccaggattgg | 1200 |
| gcacagcttg | ccgagcccta | ccgccagcgg | atcgcgcgct | tcctcgaagg | ctcggtgctg | 1260 |
| ccggggctgt | ccgacgccct | cgtcacctcg | cgggtgacga | cgccgcagga | cttttccgac | 1320 |
| gacttcctga | gcttccgcgg | ctccgggttc | gggctggagc | cggtgctgac | gcaatcggcg | 1380 |
| tggttccgtc | cgcacaaccg | ctcggaagac | gtggccaacc | tcttcctcgt | cggcgcgggg | 1440 |
| acgcatcccg | gcgccggtct | gccgggcgtg | ctgtcctcgg | cgcgtgtcct | cgattccgtg | 1500 |
| gtgccggatg | cccgtgtttg | cgcctgaccc | tttcgccgcc | agcgcggcgg | accgctctgc | 1560 |
| ctgccgggcc | gcgatccgcg | ccggctccaa | gagcttcttc | gcggcctcgc | tgctgctgcc | 1620 |
| gccctcagtg | cgggtctcgg | cctacggcct | ctacgccttc | tgccgccttt | ccgacgatgc | 1680 |
| ggtggacgag | gcgggggcca | accgtgctgc | ggccctcgcc | cgcctggaac | gacggctgac | 1740 |
| agcggcctgt | gccggccggc | ccgacaacca | cccggccgac | cgggcgctcg | ccgaggtgct | 1800 |
| cgcccgccac | gccatcccgg | aaaagctgcc | gcgggcgctg | ctcgaagggt | tggcctggga | 1860 |
| cacgcaaggc | cggcgctacg | acaccctgtc | ggagctggcc | gcctatgccg | cccgggtcgc | 1920 |
| gggcgcggtc | gggcgatga | tgacactggt | gatgggggtg | cgcgacggcc | ccgcgctcgc | 1980 |
| ccgcgcctgc | gatctcggcg | tggccatgca | attcaccaac | atcgcccgcg | atgtcggcga | 2040 |

```
                                          -continued ggatgccgc gccgggcgcc tctacctgcc tcgcgagtgg ctcgacgcgg ccggcatcga     2100
cccggacgcc ttcctcgccg agcctcggct cggccccagc ctgcaacggg tggtggccga     2160
gctgctggcg gcggccgacg aactctacgc ccgcgccgaa cccggcatcg ccgcgctccc     2220
gttgagctgc cgcccggcga tccgcgccgc cggcctgatc tacgcggaga tcggccgtgc     2280
cgtggaggcg aacgagctcg attcggtcac gcgccgcgcc cgcgtcaccg gcgcgcgcaa     2340
ggccgggctt ctggccaccg cgatcctgcc cgcgggcggc ggccagggac tatcggcgcc     2400
gccattgccc gagaccgcct tcctcgtgga agccgtgacg caccatccgg tcccagccgc     2460
gcggcgcttg ccaccgtggt ggaacgtgtc ggggcaggtc gtgcgggtgc tcgacctgat     2520
cgaggtgctg gaggagcgcg acgccttccg ccgctcggcc gcgtcgtaag gaa           2573
```

HETEROLOGOUS CAROTENOID PRODUCTION IN MICROORGANISMS

CROSS-REFERENCE TO RELATED APPLICATIONS

This application is a U.S. national stage application under 35 U.S.C. § 371 of PCT/US2018/035505, filed on May 31, 2018, which claims the benefit of U.S. Provisional Application No. 62/513,892, filed on Jun. 1, 2017, which is incorporated by reference in its entirety.

SEQUENCE LISTING

The instant application contains a Sequence Listing which has been submitted electronically in ASCII format and is hereby incorporated by reference in its entirety. Said ASCII copy, created on Jul. 9, 2018, is named 05291_003WO1_SL.txt and is 174,602 bytes in size.

FIELD OF THE INVENTION

The invention relates to production of carotenoid compounds in microbial organisms, and use in feed compositions, in particular for aquaculture, animal feeds and human nutrition.

BACKGROUND

Carotenoids are a class of ubiquitous and structurally diverse natural pigments ranging in color from light yellow to orange to red. Carotenoids are responsible for the coloring of carrots, tomatoes, red peppers, and the petals of daffodils and marigolds, as well as lobsters, salmon, and other marine life.

Carotenoids are produced by all photosynthetic organisms, as well as by some bacteria and fungi. Carotenoids have roles in photosynthesis, nutrition, and protection against photooxidative damage. Animals cannot produce carotenoids themselves, but must obtain these nutritionally important compounds through their diet. Carotenoids include 40-carbon ($C_{40}$) terpenoids ultimately derived from the isoprene biosynthetic pathway, specifically from isopentenyl pyrophosphate (IPP), a five-carbon building block. This biosynthetic pathway can be divided into two portions: the upper isoprene pathway, which leads to the formation of IPP, and the lower carotenoid biosynthetic pathway, responsible for converting IPP into long chain (e.g., $C_{30}$ and $C_{40}$) carotenogenic compounds.

Carotenoid compounds, such as β-carotene, astaxanthin, canthaxanthin, zeaxanthin, and lutein, are used industrially as ingredients for food and feed stocks, both serving a nutritional role, and often increasing desirability of the product to consumers. Carotenoids, such as astaxanthin and canthaxanthin, are often added to aquaculture feeds for the purpose of providing color to the flesh of aquacultured organisms; their wild counterparts have colored flesh resulting from consumption of carotenoids that occur naturally in crustacea or algae, or in other fish that have consumed algae. For example, astaxanthin is widely used in salmon aquaculture to produce the orange to red coloration of the flesh found in wild salmon. The deposition of carotenoids in animals is dependent on the dosing, chemical species, purity of the compound, and the individual organism's biology (see, e.g., Matthews, et al. (2006) *Comp. Biochem. Physiol.* 206-14; Per Foss, et al. (1984) *Aquaculture* 41(3):213-26). Some carotenoids are also precursors of vitamin A. Moreover, some carotenoids have antioxidant properties, and may have health benefits, for example, against cardio-vascular problems, different types of cancer and some diseases of the immunological system (see, e.g., Jyonouchi, et al. (1991) *Nutr. Cancer* 16:93; Giovannucci, et al. (1995) *J. Natl. Cancer Inst.* 87:1767; Miki (1991) *Pure Appl. Chem* 63:141; Chew, et al. (1999) *Anticancer Res.* 19:1849; Wang, et al. (2000) *Antimicrob. Agents Chemother.* 44:2452; Higuera-Ciapara, et al. (2006) *Crit. Rev. in Food Science & Nutr.* 46(2):185-96). Several carotenoids (e.g., β-carotene, lycopene, and lutein) are currently sold as nutritional supplements.

A number of carotenoids have been produced in microbial organisms. For example, PCT Application No. WO 02/18617 describes a method of production of carotenoid compounds using microorganisms that metabolize single carbon substrates. Genes encoding elements of the carotenoid biosynthetic pathway have been cloned and expressed in fungi, yeast, and microbes. For example, lycopene has been produced from genetically engineered *Escherichia coli* and *Candida utilis* (see, e.g., Farmer, et al. (2001) *Biotechnol. Prog.* 17: 57-61; Wang, et al., (2000) *Biotechnol. Prog.* 16: 922-926; Misawa & Shimada (1998) *J Biotechnol.* 59: 169-181; Shimada, et al. (1998) *Appl. Environm. Microbiol.* 64: 2676-2680). Zeaxanthin has been produced from recombinant *E. coli* and *C. utilis* (see, e.g., Albrecht, et al. (1999) *Biotechnol. Lett.* 21:791-795; Miura, et al. (1998) *Appl. Environm. Microbiol.* 64: 1226-1229). Astaxanthin has been produced from *E. coli* and *Pfaffia rhodozyma* (see, e.g., U.S. Pat. No. 5,466,599). The nutrient β-carotene has been produced from *E. coli, C. utilis*, and *P. rhodozyma* (see, e.g., Albrecht, et al. (1999) *Biotechnol. Lett.* 21:791-795; Miura, et al. (1998) *Appl. Environm. Microbiol.* 64:1226-1229; U.S. Pat. No. 5,691,190).

Genes encoding geranylgeranyl pyrophosphate synthase, lycopene cyclase, and phytoene dehydrogenase from *Erwinia herbicola* have been expressed in *E. coli* (see, e.g., U.S. Pat. Nos. 5,545,816, 5,656,472, 5,530,189, and 5,530,188). Genes encoding such carotenoid products as geranylgeranyl pyrophosphate, phytoene, lycopene, β-carotene, and zeaxanthin-diglucoside, from *Erwinia uredovora*, have been expressed in *E. coli, Zymomonas mobilis*, and *Saccharomyces cerevisiae* (U.S. Pat. No. 5,429,939). Carotenoid biosynthetic genes including crtE, crtB, crtI, crtY, and crtZ taken from *Flavobacterium*, have been recombinantly expressed (see U.S. Pat. No. 6,124,113).

Although the above methods can produce useful amounts of carotenoids, a need exists for improved processes. A particular long-appreciated need is for a process that produces useful yields of carotenoids from an inexpensive feedstock and also produces one or more nutrients (e.g., lipids or protein). The resulting carotenoid- and nutrient-rich microbial or plant biomass could then be processed into feed for aquaculture or agriculture, or used as a nutrient source for humans.

There are several microorganisms that utilize single-carbon substrates as their sole energy sources. Examples of single-carbon substrates include methane, methanol, formate, thiols, and methylated amines. These organisms are referred to as methylotrophs and also herein as "C1 metabolizers." Few methylotrophs have been successfully utilized to produce nutrients on an industrial scale. Despite the fact that single-carbon substrates are cost-effective energy sources, the lack of information about methylotroph genetics and the resulting difficulty in their manipulation has limited their use primarily to the synthesis of native products.

There is also a need for and an economic benefit to be able to utilize process streams and waste effluents that result from ethanol production as alternative carbon substrates. Ethanol is commonly produced by fermenting sugars extracted from plant biomass into 'beer' from which the ethanol is removed and concentrated by distillation. The major residual material from this distillation process is called whole stillage. During production of ethanol from dry milled corn, this whole stillage is further separated by centrifugation into dry solids (wet cake or wet distiller grains (WDG)) and a liquid component called thin stillage. Thin stillage is further evaporated to form stillage syrup or condensed distiller solubles (CDS). These products are often combined to form wet distiller grains with solids (WDGS) and further dried to form dried distillers grains with solids (DDGS) to improve shelf life. WDG, CDS, WDGS, and/or DDGS are mixed into animal feed. Beer, thin stillage, and stillage syrup contains many potential carbon substrates including alcohols (glycerol, ethanol, butanediol), carbohydrates (glucose, glucan, xylose, xylan, arabinose, arabinan, galactose, galactan, maltose, cellulose, starch), organic acids (lactic acids, acetic acid), protein, peptides, amino acids and fat (see, e.g., Kim, et al. (2008) *Bioresource Technology* 99:5165-5176).

A need also exists for low-cost, complete nutrition for use in aquaculture. Aquaculture is the propagation, cultivation and marketing of aquatic animals and plants in a controlled environment. The aquaculture industry is currently the fastest growing animal protein production sector in the world. World aquaculture produces approximately 60 million tons of seafood at an annual value of more than $110 billion (USD). Presently, fish farming produces about half of all fish consumed globally and this percentage is growing as a result of declining yields from wild-caught fish in both marine and freshwater environments and the need to provide more protein to a swelling human population. Species groups produced in aquaculture include: carps and other cyprinids; oysters; clams, cockles and ark shells; scallops; shrimps and prawns; salmons, trouts and smelts; mussels; and tilapias and other cichlids.

While certain species (e.g., tilapia) can be fed an exclusively vegetarian diet, others require a carnivorous diet. Feed for carnivorous fish typically comprises fishmeal and fish oil derived from wild caught species of small pelagic fish (predominantly anchovy, jack mackerel, blue whiting, capelin, sand eel and menhaden). The fishmeal is processed into a pelleted or flaked feed, depending on the size of the fish to which it will be fed (e.g., fry, juveniles, adults). Other components of the aquaculture feed composition may include carotenoid pigments, vegetable protein, vitamins, and minerals.

Many organizations recognize the limitations to fishmeal availability and aquaculture sustainability. The National Oceanic and Atmospheric Administration and the United States Department of Agriculture have collaborated in an Alternative Feeds Initiative to " . . . identify alternative dietary ingredients that will reduce the amount of fishmeal contained in aquaculture feeds while maintaining the important human health benefits of farmed seafood." (NOAA Technical memorandum NMFS F/SPO-124, 2011).

U.S. Pat. Appl. Pub. No. 2007/0226814 discloses fish food containing at least one biomass obtained from fermenting microorganisms wherein the biomass contains at least 20% DHA relative to the total fatty acid content. Microorganisms from the genus *Stramenopiles* are mentioned as sources of DHA. U.S. Pat. Appl. Pub. No. 2009/0202672 discloses that stearidonic acid ("SDA"; 18:4 omega-3) can be added to aquaculture feed. This fatty acid can be obtained from a transgenic plant. Unfortunately, SDA is not converted efficiently to DHA in fish. U.S. Pat. No. 7,932,077 discloses that recombinantly engineered *Yarrowia lipolytica* may be a useful addition to most animal feeds, including aquaculture feeds, because it provides necessary omega-3 and/or omega-6 PUFAs, and offers unique protein:lipid:carbohydrate composition, as well as unique complex carbohydrate profile (comprising an approximate 1:4:4.6 ratio of mannan:beta-glucans:chitin).

If the growing aquaculture industry is to sustain and even increase its contribution to world fish supplies, there is a need for alternative aquaculture feed compositions that: (i) reduce wild fish inputs by replacing fish meal with non-fish derived sources; and (ii) use pigments that are not chemically synthesized, or otherwise derived from petroleum-based feedstocks, to provide pigmentation.

BRIEF SUMMARY OF THE INVENTION

Microorganisms and methods for production of C40 carotenoid compounds and compositions containing the C40 carotenoid compounds are provided.

In one aspect, a microorganism is provided that includes a heterologous polynucleotide, including a polynucleotide sequence from *Paracoccus zeaxanthinifaciens*, *Escherichia vulnaris*, or *Pantoea ananatis* that encodes a polypeptide of a C40 carotenoid biosynthetic pathway or including a polynucleotide sequence with at least about 70% sequence identity thereof or including a polynucleotide sequence that encodes a polypeptide including at least about 70% sequence identity to the polypeptide of the C40 carotenoid biosynthetic pathway, operably linked to a promoter for expression of said polynucleotide sequence, wherein the microorganism is a bacterial cell from the class Alphaproteobacteria, and wherein the bacterial cell expresses said heterologous polynucleotide sequence to produce at least one C40 carotenoid compound.

In some embodiments, the microorganism further includes a polynucleotide sequence that expresses the heterologous gene sequence idi from *Escherichia vulneris* or includes a polynucleotide sequence with at least about 70% sequence identity thereof or includes a polynucleotide sequence that encodes a polypeptide comprising at least about 70% sequence identity to the polypeptide encoded by idi from *Escherichia vulneris*.

In another aspect, a microorganism is provided that is derived from a parent microorganism that expresses a native pathway for C30 carotenoid production, wherein at least one gene sequence that encodes an enzyme of the native pathway for C30 carotenoid production has been disrupted or deleted such that C30 carotenoid production is reduced or eliminated in the microorganism in comparison to the parent microorganism from which it is derived, wherein the microorganism is a bacterial cell from the class Alphaproteobacteria.

In some embodiments, the microorganism further comprises a heterologous polynucleotide that encodes a polypeptide of a heterologous C40 carotenoid biosynthetic production pathway, wherein the microorganism expresses the heterologous polynucleotide to produce one or more C40 carotenoid compound.

In another aspect, a microorganism is provided that includes a heterologous polynucleotide containing a polynucleotide sequence that includes the gene sequence crtW from *Fulvimarina pelagi* or includes a polynucleotide sequence with at least about 70% sequence identity thereof or includes a polynucleotide sequence that encodes a polypeptide including at least about 70% sequence identity to the polypeptide encoded by crtW from *Fulvimarina pelagi*, operably linked to a promoter for expression of the polynucleotide sequence, wherein the microorganism is a Gram-negative bacterial cell, and wherein the bacterial cell expresses the heterologous polynucleotide to produce at least one C40 carotenoid compound.

In some embodiments, the microorganism further includes heterologous polynucleotide sequences that include the gene sequences crtY, crtI, and crtB from *Fulvimarina pelagi* or include polynucleotide sequences with at least about 70% sequence identity thereof or include polynucleotide sequences that encode polypeptides comprising at least about 75% sequence identity to the polypeptides encoded by crtY, crtI, and crtB from *Fulvimarina pelagi*.

In some embodiments, the microorganism includes the gene sequences crtW and crtZ from *Fulvimarina pelagi* or includes polynucleotide sequences with at least about 70% sequence identity thereof or includes polynucleotide sequences that encode polypeptides that include at least about 70% sequence identity to the polypeptides encoded by crtW and crtZ from *Fulvimarina pelagi*.

In some embodiments, the Gram-negative bacterial cell is from the phylum Proteobacteria. In some embodiments, the Gram-negative bacterial cell is from the class Alphaproteobacteria.

In some embodiments, a microorganism as disclosed herein expresses a heterologous polynucleotide to produce at least one C40 carotenoid compound selected from astaxanthin, canthaxanthin, zeaxanthin, phoenicoxanthin, adonixanthin, 3-hydroxyechinenone, echinenone, β-carotene, and lycopene.

In some embodiments, a microorganism as disclosed herein includes at least one heterologous polynucleotide including polynucleotide sequences that include the gene sequences crtZ, crtY, crtI, crtB, and crtE from *Paracoccus zeaxanthinifaciens, Escherichia vulneris*, and/or *Pantoea ananatis* or including polynucleotide sequences with at least about 70% sequence identity thereof or including polynucleotide sequences that that encode polypeptides comprising at least about 70% identity to the polypeptides encoded by crtZ, crtY, crtI, crtB, and crtE from *Paracoccus zeaxanthinifaciens, Escherichia vulneris*, and/or *Pantoea ananatis*, operably linked to a promoter for expression of said polynucleotide sequences, wherein the microorganism produces zeaxanthin.

In some embodiments, a microorganism as disclosed herein includes at least one heterologous polynucleotide including polynucleotide sequences that include the gene sequence crtW from *Fulvimarina pelagi* or including a polynucleotide sequence with at least about 70% sequence identity thereof or including a polynucleotide sequence that encodes a polypeptide comprising at least about 70% sequence identity to the polypeptide encoded by crtW from *Fulvimarina pelagi*, wherein the microorganism produces astaxanthin.

In some embodiments, a microorganism as disclosed herein includes at least one heterologous polynucleotide including polynucleotide sequences that include the gene sequences crtY, crtI, crtB, and crtE from *Paracoccus zeaxanthinifaciens, Escherichia vulneris*, and/or *Pantoea ananatis* or including polynucleotide sequences with at least about 70% sequence identity thereof or including polynucleotide sequences that encode polypeptides include at least about 70% identity to the polypeptides encoded by crtY, crtI, crtB, and crtE from *Paracoccus zeaxanthinifaciens, Escherichia vulnearis*, and/or *Pantoea ananatis*, operably linked to a promoter for expression of said polynucleotide sequences, wherein the microorganism produces β-carotene.

In some embodiments, a microorganism as disclosed herein includes a heterologous sequence that includes the gene sequence crtW from *Fulvimarina pelagi* or includes a polynucleotide sequence with at least about 70% sequence identity thereof or includes a polynucleotide sequence that encodes a polypeptide including at least about 70% sequence identity to the polypeptide encoded by crtW from *Fulvimarina pelagi*, wherein the microorganism produces canthaxanthin.

In another aspect, a microorganism is provided that includes a heterologous polynucleotide including a polynucleotide sequence from *Sphingomonas astaxanthinifaciens, Siansivirga zeaxanthinifaciens*, or *Mesoflavibacter zeaxanthinifaciens* that encodes a polypeptide of a C40 carotenoid biosynthetic pathway or including a polynucleotide sequence with at least about 70% sequence identity thereof or including a polynucleotide sequence that encodes a polypeptide including at least about 70% sequence identity to the polypeptide of the C40 carotenoid biosynthetic pathway, operably linked to a promoter for expression of the polynucleotide sequence, wherein the microorganism expresses the heterologous polynucleotide sequence to produce at least one C40 carotenoid compound.

In some embodiments, the microorganism is a bacterial cell. In some embodiments, the bacterial cell is from the phylum Proteobacteria. In some embodiments, the bacterial cell is from the class Alphaproteobacteria.

In some embodiment, the microorganism comprising a heterologous polynucleotide including polynucleotide sequences that encode the gene sequences crtZ, crtY, crtI, and crtB from *Siansivirga zeaxanthinifaciens*, and/or *Mesoflavibacter zeaxanthinifaciens* or including polynucleotide sequences with at least about 70% sequence identity thereof or including polynucleotide sequences that encode polypeptides including at least about 70% sequence identity to the polypeptides encoded by crtZ, crtY, crtI, and crtB from *Siansivirga zeaxanthinifaciens* and/or *Mesoflavibacter zeaxanthinifaciens*, wherein the microorganism produces astaxanthin, canthaxanthin, zeaxanthin, lycopene, beta-carotene or intermediates of these C40 carotenoids.

In some embodiment, the microorganism includes a heterologous polynucleotide including polynucleotide sequences that encode the gene sequences crtZ, crtY, crtI, crtB, and crtW from *Sphingomonas astaxanthinifaciens* or including polynucleotide sequences with at least about 70% sequence identity thereof or including polynucleotide sequences that encodes polypeptides comprising at least about 70% identity to the polypeptides encoded by crtZ, crtY, crtI, crtB, and crtW from *Sphingomonas astaxanthinifaciens*, wherein the microorganism produces astaxanthin, canthaxanthin, zeaxanthin, lycopene, beta-carotene or intermediates of these C40 carotenoids.

In some embodiments, a microorganism as disclosed herein is capable of producing at least one C40 carotenoid compound utilizing at least one C1 carbon sources, such as, but not limited to, methanol, methane, methylamine, and/or formate. In some embodiments, a microorganism as disclosed herein is capable of producing at least one C40 carotenoid compound utilizing at least one C2 carbon source, such as, but not limited to, ethanol, ethylamine, ethylene glycol, and/or acetate. In some embodiments, a microorganism as disclosed herein is capable of producing at least one C40 carotenoid compound utilizing a combination of C1 and C2 carbon sources. In some embodiment, a microorganism as disclosed herein is capable of producing at least one C40 carotenoid compound utilizing at least one C1 and/or C2 alcohol, such as, but not limited to, methanol and/or ethanol.

In some embodiments, a microorganism as disclosed herein is capable of producing at least one C40 carotenoid compound utilizing one or more process streams of fermentation to produce a bioproduct of interest, such as an alcohol or a biofuel, for example, ethanol fermentation and/or distillation, such as beer, wet stillage, thin stillage, and/or thin stillage syrup as a carbon source or media component for growth. In some embodiments, a microorganism as disclosed herein is capable of producing at least one C40 carotenoid compound utilizing one of more process streams of ethanol fermentation and/or distillation, in combination with additional C1 and/or C2 carbon sources, such as, but not limited to, methanol, ethanol, methane, methylamine, formate, ethylamine, ethylene glycol, and/or acetate. In some embodiments, a microorganism as disclosed herein is capable of producing at least one C40 carotenoid compound utilizing ethanol beer resulting from fermentation of plant biomass, and one or more alcohols, such as, but not limited to, methanol and/or ethanol. In some embodiments, a microorganism as disclosed herein is capable of producing at least one C40 carotenoid compound utilizing wet stillage resulting from distillation following fermentation of plant biomass, and one or more alcohols, such as, but not limited to, methanol and/or ethanol. In some embodiments, a microorganism as disclosed herein is capable of producing at least one C40 carotenoid compound utilizing thin stillage resulting from distillation following fermentation of plant biomass, and one or more alcohols, such as, but not limited to, methanol and/or ethanol. In some embodiments, a microorganism as disclosed herein is capable of producing at least one C40 carotenoid compound utilizing thin stillage syrup resulting from distillation following fermentation of plant biomass, and one or more alcohols, such as, but not limited to methanol and/or ethanol.

In some embodiments, a microorganism as disclosed herein is a bacterial cell in the genus *Methylobacteria*, such as, but not limited to, a *Methylobacterium extorquens* cell.

In another aspect, a method is provided for producing biomass that includes at least one C40 carotenoid compound, including culturing a microorganism as disclosed herein that includes a heterologous polynucleotide for C40 carotenoid in a culture medium under conditions suitable for growth of the bacterial cell or microorganism and production of the C40 carotenoid compound, wherein biomass including the C40 carotenoid compound is produced in the culture.

In some embodiments, the method includes utilizing at least one C1 compound and/or at least one C2 compound as carbon source(s) for the microorganism culture. In some embodiments, the method includes utilizing at least one C1 and/or C2 alcohol as carbon source(s) for the microorganism culture.

In some embodiments, the method includes utilizing at least one process stream of a fermentation to produce a bioproduct of interest, such as an alcohol or a biofuel, e.g., ethanol fermentation and/or distillation as carbon source(s) for the microorganism culture. In some embodiments, the method includes utilizing at least one process stream of ethanol fermentation and/or distillation as carbon source(s), in combination with at least one C1 and/or C2 compound as carbon source(s) for the microorganism culture. In some embodiments, the method includes utilizing at least one process stream of ethanol fermentation and/or distillation as carbon source(s), in combination with at least one C1 and/or C2 alcohol as carbon source(s) for the microorganism culture.

In some embodiments, the microorganism is in the genus *Methylobacteria*, such as, but not limited to, *Methylobacterium extorquens*.

In another aspect, biomass that includes at least one C40 carotenoid compound is provided, wherein the biomass is produced according to a method as described herein for producing biomass in a microorganism that includes a heterologous polynucleotide for C40 carotenoid production.

In another aspect, a feed or nutritional supplement composition is provided that includes biomass produced according to a method as described herein for producing biomass in a microorganism that includes a heterologous polynucleotide for C40 carotenoid production.

In another aspect, a method is provided for producing biomass in a microorganism that is derived from a parent microorganism that expresses a native pathway for C30 carotenoid production, wherein at least one gene sequence that encodes an enzyme of the native pathway for C30 carotenoid production has been disrupted or deleted such that C30 carotenoid production is reduced or eliminated in the microorganism in comparison to the parent microorganism from which it is derived, including culturing the microorganism according in a culture medium under conditions suitable for growth of the microorganism, wherein said biomass is produced in the culture.

In some embodiments, the method includes utilizing at least one C1 compound and/or at least one C2 compound as carbon source(s) for the microorganism culture. In some embodiments, the method includes utilizing at least one C1 and/or C2 alcohol as carbon source(s) for the microorganism culture.

In some embodiments, the method includes utilizing at least one process stream of a fermentation to produce a bioproduct of interest, such as an alcohol or a biofuel, e.g., ethanol fermentation and/or distillation as carbon source(s) for the microorganism culture. In some embodiments, the method includes utilizing at least one process stream of ethanol fermentation and/or distillation as carbon source(s), in combination with at least one C1 and/or or C2 compound as carbon source(s) for the microorganism culture. In some embodiments, the method includes utilizing at least one process stream of ethanol fermentation and/or distillation as carbon source(s), in combination with at least one C1 and/or C2 alcohol as carbon source(s) for the microorganism culture.

In some embodiments, the microorganism is in the genus *Methylobacteria*, such as, but not limited to, *Methylobacterium extorquens*.

In another aspect, biomass is provided, wherein the biomass is produced according to a method as described herein for producing biomass in a microorganism that is derived from a parent microorganism that expresses a native pathway for C30 carotenoid production, wherein at least one gene sequence that encodes an enzyme of the native pathway for C30 carotenoid production has been disrupted or deleted such that C30 carotenoid production is reduced or eliminated in the microorganism in comparison to the parent microorganism from which it is derived.

In another aspect, a feed or nutritional supplement composition is provided that includes biomass produced according to a method as described herein for producing biomass in a microorganism that is derived from a parent microorganism that expresses a native pathway for C30 carotenoid production, wherein at least one gene sequence that encodes an enzyme of the native pathway for C30 carotenoid production has been disrupted or deleted such that C30 carotenoid production is reduced or eliminated in the microorganism in comparison to the parent microorganism from which it is derived

DETAILED DESCRIPTION

Figure 1:
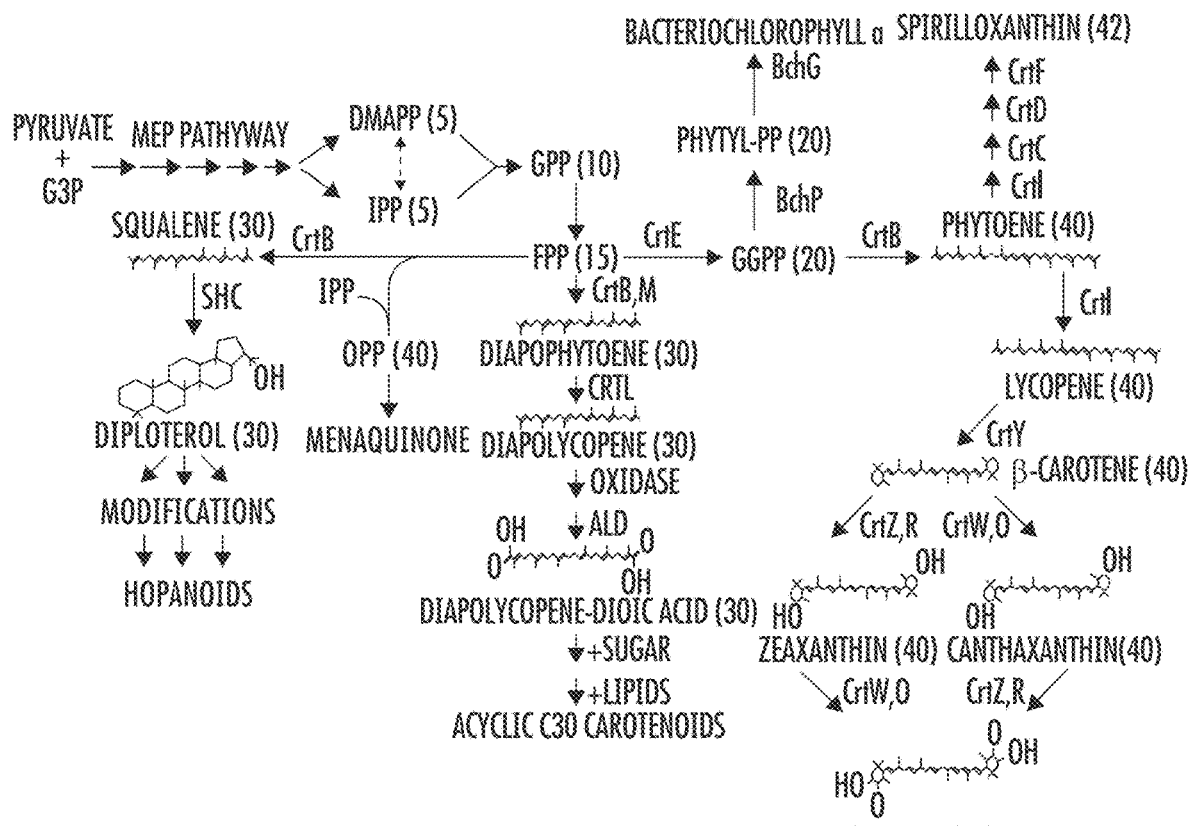
FIG. 1 schematically depicts the carotenoid biosynthetic pathway for production of C30 and C40 carotenoid compounds.

Provided herein are non-naturally occurring microorganisms that are capable of producing C40 carotenoid compound(s), e.g., astaxanthin, canthaxanthin, zeaxanthin, adonixanthin, 3-hydroxyechinenone, echinenone, β-carotene, lycopene, or any combinations thereof.

Also provided are methods of engineering and culturing such microorganisms, methods of using such microorganisms to produce C40 carotenoid compounds, and methods of producing C40 carotenoid-containing compositions, such as feed or nutritional compositions that contain the microorganisms or compositions that contain C40 carotenoid compounds recovered from such organisms.

Also provided herein are non-naturally occurring microorganisms in which C30 carotenoid production has been reduced or eliminated, methods of culturing such microorganisms, and compositions, such as feed or nutritional compositions, that contain the microorganisms.

One aspect pertains to the field of aquaculture. Another aspect is the field of pet foods, for example, for cats and dogs. A further aspect is in the field of human nutrition and supplements. More specifically, aquaculture feeds, pet food, and nutritional supplement compositions are provided that include C40 carotenoid-containing microbial biomass and/or biomass from microorganisms in which C30 carotenoid production has been reduced or eliminated, and a complete protein nutrition, that is, containing most or all amino acids necessary for healthy growth of the animal to which it is administered. The microbial biomass can be blended with other ingredients to form a portion or whole of a feed, or may be consumed directly as a protein-rich powder.

In some embodiments, microorganisms that are capable of being grown on inexpensive C1 and/or C2 feed stocks at an industrial scale that replace the (i) protein and (ii) pigment components are described.

In some embodiments, microorganisms that are capable of being grown on a process stream from a fermentation to produce a bioproduct of interest, such as an alcohol or a biofuel, e.g., inexpensive ethanol fermentation and/or distillation process streams (e.g., one or more of ethanol beer, wet stillage, thin stillage, thin stillage syrup) at an industrial scale that replace the (i) protein and (ii) pigment components are described. In some embodiments, microorganisms that are capable of being grown on ethanol fermentation and/or distillation process streams (e.g., one or more of ethanol beer, wet stillage, thin stillage, thin stillage syrup) in combination with C1 and/or C2 feed stocks at an industrial scale that replace the (i) protein and (ii) pigment components are described.

Definitions

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present invention.

The practice of the present invention will employ, unless otherwise indicated, conventional techniques of molecular biology (including recombinant techniques).

"A," "an" and "the" include plural references unless the context clearly dictates otherwise.

As used herein, the term "polynucleotide" refers to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms "polynucleotide," "nucleic acid," and "oligonucleotide" are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or a substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, a "vector" refers to a polynucleotide sequence designed to introduce nucleic acids into one or more cell types. Vectors include cloning vectors, expression vectors, shuttle vectors, plasmids, phage particles, cassettes and the like.

As used herein, the term "expression" refers to the process by which a polypeptide is produced based on the nucleic acid sequence of a gene. The process includes both transcription and translation.

As used herein, "expression vector" refers to a DNA construct containing a DNA coding sequence (e.g., gene sequence) that is operably linked to one or more suitable control sequence(s) capable of effecting expression of the coding sequence in a host. Such control sequences include a promoter to affect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. The plasmid is the most commonly used form of expression vector. However, the invention is intended to include such other forms of expression vectors that serve equivalent functions and which are, or become, known in the art.

A "promoter" refers to a regulatory sequence that is involved in binding RNA polymerase to initiate transcription of a gene. A promoter may be an inducible promoter or a constitutive promoter. An "inducible promoter" is a promoter that is active under environmental or developmental regulatory conditions.

The term "operably linked" refers to a juxtaposition or arrangement of specified elements that allows them to perform in concert to bring about an effect. For example, a promoter is operably linked to a coding sequence if it controls the transcription of the coding sequence.

"Under transcriptional control" is a term well understood in the art that indicates that transcription of a polynucleotide sequence depends on its being operably linked to an element which contributes to the initiation of, or promotes transcription.

"Under translational control" is a term well understood in the art that indicates a regulatory process which occurs after mRNA has been formed.

A "gene" refers to a DNA segment that is involved in producing a polypeptide and includes regions preceding and following the coding regions as well as intervening sequences (introns) between individual coding segments (exons).

As used herein, the term "host cell" or "parent cell," used interchangeably herein, refers to a cell or cell line into which a recombinant expression vector for production of a polypeptide may be transfected for expression of the polypeptide. Host cells include progeny of a single host cell, and the progeny may not necessarily be completely identical (in morphology or in total genomic DNA complement) to the original parent cell due to natural, accidental, or deliberate mutation. A host cell includes cells transfected or transformed in vivo with an expression vector.

The term "recombinant," refers to genetic material (i.e., nucleic acids, the polypeptides they encode, and vectors and cells comprising such polynucleotides) that has been modified to alter its sequence or expression characteristics, such as by mutating the coding sequence to produce an altered polypeptide, fusing the coding sequence to that of another gene, placing a gene under the control of a different promoter, expressing a gene in a heterologous organism, expressing a gene at a decreased or elevated levels, expressing a gene conditionally or constitutively in manner different from its natural expression profile, and the like. Generally recombinant nucleic acids, polypeptides, and cells based thereon, have been manipulated by man such that they are not identical to related nucleic acids, polypeptides, and cells found in nature.

A "signal sequence" refers to a sequence of amino acids bound to the N-terminal portion of a protein which facilitates the secretion of the mature form of the protein from the cell. The mature form of the extracellular protein lacks the signal sequence which is cleaved off during the secretion process.

The term "selective marker" or "selectable marker" refers to a gene capable of expression in a host cell that allows for ease of selection of those hosts containing an introduced nucleic acid or vector. Examples of selectable markers include but are not limited to antimicrobial substances (e.g., hygromycin, bleomycin, or chloramphenicol) and/or genes that confer a metabolic advantage, such as a nutritional advantage, on the host cell.

The term "derived from" encompasses the terms "originated from," "obtained from," "obtainable from," "isolated from," and "created from," and generally indicates that one specified material finds its origin in another specified material or has features that can be described with reference to another specified material.

The term "culturing" refers to growing a population of cells, e.g., microbial cells, under suitable conditions for growth, in a liquid or solid medium.

The term "heterologous" or "exogenous," with reference to a polynucleotide or protein, refers to a polynucleotide or protein that does not naturally occur in a specified cell, e.g., a host cell. It is intended that the term encompass proteins that are encoded by naturally occurring genes, mutated genes, and/or synthetic genes. In contrast, the term "homologous," with reference to a polynucleotide or protein, refers to a polynucleotide or protein that occurs naturally in the cell.

The term "introduced," in the context of inserting a nucleic acid sequence into a cell, includes "transfection," "transformation," or "transduction" and refers to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed.

"Transfection" or "transformation" refers to the insertion of an exogenous polynucleotide into a host cell. The exogenous polynucleotide may be maintained as a non-integrated vector, for example, a plasmid, or alternatively, may be integrated into the host cell genome. The term "transfecting" or "transfection" is intended to encompass all conventional techniques for introducing nucleic acid into host cells. Examples of transfection techniques include, but are not limited to, calcium phosphate precipitation, DEAE-dextran-mediated transfection, lipofection, electroporation, and microinjection.

As used herein, the terms "transformed," "stably transformed," and "transgenic" refer to a cell that has a non-native (e.g., heterologous) nucleic acid sequence integrated into its genome or as an episomal plasmid that is maintained through multiple generations.

The terms "recovered," "isolated," "purified," and "separated" as used herein refer to a material (e.g., a protein, nucleic acid, or cell) that is removed from at least one component with which it is naturally associated. For example, these terms may refer to a material which is substantially or essentially free from components which normally accompany it as found in its native state, such as, for example, an intact biological system.

A "signal sequence" (also termed "presequence," "signal peptide," "leader sequence," or "leader peptide") refers to a sequence of amino acids at the amino terminus of a nascent polypeptide that targets the polypeptide to the secretory pathway and is cleaved from the nascent polypeptide once it is translocated in the endoplasmic reticulum membrane.

Related (and derivative) proteins encompass "variant" proteins. Variant proteins differ from a parent protein and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively, or additionally, variants may have a specified degree of sequence identity with a reference protein or nucleic acid, e.g., as determined using a sequence alignment tool, such as BLAST, ALIGN, and CLUSTAL (see, infra). For example, variant proteins or nucleic acid may have at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence.

As used herein, the term "analogous sequence" refers to a polypeptide sequence within a protein that provides a similar function, tertiary structure, and/or conserved residues with respect to a reference protein. For example, in epitope regions that contain an alpha helix or a beta sheet structure, replacement amino acid(s) in an analogous sequence maintain the same structural element. In some embodiments, analogous sequences are provided that result in a variant enzyme exhibiting a similar or improved function with respect to the parent protein from which the variant is derived.

As used herein, "homologous protein" refers to a protein that has similar function and/or structure as a reference protein. Homologs may be from evolutionarily related or unrelated species. In some embodiments, a homolog has a quaternary, tertiary and/or primary structure similar to that of a reference protein, thereby potentially allowing for replacement of a segment or fragment in the reference protein with an analogous segment or fragment from the homolog, with reduced disruptiveness of structure and/or function of the reference protein in comparison with replacement of the segment or fragment with a sequence from a non-homologous protein.

As used herein, "wild-type," "native," and "naturally-occurring" proteins are those found in nature. The terms "wild-type sequence" refers to an amino acid or nucleic acid sequence that is found in nature or naturally occurring. In some embodiments, a wild-type sequence is the starting point of a protein engineering project, for example, production of variant proteins.

The phrases "substantially similar" and "substantially identical" in the context of at least two nucleic acids or polypeptides typically means that a polynucleotide, polypeptide, or region or domain of a polypeptide that comprises a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) polynucleotide, polypeptide, or region or domain of a polypeptide. A region or domain of a polypeptide may contain, for example, at least about 20, 50, 100, or 200 amino acids within a longer polypeptide sequence. Sequence identity may be determined using known programs such as BLAST, ALIGN, and CLUSTAL using standard parameters. (See, e.g., Altshul, et al. (1990) *J. Mol. Biol.* 215:403-410; Henikoff, et al. (1989) *Proc. Natl. Acad. Sci.* 89:10915; Karin, et al. (1993) *Proc. Natl. Acad. Sci.* 90:5873; and Higgins, et al. (1988) *Gene* 73:237). Software for performing BLAST analyses is publicly available through the National Center for Biotechnology Information. Also, databases may be searched using FASTA (Pearson, et al. (1988) *Proc. Natl. Acad. Sci.* 85:2444-2448.) In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

The term "carotenoid" is understood in the art to refer to a structurally diverse class of pigments derived from isoprenoid pathway intermediates. The commitment step in carotenoid biosynthesis is the formation of phytoene from geranylgeranyl pyrophosphate. Carotenoids can be acyclic or cyclic, and may or may not contain oxygen, so that the term carotenoids include both carotenes and xanthophylls. In general, carotenoids are hydrocarbon compounds having a conjugated polyene carbon skeleton formally derived from the five-carbon compound IPP, including triterpenes ($C_{30}$ diapocarotenoids) and tetraterpenes ($C_{40}$ carotenoids) as well as their oxygenated derivatives and other compounds that are, for example, $C_{35}$, $C_{50}$, $C_{60}$, $C_{70}$, $C_{80}$ in length or other lengths. Many carotenoids have strong light absorbing properties and may range in length in excess of $C_{80}$-$C_{100}$ [See Sliwka et al. (2012) Acta ABP Biochimica Polonica 59:1 p 17-20; Zeeshan et al. (2012) Organic Letters 14:21 p 5496-5498]. Diapocarotenoids typically consist of six isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes. $C_{40}$ carotenoids typically consist of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{40}$ carotenoids may be formally derived from the acyclic $C_{40}H_{56}$ structure, having a long central chain of conjugated double bonds, by (i) hydrogenation, (ii) dehydrogenation, (iii) cyclization, (iv) oxidation, (v) esterification/glycosylation, or any combination of these processes. The class of $C_{40}$ carotenoids also includes certain compounds that arise from rearrangements of the carbon skeleton, or by the (formal) removal of part of this structure. More than 600 different carotenoids have been identified in nature. Carotenoids include but are not limited to: antheraxanthin, adonirubin, adonixanthin, astaxanthin, canthaxanthin, capsorubin, β-cryptoxanthin, α-carotene, β-carotene, β,ψ-carotene, δ-carotene, ε-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, and C30 carotenoids. Additionally, carotenoid compounds include derivatives of these molecules, which may include hydroxy-, methoxy-, oxo-, epoxy-, carboxy-, or aldehydic functional groups. Further, included carotenoid compounds include ester (e.g., glycoside ester, fatty acid ester) and sulfate derivatives (e.g., esterified xanthophylls).

The "isoprenoid pathway" is understood in the art to refer to a metabolic pathway that either produces or utilizes the five-carbon metabolite isopentyl pyrophosphate (IPP). As discussed herein, two different pathways can produce the common isoprenoid precursor IPP—the "mevalonate pathway" and the "non-mevalonate pathway." The term "isoprenoid pathway" is sufficiently general to encompass both types of pathway. Biosynthesis of isoprenoids from IPP occurs by polymerization of several five-carbon isoprene subunits. Isoprenoid metabolites derived from IPP vary greatly in chemical structure, including both cyclic and acyclic molecules. Isoprenoid metabolites include, but are not limited to, monoterpenes, sesquiterpenes, diterpenes, sterols, and polyprenols such as carotenoids.

The term "isoprenoid compound" refers to any compound which is derived via the pathway beginning with isopentenyl pyrophosphate (IPP) and formed by the head-to-tail condensation of isoprene units which may be of 5, 10, 15, 20, 30 or 40 carbons in length. There term "isoprenoid pigment" refers to a class of isoprenoid compounds which typically have strong light absorbing properties.

The term "feed premix" refers to the crude mixture of aquaculture feed or animal/pet food components prior to processing, optionally at high temperature, into an aquaculture feed or animal or pet food composition that is in the form of pellets or flakes.

An aquaculture feed composition is used in the production of an "aquaculture product," wherein the product is a harvestable aquacultured species (e.g., finfish, crustaceans), which is often sold for human consumption. For example, salmon are intensively produced in aquaculture and thus are aquaculture products. Aquaculture compositions may also be used as feed for aquaculture feed organisms such as small fish like krill, rotifers, and the like, that are food sources for larger aquaculture organisms such as carnivorous fish. In addition, aquaculture compositions described herein can be used as feed for ornamental fish, shrimp, hobbyist aquaculture, and the like, that are not intended as food for other organisms.

The term "aquaculture meat product" refers to food products intended for human consumption comprising at least a portion of meat from an aquaculture product as defined above. An aquaculture meat product may be, for example, a whole fish or a filet cut from a fish, each of which may be consumed as food. In some embodiments, such a product can be referred to as a fish or seafood product.

The term "biomass" refers to microbial cellular material. Biomass may be produced naturally, or may be produced from the fermentation of a native host or a recombinant production host. The biomass may be in the form of whole cells, whole cell lysates, homogenized cells, partially hydrolyzed cellular material, and/or partially purified cellular material.

The term "processed biomass" refers to biomass that has been subjected to additional processing such as drying, pasteurization, disruption, etc., each of which is discussed in greater detail below.

The term "C1 carbon substrate" refers to any carbon-containing molecule that lacks a carbon-carbon bond. Examples are methane, methanol, formaldehyde, formic acid, formate, methylated amines (e.g., mono-, di-, and tri-methyl amine), methylated thiols, and carbon dioxide.

The term "C1 metabolizer" refers to a microorganism that has the ability to use a single carbon substrate as a sole source of energy and biomass. C1 metabolizers include methylotrophs and/or methanotrophs capable of growth on a single carbon substrate.

The term "C2 carbon substrate" refers to any carbon-containing molecule that contain two linked carbon molecules. Examples include ethanol, ethylamine, acetate, acetic acid, acetaldehyde, ethylene glycol, and ethanethiol. Diethylamine and triethylamine can also be considered C2 carbon substrates.

The term "methylotroph" means an organism capable of oxidizing organic compounds which do not contain carbon-carbon bonds. Where the methylotroph is able to oxidize $CH_4$, the methylotroph is also a methanotroph.

The term "methanotroph" means a prokaryote capable of utilizing methane as a substrate. Complete oxidation of methane to carbon dioxide occurs by aerobic degradation pathways. Examples of methanotrophs include, but are not limited to, the genera *Methylomonas, Methylobacter, Methylococcus*, and *Methylosinus*.

The term "high growth methanotrophic bacterial strain" refers to a bacterium capable of growth using methane as its sole carbon and energy source.

The term "Gram-negative bacteria" are bacteria that do not retain the crystal violet stain used in the Gram staining method of bacterial differentiation. They are characterized by their cell envelopes, which are composed of a thin peptidoglycan cell wall sandwiched between an inner cytoplasmic cell membrane and a bacterial outer membrane. In contrast, Gram-positive bacteria such as most bacteria in the phyla Actinobacteria or Firmicutes retain crystal violet due to their relatively thicker peptidoglycan cell wall layer. In general, Gram-positive bacteria are monoderms and have a single lipid bilayer whereas Gram-negative bacteria are diderms and have two lipid bilayers. As used here "Gram-negative bacteria" refers to all bacteria except those in the phyla Actinobacteria, Firmicutes, or Tenericutes. Examples of Gram-negative phyla include Proteobacteria, Aquificae, Bacteroidetes, Chlamydiae, Chlorobi, Cyanobacteria, Deinococcus-Thermus, Fibrobacteres, Fusobacteria, Gemmatimonadetes, Nitrospirae, Planctomycetes, Spirochaetes, Synergistetes, and Verrucomicrobia.

The term "process stream" (e.g., "ethanol fermentation and/or distillation process stream") refers to the products or waste effluents generated during the fermentation of sugars extracted from biomass to a bioproduct of interest, e.g., ethanol, distillation to remove and concentrate the bioproduct (e.g., ethanol), or the solid separation and drying of the resulting residuals. Examples include beer (e.g., ethanol beer), an alcohol (e.g., ethanol), whole stillage, wet cake or wet distiller grains (WDG), thin stillage, thin stillage syrup or condensed distiller solubles (CDS), wet distillers grains with solubles (WDGS), and dried distiller grains with solubles (DDGS).

The term "ethanol beer" refers to the result of fermentation of biomass containing sugars into a liquid containing an increased content of ethanol.

The term "whole stillage" refers to the residuals or left-overs from distillation of "ethanol beer" to remove and concentrate the ethanol.

The term "wet cake" or "wet distiller grains" or "WDG" refers to the solid component of "whole stillage" that is separated by centrifugation.

The term "thin stillage" refers to the liquid component of "whole stillage" that is separated from the solid "wet cake" or "wet distiller grains" by centrifugation.

The term "thin stillage syrup" or "syrup" or "condensed distiller solids" or "CDS" refers to concentrated "thin stillage" where liquid (e.g., water) has been removed.

The term "wet distiller grains with solubles" or "WDGS" refers to a combination of "thin stillage syrup" with "wet distiller grains"

The term "dried distiller grains with solids" or "DDGS" refers to "wet distiller grains with solubles" that have been further dried.

Microorganisms

Non-naturally occurring microorganisms are provided for the production of C40 carotenoid compound(s) and/or for reduced or eliminated production of C30 carotenoid compound(s). In some embodiments, non-naturally occurring, e.g., recombinant, microorganisms herein include, e.g., bacteria, yeast, Archaea, that have been engineered to express at least one (i.e., one or more) enzyme(s) for biosynthesis of one or more C40 carotenoid compound(s) and that produce the C40 carotenoid compound(s) when cultured under conditions suitable for microbial growth and carotenoid production.

Non-naturally occurring microorganisms as described herein include one or more exogenous polynucleotide(s) that encode and express one or more enzyme or enzyme activity for biosynthesis of C40 carotenoid compound(s). The exogenous polynucleotide(s) may include one or more coding sequence for one or more enzyme or enzyme activity for biosynthesis of C40 carotenoid compound(s), operably linked to one or more promoter for expression in the non-naturally occurring microorganism. Such promoters may include, but are not limited to PR and PmxaF. In some embodiments, the polynucleotide(s) are codon optimized for expression in the microorganism.

In some embodiments, the non-naturally occurring microorganism includes one or more exogenous polynucleotide(s) that encodes one or more enzymes or enzyme activities for C40 carotenoid biosynthesis, as described herein, that has been modified for improved stability and/or activity relative to the stability and/or activity of the enzyme or enzyme activity in the host cell from which it is derived or relative to the wild-type stability and/or activity of the enzyme or enzyme activity. For example, the non-naturally occurring microorganism may express a variant of an enzyme of C40 carotenoid biosynthesis that has greater stability and/or activity than the wild-type enzyme from which it is derived.

In some embodiments, the host cell from which a non-naturally occurring microorganism as described herein is derived produces one or more C30 carotenoid compound(s). In some embodiments, the non-naturally occurring microorganism includes deletion or inactivation of one or more gene(s) that encode enzyme(s) of C30 carotenoid biosynthesis. In some embodiments, the host cell is *Methylobacterium extorquens* and the non-naturally occurring microorganism derived from the host cell includes deletion or modification of one or more gene(s) that encode squalene synthase, diapophytoene synthase, diapophytoene desaturase, C30 carotenoid oxidase, glycosyl transferase, or phospholipid glycerol acetyltransferase in the host cell. In some embodiments, a deletion or replacement of the region encompassing Mext_3434 to Mext_3441 in *M. extorquens* PA1 removes the C30 carotenoid oxidase, diaphophytoene desaturase, glycosyl transferase, and phospholipid glyercol acetyltransferase, resulting in complete blockage of C30 carotenoid production.

In certain embodiments, the host cell comprises one or more endogenous gene(s) in the described pathway, and the exogenous gene(s) that are added complement the endogenous pathway for production of C40 carotenoid compound(s).

Microorganisms herein may be bacterial or fungal. In some embodiments, the microorganism is a bacterial microorganism from the phylum Proteobacteria. In some embodiments, the microorganism is a bacterial microorganism from the class Alphaproteobacteria. In some embodiments, the microorganism is a Gram-negative bacterium.

Non-limiting examples of genera from which the non-naturally occurring microorganism may be derived include *Methylobacterium, Methylomonas, Methylobacter. Methylococcus, Methylosinus, Methylocyctis, Methylomicrobium, Methylophilus, Methylobacillus, Hyphomicrobium, Xanthobacter, Bacillus, Paracoccus, Nocardia, Arthrobacter, Rhodopseudomonas, Pseudomonas, Candida, Hansenula, Pichia, Torulopsis, Rhodotorula, Escherichia,* and *Saccharomyces*. Non-limiting examples of microbial species from which the non-naturally occurring microorganism may be derived include *Methylobacterium extorquens* (e.g., strains AM1, DM4, DSMZ1340, CM4, PA1, or BJ001 (formerly *Methylobacterium populi*)), *Methylobacterium radiotolerans, Methylobacterium nodulans, Methylobacterium* spp. 4-46, and *Escherichia coli*.

In some embodiments, the non-naturally occurring microorganism is a methylotrophic bacterium.

In various embodiments, genes of C40 carotenoid biosynthesis may be incorporated into a host microorganism for production of C40 carotenoid(s). For example, one or more of the gene(s) crtZ, crtY, crtI, crtB, crtE, idi, and crtW, or polynucleotides that encode polypeptides with functionally equivalent activities thereof may be introduced (e.g., transformed) into a host cell, thereby producing a cell that produces C40 carotenoid compound(s). Introduction of different subsets of these genes or functional equivalents thereof will result in production of different predominant C40 carotenoid compound(s). For example, expression of crtZYIBE will produce zeaxanthin. Expression of crtYIBE will produce β-carotene. Expression of crtIBE will produce lycopene. Expression of crtYIBEW will produce canthaxanthin and/or echinenone. Expression of crtZYIBEW will produce astaxanthin. Expression of crtZYIBW of *S. astaxanthinifaciens* will produce astaxanthin in a strain that expresses a native or heterologous crtE on a plasmid or second integration site. Expression of crtZYIB of *S. zeaxanthinifaciens* or *M. zeaxanthinifaciens* will produce zeaxanthin in a strain that expresses native of heterologous crtE on a plasmid or second integration site. Expression of crtYIB and crtWZ from *F. pelagi* will produce astaxanthin in a strain that expresses a native or heterologous crtE on a plasmid or second integration site. The gene or functional equivalents thereof that are introduced into a host microorganism may be derived from the same or different microorganism species or strain.

In some embodiments, the host microorganism may be a non-naturally occurring microorganism that has been engineered to reduce or eliminate native C30 carotenoid production, which may, in some embodiments, increase flux to C40 carotenoid compound(s).

In some embodiments, the gene idi or a polynucleotide that encodes a polypeptide with functionally equivalent isopentenyl-diphosphate delta-isomerase activity may be incorporated, which may increase carotenoid biosynthesis, in comparison with an identical cell that does not include or express the idi gene or functional equivalent thereof.

In one embodiment, the non-naturally occurring microorganism includes at least one heterologous polynucleotide that encodes one or more polypeptide encoded by the gene(s) crtZ, crtY, crtI, crtB, and/or crtE of *Paracoccus zeaxanthinifaciens* or *Pantoea ananatis*, e.g., *P. ananatis* ATCC 19321, or crtZ, crtY, crtI, crtB, crtE, and/or idi of *Escherichia vulneris*, or one or more polypeptide having at least about 70%, 75%, 80%, 85%, 90%, 95%, 98%, or 99% amino acid sequence identity to the polypeptide(s) encoded by crtZ, crtY, crtI, crtB, and/or crtE of *Paracoccus zeaxanthinifaciens* or *Pantoea ananatis*, e.g., *P. ananatis* ATCC 19321, or crtZ, crtY, crtI, crtB, crtE, and/or idi of *Escherichia vulneris*, and retaining the functional activity thereof for production of C40 carotenoid compound(s). In some embodiments, the heterologous polynucleotide(s) includes one or more polynucleotide sequence(s) having at least about 70%, 75%, 80%, 85%, 90%, 95%, 98%, or 99% nucleotide sequence identity to the gene sequence(s) crtZ, crtY, crtI, crtB, and/or crtE of *Paracoccus zeaxanthinifaciens* or *Pantoea ananatis*, e.g., *P. ananatis* ATCC 19321, or crtZ, crtY, crtI, crtB, crtE, and/or idi of *Escherichia vulneris*. In some embodiments, the microorganism is a bacterial microorganism. In some examples, the bacterial microorganism may be from the class Alphaproteobacteria. In one example, the bacterial microorganism is from the genus *Methylobacterium*, for example, *Methylobacterium extorquens*. In some embodiments, the coding sequences of the heterologous polynucleotide(s) are codon optimized for expression in the microorganism, for example, codon optimized for expression in *Methylobacterium extorquens*.

In one embodiment, the microorganism includes and expresses heterologous crtZYIBE from *Paracoccus zeaxanthinifaciens, Pantoea ananatis*, e.g., *P. ananatis* ATCC 19321, and/or *Escherichia vulneris*, or polypeptides having at least about 70%, 75%, 80%, 85%, 90%, 95%, 98%, or 99% sequence identity thereof and retaining the functional activity thereof, and the microorganism produces zeaxanthin. In some embodiments, the microorganism further includes and expresses a heterologous polynucleotide that encodes a crtW gene, for example the crtW gene from *Fulvimarina pelagi*, or a polypeptide having at least about 70%, 75%, 80%, 85%, 90%, 95%, 98%, or 99% identity to the polypeptide encoded by crtW of *Fulvimarina pelagi* and retaining the functional activity thereof for production of C40 carotenoid compound(s), or having a polynucleotide sequence having at least about 70% sequence identity with the polynucleotide sequence of crtW of *Fulvimarina pelagi*, and the microorganism produces astaxanthin. In some embodiments, the microorganism further includes and expresses a heterologous polynucleotide that encodes a idi gene, for example, the idi gene from *Escherichia vulneris*, or a polypeptide having at least about 70% identity to the polypeptide encoded by idi of *Escherichia vulneris* and retaining the functional activity thereof for production of C40 carotenoid compound(s), or having a polynucleotide sequence having at least about 70%, 75%, 80%, 85%, 90%, 95%, 98%, or 99% sequence identity with the polynucleotide sequence of idi of *Escherichia vulneris*, and the microorganism produces a greater amount of C40 carotenoid compound(s) than an identical microorganism that does not include the idi gene or functional equivalent thereof.

In one embodiment, the microorganism includes and expresses heterologous crtYIBE from *Paracoccus zeaxanthinifaciens, Pantoea ananatis*, e.g., *P. ananatis* ATCC 19321, and/or *Escherichia vulneris*, or polypeptides having at least about 70%, 75%, 80%, 85%, 90%, 95%, 98%, or 99% sequence identity thereof and retaining the functional activity thereof, and the microorganism produces β-carotene. In some embodiments, the microorganism further includes a heterologous polynucleotide that encodes a crtW gene, for example the crtW gene from *Fulvimarina pelagi*, or a polypeptide having at least about 70%, 75%, 80%, 85%, 90%, 95%, 98%, or 99% identity to the polypeptide encoded by crtW of *Fulvimarina pelagi* and retaining the functional activity thereof for production of C40 carotenoid compound(s), or having a polynucleotide sequence having at least about 70%, 75%, 80%, 85%, 90%, 95%, 98%, or 99% sequence identity with the polynucleotide sequence of crtW of *Fulvimarina pelagi*, and the microorganism produces canthaxanthin and/or echinenone. In some embodiments, the microorganism further includes and expresses a heterologous polynucleotide that encodes a idi gene, for example, the idi gene from *Escherichia vulneris*, or a polypeptide having at least about 70%, 75%, 80%, 85%, 90%, 95%, 98%, or 99% identity to the polypeptide encoded by idi of *Escherichia vulneris* and retaining the functional activity thereof for production of C40 carotenoid compound(s), or having a polynucleotide sequence having at least about 70%, 75%, 80%, 85%, 90%, 95%, 98%, or 99% sequence identity with the polynucleotide sequence of idi of *Escherichia vulneris*, and the microorganism produces a greater amount of C40 carotenoid compound(s) than an identical microorganism that does not include the idi gene or functional equivalent thereof.

In one embodiment, the microorganism includes and expresses heterologous crtIBE from *Paracoccus zeaxanthinifaciens, Pantoea ananatis*, e.g., *P. ananatis* ATCC 19321, and/or *Escherichia vulneris*, or polypeptides having at least about 70%, 75%, 80%, 85%, 90%, 95%, 98%, or 99% sequence identity thereof and retaining the functional activity thereof, and the microorganism produces lycopene. In some embodiments, the microorganism further includes and expresses a heterologous polynucleotide that encodes a idi gene, for example, the idi gene from *Escherichia vulneris*, or a polypeptide having at least about 70% identity to the polypeptide encoded by idi of *Escherichia vulneris* and retaining the functional activity thereof for production of C40 carotenoid compound(s), or having a polynucleotide sequence having at least about 70%, 75%, 80%, 85%, 90%, 95%, 98%, or 99% sequence identity with the polynucleotide sequence of idi of *Escherichia vulneris*, and the microorganism produces a greater amount of C40 carotenoid compound(s) than an identical microorganism that does not include the idi gene or functional equivalent thereof.

In one embodiment, the non-naturally occurring microorganism includes at least one heterologous polynucleotide that encodes the polypeptides encoded by the gene(s) crtYIB and crtWZ of *Fulvimarina pelagi*, or polypeptides having at least about 75%, 80%, 85%, 90%, 95%, 98%, or 99% amino acid sequence identity to the polypeptides encoded by crtYIB and crtWZ of *Fulvimarina pelagi*, and retaining the functional activities thereof for production of C40 carotenoid compound(s), and the microorganism produces astaxanthin, canthaxanthin, zeaxanthin, lycopene, or beta-carotene or intermediates of these C40 carotenoids. In some embodiments, the heterologous polynucleotide(s) includes polynucleotide sequences having at least about 70%, 75%, 80%, 85%, 90%, 95%, 98%, or 99% nucleotide sequence identity to the gene sequence(s) crtYIB and crtWZ of *Fulvimarina pelagi*. In some embodiments, the microorganism is a bacterial microorganism. In some examples, the bacterial microorganism may be a Gram-negative bacterial microorganism. In one example, the bacterial microorganism may be from the phylum Proteobacteria. In one example the bacterial microorganism may be from the class Alphaproteobacteria. In one example, the bacterial microorganism is from the genus *Methylobacterium*, for example, *Methylobacterium extorquens*. In some embodiments, the coding sequences of the heterologous polynucleotide(s) are codon optimized for expression in the microorganism, for example, codon optimized for expression in *Methylobacterium extorquens*.

In one embodiment, the non-naturally occurring microorganism includes at least one heterologous polynucleotide that encodes one or more polypeptide encoded by the gene(s) crtZ, crtY, crtI, crtB, and/or crtW of *Sphingomonas astaxanthinifaciens*, e.g., *S. astaxanthinifaciens* DSM 22298, or one or more polypeptide having at least about 70% amino acid sequence identity to the polypeptide(s) encoded by crtZ, crtY, crtI, crtB, and/or crtW of *Sphingomonas astaxanthinifaciens*, e.g., *S. astaxanthinifaciens* DSM 22298 and retaining the functional activity thereof for production of C40 carotenoid compound(s). In some embodiments, the heterologous polynucleotide includes one or more polynucleotide sequence(s) having at least about 70%, 75%, 80%, 85%, 90%, 95%, 98%, or 99% nucleotide sequence identity to the gene sequence(s) crtZ, crtY, crtI, crtB, and/or crtW of *Sphingomonas astaxanthinifaciens*, e.g., *S. astaxanthinifaciens* DSM 22298. In one embodiment, the microorganism includes and expresses heterologous crtZYIBW from *Sphingomonas astaxanthinifaciens* or polypeptides having at least about 70%, 75%, 80%, 85%, 90%, 95%, 98%, or 99% sequence identity thereof and retaining the functional activity thereof, and the microorganism produces astaxanthin, canthaxanthin, zeaxanthin, lycopene, beta-carotene, or intermediates of these C40 carotenoids. In some embodiments, the microorganism expresses crt Y, crtI, and crtB of *Sphingomonas astaxanthinifaciens* or polypeptides having at least about 70%, 75%, 80%, 85%, 90%, 95%, 98%, or 99% sequence identity thereof and retaining the functional activity thereof, and the microorganism produces beta-carotene. In some embodiments, crtW is expressed that results in production of canthaxanthin. In some embodiments, crtZ is expressed that results in production of zeaxanthin. In some embodiments, crtW and crtZ are expressed to produce a ratio of the gene products thereof that produces astaxanthin. In some embodiments, the microorganism is a bacterial microorganism. In some examples, the bacterial microorganism may be from the phylum proteobacteria, optionally from the class Alphaproteobacteria. In one example, the bacterial microorganism is from the genus *Methylobacterium*, for example, *Methylobacterium extorquens*. In some embodiments, the coding sequences of the heterologous polynucleotide(s) are codon optimized for expression in the microorganism, for example, codon optimized for expression in *Methylobacterium* extorquens.

In one embodiment, the non-naturally occurring microorganism includes at least one heterologous polynucleotide that encodes one or more polypeptide encoded by the gene(s) crtZ, crtY, crtI, and/or crtB of *Siansivirga zeaxanthinifaciens*, e.g., *S. zeaxanthinifaciens* CC-SAMT-1, or of *Mesoflavibacter zeaxanthinifaciens*, e.g., *M. zeaxanthinifa-*

*ciens* DSM 18436, or one or more polypeptide having at least about 70%, 75%, 80%, 85%, 90%, 95%, 98%, or 99% amino acid sequence identity to the polypeptide(s) encoded by crtZ, crtY, crtI, and/or crtB, of *Siansivirga zeaxanthinifaciens*, e.g., *S. zeaxanthinifaciens* CC-SAMT-1, or of *Mesoflavibacter zeaxanthinifaciens*, e.g., *M. zeaxanthinifaciens* DSM 18436, and retaining the functional activity thereof for production of C40 carotenoid compound(s). In some embodiments, the heterologous polynucleotide includes one or more polynucleotide sequence(s) having at least about 70%, 75%, 80%, 85%, 90%, 95%, 98%, or 99% nucleotide sequence identity to the gene sequence(s) crtZ, crtY, crtI, and/or crtB of *Siansivirga zeaxanthinifaciens*, e.g., *S. zeaxanthinifaciens* CC-SAMT-1, or of *Mesoflavibacter zeaxanthinifaciens*, e.g., *M. zeaxanthinifaciens* DSM 18436. In one embodiment, the microorganism includes and expresses heterologous crtZYIB from *Siansivirga zeaxanthinifaciens*, e.g., *S. zeaxanthinifaciens* CC-SAMT-1, or of *Mesoflavibacter zeaxanthinifaciens*, e.g., *M. zeaxanthinifaciens* DSM 18436 or polypeptides having at least about 70% sequence identity thereof and retaining the functional activity thereof, and the microorganism produces astaxanthin, canthaxanthin, zeaxanthin, lycopene, beta-carotene, or intermediates of these C40 carotenoids. In some embodiments, the microorganism is a bacterial microorganism. In some examples, the bacterial microorganism may be from the phylum Proteobacteria, optionally from the class Alphaproteobacteria. In one example, the bacterial microorganism is from the genus *Methylobacterium*, for example, *Methylobacterium extorquens*. In some embodiments, the coding sequences of the heterologous polynucleotide(s) are codon optimized for expression in the microorganism, for example, codon optimized for expression in *Methylobacterium* extorquens.

Transformation of Microorganisms

Numerous transformation protocols and constructs for introducing and expressing exogenous polynucleotides in host cells are known in the art.

In certain embodiments, genetic modifications will take advantage of freely replicating plasmid vectors for cloning. These may include small IncP vectors developed for use in *Methylobacterium*. These vectors may include pCM62, pCM66, or pHC41 for cloning. (Marx & Lidstrom (2001) *Microbiology* 147:2065-2075; Chou, et al. (2009) *PLoS Genetics* 5: e1000652).

In certain embodiments, genetic modifications will take advantage of freely replicating expression plasmids such as pCM80, pCM160, pHC90, or pHC91. (Marx & Lidstrom (2001) *Microbiology* 147:2065-2075; Chou, et al. (2009) *PLoS Genetics* 5: e1000652).

In certain embodiments, genetic modifications will utilize freely replicating expression plasmids that have the ability to respond to levels of inducing molecules such as cumate or anhydrotetracycline. These include pHC115, pLC290, pLC291. (Chou, et al. (2009) *PLoS Genetics* 5: e1000652; Chubiz, et al. (2013) *BMC Research Notes* 6:183).

In certain embodiments, genetic modifications will utilize recyclable antibiotic marker systems such as the cre-lox system. This may include use of the pCM157, pCM158, pCM184, pCM351 series of plasmids developed for use in *M. extorquens*. (Marx & Lidstrom (2002) *BioTechniques* 33:1062-1067).

In certain embodiments, genetic modifications will utilize transposon mutagenesis. This may include mini-Tn5 delivery systems such as pCM639 (D'Argenio, et al. (2001) 1 *Bacteriol.* 183: 1466-1471) demonstrated in *M. extorquens*. (Marx, et al. (2003) *J. Bacteriol.* 185: 669-673).

In certain embodiments, genetic modifications will utilize expression systems introduced directly into a chromosomal locus. This may include pCM168, pCM172, and pHC01 plasmids developed for *M. extorquens* AM1. (Marx & Lidstrom (2001) *Microbiology* 147: 2065-2075; Lee, et al. (2009) *Evolution* 63: 2813-2830).

In certain embodiments, genetic modifications will utilize a sacB-based system for unmarked exchange of alleles due to the sucrose sensitivity provided by sacB expression. This may include the pCM433 vector originally tested with *M. extorquens*. (Marx, et al. (2008) *BMC Research Notes* 1:1).

Microbial Cultures

Methods for producing biomass are provided. The methods include culturing a microorganism as described herein in a culture medium under conditions suitable for growth of the microorganism and production of biomass that contains one or more C40 carotenoid compound(s) as described herein. In some embodiments, one or more of the C40 carotenoid compound(s) astaxanthin, canthaxanthin, zeaxanthin, phoenicoxanthin, adonixanthin, 3-hydroxyechinenone, echinenone, β-carotene, and lycopene, or a combination thereof, is produced.

The microorganisms herein are non-naturally occurring and contain at least one heterologous polynucleotide that encodes one or more heterologous enzyme for C40 carotenoid production in the microorganism. In some embodiments, the microorganism produces C40 carotenoid compound(s) exclusively from enzymes that are encoded by the heterologous polynucleotide(s). In some embodiments, the microorganism produces carotenoid compound(s) from a combination of enzymes that are encoded by the heterologous polynucleotide(s) and native enzyme(s) encoded by the genome of the parent microorganism. In some embodiments, the microorganism also produces one or more C30 carotenoid compound from a native biosynthetic pathway in the parent microorganism. In some embodiments, the native C30 carotenoid pathway of the parent microorganism has been disrupted or deleted such that C30 carotenoid production is reduced or eliminated in comparison to the parent microorganism.

The culture medium includes carbon source(s), nitrogen source(s), inorganic substances (e.g., inorganic salts), and any other substances required for the growth of the microorganism (e.g., vitamins, amino acids, etc.).

The carbon source may include sugars, such as glucose, sucrose, lactose, fructose, trehalose, mannose, mannitol, and maltose; organic acids, such as acetic acid, lactic acid, fumaric acid, citric acid, propionic acid, malic acid, pyruvic acid, malonic acid, succinic acid and ascorbic acid; alcohols, such as methanol, ethanol, propanol, butanol, pentanol, hexanol, isobutanol, and glycerol; oil or fat, such as soybean oil, rice bran oil, olive oil, corn oil, sesame oil, linseed oil, and the like. The amount of the carbon source added varies according to the kind of the carbon source, for example, about 1 to about 100 gm, or about 2 to about 50 gm per liter of medium.

In various embodiments, the culture conditions may include one or more of: aeration of the culture medium (e.g., resulting in a dissolved oxygen concentration of about 5% to about 50%); temperature of the culture medium (e.g., temperature of about 20° C. to about 50° C.); carbon source comprising, consisting of, or consisting essentially of one or more alcohol(s) (e.g., methanol, ethanol, glycerol, or a combination thereof); or semi-continuous or continuous fermentation conditions.

In some embodiments, a C1 carbon substrate is provided to a microorganism that is capable of converting such a substrate to organic products (e.g., microorganisms of the genera *Methylobacterium, Methylomonas, Methylobacter, Methylococcus, Methylosinus, Methylocyctis, Methylomicrobium*). In certain embodiments, the C1 carbon substrate is selected from methane, methanol, formaldehyde, formic acid, methylated amines, methylated thiols, and carbon dioxide. In certain embodiments, the C1 carbon substrate is selected from methanol, formaldehyde, and methylated amines. In certain embodiments, the C1 carbon substrate is methanol.

In some embodiments, a C2 carbon substrate is provided to a microorganism that is capable of converting such a substrate to organic products (e.g., microorganisms of the genera *Methylobacterium, Methylomonas, Methylobacter, Methylococcus, Methylosinus, Methylocyctis, Methylomicrobium*). In certain embodiments, the C2 carbon substrate is selected from ethylamine, acetate, acetic acid, acetaldehyde, ethylene glycol, and ethanethiol. Diethylamine and triethylamine can also be considered C2 carbon substrates. In certain embodiments, the C1 carbon substrate is selected from methanol.

In some embodiments, one or more C1 and C2 carbon substrate are provided together or sequentially to a microorganism that is capable of converting such a substrate to organic products (e.g., microorganisms of the genera *Methylobacteriurn, Methylomonas, Methylobacter, Methylococcus, Methylosinus, Methylocyctis, Methylomicrobium*). In certain embodiments, the C1 and C2 source(s) may include methane, methanol, formaldehyde, formic acid, methylated amines, methylated thiols, carbon dioxide, ethanol, ethylamine, acetate, acetic acid, acetaldehyde, ethylene glycol, ethanethiol, diethylamine, or triethylamine. In some embodiments the C1 and C2 sources are methanol and ethanol, respectively.

In some embodiments, one or more process stream from a fermentation to produce a bioproduct of interest, such as an alcohol or a biofuel (e.g., ethanol fermentation and/or distillation process stream(s)) is provided as a carbon substrate to a microorganism that is capable of converting such a substrate to organic products (e.g., microorganisms of the genera *Methylobacterium, Methylomonas, Methylobacter, Methylococcus, Methylosinus, Methylocyctis, Methylomicrobium*). In certain embodiments, the ethanol fermentation and/or distillation process stream is selected from one or more of ethanol beer, ethanol, whole stillage, wet cake or wet distiller grains (WDG), thin stillage, thin stillage syrup or condensed distiller solubles (CDS), wet distillers grains with solubles (WDGS), and dried distiller grains with solubles (DDGS). In certain embodiments, the ethanol fermentation and/or distillation process stream is selected from thin stillage or thin stillage syrup. In certain embodiments, the ethanol fermentation and/or distillation process stream is thin stillage syrup.

In some embodiments, one or more C1, one or more C2, or one or more C1 and C2 carbon substrate are provided together or sequentially to a microorganism with one or more process stream from a fermentation to produce a bioproduct of interest, such as an alcohol or a biofuel (e.g., ethanol fermentation and/or distillation process stream(s)) that is capable of converting such a substrate to organic products (e.g., microorganisms of the genera *Methylobacterium, Methylomonas, Methylobacter, Methylococcus, Methylosinus, Methylocyctis, Methylomicrobium*). In certain embodiments, the C1, C2, or C1 and C2 source(s), and ethanol fermentation and/or distillation process stream(s) may include methane, methanol, formaldehyde, formic acid, methylated amines, methylated thiols, carbon dioxide, ethanol, ethylamine, acetate, acetic acid, acetaldehyde, ethylene glycol, ethanethiol, diethylamine, triethylamine, ethanol beer, ethanol, whole stillage, wet cake or wet distiller grains (WDG), thin stillage, thin stillage syrup or condensed distiller solubles (CDS), wet distillers grains with solubles (WDGS), and/or dried distiller grains with solubles (DDGS). In some embodiments, the C1 and C2 sources are methanol and ethanol, respectively and the ethanol fermentation and/or distillation process stream is thin stillage. In some embodiments the C1 and C2 sources are methanol and ethanol, respectively, and the ethanol fermentation and/or distillation process stream is thin stillage syrup.

The nitrogen source may include potassium nitrate, ammonium nitrate, ammonium chloride, ammonium sulfate, ammonium phosphate, ammonia, urea, spent yeast cells and the like, alone or in combination. Amount of the nitrogen source added varies according to the kind of the nitrogen source, for example, about 0.1 to about 30 gm, or about 1 to about 10 gm per liter of medium.

Inorganic salts may include potassium dihydrogen phosphate, dipotassium hydrogen phosphate, disodium hydrogen phosphate, sodium dihydrogen phosphate, magnesium sulfate, magnesium chloride, ferric sulfate, ferrous sulfate, ferric chloride, ferrous chloride, manganese sulfate, manganese chloride, zinc sulfate, zinc chloride, cupric sulfate, calcium chloride, calcium carbonate, sodium carbonate, sodium sulfate, and the like, alone or in combination. Amount of inorganic salt varies according to the kind of the inorganic salt, for example, about 0.00001 to about 10 gm per liter of medium.

Special required substances, for example, vitamins, nucleic acids, yeast extract, peptone, meat extract, malt extract, corn steep liquor, soybean meal, dried yeast etc., may be included alone or in combination. Amount of the special required substance used varies according to the kind of the substance, for example, about 0.2 gm to about 200 gm, or about 3 gm to about 10 gm per liter of medium.

In some embodiments, the culture conditions include a carbon source that comprises, consists of, or consists essentially of one or more alcohol(s), such as, but not limited to, methanol, ethanol, and/or glycerol, or a combination thereof, e.g., a combination of methanol and ethanol.

In some embodiments, culture conditions that result in a desired C40 carotenoid level are employed. For example, a total C40 carotenoid level of 0.1-1% (w/v) or greater in the biomass may be achieved.

Figure 2:
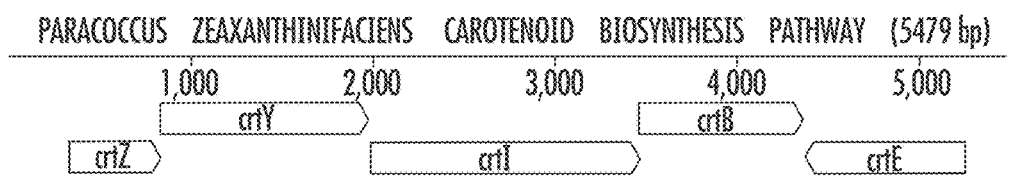
FIG. 2 schematically depicts the C40 carotenoid biosynthetic gene cluster in *Paracoccus zeaxanthinifaciens.*

In some embodiments, the pH of the culture medium is adjusted to pH about 2 to about 12, or about 6 to about 9. The medium may further include one or more buffer(s) to maintain the culture at the desired pH. Numerous buffers are known in the art and include phosphate, carbonate, acetate, PIPES, HEPES, and Tris buffers. A suitable buffer for a given microorganism can easily be determined by one of ordinary skill in the art. For *Methylobacterium*, a common medium, described by Lee, et al. (2009) *Evolution* 63:2813-2830, is a phosphate buffered medium that consists of 1 mL of trace metal solution (to 1 liter of deionized water the following are added in this order: 12.738 gm of EDTA disodium salt dihydrate, 4.4 gm of $ZnS0-7H_2O$, 1.466 gm of $CaCl_2-2H_2O$, 1.012 gm of $MnCl_2-4H_2O$, 0.22 gm of $(NH_4)_6Mo_7O_{24}-4H_2O$, 0.314 gm of $CuSO_4-5H_2O$, 0.322 gm of $CoCl_2-6H_2O$, and 0.998 gm of $Fe_3(SO_4)_2-7H_2O$; pH 5.0 is maintained after every addition), 100 mL of phosphate buffer (25.3 g of $K_2HPO_4$ and 22.5 g of $NaH_2PO_4$ in 1 liter of deionized water), 100 mL of sulfate solution (5 gm of $(NH_4)_2(SO_4)$ and 0.98 gm of $Mg(SO_4)_2$ in 1 liter of deionized water), and 799 mL of deionized water. All components are heat sterilized separately and then pooled together. An alternative medium recently developed for use with *Methylobacterium extorquens* takes advantage of an organic buffer and has a citrate-chelated trace metal mix. Culturing is carried out at temperature of 15° to 40° C., and preferably 20° to 35° C., usually for 1 to 20 days, and preferably 1 to 4 days, under aerobic conditions provided by shaking or aeration/agitation. Common practice with *Methylobacterium* is at 30° C. The protocol for making M-PIPES medium is described in Table Si of Delaney et al. (2013) *PLoS One* 8:e62957. FIG. 2 in U.S. Ser. No. 61/863,701 shows an exemplary recipe for medium optimized for use with *M. extorquens*.

In order to generate dense cultures of microorganisms, such as *Methylobacterium*, it may be advantageous to use a fed-batch method. Methanol can be tolerated well at 0.1-10% v/v (~24.7 mM-2.47M), and thus this step size of addition can be used repeatedly. Ethanol can be tolerated well at 0.1-20% v/v (~1.71 mM-3.42M), and thus this step size of addition can be used repeatedly. Critically, pH levels drop during culturing on methanol and/or ethanol, such that the use of a base such as KOH, $NH_4OH$, or NaOH would be important to maintain the pH around 6.5. Aeration can be achieved via physical agitation, such as an impeller, via bubbling of filtered air or pure oxygen, or in combination. In order to reduce production costs, the buffer can be replaced from phosphates or PIPES to a carbonate-buffered medium.

In some embodiments, a "fill and draw" method is used, in which a portion of the culture medium (e.g., about 10% to about 90%) is removed when the culture reaches a desired optical density at 600 nm (e.g., about 50 to about 200), followed by replacement with an equivalent amount of fresh medium, thereby maintaining C40 carotenoids at a relatively constant level in the culture, thereby resulting in biomass that contains a desired level of C40 carotenoids.

In some embodiments, a "continuous" method is used, in which fresh medium is continuously added, while culture medium and microorganisms are continuously removed at the same rate, keeping the culture volume relatively constant, thereby resulting in biomass that contains a desired level of C40 carotenoids.

Microbial cells may be separated from the culture, for example, by a conventional means such as centrifugation or filtration. The cells may be isolated whole, or may be lysed to release their contents for extraction or further processing. The cells or the medium may be subjected to an extraction with a suitable solvent.

Compositions

Compositions are provided for use as feed in aquaculture, or as animal feed, or as human nutritional supplements containing processed or unprocessed biomass from microorganism cells cultured as described herein, as are methods of preparation of the feed or nutritional supplement compositions.

In some embodiments, the feed compositions or nutritional supplements include C40 carotenoid-containing biomass, produced by culturing one or more microorganism(s) as described herein, i.e., produced by culturing a non-naturally occurring microorganism as described herein that result in a desired C40 carotenoid level, as described herein.

In some embodiments in which the C30 carotenoid biosynthetic pathway has been disrupted or deleted, the feed composition or nutritional supplement contains biomass that does not contain C30 carotenoids or which contains reduced levels of C30 carotenoids in comparison to the biomass produced from the parent strain from which the microorganism is derived under identical culture conditions.

In some embodiments, the microbial cell produces a polyhydroxyalkanoate (PHA), e.g., polyhydroxybutyrate (PHB), and the composition contains PHA (e.g., PHB) in the biomass that is incorporated into the composition. In some embodiments, the composition contains one or more C40 carotenoid(s) and contains PHA (e.g., PHB).

In various embodiments, the composition contains one or more of astaxanthin, canthaxanthin, zeaxanthin, phoenicoxanthin, adonixanthin, 3-hydroyechinenone, echinenone, β-carotene, and lycopene, or combinations thereof.

In certain embodiments, biomass that is incorporated into a feed or nutritional supplement composition can be in a dry, or substantially dry, form, e.g., containing less than about 20%, 10%, 5%, or 2% of moisture. In certain embodiments, the cultures are isolated by removing substantially all supernatant, such as by filtering, sedimentation, or centrifugation. In certain embodiments, the collection of cultures and further processing of biomass includes a bacterial lysis step, e.g., by use of detergents or ultrasound. In certain embodiments, the processed microbial cells maintain substantially whole cell membranes. In some embodiments, a substantial portion (e.g., more than about 5%, 10%, 20%, 30%, 50%, or 80%) of bacterial cells may maintain viability in the processed biomass.

The feed composition may contain at least about 1% of the biomass by weight. In certain embodiments, the feed composition is optimized for consumption by fish, seafood, humans, poultry, swine, cattle or other animals. For example, the feed may include one or more of EPA, DHA, and one or more essential amino acids.

Methods for preparing a feed composition are also provided. In some embodiments, the method includes: (a) culturing in an appropriate medium at least one non-naturally occurring microorganism as described above; (b) concentrating the medium to provide a biomass; (c) optionally providing additional feed components; and (d) producing the feed composition from the biomass. In certain embodiments, step (b) includes centrifugation. In certain embodiments, step (b) includes allowing the biomass to settle. In certain embodiments, step (b) includes filtration. In certain embodiments, the method further includes a pre-treatment of the biomass after step (a) with a chemical agent (e.g., a surfactant or solvent) to disrupt the cell membranes of the biomass. In certain embodiments, the method further includes mechanical disruption of the cell membranes of the biomass after step (a).

Examples of feedstuffs into which single cell protein enriched with one or more C40 carotenoid compound(s), produced as described herein, may be incorporated include, for example, pet foods, such as cat foods, dog foods and the like, feeds for aquarium fish, cultured fish or crustaceans, etc., feed for farm-raised animals (including livestock and further including fish or crustaceans raised in aquaculture). The state of the biomass can be in whole cell, lysed or partially processed. C40 carotenoid-enriched biomass or C40 carotenoid-enriched protein, produced as described herein can also be incorporated into food or vitamin supplements for human consumption, optionally with additional caloric or nutritional supplements. Food or feed material that includes one or more C40 carotenoid compound(s) or biomass that includes one or more C40 carotenoid compound(s), produced as described herein is incorporated, is preferably palatable to the organism that is the intended recipient. This food or feed material may have any physical properties currently known for a food material (e.g., solid, liquid, soft). In some embodiments, feed produced as described herein will undergo a pelletization process, e.g., through a hot or cold extrusion process at an inclusion rate of less than about 1%, 5%, 10%, 20%, 25%, 30%, 40%, 50%, 60%, or 75%. In other scenarios, C40 carotenoid-enriched biomass or C40 carotenoid-enriched protein, produced as described herein, can be consumed directly at 100% or combined with another substance in the form of liquid, baked goods or other to form, including but not limited to, various types of tablets, capsules, drinkable agents, gargles, etc.

In some embodiments, the feed or nutritional composition or the biomass that is incorporated into the feed or nutritional composition includes about 0.0001% to about 1% C40 carotenoids by weight. In some embodiments the final feed composition, the C40 carotenoids are by weight 0.00001% to 0.0001%.

In some embodiments, all of the C40 carotenoids in the final feed are provided by biomass of the microorganisms described herein. In some embodiments, at least 1% (w/w) of the C40 carotenoids in the final feed composition are provided by the biomass of the microorganisms described herein.

In some embodiments, a feed or nutritional composition as described herein includes a plurality of microorganisms that each produce different levels of different C40 carotenoid compound(s) as described herein, which may be cultured together or may be cultured separately and combined for production of the feed or nutritional composition.

Methods of producing fish or seafood are also provided, including farming fish or seafood, and providing a diet, which includes a feed composition as described herein, to the fish or seafood.

The following examples are intended to illustrate, but not limit, the invention.

EXAMPLES

Vectors and nucleotide sequences used in the examples below are provided in Table 1. Gene or gene cluster origin is noted by initials of the native organism.

TABLE 1

| Plasmid name | Insert Origin | Description | Example | SEQ ID NO: |
|---|---|---|---|---|
| pI | | Integration plasmid backbone | | 1 |
| pA | | Circulating plasmid backbone with HP1 promoter | | 7 |
| pB | | Circulating plasmid backbone with HP2 promoter | | 8 |
| PC | | Circulating plasmid backbone with pmxaF promoter | | 3 |
| pD | | Circulating plasmid backbone with pR-faeRBS promoter | | 2, 4 |
| pD00 | *Paracoccus zeaxanthinifaciens* | pR-faeRBS-crtZYIB_Pz-pmxaF-crtE_Pz | 1 | 4, 10, 11, 12, 13, 14, 3 |
| pD00* | *Paracoccus zeaxanthinifaciens* | pR-faeRBS-crtZ*YIB_Pz-pmxaF-crtE_Pz | 1 | 4, 10, 11, 12, 13, 14, 3 |
| pA01 | *P. zeaxanthinifaciens* | HP1-crtYIB_Pz-HP2-crtE_Pz | 2 | 7, 11, 12, 13, 8, 14 |
| pA02 | *F. vulneris, P. zeaxanthinifaciens* | HP1-crtYIB_Ev-HP2-crtE_Pz | 2 | 7, 33, 34, 35, 8, 14 |
| pA03 | *P. ananatis, P. zeaxanthinifaciens* | HP1-crtYIB_Pa-HP2-crtE_Pz | 2 | 7, 40, 41, 42, 8, 14 |
| pA04 | *S. zeaxanthinifaciens, P. zeaxanthinifaciens* | HP1-crtIBZY_Sz-HP2-crtE_Pz | 2 | 7, 22, 23, 24, 25, 8, 14 |
| pA05 | *S. astaxanthinifaciens, P. zeaxanthinifaciens* | HP1-crtYIB_Sa-HP2-crtE_Pz | 2 | 7, 17, 18, 19, 8, 14 |
| pA06 | *F. pelagi, P. zeaxanthinifaciens* | HP1-crtYIB_Fp-HP2-crtE_Pz | 2 | 7, 46, 47, 48, 8, 14 |
| pA07 | *M. zeaxanthinifaciens, P. zeaxanthinifaciens* | HP1-crtIBY_Mz-HP2-crtE_Pz | 3 | 7, 28, 29, 30, 8, 14 |
| pI08 | *P. zeaxanthinifaciens, M. extwquens* | HP1-crtZYIB_Pz-HP2-crtE_Pz (C30 integration flanks) | 3 | 1, 5, 9, 6 |
| pB09 | *E. vulneris* | HP2-idi_Ev | 4 | 8, 37 |
| pD10 | *F. pelagi* | pR-faeRBS-crtWZ_Fp | 5 | 4, 49, 50 |
| pC11 | *S. astaxanthinifaciens* | pmxaF-crtW_Sa | 6 | 3, 20 |
| pI12 | *F. pelagi* | pR-faeRBS-crtW_Fp (3010-3011 integration flanks) | 8 | 1, 51, 4, 49, 52 |
| pI13 | *P. zeaxanthinifaciens* | ΔcrtZ (integration) | 8 | 1, 7, 11 (partial) |
| pI14 | *P. zeaxanthinifaciens* | crtIBE_Pz-HP1-HP2 (C30 integration flanks) | 8 | 1, 5, 7, 12, 13, 14, 8, 6 |
| pA15 | *S. astaxanthinifaciens* | HP1-crtZ_Sa-crtY_Pz | 9 | 7, 16, 11 |
| pA16 | *F. pelagi* | HP1-crtZ_Fp-crtY_Pz | 9 | 7, 50, 11 |
| pA17 | *E. vulneris* | HP1-crtZ_Ev-crtY_Pz | 9 | 7, 32, 11 |
| pA18 | *M. zeaxanthinifaciens* | HP1-crtZ_Mz-crtY_Pz | 9 | 7, 27, 11 |

TABLE 1-continued

| Plasmid name | Insert Origin | Description | Example | SEQ ID NO: |
|---|---|---|---|---|
| pB19 | E. vulneris | HP2-crtE_Ev | 10 | 8, 36 |
| pB20 | | HP2-crtE_Pa | 10 | 8, 43 |

A list of strains used in the examples below with genotypes related to carotenoid production is provided in Table 2.

TABLE 2

| Strain Name | Relevant Genotype | Strain derived from | Main carotenoid produced |
|---|---|---|---|
| Str01 | | PA1 | C30 mix |
| Str02 | Δbch-cluster | Str01 | C30 mix |
| Str03 | ΔC30 Δbch-cluster Δhpt::PR-crtY_Pz pR-faeRBS-crtEBI_Me | Str01 | B-carotene |
| Str04 | ΔC30 | Str01 | — |
| Str05 | HP1-crtZYIB_Pz-HP2-crtE_Pz | Str03 | Zeaxanthin |
| Str06 | HP1-crtZYIB_Pz-HP2-crtE_Pz | Str01 | Zeaxanthin |
| Str07 | HP1-crtZYIB_Pz-HP2-crtE_Pz pR-crtW_Fp | Str06 | Astaxanthin |
| Str08 | HP1-crtIB_Pz-HP2-crtE_Pz pR-crtW_Fp | Str07 | Lycopene |
| Str09 | HP1-crtYIB_Pz-HP2-crtE_Pz pR-crtW_Fp | Str07 | Canthaxanthin |
| Str10 | HP1-crtIB_Pz-HP2-crtE*_Pz pR-crtW_Fp | Str07 | — |

Carotenoid production of crtYIB and crtIBZY clusters from various organisms in *E. coli* and *M. extorquens* with and without native C30 carotenoid production pathway, as described in the examples below, is shown in Table 3. Production of C40 carotenoids is reported on dry-cell basis for best producing isolates.

TABLE 3

| Plasmid | Strain | Beta carotene (ppm) | Zeaxanthin (ppm) |
|---|---|---|---|
| pA01 | Str02 | 165 | |
| | Str04 | 730 | |
| | E. coli BL21 | 44 | |
| pA02 | Str02 | 588 | |
| | Str04 | 111 | |
| | E. coli BL21 | 188 | |
| pA03 | Str02 | 165 | |
| | Str04 | 304 | |
| | E. coli BL21 | 289 | |
| pA04 | Str04 | | 200 |
| | E. coli BL21 | | 120 |
| pA05 | Str02 | 15 | |
| | E. coli BL21 | 114 | |
| pA06 | Str04 | 895 | |
| pA07 | Str02 | 739 | |
| | E. coli BL21 | 39 | |

Carotenoid production of various integrated strains with plasmid-based overexpression of various genes, as described in the examples below, is provided in Table 4. crtE* indicates non-functional mutant.

TABLE 4

| Strain | Plasmid | Lycopene (ppm) | Beta Carotene (ppm) | Zeaxanthin (ppm) | Canthaxanthin (ppm) | Astaxanthin (ppm) |
|---|---|---|---|---|---|---|
| Str06 | pB | | | 1,475 | | |
| Str06 | pB09 | | | 2,743 | | |
| Str06 | pD10 | | | 668 | 1,424 | |
| Str06 | pC11 | | | | 1,232 | |
| Str08 | pA | 4,896 | | | | |
| Str08 | pA15 | | 99 | | 2,048 | 216 |
| Str08 | pA16 | | 4 | | | 1,404 |
| Str08 | pA17 | | 64 | | | 776 |
| Str08 | pA18 | | 12 | | | 169 |
| Str10 | pB | | | | | |
| Str10 | pB19 | | | | 321 | 1,097 |
| Str10 | pB20 | | | | 38 | 579 |

Carotenoid production of integrated pathways in *M. extorquens* on various media compositions, as described in the examples below, is provided in Table 5.

TABLE 5

| Sample Name | Carbon Source | Total Carotenoids (ppm) 2500E | Lycopene (ppm) | Zeaxanthin (ppm) | Canthaxanthin (ppm) | Astaxanthin (ppm) |
|---|---|---|---|---|---|---|
| Str06 | Methanol | 2,726 | | 2,295 | | |
| Str06 | Cofeed | | | 1,171 | | |
| Str06 | Stillage | | | 1,780 | | |
| Str06 | Stillage + Methanol | | | 2,621 | | |
| Str06 | Stillage + Cofeed | | | 1,490 | | |
| Str06 | Stillage + Ethanol | | | 533 | | |
| Str07 | Methanol | 3,669 | | 970 | 369 | 2,311 |
| Str07 | Cofeed | | | 630 | 154 | 2,570 |
| Str07 | Stillage | | | 159 | 134 | 1,630 |
| Str07 | Stillage + Methanol | | | 701 | 130 | 2,765 |
| Str07 | Stillage + Cofeed | | | 420 | 159 | 1,934 |
| Str07 | Stillage + Ethanol | | | 59 | 95 | 537 |
| Str08 | Methanol | 5,789 | 5,857 | | | |
| Str08 | Cofeed | | 5,942 | | | |
| Str08 | Stillage | | 2,271 | | | |

TABLE 5-continued

| Sample Name | Carbon Source | Total Carotenoids (ppm) 2500E | Lyco- pene (ppm) | Zea- xanthin (ppm) | Cantha- xanthin (ppm) | Asta- xanthin (ppm) |
|---|---|---|---|---|---|---|
| Str08 | Stillage + Methanol | | 3,884 | | | |
| Str08 | Stillage + Cofeed | | 2,517 | | | |
| Str08 | Stillage + Ethanol | | 1,631 | | | |
| Str09 | Methanol | 4,652 | | 4,470 | | |
| Str09 | Cofeed | | | 3,313 | | |
| Str09 | Stillage | | | 3,232 | | |
| Str09 | Stillage + Methanol | | | 5,363 | | |
| Str09 | Stillage + Cofeed | | | 3,463 | | |
| Str09 | Stillage + Ethanol | | | 2,609 | | |

Example 1

Summary:

*Paracoccus zeaxanthinifaciens* crtZYIBE genes were cloned into a plasmid with constitutive promoters previously characterized in *M. extorquens*. The plasmid was transformed into *M. extorquens*, with and without native C30 carotenoid pathway. Fermentations of these plasmid-bearing strains produced zeaxanthin.

*P. zeaxanthinifaciens* ATCC 21588 crtZYIBE genes (SEQ ID NO:9) were amplified via polymerase chain reaction (PCR) in several parts, with junctions introduced where AarI recognition sites natively occurred in the target sequence. As this gene cluster consists of two convergent operons (FIG. 2), promoter region from *M. extorquens* mxaF gene (SEQ ID NO:3) was amplified via PCR to drive the expression of the crtE gene. All amplification primers were designed with 18-25 base pair binding regions and an overhang including a recognition site, spacer regions and restriction site to enable restriction and ligation by AarI Gateway cloning. Single nucleotide polymorphisms (SNPs) were introduced at the junctions located in AarI recognition sites to remove recognition without changing coded amino acids.

Figure 10A:
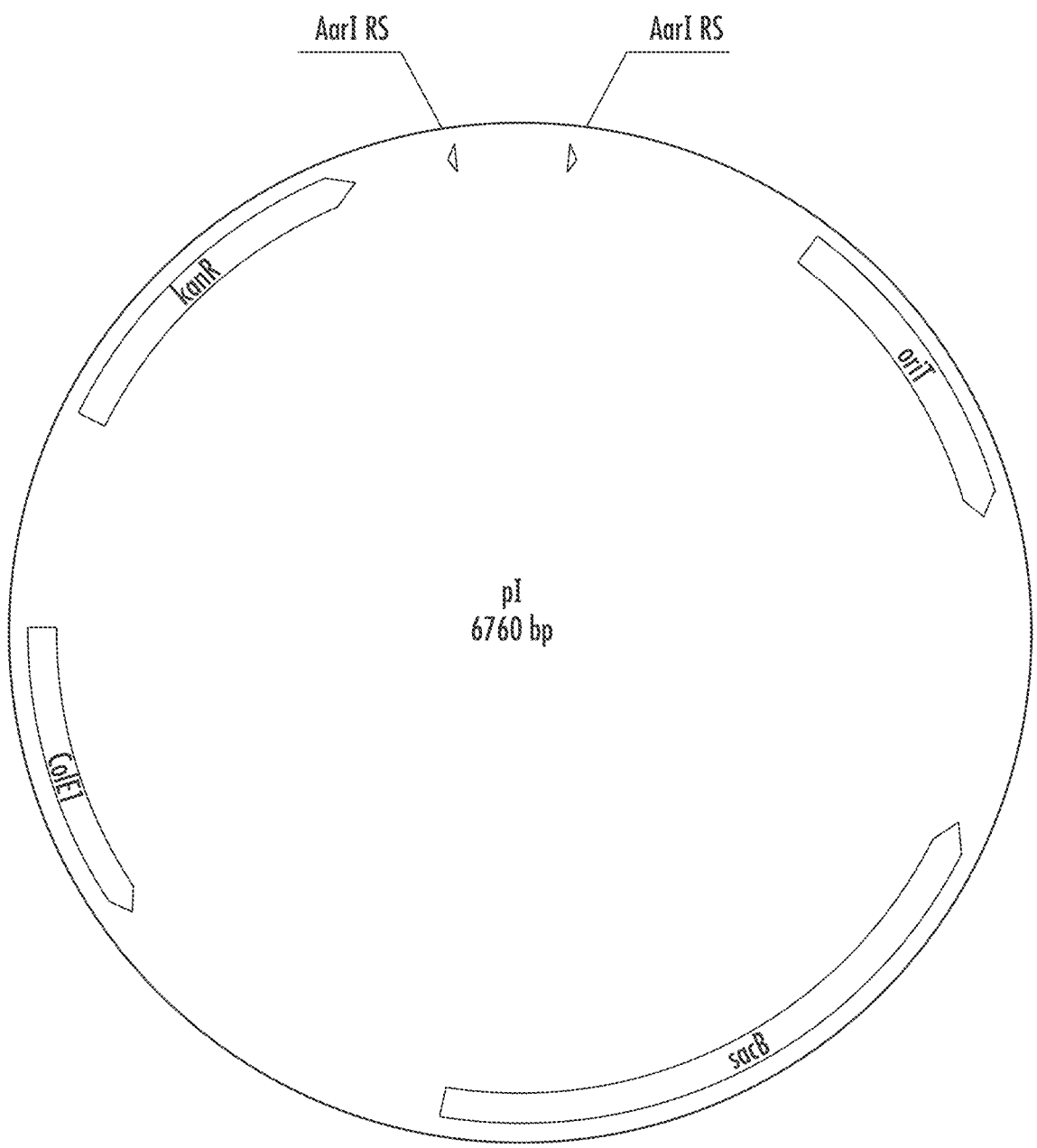
FIG. 10A shows a map of plasmid pI, as described in Example 3.

Operon fragments and pmxaF were ligated with AarI Gateway assembly into vector pD (FIG. 10B), which contains the promoter-RBS region pR-faeRBS (SEQ ID NO:4) derived from the viral promoter pR and the RBS region from *M. extorquens* gene fae. Genes were assembled in their native convergent structure with crtZYIB downstream of pR-faeRBS and crtE downstream of pmxaF. (FIG. 10C shows a map of plasmid pA01 as an example schematic.) The vector backbone was derived from plasmid pLC291 (see Chubiz, et al. (2013) *BMC Research Notes*, 6(1):183), which included the gene kanR, which confers kanamycin resistance, origin of replication ColEI, which allows *E. coli* to maintain the plasmid at high copy numbers, and IncP origin of vegetation (oriV), which allows *M. extorquens* to maintain the plasmid at low copy numbers (*M. extorquens* does not recognize the ColEI origin).

Ligation products were transformed into New England Biolab's 10-beta Competent *E. coli* cells, single colonies were screened for correct assembly, and plasmid DNA was extracted by mini-prep and sequenced.

Verified plasmid. Designated pD00, was transformed into competent *M. extorquens* PA1 (Taxonomy ID: 419610) variants. All *M. extorquens* PA1 strains tested in these studies were derived from a strain designated Str01, which includes two deletions, the celABC and crtCDF deletions that reduce flocculation of cells in liquid culture and eliminate spirilloxanthin pathway, respectively. The strain used in this study is designated Str03 and includes overexpression of the native crtEBI genes on the heterologous pR promoter integrated into the crtBI locus (Mext_3011-Mext_3012) and the crtY from *P. zeaxanthinifaciens* also expressed on the heterologous pR promoter integrated at the hpt locus. Additionally, Str03 has a deleted carotenoid cluster and does not produce native C30 compounds. Most transformed colonies appeared yellow on solid media, however an orange mutant was identified and isolated for study. The mutant plasmid was designated pD00*.

Isolated colonies were picked into 3-5 mL precultures, grown with shaking 3 days at 30° C., then 250-500 µL transferred to 25-50 mL minimal media in flasks for 2-3 day fermentation with shaking at 30° C. (with kanamycin selection to maintain the plasmid). Minimal media used in all fermentations was modified from Choi et al., (1989) *Kor. J. Appl. Microbiol. Bioeng.* 17:392-396. Cultures were fed twice daily with 0.5% methanol as carbon source unless otherwise noted.

Absorbance at 600 nm over 1 cm path length was measured by spectrophotometry to estimate cell density, and 0.1-10 mL culture was harvested by centrifugation. Total biomass harvested was calculated from absorbance using a conversion value of 0.3 mg/($OD_{600}$*mL) according to internal data.

Carotenoids were extracted from the cell pellet and analyzed as follows: the cell pellet was resuspended in methanol, mixed with an equal volume of chloroform, and sonicated to lyse. Cell debris was removed by centrifugation and the resulting supernatant was dried completely. Residue was resuspended in dichloromethane and ethyl acetate (1:4 ratio) with sonication, debris again removed by centrifugation, and resultant supernatant dried completely. Residue was resuspended in 1:1 methanol chloroform mixture with sonication, centrifuged to remove any remaining debris, and analyzed by UPLC.

Figure 3:
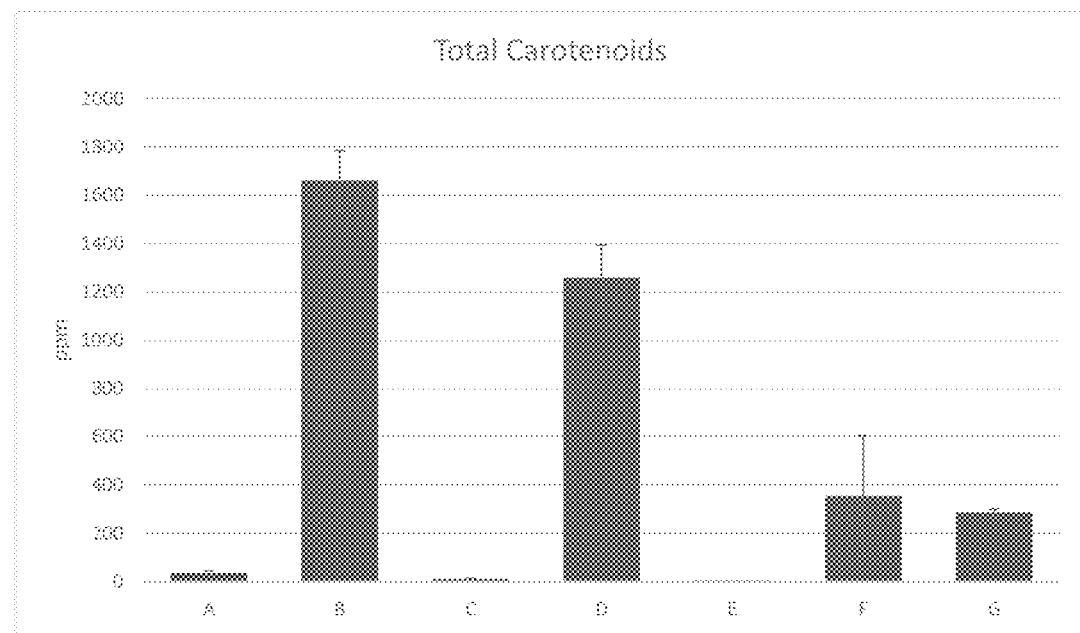
FIG. 3 shows data from the experiment described in Examples 1 and 3. (A) Str01, parent strain, *Methylobacterium extorquens* PA1, producing 100% C30 carotenoids; (B) Str06, strain (A) with C30 carotenoid production removed and *P. zeaxanthinifaciens* carotenoid gene cluster crtZYIBE integrated into the bacterial chromosome, producing >95% zeaxanthin; (C) Str03, strain (A) with C30 carotenoid production removed and *P. zeaxanthinifaciens* crtY gene integrated into the bacterial chromosome, driven by native crtEBI, producing trace amount of β-carotene; (D) Str05, strain (C) with *P. zeaxanthinifaciens* crtZYIBE integrated into the bacterial chromosome, producing >95% zeaxanthin; (E) Strain (C) with empty control plasmid, producing trace amount of β-carotene; (F) Strain (C) with plasmid pD00* containing *P. zeaxanthinifaciens* crtYIBE, producing >80% β-carotene; (G) Strain (C) with plasmid pD00 containing *P. zeaxanthinifaciens* crtZYIBE, producing >95% zeaxanthin.

1-4 µL of the cell extract was injected on Waters Acuity Ultra Performance Liquid Chromatography (UPLC) system. Analytes were separated by a gradient of ultrapure water with 0.1% formic acid, methanol with 0.1% formic acid and acetonitrile on a C18 column held at 32° C. Compounds were identified by tunable UV (TUV) detector (470 nm wavelength) and mass spectrometry. The resultant chromatography peaks were quantified by comparison of UV signal to standard curves of astaxanthin, zeaxanthin, canthaxanthin and beta-carotene. Parent strain Str03 with empty control vector produced trace beta-carotene, while this strains bearing pD00 plasmid produced zeaxanthin and those bearing pD00* produced more beta-carotene than the control vector (FIG. 3(E-G)).

Example 2

Summary: crtYIB or crtIBZY gene clusters from *Paracoccus zeaxanthinifaciens, Escherichia vulgaris, Pantoea ananatis, Fulvimarina pelagi, Sphingomonas astaxanthinifaciens, Siansivirga zeaxanthinifaciens* and *Mesoflavibacter zeaxanthinifaciens* were cloned into plasmids with crtE from *P. zeaxanthinifaciens* with promoter regions from *P. zeaxanthinifaciens*. The plasmids were transformed into *M. extorquens* with and without native C30 carotenoid pathway and *Escherichia coli* BL21. Fermentations of these plasmid-bearing strains produced beta carotene and zeaxanthin.

Carotenoid production genes were identified in strains *Paracoccus zeaxanthinifaciens, Escherichia vulgaris, Pantoea ananatis, Fulvimarina pelagi, Sphingomonas astaxanthinifaciens, Siansivirga zeaxanthinifaciens* and *Mesoflavibacter zeaxanthinifaciens*. crtYIB or crtIBZY gene clusters (SEQ IDs in Table 1) were amplified via polymerase chain reaction (PCR) in several parts, with junctions introduced where AarI recognition sites natively occurred in the target sequence. The crtE gene from *P. zeaxanthinifaciens* (SEQ ID NO: 14) was amplified with adjacent non-coding promoter region which was designated HP2 (SEQ ID NO: 8). As in Example 1, SNPs were introduced at junctions to remove natively-occurring AarI sites without changing coded amino acids and extension primers were designed to enable restriction and ligation by AarI Gateway cloning.

Each cluster was assembled with HP2-crtE fragment using AarI Gateway assembly into vector pA, which contains the non-coding promoter region upstream of *P. zeaxanthinifaciens* crtZYIBE cluster, designated HP1 (SEQ ID NO: 7), and shares other backbone features with plasmid pD described in Example 1. As in pD00, fragments were arranged in a convergent operon structure (FIG. 10C shows a map of plasmid pA01 as example schematic).

Ligation products were transformed into competent *E. coli* cells, single colonies were screened for correct assembly, and plasmid DNA was extracted by mini-prep and sequenced.

Verified plasmids were introduced into *M. extorquens* PA1 (Taxonomy ID: 419610) variants. Variant Str02 contains the *M. extorquens* carotenoid cluster and no bch cluster, while variant Str04 has a deleted carotenoid cluster and does not produce native C30 compounds. Plasmids were also transformed into competent *E. coli* BL21.

Isolated colonies of *M. extorquens* transformations were picked into 3 mL of minimal media in 24 deep well plates, covered with breathable film and grown with shaking at 30° C. for three days. Isolated colonies of *E. coli* transformations were picked into 3 mL of LB media in capped tubes and grown with shaking at 37° C. overnight.

Cultures were harvested as in Example 1 and extracted from the cell pellet by an abbreviated method suitable for target C40 compounds as follows: the cell pellet was resuspended in methanol, mixed with an equal volume of ethyl acetate, and sonicated to lyse. Cell debris was removed by centrifugation, the resulting supernatant was diluted in 1:1 methanol:ethyl acetate as necessary and analyzed by UPLC as in Example 1. Parent strains with empty control vector produced no detectable C40 carotenoids, while strains with plasmids produced beta carotene or zeaxanthin (Table 3).

Example 3

Summary:

*P. zeaxanthinifaciens* crtZYIBE genes were cloned into an integration plasmid with non-coding regions upstream and downstream of operons from *P. zeaxanthinifaciens*. The cassette was integrated into *M. extorquens* in the C30 gene cluster region using scarless integration methods. Fermentations of these strains produced zeaxanthin.

The *P. zeaxanthinifaciens* crtZYIBE operon with up- and down-stream non-coding regions (HP1 and HP2), was amplified with PCR in fragments with junctions at natively-occurring AarI sites (SEQ ID NO:9). 500 base pair flanking regions upstream of MEXT_3434 (SEQ ID NO:5) and downstream of MEXT_3441 (SEQ ID NO:6) (flanking the C30-producing gene cluster region) were designed to target insertion of operons into *M. extorquens* chromosome.

As in Example 1, SNPs were introduced at junctions in crtZ and crtB to remove natively-occurring AarI sites without changing coded amino acids, and extension primers were designed to enable restriction and ligation by AarI Gateway cloning.

Operon fragments were assembled with flanking regions by Gateway assembly to form integration cassettes in plasmid pI (SEQ ID NO:1; FIG. 10A), which replicates in *E. coli* but not in *M. extorquens*, and which includes a kanamycin resistance cassette, a sacB counter selection cassette, and the origin of replication ColE1 for maintenance in *E. coli*. Ligation products were transformed into competent *E. coli* cells, single colonies were screened for correct assembly, and plasmid DNA was extracted by mini-prep and sequenced.

The resulting plasmid, pI08, was introduced into several strains of *M. extorquens* by electroporation, including Str01 (with addition of crtZYIBE cassette this was designated Str06) and Str03 (with addition of crtZYIBE cassette this was designated Str05) described in Example 1. Integrants were selected on kanamycin selective media and passaged onto sucrose media plates to remove markers. Yellow isolates were selected and the integration locus verified with PCR.

Verified integration strains and parent strains were grown with no antibiotics and assessed for zeaxanthin production as described in Example 1. Parent strains produced no zeaxanthin, while integrated strains produced zeaxanthin (FIG. 3 (A-D)).

Example 4

Summary:

*E. vulneris* idi gene was cloned on a plasmid and transformed into a zeaxanthin producing strain. Fermentations with this plasmid improved production of zeaxanthin up to 70% over control plasmid fermentations.

The gene idi from *E. vulneris* (SEQ ID NO: 37) was amplified via PCR with AarI Gateway extension primers. The gene was assembled by Gateway assembly into plasmid pB, which contains promoter region HP2 and shares other backbone features with plasmid pD, described in Example 1, to generate pB09. Ligation products were transformed into competent *E. coli* cells, single colonies were screened for correct assembly, and plasmid DNA was extracted by mini-prep and sequenced.

Verified idi plasmid and empty control plasmid were transformed into integrated zeaxanthin-producing strain Str06. Transformants were grown with kanamycin and assessed for zeaxanthin production as described in Example 2. Fermentations with idi overexpression yielded elevated zeaxanthin yields when compared to control plasmid fermentations (Table 4).

Example 5

Summary:

*Fulvimarina pelagi* crtWZ genes were cloned into a plasmid with a constitutive promoter previously characterized in *M. extorquens*. The plasmid was transformed into *M. extorquens* and fermentations of plasmid-bearing strains were analyzed for carotenoid content. *M. extorquens* with this plasmid produced 1200 ppm astaxanthin.

crtW and crtZ genes from *F. pelagi* were amplified with PCR with Gateway extension primers, as described in Example 1. Gene fragments from *F. pelagi* were ligated into plasmid pD, which contains promoter/RBS pair pR-faeRBS (SEQ ID NO:4) to generate pD10 using Gateway assembly. The vector backbone was as described in Example 1, and contained a kanamycin resistance cassette and oriV for replication in *M. extorquens*. Insertion was verified by PCR and sequence verified. Ligation products were transformed into competent *E. coli* cells, single colonies were screened for correct assembly, and plasmid DNA was extracted by mini-prep and sequenced.

Verified plasmids were transformed into strain Str05 from Example 3 and isolated colonies grown in presence of kanamycin and assessed for astaxanthin production as described in Example 2. Fermentations with this plasmid-bearing strain are described in Example 7.

Example 6

Summary:

*S. astaxanthinifaciens* crtW gene was cloned into plasmids and transformed alongside pD10 into zeaxanthin producing *M. extorquens*. Fermentations of plasmid-bearing strains produced astaxanthin.

crtW from *S. astaxanthinifaciens* (SEQ ID NO: 20) was amplified via PCR with Gateway extension primers as described in Example 1. The gene was ligated with Gateway assembly into plasmid pC, which contains the promoter pmxaF (SEQ ID NO: 3) and shares other backbone features with plasmid pA, described in Example 2, to generate pC11.

Ligation products were transformed into competent *E. coli* cells, single colonies were screened for correct assembly, and plasmid DNA was extracted by mini-prep and sequenced.

Verified pD10 and pC11 were transformed into Str06, described in Example 3. Transformants were grown with kanamycin and assessed for carotenoid production as in Example 2. Fermentations with these plasmids produced astaxanthin and mixed precursors (Table 4).

Example 7

Summary:

Zeaxanthin and astaxanthin-producing strains were fermented as described in Example 1 with either methanol alone, or methanol and ethanol fed together. Zeaxanthin and astaxanthin production were altered in cultures fed with methanol and ethanol together versus those fed methanol alone.

Zeaxanthin producing strains Str05 and Str06 from Example 3 and plasmid-bearing strain from Example 5 were struck on solid minimal media with methanol to isolate single colonies.

Three single colonies from each plate were picked into 3-5 mL minimal media with 0.5% methanol and grown 3 days at 30° C. Flasks with minimal media containing either 0.5% methanol or 0.25% methanol and 0.1% ethanol were inoculated with 1% of preculture (each preculture used to inoculate one methanol and one methanol/ethanol flask).

Cultures were sampled and fed with additional bolus of carbon equivalent to starting quantity (0.4% methanol or 0.25% methanol and 0.1% ethanol) after one day. Additional samples were taken after three and four days. Cell density was measured by absorbance at 600 nm.

Carotenoids were harvested from cell extracts using an abbreviated method suitable for high-titer cultures: 1 mL culture was pelleted and supernatant removed. Pellet was resuspended in ethanol then lysed with equal volume of ethyl acetate and sonication. Cell debris was removed by centrifugation.

Figure 6:
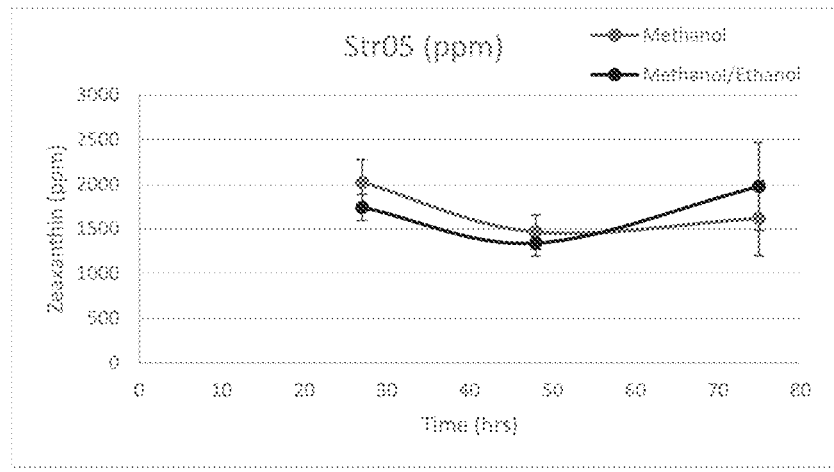
FIG. 6 shows zeaxanthin production in methanol and methanol/ethanol for strain Str05 as described in Example 7.
Figure 7:
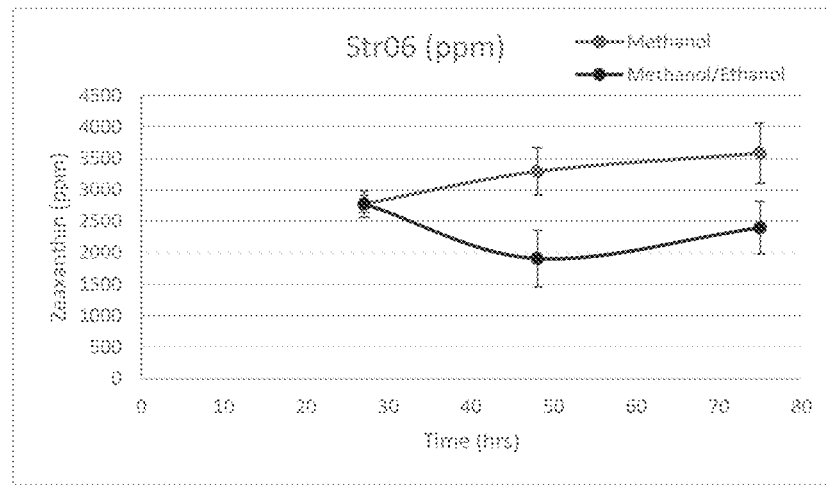
FIG. 7 shows zeaxanthin production in methanol and methanol/ethanol for strain Str06 as described in Example 7.
Figure 8:
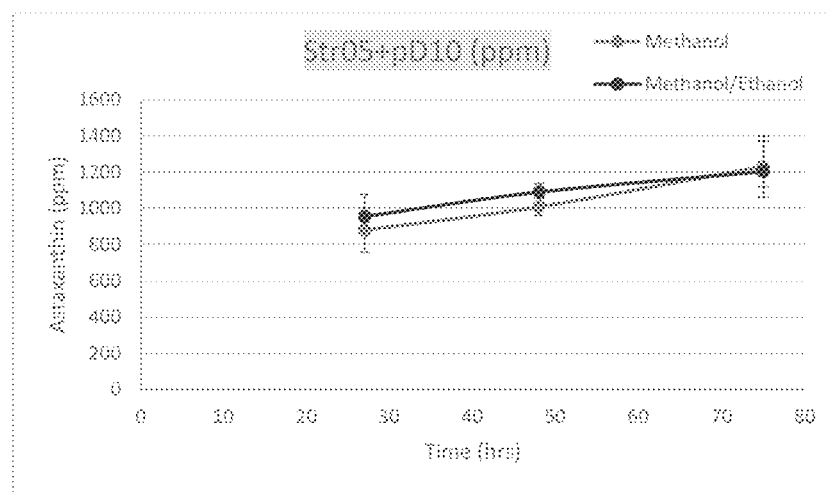
FIG. 8 shows astaxanthin production in methanol and methanol/ethanol for strain Str05+plasmid pD10 as described in Example 7.

Carotenoids were extracted from cell pellets as described in Example 2. Zeaxanthin production in strains Str05 and Str06 on methanol and methanol/ethanol is shown in FIG. 6 and FIG. 7, respectively. Astaxanthin production in strain Str05+plasmid pD10 on methanol and methanol/ethanol is shown in FIG. 8.

Figure 4A:
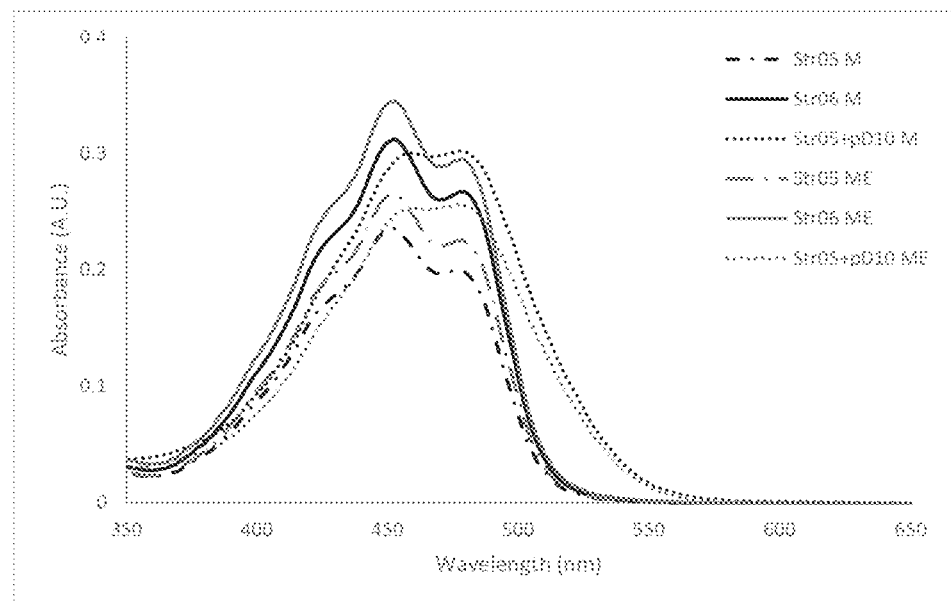
FIG. 4A shows the absorbance spectra for the strains described in Example 7.
Figure 5:
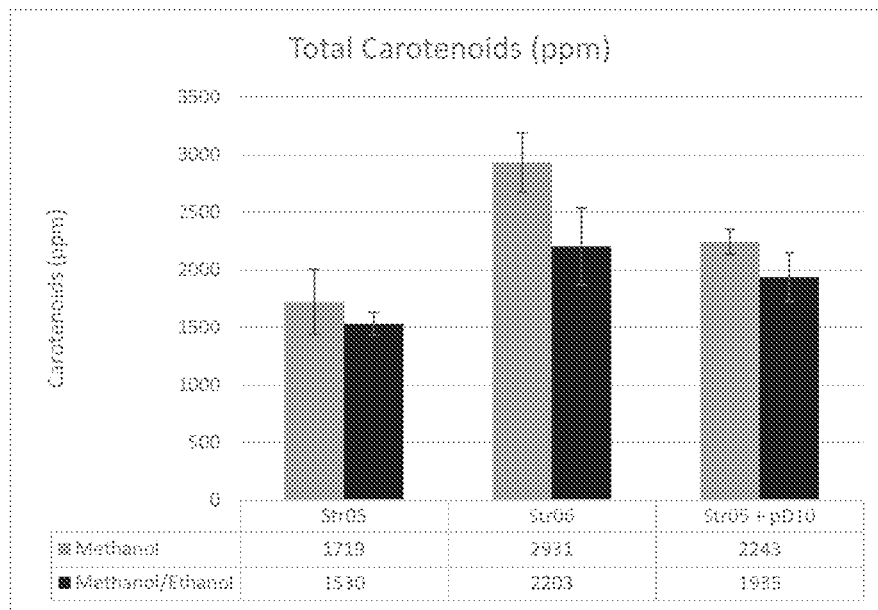
FIG. 5 shows total carotenoid production for the strains described in Example 7.

Aliquots of final time point were diluted 10× into ethyl acetate and absorbance was measured from 350-800 nm wavelengths at 1 nm intervals. Representative absorbance spectra are plotted (FIG. 4A), showing relative carotenoid levels of certain samples and peaks indicating chemical differences in carotenoids as known in the art (Rodriguez (2001) A Guide to Carotenoid Analysis in Foods). Total carotenoids were estimated based on peak absorbance and extinction coefficients reported in literature (Davies (1976) Carotenoids. In: T. W. Goodwin (Ed.) Chemistry and Biochemistry of Plant Pigments, Academic Press, London, pp. 38-165). Results are shown in FIG. 5.

Example 8

Summary:

Strains that produce astaxanthin, canthaxanthin, and lycopene were generated. *Fulvimarina pelagi* crtW gene was integrated into a zeaxanthin producing strain of *M. extorquens*. The crtZ gene and the crtZY genes were removed from the astaxanthin strain. Integrated strains were fermented in six conditions: minimal media with methanol alone or methanol and ethanol cofeed; or media made with 2% stillage syrup and methanol alone, methanol and ethanol cofeed, ethanol alone or no supplemental carbon.

The *F. pelagi* crtW, pR-faeRBS fragment and two flanking regions overlapping MEXT_3010 (SEQ ID NO: 51) and MEXT_3011 (SEQ ID NO: 52) were amplified with PCR. As in Example 1, extension primers were designed to enable restriction and ligation by AarI Gateway cloning.

Promoter and crtW were assembled with flanking regions by Gateway assembly to form integration cassette in plasmid pI. Ligation products were transformed into competent *E. coli* cells, single colonies were screened for correct assembly, and plasmid DNA was extracted by mini-prep and sequenced. The plasmid was introduced into Str06 by electroporation. Integrants were selected on kanamycin selective media and passaged onto sucrose media plates to remove markers. Red-orange isolates were selected, and the integration locus verified with PCR. Verified integration strain was designated Str07.

Deletion fragments overlapping the MEXT_3434-HP1 region (SEQ ID NOs: 5 and 7) and crtY region (SEQ ID NO: 11) were designed to delete the crtZ gene from STR07. Fragments were amplified with PCR. As in Example 1, extension primers were designed to enable restriction and ligation by AarI Gateway cloning. Deletion fragments were assembled by Gateway assembly to form deletion cassette in plasmid pI. Ligation products were transformed into competent *E. coli* cells, single colonies were screened for correct assembly, and plasmid DNA was extracted by mini-prep and sequenced. The plasmid was introduced into Str07 by electroporation. Integrants were selected on kanamycin selective media and passaged onto sucrose media plates to remove markers. Isolates were screened by PCR for the absence of crtZ and the locus sequenced to confirm deletion. Verified deletion strain was designated Str09.

A truncated section of the *P. zeaxanthinifaciens* crtZYIBE operon consisting only of the crtIBE genes with up- and down-stream non-coding regions (HP1 and HP2) was amplified with PCR and assembled into pI with 500 base pair flanking regions upstream of MEXT_3434 (SEQ ID NO: 5) and downstream of MEXT_3441 (SEQ ID NO: 6) as in Example 1. Ligation products were transformed into competent E. coli cells, single colonies were screened for correct assembly, and plasmid DNA was extracted by mini-prep and sequenced. The plasmid was introduced into Str07 by electroporation to replace full-length crtZYIBE_Pz pathway. Integrants were selected on kanamycin selective media and passaged onto sucrose media plates to remove markers. Pink isolates were selected, and the integration locus verified with PCR. Verified strain was designated Str08.

Figure 4B:
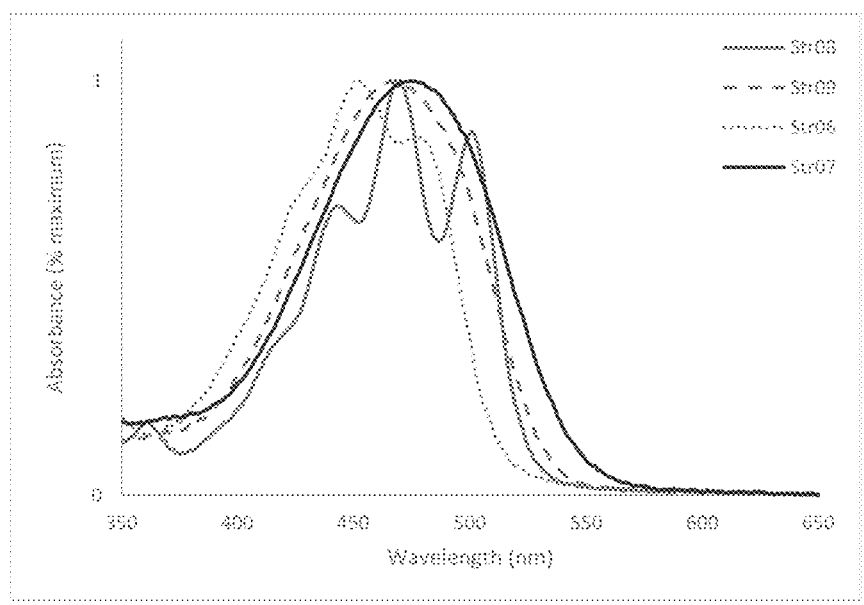
FIG. 4B shows the absorbance spectra for the strains fermented with methanol described in Example 8.

Integrated carotenoid-producing strains Str08, Str09, Str06, and Str07 were struck on solid minimal media with methanol to isolate single colonies. One colony from each plate was picked into 5 mL minimal media precultures with 0.5% methanol and grown 3 days at 30° C. Concentrated stillage syrup with sterile water and mineral solutions to a final media composition of 2% stillage syrup with supplementation of $(NH_4)_2SO_4$, $KH_2PO_4$ and $Na_2HPO_4$. Stillage media was supplemented with nothing (Stillage), 0.25% methanol (Stillage+Methanol), 0.1% methanol and 0.0625% ethanol (Stillage+Cofeed) or 0.125% ethanol (Stillage+Ethanol). Minimal media were prepared with either 0.5% methanol as the sole carbon source or 0.125% methanol and 0.2% ethanol (Cofeed). Each of the four precultures was used to inoculate one flask of each media and the set was grown with shaking for 3 days at 30° C. Cell density was measured by absorbance at 600 nm at the end of fermentation and carotenoid production assessed as described in Example 2. Absorbance spectrum measurements of extracts from minimal media methanol-fed cultures were taken as in Example 7. Representative absorbance spectra are plotted in FIG. 4B.

Figure 9:
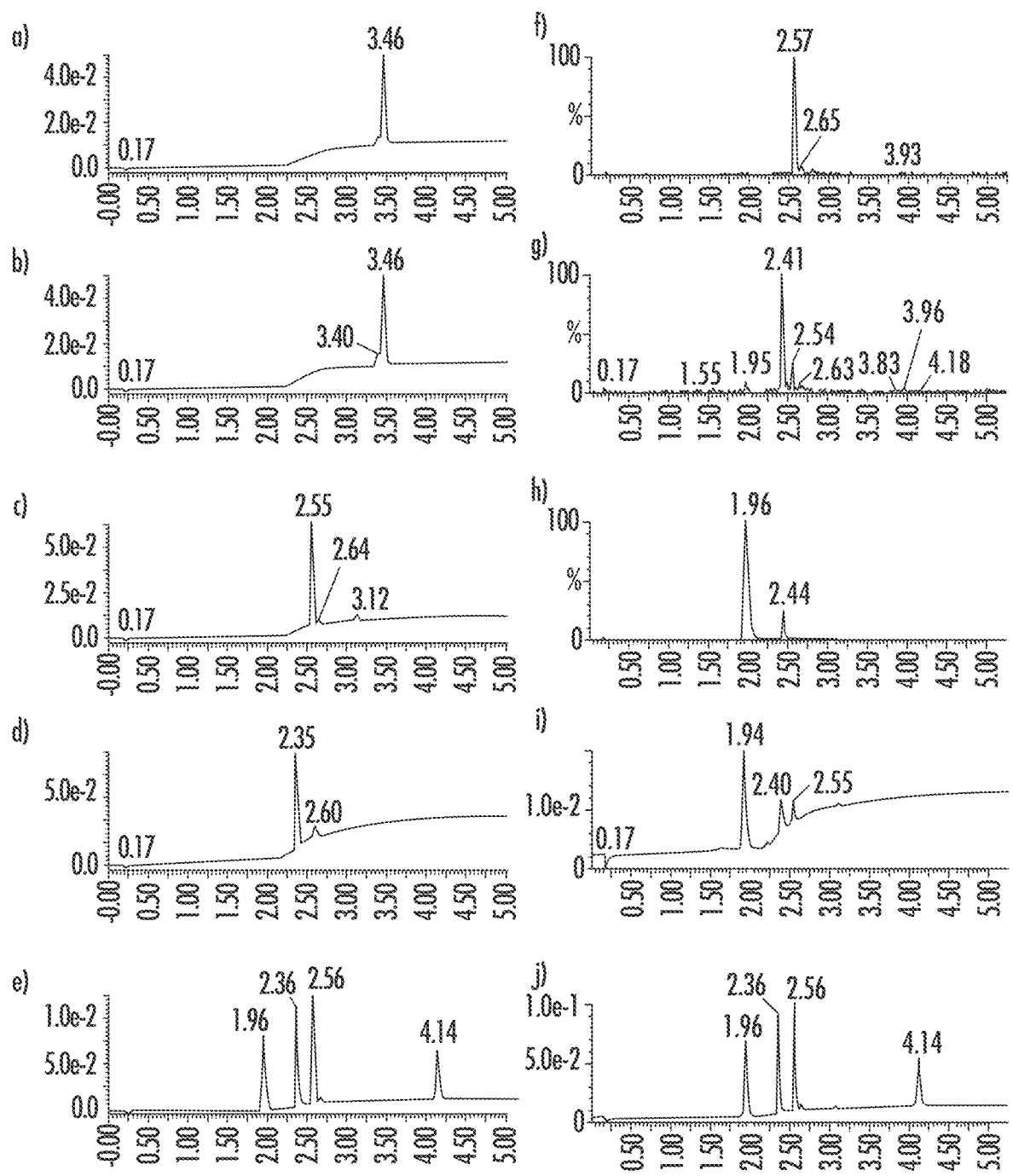
FIG. 9 shows UPLC traces of standard compound mixtures and extracts of various strains grown in minimal media with methanol as sole carbon source. Traces show absorbance at 470 nm wavelength or targeted ions.
   a. Absorbance trace of lycopene standard.
   b. Absorbance trace of Str08 extract.
   c. Absorbance trace of Str09 extract. Minor peak with retention time 3.12 minutes predicted to be cis-isomer of canthaxanthin.
   d. Absorbance trace of Str06 extract. Minor peak with retention time 2.60 minutes predicted to be cis-isomer of zeaxanthin.
   e. Absorbance trace of reference mixture of standard compounds (all trans-isomers).
   f. Mass spectrometry trace of 565.24 m/z ions of Str07 extract. Exact mass of canthaxanthin ($C_{40}H_{52}O_2$) is 564.40 Da.
   g. Mass spectrometry trace of 580.2 m/z ions of Str07 extract. Exact mass of phoenicaxanthin ($C_{40}H_{52}O_3$ is 580.39.
   h. Mass spectrometry trace of 597.4 m/z ions of Str07 extract. Exact mass of astaxanthin ($C_{40}H_{52}O_4$) is 597.38.
   i. Absorbance trace of Str07 extract.
   j. Absorbance trace of reference mixture of standard compounds (all trans-isomers): astaxanthin (retention time 1.96 minutes); zeaxanthin (retention time 2.36 minutes); canthaxanthin (retention time 2.56 minutes); beta-carotene (retention time 4.14 minutes).

Total carotenoid content calculated from absorbance spectra of methanol-fed samples and individual carotenoid content calculated from UPLC traces of all samples are reported in Table 5 and FIG. 9. Str06 produced zeaxanthin; Str07 produced mostly astaxanthin, some canthaxantin and another molecule predicted by mass spectrometry data to be phoenicaxanthin; Str08 produced lycopene, and Str09 produced canthaxanthin.

Example 9

Summary:
S. astaxanthinifaciens, F. pelagi, E. vulneris and M. zeaxanthinifaciens crtZ genes were cloned into plasmids with crtY gene from P. zeaxanthinifaciens. Plasmids were transformed into lycopene-producing strain from Example 8. Fermentations of these plasmid-bearing strains produced astaxanthin.

crtZ genes from S. astaxanthinifaciens (SEQ ID NO: 16), F. pelagi (SEQ ID NO: 50), E. vulneris (SEQ ID NO: 32) and M. zeaxanthinifaciens (SEQ ID NO: 27) were amplified via PCR with Gateway extension primers as described in Example 1. The crtY from P. zeaxanthinifaciens (SEQ ID NO: 11) was also amplified with Gateway extension primers and the faeRBS (SEQ ID NO: 4). Each crtZ was ligated with the faeRBS-crtY fragment into plasmid pA using Gateway assembly. Ligation products were transformed into competent E. coli cells, single colonies were screened for correct assembly, and plasmid DNA was extracted by mini-prep and sequenced.

Verified plasmids pA15-18 were transformed into Str08 from Example 8. Transformants were grown with kanamycin and assessed for carotenoid production as in Example 1. Fermentations with these plasmids produced astaxanthin and mixed precursors (Table 4).

Example 10

Summary:
Descendant of astaxanthin-producing strain from Example 8 with non-producing phenotype was identified to have null mutation in the crtE gene. Complementation of non-producer with E. vulneris and P. ananatis crtE genes expressed on plasmids recovered production of astaxanthin.

Astaxanthin-producing strain Str07 was grown in minimal media to high density and passaged to allow for random mutation before plating. Pale colonies were selected, and the carotenoid genes were sequenced. A white isolate with a frame-shift mutation in the crtE gene was identified and designated Str10.

The crtE gene from E. vulneris (SEQ ID NO: 36) and from P. ananatis (SEQ ID NO: 43) were amplified via PCR with Gateway extension primers as described in Example 1 and ligated into plasmid pB using Gateway assembly. Ligation products of E. vulneris gene were transformed into competent E. coli cells, single colonies were screened for correct assembly, and plasmid DNA was extracted by mini-prep and sequenced. The verified plasmids pB19 was transformed into Str10. Ligation products of P. ananatis gene were directly transformed into Str07 and pB20 containing colonies were screened for orange color.

Transformants were grown with kanamycin and assessed for carotenoid production as in Example 2. Fermentations with these plasmids produced astaxanthin and mixed precursors (Table 4).

Although the foregoing invention has been described in some detail by way of illustration and examples for purposes of clarity of understanding, it will be apparent to those skilled in the art that certain changes and modifications may be practiced without departing from the spirit and scope of the invention, which is delineated in the appended claims. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

```
Nucleotide and Amino Acid Sequences
pKB40 - plasmid sequences (FIG. 10A)
                                                                        SEQ ID NO: 1
acccacgctcaccggctccagatttatcagcaataaaccagccagccggaagggccgagcgcagaagtggtcctgcaactttatccgcctccatccagtctatt aatatccccgtgtcggacctgcagggggggggggaaagccacgttgtgtctcaaaatctctgatgttacattgcacaagataaaaatatatcatcatgaacaa taaaactgtctgcttacataaacagtaatacaagggtgttatgagccatattcaacgggaaacgtcttgctcgaggccgcgattaaattccaacatggatgct gatttatatgggtataaatgggctcgcgataatgtcgggcaatcaggtgcgacaatctatcgattgtatgggaagcccgatgcgccagagttgtttctgaaaca
```

-continued tggcaaaggtagcgttgccaatgatgttacagatgagatggtcagactaaactggctgacggaatttatgcctcttccgaccatcaagcattttatccgtactc ctgatgatgcatggttactcaccactgcgatccccgggaaaacagcattccaggtattagaagaatatcctgattcaggtgaaaatattgttgatgcgctggca gtgttcctgcgccggttgcattcgattcctgtttgtaattgtccttttaacagcgatcgcgtatttcgtctcgctcaggcgcaatcacgaatgaataacggttt ggttgatgcgagtgattttgatgacgagcgtaatggctggcctgttgaacaagtctggaaagaaatgcataagcttttgccattctcaccggattcagtcgtca ctcatggtgatttctcacttgataaccttattttttgacgaggggaaattaataggttgtattgatgttggacgagtcggaatcgcagaccgataccaggatctt gccatcctatggaactgcctcggtgagttttctccttcattacagaaacggcttttcaaaaatatggtattgataatcctgatatgaataaattgcagtttca tttgatgctcgatgagttttttctaatcagaattggttaattggttgtaacactggcagagcattacgctgacttgacgggacggaatattattgaagcatttat cagggttattgtctcatgagcggatacatatttgaatgtatttagaaaaataaacaaatagggggttccgcgcacatttccccgaaaagtgccacctgacgtcta gatctgaattcagctgtacaattggtaccatggatgGGAGggcagcaggtgGGAAAGCGGGCAGTGAGCGCAACGCAATTAATGTGAGTTAGCTCACTCATTAG

GCACCCCAGGCTTTACACTTTATGCTTCCGGCTCGTATGTTGTGTGGAATTGTGAGCGGATAACAATTTCA

CACAGGAAACAGCTATGACCATGATTACGCCAAGCTATTTAGGTGACACTATAGAATACTCAAG

CTATGCATCAAGCTTGGTACCGAGCTCGGATCCACTAGTAACGGCCGCCAGTGTGCTGGAATTCG

Figure 10B:
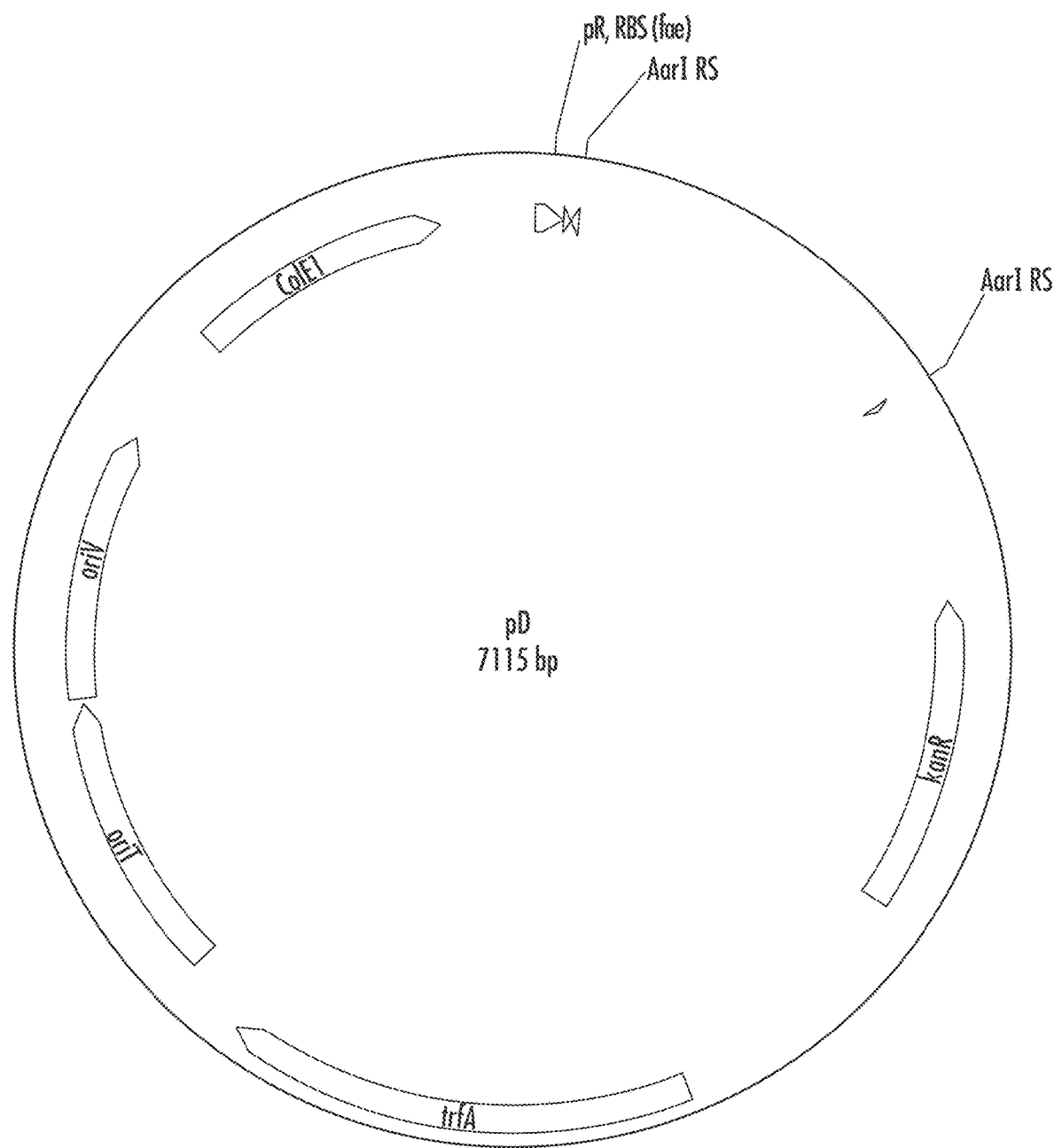
FIG. 10B shows a map of plasmid pD, as described in Examples 1 and 5.
Figure 10C:
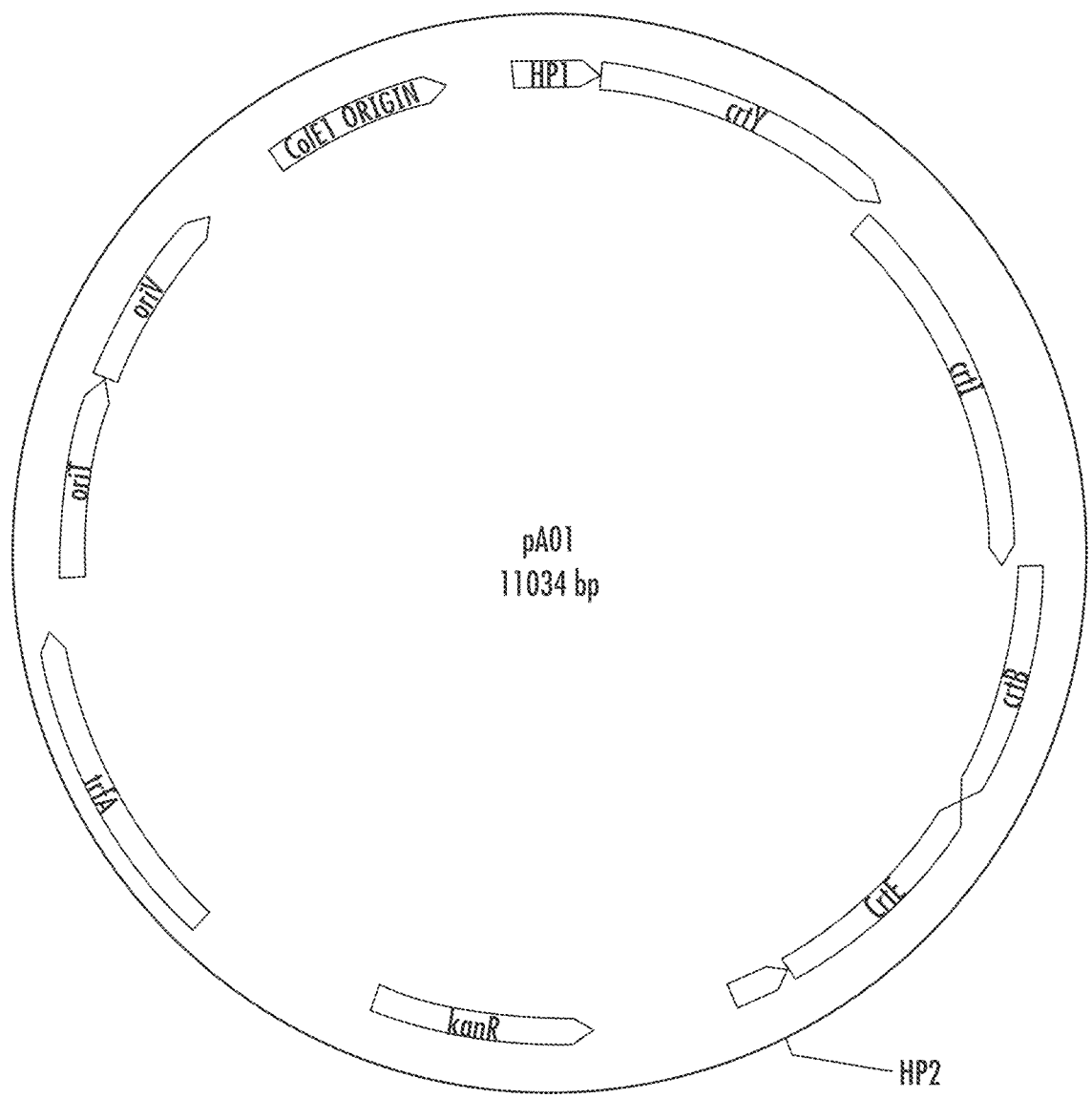
FIG. 10C shows a map of plasmid pA01, as described in Example 2. Location of AarI restriction sites labeled "AarI-RS."

CCCTTcacctgctgccAGTAcatatgctgcagctcgagcggccgcgggccctacgtacgcgtgttaaccggtgagctcactagaggatccagccgac caggcttttccacgcccgcgtgccgctccatgtcgttcgcgcggttctcggaaacgcgctgccgcgtttcgtgattgtcacgctcaagcccgtagtcccgttcg agcgtcgcgcagaggtcagcgagggcgcggtaggcccgatacggctcatggatggtgtttcgggtcgggtgaatcttgttgatggcgatatggatgtgcaggt tgtcggtgtcgtgatgcacggcactgacgcgctgatgctcggcgaagccaagcccagcgcagatgcggtcctcaatcgcgcgaacgtctccgcgtcgggctt ctctcccgcgcggaagctaaccagcacgtgataggtcttgtcggcctcggaacgggtgttgccgtgctgggtcgccatcacctcggccatgacagcgggcagg gtgtttgcctcgcagttcgtgacgcgcacgtgacccaggcgctcggtcttgccttgctcgtcggtgatgtacttcaccagctccgcgaagtcgctcttcttga tggagcgcatggggacgtgcttggcaatcacgcgcaccccccggccgttttagcggctaaaaaagtcatggctctgccctcgggcggaccacgcccatcatga ccttgccaagctcgtcctgcttctcttcgatcttcgccagcagggcgaggatcgtggcatcaccgaaccgcgccgtgcgcgggtcgtcggtgagccagagttt cagcaggccgcccaggcggcccaggtcgccattgatgcgggccagctcgcggacgtgctcatagtccacgacgccgtgattttgtagccctggccgacggcc agcaggtaggccgacaggctcatgccggccgccgccgccttttcctcaatcgctcttcgttcgtctggaaggcagtacaccttgataggtgggctgcccttcc tggttggcttggtttcatcagccatccgcttgccctcatctgttacgccggcggtagccggccagcctcgcagagcaggattcccgttgagcaccgccaggtg cgaataagggacagtgaagaaggaacaccccgctcgcgggtgggcctacttcacctatcctgcccggctgacgccgttggatacaccaaggaaagtctacacga acccttttggcaaaatcctgtatatcgtgcgaaaaaggatggatataccgaaaaaatcgctataatgaccccgaagcagggttatgcagcggaaaagcgctgct tccctgctgttttgtggaatatctaccgactggaaacaggcaaatgcaggaaattactgaactgaggggacaggcgagagacgatgccaaagagctacaccga cgagctggccgagtgggttgaatcccgcgcggccaagaagcgccggcgtgatgaggctgcggttgcgttcctggcggtgagggcggatgtcgaggcggcgtta gcgtccggctatgcgctcgtcaccatttgggagcacatgcgggaaacggggaaggtcaagttctcctacgagacgttccgctcgcacgccaggcggcacatca aggccaagcccgccgatgtgcccgcaccgcaggccaaggctgcggaacccgcgccggcacccaagacgccggagccacgcgcggccgaagcagggggcaa ggctgaaaagccggcccccgctgcggccccgaccggcttcaccttcaacccaacaccggacaaaaaggatccccaattctcatgtttgacagcttatcatcgat aagctttaatgcggtagtttatcacagttaaattgctaacgcagtcaggcaccgtgtatgaaatctaacaatgcgctcatcgtcatcctcggcaccgtcaccct ggatgctgtaggcataggcttggttatgccggtactgccgggcctcttgcgggatatcggcattttcttttgcgttttatttgttaactgttaattgtccttg ttcaaggatgctgtctttgacaacagatgttttcttgcctttgatgttcagcaggaagcttggcgcaaacgttgattgtttgtctgcgtagaatcctctgtttg tcatatagcttgtaatcacgacattgtttcctttcgcttgaggtacagcgaagtgtgagtaagtaaaggttacatcgttaggatcaagatccattttttaacaca aggccagttttgttcatgcggcttgtagggccagttaaagaattagaaacataaccaagcatgtaaatatcgttagacgtaatgccgtcaatcgtcatttttga tccgcgggagtcagtgaacaggtaccattgccgttcatttttaaagacgttcgcgcgttcaatttcatctgttactgtgttagatgcaatcagcggtttcatca ctttttttcagtgtgtaatcatcgtttagctcaatcataccgagagcgccgtttgctaactcagccgtgcgttttttatcgctttgcagaagttttgactttct tgacggaagaatgatgtgcttttgccatagtatgctttgttaaataaagattcttcgccttggtagccatcttcagttccagtgtttgcttcaaatactaagta tttgtggcctttatcttctacgtagtgaggatctctcagcgtatggttgtcgcctgagctgtagttgccttcatcgatgaactgctgtacattttgatacgttt ttccgtcaccgtcaaagattgatttataatcctctacaccgttgatgttcaaagagctgtctgatgctgatacgttaacttgtgcagttgtcagtgtttgtttg -continued ccgtaatgtttaccggagaaatcagtgtagaataaacggattttttccgtcagatgtaaatgtggctgaacctgaccattcttgtgtttggtcttttaggataga atcatttgcatcgaatttgtcgctgtctttaaagacgcggccagcgttttttccagctgtcaatagaagtttcgccgacttttttgatagaacatgtaaatcgatg tgtcatccgcatttttaggatctccggctaatgcaaagacgatgtggtagccgtgatagtttgcgacagtgccgtcagcgttttgtaatggccagctgtcccaa acgtccaggccttttgcagaagagatatttttaattgtggacgaatcgaattcaggaacttgatatttttcattttttttgctgttcagggatttgcagcatatc atggcgtgtaatatgggaaatgccgtatgtttccttatatggcttttggttcgtttctttcgcaaacgcttgagttgcgcctcctgccagcagtgcggtagtaa aggttaatactgttgcttgttttgcaaacttttttgatgttcatcgttcatgtctccttttttatgtactgtgttagcggtctgcttcttccagccctcctgttt gaagatggcaagttagttacgcacaataaaaaaagacctaaaatatgtaaggggtgacgccaaagtatacactttgcccttttacacattttaggtcttgcctgc tttatcagtaacaaacccgcgcgatttacttttcgacctcattctattagactctcgtttggattgcaactggtctattttcctcttttgtttgatagaaaatc ataaaaggatttgcagactacgggcctaaagaactaaaaaatctatctgtttcttttcattctctgtattttttatagtttctgttgcatgggcataaagttgc ctttttaatcacaattcagaaaatatcataatatctcatttcactaaataatagtgaacggcaggtatatgtgatgggttaaaaaggatcgatcctctagccac gggtgcgcatgatcgtgctcctgtcgttgaggacccggctaggctggcggggttgccttactggttagcagaatgaatcaccgatacgcgagcgaacgtgaagc gactgctgctgcaaaacgtctgcgacctgagcaacaacatgaatggtcttcggtttccgtgtttcgtaaagtctggaaacgcggaagtcagcgctcttccgctt cctcgctcactgactcgctgcgctcggtcgttcggctgcggcgagcggtatcagctcactcaaaggcggtaatacggnatccacagaatcaggggataacgcag gaaagaacatgtgagcaaaaggccagcaaaaggccaggaaccgtaaaaaggccgcgttgctggcgtttttccataggctccgcccccctgacgagcatcacaaa aatcgacgctcaagtcagaggtggcgaaacccgacaggactataaagataccaggcgtttccccctggaagctccctcgtgcgctctcctgttccgaccctgcc gcttaccggatacctgtccgcctttctcccttcgggaagcgtggcgctttctcatagctcacgctgtaggtatctcagttcggtgtaggtcgttcgctccaagc tgggctgtgtgcacgaaccccccgttcagcccgaccgctgcgccttatccggtaactatcgtcttgagtccaacccggtaagacacgacttatcgccactggca gcagccactggtaacaggattagcagagcgaggtatgtaggcggtgctacagagttcttgaagtggtggcctaactacggctacactagaaggacagtatttgg tatctgcgctctgctgaagccagttaccttcggaaaaagagttggtagctcttgatccggcaaacaaaccaccgctggtagcggtggtttatttgtitgcaagca gcagattacgcgcagaaaaaaaggatctcaagaagatcctttgatcttttctacggggtctgacgctcagtggaacgaaaactcacgttaagggattnggtcat gagattatcaaaaaggatcttcacctagatcctataaattaaaaatgaagttttaaatcaatctaaagtatatatgagtaaacttggtctgacagnaccaatgc ttaatcagtgaggcacctatctcagcgatctgtctatttcgttcatccatagttgcctgactccccgtcgtgtagataactacgatacggagggcttaccatc tggccccagtgctgcaatgataccgcgag pKB127 - plasmid sequences (FIG. 10B)

SEQ ID NO: 2 gtgtcgatggtcatcgacttcgccaaacctgccgcctcctgttcgagacgacgcgaacgctccacgcgcggccgatggcgcgcgggcagggcaggggagcca gttgcacgctgtcgcgctcgatcttggccgtagcttgctggaccatcgagccgacggactggaaggtttcgcggggcgcacgcatgacggtgcggcttgcgat ggtttcggcatcctcggcggaaaaccccgcgtcgatcagttcttgcctgtatgccttccggtcaaacgtccgattcattcaccctccttgcgggattgccccga ctcacgccggggcaatgtgcccttattcctgatttgaccgcctggtgccttggtgtccagataatccacttatcggcaatgaagtcggtcccgtagaccgtc tggccgtccttctcgtacttggtattccgaatcttgccctgcacgaataccagctccgcgaagtcgctcttcttgatggagcgcatgggacgtgcttggcaat cacgcgcaccccccggccgttttagcggctaaaaaagtcatggctctgccctcgggcggaccacgcccatcatgaccttgccaagctcgtcctgcttctcttcg atcttcgccagcagggcgaggatcgtggcatcaccgaaccgcgccgtgcgcgggtcgtcggtgagccagagtttcagcaggccgcccaggcggcccaggtcgcc attgatgcgggccagctcgcggacgtgctcatagtccacgacgcccgtgattttgtagccctggccgacggccagcaggtaggcctacaggtcatgccggccg ccgccgccttttcctcaatcgctcttcgttcgtctggaaggcagtacaccttgataggtgggctgcccttcctggttggcttggtttcatcagccatccgcttg ccctcatctgttacgccggcggtagccggccagcctcgcagagcaggattcccgttgagcaccgccaggtgcgaataagggacagtgaagaaggaacacccgct cgcgggtgggcctacttcacctatcctgcccggctgacgccgttggatacaccaaggaaagtctacacgaacccttggcaaaatcctgtatatcgtgcgaaaa aggatggatataccgaaaaaatcgctataatgaccccgaagcagggttatgcagcggaaaagatccgtcgacccttccgacgctcaccgggctggttgccctc gccgctgggctggcggccgtctatggccctgcaaacgcgccagaaacgccgtcgaagccgtgtgcgagacaccgcggccgccggcgttgtggatacctcgcgga aaacttggccctcactgacagatgaggggcggacgttgacacttgaggggccgactcacccggcgcggcgttgacagatgaggggcaggctcgatttcggccg gcgacgtggagctggccagcctcgcaaatcggcgaaaacgcctgattttacgcgagtttcccacagatgatgtggacaagcctggggataagtgccctgcggt attgacacttgagggggcgcgactactgacagatgaggggcgcgatccttgacacttgaggggcagagtgctgacagatgaggggcgcaccctattgacatttga ggggctgtccacaggcagaaaatccagcatttgcaagggtttccgcccgttttcggccaccgctaacctgtcttttaacctgcttttaaaccaatatttataa -continued accttgttttaaccagggctgcgccctgtgcgcgtgaccgcgcacgccgaaggggggtgccccccttctcgaaccctcccggcccgctaacgcgggcctccc atcccccagggctgcgccctcggccgcgaacggcctcaccccaaaaatggcagccaagctgaccacttctgcgctcggcccttccggctggctggtttatt gctgataaatctggagccggtgagcgtgggtctcgcggtatcattgcagcactggggccagatggtaagccctcccgtatcgtagttatctacacgacggggag tcaggcaactatggatgaacgaaatagacagatcgctgagataggtgcctcactgattaagcattggtaactgtcagaccaagtttactcatatatactttaga ttgatttaaaacttcattttaatttaaaaggatctaggtgaagatccttttgataatctcatgaccaaaatcccttaacgtgagttttcgttccactgagcg tcagaccccgtagaaaagatcaaaggatcttcttgagatcctttttttctgcgcgtaatctgctgcttgcaaacaaaaaaaccaccgctaccagcggtggtttg tttgccggatcaagagctaccaactctttttccgaaggtaactggcttcagcagagcgcagataccaaatactgttcttctagtgtagccgtagttaggccacc acttcaagaactctgtagcaccgcctacatacctcgctctgctaatcctgttaccagtggctgctgccagtggcgataagtcgtgtcttaccgggttggactca agacgatagttaccggagcagcggtcgggctgaacgggggggttcgtgcacacagcccagcttggagcgaacgacctacaccgaactgagatacctacagcgtga gctatgagaaagcgtaaggcccacgcttcccgaagggagaaaggcggacaggtatccggtaagcggcagggtcggaacaggagagcgcacgagggagcttccag ggggaaacgcctggtatctttatagtcctgtcgggtttcgccacctctgacttgagcgtcgatttttgtgatgctcgtcaggggggcggagcctatggaaaaac gccagcaacgcggcctttttacggttcctggccttttgctggccttttgctcacatgttctttcctgcgttatcccctgattctgtggataaccgtattaccgc ctttgagtgagctgataccgctcgccgcagccgaacgaccgagcgcagcgagtcagtgagcgaggaagcggaagagcgcccaatacgcaaaccgcctctccccg cgcgttggccgattcattaatgcagctggcacgacaggtttcccgactACTAGTccaacaacttataccatggcctacaaaaaggcaaacaatggtacttgacg actcatcacaacaattgtagngtagcagggagagaccccgaGGTACCgatCCTAGCAGGTGGTGCCGCTGGCGACCTGCGTTTCACCCTGC

CATAAAGAAACTGTTACCCGTAGGTAGTCACGCAACTCGCCGCACATCTGAACTTCAGCCTCCAG

TACAGCGCGGCTGAAATCATCATTAAAGCGAGTGGCAACATGGAAATCGCTGATTTGTGTAGTC

GGTTTATGCAGCAACGAGACGTCACGGAAAATGCCGCTCATCCGCCACATATCCTGATCTTCCAG

ATAACTGCCGTCATTCCAGCGCAGCACCATCACCGCGAGGCGGTTTTCTCCGGCGCGTAAAAATG

CGCTCAGGTCAAATTCAGACGGCAAACGACTGTCCTGGCCGTAACCGACCCAGCGCCCGTTGCA

CCACAGATGAAACGCCGAGTTAACGCCATCAAAAATAATTCGCGTCTGGCCTTCCTGTAGCCAGC

TTTCATCAACATTAAATGTGAGCGAGTAACAACCCGTCGGATTCTCCGTGGGAACAAACGGCGG

ATTGACCGTAATGGGATAGGTCACGTTGGTGTAGATGGGCGCATCGTAACCGTGCATCTGCCAGT

TTGAGGGGACGACGACAGTATCGGCCTCAGGAAGATCGCACTCCAGCCAGCTTTCCGGCACCGC

TTCTGGTGCCGGAAACCAGGCAAAGCGCCATTCGCCATTCAGGCTGCGCAACTGTTGGGAAGGG

CGATCGGTGCGGGCCTCTTCGCTATTACGCCAGCTGGCGAAAGGGGGATGTGCTGCAAGGCGAT

TAAGTTGGGTAACGCCAGGGTTTTCCCAGTCACGACGTTGTAAAACGACGGCCAGTGAATCCGT

AATCATGGTCATAGCTGTTTCCTGTGTAAAATTGTTATCCGCTCACAATTCCACACAACATACGA

GCCGGAAGCATAAAGTGTAAAGCCTGGGGTGCCTAATGAGTGAGCTAACTCACATTAATTGCGT

TGCGCTCACCTGCTAGGGCCTGGATCCATGGTTTAAACtcaggaattcacgtgcgcacctgtgctgggcgcgctgtcggat cgtdcgggcggcggccaatcttgctcgtctcgctggccggcgccactgtcgactacgccatcatggcgacagcgcctttcctttgggttctctatatcgggcgga tcgtggccggcatcaccggggcgactggggcggtagccggcgcttatattgccgatgacctgcaggggggggggcgctgaggtctgcctcgtgaagaa ggigttgctgactcataccaggcctgaatcgcccatcatccagccagaaagtgagggagccacggttgatgagagctttgngtaggtggaccagttggtgattt tgaactittgctttgccacggaacggtctgcgttgtcgggaagatgcgtgatctgatccttcaactcagcaaaagttcgatttattcaacaaagccgccgtcccg tcaagtcagcgtaatgctctgccagtgttacaaccaattaaccaattctgattagaaaaactcatcgagcatcaaatgaaactgcaatttattcatatcaggatt atcaataccatatttttgaaaaagccgtttctgtaatgaaggagaaaaactcaccgaggcagttccataggatggcaagatcctggtatcggtctgcgattccgac tcgtccaacatcaatacaacctattaatttccctcgtcaaaaataaggttatcaagtgagaaatcaccatgagtgacgactgaatccggtgagaatggcaaaag cttatgcatttctttccagacttgttcaacaggccagccattacgctcgtcatcaaaatcactcgcatcaaccaaaccgttattcattcgtgattgcgcctgagc gagacgaaatacgcgatcgctgttaaaaggacaattacaaacaggaatcgaatgcaaccggcgcaggaacactgccagcgcatcaacaatattttcacctgaatc aggatattcttctaatacctggaatgctgttttcccggggatcgcagtggtgagtaaccatgcatcatcaggagtacggataaaatgcttgatggtcggaagagg -continued

```
cataaattccgtcagccagtttagtctgaccatctcatctgtaacatcattggcaacgctacctttgccatgtttcagaaacaactctggcgcatcgggcttccc atacaatcgatagattgtcgcacctgattgcccgacattatcgcgagcccatttatacccatataaatcagcatccatgttggaatttaatcgcggcctcgagca agacgtttcccgttgaatatggctcataacacccccttgtattactgtttatgtaagcagacagttttattgttcatgatgatatattttttatcttgtgcaatgta acatcagagattttgagacacaacgtggctttccccccccccctgcaggtccgacacggggatggatggcgttcccgatcatggtcctgcttgcttcgggtggc atcggaatgccggcgctgcaagcaatgttgtccaggcacgtggatgaggaacgtcagggcagctgcaaggctcactggcggcgctcaccagcctgacctcgatc cgtcggacccctcctcttcacggcgattatgcggcttctataacaacgtggaacgggtgggcatggattgcaggcgctgccctctacttgctctgcctgccggcg ctgcgtcgcgggctttggagcggcgcagggcaacgagccgatcgctgatcgtggaaacgataggcctatgccatgcgggtcaaggcgacttccggcaagctatac gcgccctagaattgtcaatttttaatcctctgtttatcggcagttcgtagagcgcgccgtgcgtcccgagcgatactgagcgaagcaagtgcgtcgagcagtgccc gcttgttcctgaaatgccagtaaagcgctggctgctgaaccccagccggaactgaccccacaaggccctagcgtttgcaatgcaccaggtcatcattgacccag gcgtgttccaccaggccgctgcctcgcaactcttcgcaggcttcgccgacctgctcgcgccacttcttcacgcgggtggaatccgatccgcacatgaggcggaag gtttccagcttgagcgggtacggctcccggtgcgagctgaaatagtcgaacatccgtcgggccgtcggcgacagcttgcggtacttctcccatatgaatttcgtg tagtggtcgccagcaaacagcacgacgatttcctcgtcgatcaggacctggcaacgggacgttttcttgccacggtccaggacgcggaagcggtgcagcagcgac accgattccaggtgcccaacgcggtcggacgtgaagcccatcgccgtcgcctgtaggcgcgacaggcattcctcggccttcgtgtaataccggccattgatcgac cagcccaggtcctggcaaagctcgtagaacgtgaaggtgatcggctcgccgatagggtgcgcttcgcgtactccaacagctgctgccacaccagttcgtcatcg tcggcccgcagctcgacgccggtgtaggtgatcttcacgtccttgttgacgtggaaaatgaccttgttttgcagcgcctcgcgcgggattttcttgttgcgcgtg gtgaacagggcagagcgggccgtgtcgtttggcatcgctcgcatcgtgtccggccacggcgcaatatcgaacaaggaaagctgcatttccttgatctgctgcttc gtgtgtttcagcaacgcggcctgcttggcctcgctgacctgttttgccaggtcctcgccggcggttttcgcttcttggtcgtcatagttcctcgc
``` pmxaF - promoter
Source: *Methylobacterium extorquens* PA1

SEQ ID NO: 3

```
gttgacgacaacggtgcgatgggtcccggccccggtcaagacgatgccaatacgttgcgacactacgccttggcacttttagaattgccttatcgtcctgataag aaatgtccgaccagctaaagacatcgcgtccaatcaaagcctagaaaatataggcgaagggacgctaataagtctttcataagaccgcgcaaatctaagaatatc cttagattcacgatgcggcacttcggatgacttccgagcgagcctggaacctcagaaaaacgtctgagagataccgcgaggccgaaaggcgaggcggttcag cgaggagacgcagg
```

Pr-faeRBS - promoter-ribosome binding site from MEXT_1384

SEQ ID NO: 4

```
ccaacaacttataccatggcctacaaaaaggcaaacaatggtacttgacgactcatcacaacaattgtagttgtagcagggagagaccccga
```

Flank 1 - 500bp flanking region upstream of MEXT_3434
Source: *Methylobacterium extorquens* PA1

SEQ ID NO: 5

```
caccgcgcgggacttcatcttgccccggcagatgcgcagggcctccaccgtgcgctcgatcgccgcctcggtgaggcgattggaattgcccaatccctcgcc gagccggacgatgcgggagaaggcgtcgatcacccggaagccgttgggcgtcggctcggcgaccagaaggcggcaattgttggtgccgagatcgagcgc ggcataggcgtcgcgtcggccgtgccgaccggtttcgtagcggggagggaagctctcgatcgggcgtccgcccgtgaccgtgcgggaaccctcccgcgctg tctgcgggtcggcggtggggcgggccgacacggcggcggcgctctcatccctcatcgacgcgaccgaacttcctggcgatgcagcccggcaagacgccgg gccgacgtggcaccaaggctacaggcgttattcaggaactgcaaaggctggatggccggccttacacgatttgccgcatggattgtttcgcgaaaagtccc
```

Flank2 - 500bp flanking region downstream of MEXT_3441
Source: *Methylobacterium extorquens* PA1

SEQ ID NO: 6

```
cgccccaagactcccaacctgatatcgtcggcgcaatcttggccggaagcgggcgaggggcaagaggcacggattgtcgcgtgccgccggtctcgaccggt tccggccgcgttcagggccgccgccgacgcagcgggagcacggcagcggcgccgatctgtgggccggtctcggcgtcgagatcgggcacggcgatgatc ggcgcgccgcgcaggtcccggcgcatgacgatagcgccgcgctcctccagatagcccagcatgcgccgggcacgccccgccgaggaggtgccgtaggc ctccgcgagcgccgcgtcggaagggcagggcgaaccttcgagcgccgtgcgggcgatgagcaggaacaacccggccagatcctccggcagaccggcgg cgatctcctgcgcccgctcccaaccgggtccctcggcggtggcgcccgtggacgccggcccgcgccacggcgagccgccgcttgaactcgggcaggcccat cgcc
```

-continued

CrtZ, pPzZ, HP1
Source: *Paracoccus zeaxanthinifaciens*

SEQ ID NO: 7 gactaggtctttcccttgccggaacaatcggctaaagccttccgcagtcggggcgtagcgcagcctggtagcgcgacggttttgggtaccgtaggtcggaggtt cgaatcctctcgccccgaccatcttcgggaaaacattaatatttccagcgacggaacgcgtgatgcgcctgccg crtE, pPzE, HP2
Source: *Paracoccus zeaxanthinifaciens*

SEQ ID NO: 8 ccgcatccgtctgcatcggcggggcgaggcgacggccatcgcgctggaacggctgagctaattcatttgcgcgaatccgcgttttttcgtgcacgatggggga accggaaacggccacgcctgttgtggttgcgtcgacctgtcttcgggccatgcccgtgacgcgatgtggcaggcgcatgggcgttgccgatccggtcgcatg actgacgcaacgaaggcaccg crtZYIBE, PzC40 cluster
Source: *Paracoccus zeaxanthinifaciens*

SEQ ID NO: 9 gactaggtctttcccttgccggaacaatcggctaaagccttccgcagtcggggcgtagcgcagcctggtagcgcgacggttttgggtaccgtaggtcggaggtt cgaatcctctcgccccgaccatcttcgggaaaacattaatatttccagcgacggaacgcgtgatgcgcctgccgcgttcggcggcgaatgtcacggatgatccg cctatgagccctgaacgcagatgtcacgcgatgccctttggtcgcaccccgatgggctggtcatgcaccgcgcggcagcgtagcctgttccctgtcatatcaag caaggggccggcatgagcacttgggccgcaatcctgaccgtcatcctgaccgtcgccgcgatggagctgacggcctactccgtccatcggtggatcatgcatg gcccctgggctggggctggcataaatcgcaccacgacgaggatcacgaccacgcgctcgagaagaacgacctctatggcgtcatcttcgcggtaatctcgat cgtgctgttcgcgatcggcgcgatggggtcggatctggcctggtggctggcggtgggggtcacctgctacgggctgatctactatttcctgcatgacggcttggt gcatgggcgctggccgttccgctatgtccccaagcgcggctatcttcgtcgcgtctaccaggcacacaggatgcatcacgcggtccatgccgcgagaactgc gtcagcttcggtttcatctgggcgccctcggtcgacagcctcaaggcagagctgaaacgctcgggcgcgctgctgaaggaccgcgaaggggcggatcgcaa tacatgagccatgatctgctgatcgcgggcgcggggctgtccggtgcgctgatcgcgcttgccgttcgcgaccgcagaccggatgcgcgcatcgtgatgctcg acgcgcggtccggcccctcggaccagcacacctggtcctgccacgacacggatcttttcgcccgaatggctggcgcgcctgtcgcccattcgtcgcggcgaat ggacggatcaggaggtcgcgtttcccgaccattcgcgccgcctgacgacaggctatggctcgatcgaggcgggcgcgctgatcgggctgctgcagggtgtc gatctgcggtggaatacgcatgtcgcgacgctggacgataccggcgcgacgctgacggacggctcgcggatcgaggctgcctgcgtgatcgacgcccgtgg tgccgtcgagaccccgcacctgaccgtgggtttccagaaattcgtgggcgtcgagatcgagaccgacgcccccatggcgtcgagcgcccgatgatcatgga cgcgaccgttccgcagatggacgggtaccgcttcatctatctgctgcccttcagtcccacccgcatcctgatcgaggatacgcgctacagcgacggcggcgatc tggacgatggcgcgctggcgcaggcgtcgctggactatgccgccaggcggggctggaccgggcaggagatgcggcgcgaaaggggcatcctgcccatcg cgctggcccatgacgccataggcttctggcgcgaccacgcgcaggggcggtgccggttgggctgggggcagggctgttccacccgtcaccggatattcg ctgccctatgccgcgcaggtcgcggatgccatcgcggcgcgcgacctgacgaccgcgtccgcccgtcgcgcggtgcgcggctgggccatcgatcgcgcgg atcgcgaccgcttcctgcggctgctgaaccggatgctgttccgcggctgcccgcccgaccgtcgctatcgcctgctgcagcggttctaccgcctgccgcagcc gctgatcgagcgcttctatgccgggcgcctgacattggccgaccggcttcgcatcgtcaccggacgcccgcccattccgctgtcgcaggccgtgcgctgcctg cccgaacgcccccctgctgcaggagagagcatgagttccgccatcgtcatcggcgcaggtttcggcgggcttgcgcttgccatccgcctgcaatcggccgcat cgcgaccaccatcgtcgaggcccgcgacaagcccggcggccgcgcctatgtctggaacgatcagggccacgtcttcgatgcaggcccgacggtcgtgacc gaccccgacagcctgcgagagctgtgggccctcagcggccaaccgatggagcgtgacgtgacgctgctgccggtctcgccttctaccggctgacatgggc ggacggccgcagcttcgaatacgtgaacgacgacgacgagctgatccgccaggtcgcctccttcaatccgccgatgtcgatggctatcgccgcttccacgatt acgccgaggaggtctatcgcgaggggtatctgaagctggggaccacgcccttcctgaagctgggccagatgctgaacgccgcccgcgctgatgcgcctg caggcataccgctcggtccacagcatggtggcgcgcttcatccaggacccgcatctgcggcaggccttctcgttccacacgctgctggtcggcgggaacccgt tttcgaccagctcgatctatgcgctgatccatgcgctggaacggcgcggcggcgtctggttcgcaagggcggcaccaaccagctggtcgcgggcatggtcg ccctgttcgagcgtcttggcggcacgctgctgctgaatgcccgcgtcacgcggatcgacaccgagggcgatcgcgccacgggcgtcacgctgctggacggg cggcagttgcgcgcggatacggtggccagcaacggcgacgtgatgcacagctatcgcgacctgctgggccataccgccgcgggcgcaccaaggccgcg atcctgaaccggcagcgctggtcgatgtcgctgttcgtgctgcatttcggcctgtccaagcgccccgagaacctggcccaccacagcgtcatcttcggcccgcg ctacaaggggctggtgaacgagatcttcaacgggccacgcctgccggacgatttctcgatgtatctgcattcgcctgcgtgaccgatcccagcctggccccg aggggatgtccacgcattacgtccttgcgcccgttccgcatctgggccgcgccgatgtcgattgggaagccgaggccccgggctatgccgagcgcatcttcga

```
ggaactggagcgccgcgccatccccgacctgcgcaagcacctgaccgtcagccgcatcttcagccccgccgatttcagcaccgaactgtcggcccatcacgg
cagcgccttctcggtcgagccgatcctgacgcaatccgcctggttccgcccgcataaccgcgaccgcgcgatcccgaacttctacatcgtgggggcgggcac
gcatccgggtgcgggcatcccgggtgtcgttggcagcgccaaggccacggcgcaggtcatgctgtcggacctggccgtcgcatgaccgatctgacggcgac
ttccgaagcggccatcgcgcagggttcgcaaagcttcgcgcaggcggccaagctgatgccgcccggcatccgcgaggatacggtcatgctctatgcctggtg
caggcatgcggatgacgtgatcgacgggcaggtCatgggttctgccccgaggcgggcggcgacccacaggcgcggctggatgcgctgcgcgccgacac
gctggccgcgctgcacgaggacggcccgatgtcgccgcccttcgcggcgctgcgccaggtcgcccggcggcatgatttcccggacctttggccgatggacc
tgatcgagggtttcgcgatggatgtcgcggatcgcgaataccgcagcctggatgacgtgctggaatattcctaccacgtcgcggggtcgtgggcgtgatgatg
gcgcgggtgatgggcgtgcaggacgatgcggtgctggatcgcgcctgcgatctgggccttgcgttccagctgacgaacatcgctcgcgacgtgatcgacgat
gccgccatcgggcgctgctatctgcctgccgactggctggccgaggcggggcgacggttgagggtccgtgccttcggacgcgctctattccgtcatcatcc
gcctgcttgacgcggccgagccctattatgcctcggcgcggcaggggcttccgcatctgccgccgcgctgcgcgtggtcgatcgccgccgcgctgcgtatcta
tcgcgcaatcgggacgcgcatccggcagggtggccccgaggcctatcgcagcggatcagcacgtcgaaggctgccaagatcgggcttctggcgcgcgga
ggcttggacgcggccgcatcgcgcctgcgcggcggtgaaatcagccgcgacggcctgtggacccgaccgcgcgcctaggcgctgcggcggatgtcatgc
ggcagcacgcgggccagcaggtccgcgatctgcccccgcggaacagccgggtgcgcatcagctcgtccagttgcgcgcggctggcgcggtaatgctgcg
ccacgtcgcccatctgtccgaccgccatcaggccgcgctttgggccgggggcggcggtgtcgcgccccgtatccttgccggtgctggccttgtcgccgatcac
gtccagcaggtcgtcataggactggaagacccgaccaagctgacgcccgaaggccatgagctgctcggtctcggccttgtccagaccccttaataatggacagc
atctcgaggcccgcgacgaacagcacgccggtcttgaggtcctgttcacgttcgatcccggcggcgtccttgggggcgtgcaggtccagatcctgccctgcgc
acagccccaccggtcccatcgcgcgcgacatggatgcgaccagccttgcgcgctgatccggcgtcgccgcgcgcctcgcccaaaatccgcatggcctcg
gtgatcagggcgatgcccgcaagcaccgcgcgcccctcgccatgggcgacatggtggcgggctgaccgcgacgggtcctggcatcgtccatgcagggca
tgtcgtcgaagatcagcgatgcggcatggaccatctcgaccgcgcaggcggcatcgaccatcgcatcgcagaccccgcccgagctttcggcgaccatcagca
tcagcacggcgcgaaagcgtttgccggggacagggcggcatcgctcatggccgcgccgagcggggccgagaccacgccgaactggcccgagatctgc
gccagcctgatctcgaccagatcgcgtaggggaattgctgcttgggcgtcatcggtgccttcgttgcgtcagtcatgcgaccggatcggcaacgcccatgcg
cctgccacatcgcgtcacgggcatggcccgaagacaggtcgacgcaaccacaacaggcgtggccgtttccggttcccccatcgtgcacgaaaaacgcggatt
cgcgcaaatgaattagctcagccgttccagcgcgatggccgtcgcctcgcccccgccgatgcagacggatgcgg
``` crtZ_Pz
Source: *Paracoccus zeaxanthinifaciens*
SEQ ID NO: 10

MSTWAAILTVILTVAAMELTAYSVHRWIMEGPLGWGWHKSHHDEDHDHALEKNDLYGVIFAVISIV

LFAIGAMGSDLAWWLAVGVTCYGLIYYFLHDGLVHGRWPFRYVPKRGYLRRVYQAHRMHHAVHG

RENCVSFGFIWAPSVDSLKAELKRSGALLKDREGADRNT* crtY_Pz
Source: *Paracoccus zeaxanthinifaciens*
SEQ ID NO: 11

MSHDLLIAGAGLSGALIALAVRDRRPDARIVMLDARSGPSDQHTWSCHDTDLSPEWLARLSPIRRGE

WTDQEVAFPDHSRRLTTGYGSIEAGALIGLLQGVDLRWNTHVATLDDTGATLTDGSRIEAACVIDAR

GAVETPHLTVGFQKFVGVEIETDAPHGVERPMIMDATVPQMDGYRFIYLLPFSPTRILIEDTRYSDGG

DLDDGALAQASLDYAARRGWTGQEMRRERGILPIALAHDAIGFWRDHAQGAVPVGLGAGLFHPVT

GYSLPYAAQVADAIAARDLTTASARRAVRGWAIDRADRDRFLRLLNRMLFRGCPPDRRYRLLQRFY

RLPQPLIERFYAGRLTLADRLRIVTGRPPIPLSQAVRCLPERPLLQERA* crtI_Pz
Source: *Paracoccus zeaxanthinifaciens*
SEQ ID NO: 12

MSSAIVIGAGFGGLALAIRLQSAGIATTIVEARDKPGGRAYVWNDQGHVFDAGPTVVTDPDSLRELW

ALSGQPMERDVTLLPVSPFYRLTWADGRSFEYVNDDDELIRQVASFNPADVDGYRRFHDYAEEVYR

EGYLKLGTTPFLKLGQMLNAAPALMRLQAYRSVHSMVARFIQDPHLRQAFSFHTLLVGGNPFSTSSI

YALIHALERRGGVWFAKGGTNQLVAGMVALFERLGGTLLLNARVTRIDTEGDRATGVTLLDGRQLR

ADTVASNGDVMESYRDLLGHTRRGRTKAAILNRQRWSMSLFVLHFGLSKRPENLAHHSVIFGPRYK

GLVNEIFNGPRLPDDFSMYLHSPCVTDPSLAPEGMSTHYVLAPVPHLGRADVDWEAEAPGYAERIFE

ELERRAIPDLRKHLTVSRIFSPADFSTELSAHHGSAFSVEPILTQSAWFRPHNRDRAIPNFYIVGAGTHP

GAGIPGVVGSAKATAQVMLSDLAVA* crtB_Pz
Source: *Paracoccus zeaxanthinifaciens*
SEQ ID NO: 13

MTDLTATSEAAIAQGSQSFAQAAKLMPPGIREDTVMLYAWCRHADDVIDGQVMGSAPEAGGDPQA

RLDALRADTLAALHEDGPMSPPPFAALRQVARRHDFPDLWPMDLIEGFAMDVADREYRSLDDVLEYS

YHVAGVVGVMMARVMGVQDDAVLDRACDLGLAFQLTNIARDVIDDAAIGRCYLPADWLAEAGAT

VEGPVPSDALYSVIIRLLDAAEPYYASARQGLPHLPPRCAWSIAAALRIYRAIGTRIRQGGPEAYRQRIS

TSKAAKIGLLARGGLDAAASRLRGGEISRDGLWTRPRA* crtE_Pz
Source: *Paracoccus zeaxanthinifaciens*
SEQ ID NO: 14

MTPKQQFPLRDLVEIRLAQISGQFGVVSAPLGAAMSDAALSPGKRFRAVLMLMVAESSGGVCDAMV

DAACAVEMVHAASLIFDDMPCMDDARTRRGQPATHVAHGEGRAVLAGIALITEAMRILGEARGATP

DQRARLVASMSRAMGPVGLCAGQDLDLHAPKDAAGIEREQDLKTGVLFVAGLEMLSIIKGLDKAET

EQLMAFGRQLGRVFQSYDDLLDVIGDKASTGKDTGRDTAAPGPKRGLMAVGQMGDVAQHYRASR

AQLDELMRTRLFRGGQIADLLARVLPHDIRRSA* crtZYIBW, Sa C40 cluster
Source: *Sphingomonas astaxanthinifaciens* DSM 22298
SEQ ID NO: 15 atgatgaagcgcgcggacctggtgatcgtcggtggaggactggccggcggcctgtgcgccctcgccttcgccgccgccgccctgacctcaggctgctgctg gtcgagccggggccaagcatcggcggcaaccatctctggtccttcttcgaaagcgacgtcgcccccgccgaccgctggctgaccgacccgctgatccggcat cgctggcccgattacgaggtccgcttcccggcgcaccagcgccacctcgccgaagcctatcagaccatcgagagcgaggcgctcgacgaggccgtgcgca aggcccttccgccgaggagatcgtccgggccgaagccaccgaccttggcccgacccacgtcaccctcgcgaccggcgagcggatcgaggcgaaggcgg tgctcgacgcgcgcggggggcaaagccgaggggctcgatctcggctggcagaaattcctcggccagctgctgaccatcccgcagggccacggcctcacccgt ccgatcgtgatggacgcgacggtcgaccagcatgacggctatcgcttcgtctactgcctgcccttcagcccgaccgaactcttcgtcgaggacacttattacagc gacggggccgagctcgaccacgaccgattgcgtgaccggatcggcgattatgccgcggcacagggctggcaggtcgcggaccgcagccgcgaggagcat ggccgcgctgccagtggtgatcggcggcgatttcgaccggctgtggcccgccgccgaccatgtcgcccgggccggcgcgcgcggcggtttcttccatccgct gaccagctattcgctgcccgacgcggtccgcttcgccatctggctggcggacaaggccacgttcgacgcccggctcggggccgcgacccgcgcgcggggc cgccgccactggaggtcgggtgccttctaccggctgctcaccgcgctcctgttccacgcgccgagcccggccagcgctacctcgtgctggagcgtttctacc gcctttccggccccttgatcggccgcttctacgcggggatgagcaccggctatgacaaggcgcgcgtgctcgcgggcaagccgccggtgcccttcttccggg cactcagggtattgagggacagcttgtgaagagtgcaatcgtgatcggtgccggcttcggcggcctggcgctggccatccgcctccagtcggccggggtgaa gaccaccatcgtcgaggcccgcgaccggcccggcggccgcgcctatgtctgggaaaaggacggccacgtgttcgacgcgggcccgaccgtgatcaccgat cccgactgtctccagcggctgtggaagctgtcgggccacgacatgtcggaggatgtcgagctcgtcccggtcaagcccttctaccggctctcctggcccgacg gcgtggtgttcgattacaccaatgacgacgccgagctcaaagccgcgatggacgcactcaatcccgacgactgggcgggctaccagcgcttcctcgcctatag cgccggggtctataacgagggctatgtgaagctcgggaccaaggcgtttgaaagcctcggcgacatgctcaaggccgcgcccgcgctcgccaaatatcagg cttggcggtcggtctattcgatcgtgtcgagcttcgtgaaggacgagcacctgcgccagaccttgtccttccacacgctgctggtcggcggcaatccgatgacct gctcgtcgatctacgcgctgatccacaagctcgagcgcgacggcggggtgtggttcgcaagggcgggaccaacaagctgatcgccggcatggtccgccag ttcgagcggatcggcgggaccattcgccttggcgatccggtcactgcgatcctggccgagaacgatcgggtcaccggggtgcgcaccgcctcgggttggagc gccaccgccgacgcggtgcctccaatggcgacgtggtccacagctatggcctgatcgagggttccgaccgcggccagcaacaggtccgcgccctcaagc gcaagcgtttctcgcccggcctgttcgtgctccatttcgggctcgaggggacgtcggacctcgcccaccacgatcctgttcggcccgcgctacggcggcctc gtcaacgacatctacaagaccgggcggctcgcgaccgaccccgtcgctctacatccaccacccgaccatcaccgacccgtccatggcgccgccgggctgctc -continued

```
gaccttctacgcgcttgccccgtccccaatgccggcaaggccgatgtcgactgggcggtcgaggggccgaaatatcaggaggtcgtgctcgacacgatcgc
cgagcggctgatccccgacgtgcgccagcggatccggaccatcttccattacaccccggccgatttctcggccgacctcgccgcccacctcggctccgcattc
agcctcgagccggtgctgtggcagtcggcctggttccgcacccacaatcgcgacgacaagctcaggaacctctatttcgtcggtgccggcactcacccaggcg
cggggatcccggggggtggtcggaagcgccgaggcgactgcggggctgatgctggcgtgagcgaagctgacgaacgggcacggctggtccaggccgcgc
tggaaagcatttcggcgggctccaagagttttcgcttcgccagccagttgttcgaccagcagacccgagagcgcagctggctgctctacagctggtgccgcgc
ctgcgacgacgtgaccgacggccagaccctgggccatgatgcggagcgggtcgacgatcccgccgcccgcctcgccttcctcaaggcgaagaccgccgag
gcgttcgcgggccaaccgacgggacttgtccccttcgacgcactgcgcgtggtcgccgccgaatgcgcgattccccaggccgtcgccggcgaccatctcgcc
gggttcgagcgcgacgccgggggtggcggccgaccacgaccgacgacctcctctcttattgctaccaggttgctggcgcggtgggcgtgatgatggcgca
cgtcatgggcgtgccgcccgaggacgaggacacgctcaaccgcgcagccgacttggggatcgccttccagctcgccaatatcgcccgcgacatcgtcgacg
atgccaaggtcgggcgggtctatctgcccgccgaatggcttgccgccgagggctggccggggccgacctcgccgatcccgcgcatcgcccggccctcgc
gcgcctcgcccaccgcctcgccgacatggccgacgcctatcgcgctcggcccgggtcggcgcggcccgcctgcccttccgcagccgctgggcggtgctc
gcggccagcggcatctacggcgagatcgcgacccgcgccgccgcgctcgggccccgcgcctgggacgagcggatcaccacctcgaaggcggaaaaggc
cgcgctggtgatggaggccttctgggaagccttgtggcgggtcaggcccgctcctcgtgacgggctgtggacccgccccgcgcacgcctgagctgcgcctc
gcggctggcctggagcgcctgcttcagccgctcgaccggcggggcgtaaaggaagccgaagctcaccgcccgtcgcggctctcgaccgcatggtgcagc
ttgtgcgcctggacgatccgcttgaaataggtcgaacgcggcacgatccggtgcggcagccggccgtggacgatgacgtcgtgaaagccgaaatagatcacc
ccgtagaaggccaccccggcccccatccacgtcgcccagtcgccccagccgccattgagcccgccccagatcagcaggatcgagggcaaagcgaagacc
acggcatagaggtcgttccgctcgaaccagccggtccgcgcgcgatgatggctttcgtgccagttccagccgagccgcgagtgcatcacgaagcggtggag
gacataggcgaagccctccatcagaaggaccgtcgatacgaacagggcgagaccggcaggccaggacat
``` crtZ_Sa
Source: *Sphingomonas astaxanthinifaciens* DSM 22298

SEQ ID NO: 16

MSWPAGLALFVSTVLLMEGFAYVLHRFVMHSRLGWNWHESHHRARTGWFERNDLYAVVFALPSIL

LIWGGLNGGWGDWATWMGAGVAFYGVIYFGFHDVIVHGRLPHRIVPRSTYFKRIVQAHKLHHAVE

SRDGAVSFGFLYAPPVERLKQALQASREAQLRRARGGSTARHEERA* crtY_Sa
Source: *Sphingomonas astaxanthinifaciens* DSM 22298

SEQ ID NO: 17

MMKRADLVIVGGGLAGGLCALALRRRRPDLRLLLVEPGPSIGGNHLWSFFESDVAPADRWLTDPLIR

HRWPDYEVRFPAHQRHLAEAYQTIESEALDEAVRKALSAEEIVRAEATDLGPTHVTLATGERIEAKA

VLDARGGKAEGLDLGWQKFLGQLLTIPQGHGLTRPIVMDATVDQHDGYRFVYCLPFSPTELFVEDTY

YSDGPELDHDRLRDRIGDYAAAQGWQVADRSREEHGALPVVIGGDFDRLWPAADHVARAGARGGF

FHPLTSYSLPDAVRFAIWLADKATFDARLGAATRARGRRHWRSGAFYRLLTALLFHAAEPGQRYLV

LERFYRLSGPLIGRFYAGMSTGYDKARVLAGKPPVPFFRALRVLRDSL* crtI_Sa
Source: *Sphingomonas astaxanthinifaciens* DSM 22298

SEQ ID NO: 18

VKSAIVIGAGFGGLALAIRLQSAGVKTTIVEARDRPGGRAYVWEKDGHVFDAGPTVITDPDCLQRLW

KLSGHDMSEDVELVPVKPFYRLSWPDGVVFDYTNDDAELKAAMDALNPDDWAGYQRFLAYSAGV

YNEGYVKLGTKAFESLGDMLKAAPALAKYQAWRSVYSIVSSFVKDEHLRQTLSFHTLLVGGNPMTC

SSIYALIHKLERDGGVWFAKGGTNKLIAGMVRQFERIGGTIRLGDPVTAILAENDRVTGVRTASGWS

ATADAVASNGDVVHSYGLIEGSDRGQQQVRALKRKRFSPGLFVLHFGLEGTSDLAHHTILFGPRYGG

LVNDIYKTGRLATDPSLYIHHPTITDPSMAPPGCSTFYALAPVPNAGKADVDWAVEGPKYQEVVLDTI

AERLIPDVRQRIRTIFHYTPADFSADLAAHLGSAFSLEPVLWQSAWFRTHNRDDKLRNLYFVGAGTHP

GAGIPGVVGSAEATAGLMLA* crtB_Sa
Source: *Sphingomonas astaxanthinifaciens* DSM 22298

SEQ ID NO: 19

VSEADERARLVQAALESISAGSKSFRFASQLFDQQTRERSWLLYSWCRACDDVTDGQTLGHDAERV

DDPAARLAFLKAKTAEAFAGQPTGLVPFDALRVVAAECAIPQAVAGDHLAGFERDAGGWRPTTTDD

LLSYCYQVAGAVGVMMAHVMGVPPEDEDTLNRAADLGIAFQLANIARDIVDDAKVGRVYLPAEWL

AAEGLAGADLADPAHRPALARLAHRLADMADAYRRSARVGAARLPFRSRWAVLAASGIYGEIATR

AAALGPRAWDERITTSKAEKAALVMEAFWEALWRVRPAPRDGLWTRPAHA* crtW_Sa
Source: *Sphingomonas astaxanthinifaciens* DSM 22298

SEQ ID NO: 20

MAPMLSDAQRRRQAMIGLGLAAAITAAFVALHVWSVFFLPLEGAGWWLALPIVAVQTWLSVGLFIV

AHDAMHGSLAPGRPATNLFWGRLTLLLYAGFWLDRLSPKHFDHHRHVGTERDPDFSVDHPTRFWP

WYYAFMRRYFGLREYLVLNALVLAYVLVLKAPLGNLLLFWALPSILSSIQLFYFGTYLPHRHEDAPF

ADQHNARSNDFPVWLSLLTCFHFGYHREHHLSPGTPWWQLPRRRRELALPA crtZYIB, Sz cluster
Source: *Siansivirga zeaxanthinifaciens* CC-SAMT-1

SEQ ID NO: 21 atgaaaaaagaaataataattatcggttcaggttttcgtctctagcagcatcctgctatttggcgaaagcaggttataatgtaactttattagaaaaaacaa
cactattggaggcagagctcgacaattagttaaagacggttttactttcgatataggtccaacttggtattggatgcccgatgtatttgaacgcttcttcaatg
attttgataaaaaaccttcagattactatagtcttgaaaaactgaatcccgcatacagtgttatttttgaaaaaacgactacattaccattgaagatacatta
gcgaaatttctgaagcatttgaaaaagaagaacctggaagttcaaaaaaactaaacacctttattgaaaaagctaaaagcaactacgatatagcaattaaaga
tttggtttataaccctggcgtatcgcctctagaattggttactattgctactataaaaaaattagaccaattctttagtaacataaaaagagatgttagaaaag
aatttaaaaatgaaaggttagtaaaaattcttgaatttcctgttttatttttaggagcaaaaccaagcgatacaccttcgttttatagttttatgaattatgca
gattttggccttgggacgtttcatccaaaaaaggcatgtatcaagttatcctagcgcttgaaaatctggcaaaatctcttggtgttattataaaaacaaatgc
tcccatagaaaaaattatcattgaaaacaacgaagtaaaaggtgttatttcaaatggaaaaacaataaataccaacattgttgttagtggagccgattaccatc
ataccgaaacgttattagataaaacatacagacaatatagtgagtcttactggagtaaaaagacttttgcaccgtcatcactactattttatgtaggtttcgat
aaaaagattcaaaatgtaaatcatcacacattattttttgatgtagattttgatgtacatgcagaagccatatacgatactccaaaatggcccgaagaaccact
tttttacgcaagttttcctagtataacggatgctaacagcgcccagaaggtaaagaagctggcatatttttaatacccttagcgccaggattagaagatacag
aagcgttaagagaagcctatttgaaaaaattatgacacgttttgaggccttaactagtcaaaatattaaaaaacatgttatatttaaagagagttttgtatc
aatgattttataaaagattataattcttacaaaggaaacgcttacggaatggctaatacaattacccaaaccgcattttaagacccaaattaaaaagtaaaa
agttaaaggtttatttttacaggtcaattaacagttcctggtcccggtgtaccaccatcattaatttcaggaaagttagtagcagatttagtaaccaaacacc
attctttatgaaagcattatttgataccgtttcatacaattgcagcaaattagtaacaaaatcttatagcacttcattttcgcttgctactaaaatgctataca
aatctataagacccgatatttacaacatttacggatttgttagatttgctgatgagattgtagattcgtttcatgattttaataaagaagaactacttaacaaa
tttgaagccgatttagagcatgctctcgaacataggtaagtttaaaccctatttaaatgccttccagtacacataccataagaataaaatagagaaaagcat
ggtcgatgctttatgaaagtatgcgacttgatttacataaaactcaatacctaacaaacgaagagtacaaagaatacattacggttctgcagatgttgtag
gacttatgtgtttaaaggttttgtgaatggtgataacgaaaaatttgaagctttaaaagatacagccatggcacttggttctgcttttcaaaaagttaacttt
ttaagagatttaaaagatgattacgaaggtttaaacagaacatatttcccgaataccgatttaaataaccttgatgaacaatcgaaactagatattattcaaga
tattgaaaaagattttgaaaaaggcttaacaggaattaaaaaattaccaattgaggctaaatttggtgttttatggcttacagatattatcatcaattgctta
aaaaacttaaaaaaacacctgcttttaatattaaaaacaccagaatacgcgtttcaaatcctaaaaaaatagaattattaatgcgtagttatgtaaaatatcaa
ttaaaattaatgtaaatttatagtatgcaaacactattatggataatcattttttagcaacgtattgtatcatggaatttatggcgtggtttacgcataaata
cattatgcatggcttttatggagtttacacaaagaccatcacaagaaagatcacgatagttggttcgaaagaaacgatgctttttttatattttatgctattg
ttagcataggttgtttttttactttggaaatacgacatattttgggctggtttacccattggcgttggtatttttgcttatggattatcatactttttggtacac
gatatatttattcatcaacgttttaaattatttagaaatgccaataactggtatgctaaaggtgtaagacgtgctcacaaaatgcaccacaaacatattggaaa
agaagatggcgaatgctttggtatgttgtttgttcctttaaatacttcaagaaataattttctattaattacatgatatctaacacccatttcgattatatca -continued

```
ttattggaaatggattagcagggcttcagttggcattaaaaatgagtgctgatgtttattttaaagataaacgcatcgctttaatagatggttctaacaaaaac acaaacgataaaacctggagttttttgggaagaaaactcatctcaatgggatgccattacaactaaaagttggaatattgccaacatttacacttccaaaaaca tatttcattagcactttgcccctataaatataaatctatacgttctatagatttatataattatgcgaaattcgagcttcaaaaacattctaattttttcattta taattgattttgtatgtactaccacagaaacagaagataaaaaggtattagtagaaacttcctctaataaattcactgcctcacatgttttttgatagtagaatt ccagaagatttttttcaaaaaaataaaaattacacacacataattcaacacttttaaaggctatgtaattaaaacagaagaagcctattttaatgacgacacctt cacgatgatggattatcgattgaaagatggtgaacaaaccacatttacctatgtactgcctttttcaaaaacagaagctttaatagaattttacctattttacag aaaatttagttaatgaagccgtttatgatgcattcattgaaaaatacataaaaaactatcttaaaattgactcgtatttaattatggaaacagaataggtcaa attcctatgactaatttccccatttgcaaggttcaatacaaaaaatataacgaaaataggcactggtggtggatgggtaaaggggtctacgggttattcttttaa acataccgaaaaaaaaatatctaaaatcatcgaaaatattaaagctaacaacataccaagcgctcacttatttaagaaaaggtatcgtttttatgacaaaatat ttttaaaggttttaaaagataacaaccacaaaggcgaatggattttttgagcaattttacaacaaaaattctcctcaaaatatgtttaaatttcttgatgaagaa tctactttttttgatgaattaaaaaattatgtattcattattctctttgccttttattaaagcattttttcaagacccttttcaaataa
``` crtZ_Sz
Source: *Siansivirga zeaxanthinifaciens* CC-SAMT-1

SEQ ID NO: 22

MQTLLWIIIFLATYCIMEFMAWFTHKYIMEGFLWSLHKDHHKKDHDSWFERNDAFFIFYAIVSIGCFL

LWKYDIFWAGLPIGVGIFAYGLSYFLVHDIFIHQRFKLFRNANNWYAKGVRRAHKMEHKHIGKEDG

ECFGMLFVPFKYFKK* crtY_Sz
Source: *Siansivirga zeaxanthinifaciens* CC-SAMT-1

SEQ ID NO: 23

MISNTHFDYIIIGNGLAGLQLALKMSADVYFKDKRIALIDGSNKNTNDKTWSFWEENSSQWDAITTKS

WNIANIYTSKKHISLALCPYKYKSIRSIDLYNYAKFELQKHSNFSFIIDFVCTTTETEDKKVLVETSSNK

FTASHVFDSRIPEDFFQKNKNYTHIIQHFKGYVIKTEEAYFNDDTFTMMDYRLKDGEQTTFTYVLPFS

KTEALIEFTYFTENLVNEAVYDAFIEKYIKNYLKIDSYLIMETEIGQIPMTNFPFARFNTKNITKIGTGG

GWVKGSTGYSFKHTEKKISKIIENIKANNIPSAHLFKKRYRFYDKIFLKVLKDNNHKGEWIFEQFYNK

NSPQNMFKFLDEESTFFDELKIMYSLFSLPFIKAFFKTLFK* crtI_Sz
Source: *Siansivirga zeaxanthinifaciens* CC-SAMT-1

SEQ ID NO: 24

MKKEIIIIGSGFSSLAASCYLAKAGYNVTLLEKNNTIGGRARQLVKDGFTFDIGPTWYWMPDVFERFF

NDFDKKPSDYYSLEKLNPAYSVYFGKNDYITIEDTLAKISEAFEKEEPGSSKKLNTFIEKAKSNYDIAIK

DLVYNPGVSPLELVTIATIKKLDQFFSNIKRDVRKEFKNERLVKILEFPVLFLGAKPSDTPSFYSFMNY

ADFGLGTFHPKKGMYQVILALENLAKSLGVIIKTNAPIEKIIIENNEVKGVISNGKTINTNIVVSGADYH

HTETLLDKTYRQYSESYWSKKTFAPSSLLFYVGFDKKIQNVNHHTLFFDVDFDVHAEAIYDTPKWPE

EPLFYASFPSITDANSAPEGKEAGIFLIPLAPGLEDTEALREAYFEKIMTRFEALTSQNIKKHVIFKESFCI

NDFIKDYNSYKGNAYGMANTITQTAFLRPKLKSKKVKGLFFTGQLTVPGPGVPPSLISGKLVADLVT

KHHSL* crtB_Sz
Source: *Siansivirga zeaxanthinifaciens* CC-SAMT-1

SEQ ID NO: 25

MKALFDTVSYNCSKLVTKSYSTSFSLATKMLYKSIRPDIYNIYGFVRFADEIVDSFHDFNKEELLNKFE

ADLEHALEHRVSLNPILNAFQYTYHKNKIEKSMVDAFMKSMRLDLHKTQYLTNEEYKEYIYGSADV

VGLMCLKVFVNGDNEKFEALKDTAMALGSAFQKVNFLRDLKDDYEGLNRTYFPNTDLNNLDEQSK

LDIIQDIEKDFEKGLTGIKKLPIEAKFGVFMAYRYYHQLLKKLKKTPAFNIKNTRIRVSNPKKIELLMRS

YVKYQLKLM* crtZYIB, Mz C40 cluster
Source: *Mesoflavibacter zeaxanthinifaciens* DSM 18436

-continued

SEQ ID NO: 26
```
atgaaaaataaaatagcaataataggttctgggttttctgctttatctgctgcatgttatcttgctaaggatggatttaatgtttcagttttgaaaaaaatga
tactgtaggaggacgttgtagacagttaaaaaagatggatttacttttgatatgggaccaagctggtattggatgcctgatatatttgataagttttttaatg
attttgataaaaaaacttcagattttatcagctagacaagctttctcctgcgtataaaattttctttaatgatgaagttatcaccataggagatacaatggag
aaaatttgcgaagaatttgaacgcatagaaaaggaagttcaattcctcttaaaaaatttataaataaagctgcagataattataacattgccataaacaaaat
tgtattaaaaccaggtgtttcacccttagaattggttactaaagatactgttactagactagatcaatttttttaaaacaataagcagtgatgttagacgccagt
ttaaaaaccctaaactaatatctactttagagtttcctgttttgttttgggtgcaaaaccaagcaatacaccttcttttatagttttatgaattacgccgat
tttggcttaggtacttggcatcctaaaggcggaatgtatcaaataattcttgcaatgagacaacttgcagaagaattaggtgtttcaataaatgtaaactctaa
tgttactaatattaatgttgaaaataatacatcaacatcaattactgttaacggtaaaacttaaagtttgatgttgttttaagcggtgcagattatcatcact
cagaaacgttgttagatagaaaatatagacagtattcagaaaaatattggaacaataaaaccttgctccttcttctctcctattttacgtaggttttgataag
aaattgaaaaatgtaaaccatcataacttatttttttgataccaactttgaaacgcatgcagaagatatttacgataatccaaatggcctaaagaacctctatt
ttatgccaatttcccatctgtaacagataacagcatggcgcctaatggtaaagaaaatggttttttcttaataccaattgctcctaacttagaagatacacctc
aattaagagaacaatattttgatataatcatgtctcgttttgaaaaattaactcaacaagatgttaaaaatagtattatctttaaagaaagcttttgtgttaaa
gattttattgaagcatataattcctacaaaggaaacgcatacggaatggctaatacgctaacgcaaaccgcttttttaagaccaaatttaaagagtaaaaagt
taacaacctctactttacaggacaattaactgttcctggtccaggtgtgccgccagcacttatatctggaaaattagtagcagaattaatccaaaaacaccacc
aaaaactatgaaagcaatatttgattctgtgtcgtacaattgtagtaaagttgttactacatcttacagcacttcgttttctttagctacaaaaatgcttgcaa
agtctatcagacaggatatttataatatttatggttttgtgaggtttgcagatgagattgtagacacttttcatgattatgataaagaaactttatttaacaat
tttgaaaatgatttagaattagctctaaaaaacaaaattagcctaaatccaatattaaatgcgtttcaacatacatatcacaagtataacatcgaaaaacatat
ggttgatgcttttatgaaaagtatgcgactagatttatctaaaactaaatacactacagaccaagagtataaagattatatttatggttctgcagacgtagttg
gactaatgtgtttaaaagtctttgttaaaggagataatgatcaatacgaaaaacttaaagacacagcaatgtcattaggttctgcttttcaaaaggtgaatttt
ttacgagacttaaaagctgatcacgaattacttgatagaacttatttcccaaatacagatttaaataatctaactgaagaagataaactattcatcattaatga
tattgaaaacgattttaaaaaaggcttagaaggtataaaaacaattacctatggaggctaaatttggagtatttatggcttatagatactatcaccagttactgg
caaagcttaaaaaaacaccagcattagaaaattaaaaatactagaataagagtaccaaactacaaaaaggcagaacttttaactagaagctacgtaaagtatcag
ttaaatttattataattagacatgaaaacattgtattggatattaatattttaggcacattttctatcatggaatttatggcatggtttacacataaatacat
catgcacggatttttatggtcactacataaagaccatcatctaaaagatcacgatagctggtttgagcgtaatgatgcctttttatcttttatgcaattgtaa
gtatgacttgcttttacttatggagttacgaagatatatggtatacattaccaataggcttaggcattatggcttatggtgcagcttacttcttagtacacgat
atttttatccatcaacgctttaaaatgtttagaaatgctaataattggtacgcacgtggtgttagacgtgcacacaaaatacatcacaagcatataggcaaaga
agatggagaaaactttggcatgttagtcgtaccatttaagtacttcaaaaaatagactaaatgtctcaaaaacattatgattatatcatagttggcaatggttt
agctggacttcaattagccttagcttttgccaaggattcatatttttaataataaatccattgctttaatagacgcttctactaaaactgaaaatgataaaactt
ggagttttttgggaacaaaacaatagcacttttagtcatttaacttaccaatcctggcaacatgcaactatctacgcagaagaccaaaaaataagcttaaatcta
aaaccttatacttataaatctatacgtgcaatagacttttatacggaagctaaagcacaactcaatcagcaagacaatattacatttttggtggaaaccgtgac
ttcggttaaagaaaaagaaatagttgaagtcacaaccaaaacaaacaactatacgacaaatcatgttttttgatagtcggattccagacgcgtttttttaaagatg
aaaaagccacaactttaatacaacattttaaaggctggattatagaagctgaaaacgatgttttttaatgaaaacagcttaacaatgatggattatcgattaaaa
gataataatcaaacaaccttttatgtatgtgttaccgcatacaaaaaataaagcgttagtagaatttacatattttacggaaaacactgttaaaagtgaccatta
cgacaactatttaaagcaatatatttcagaatatttaaacattaataattataatattgtcgaaactgaagttggtcaaataccaatgacaacttttaattttc
aattgtttaactcttccaaaatcactaaaattggtacagctggcggttgggtaaaaccttctacgggatattcttttaaactcacagaaaaaagagttgcaaaa
attattgagaatataaaaaaccaatcaaccaaccacaaacggatttttttaaaaacaagtataaattttacgacaaagtatttttacaagtttaaaagataataa
tgaaaaggcgaatgggttttttaatcaattttacagtaaaaaatagcacaccaaccatgttttaaattttttagatgaagagtcttcacttttttgaagacattaaaa
ttatgtggtcgttatttagtttcagttttattaaagcttttttttaaaacgcttttaa
``` crtZ_Mz
Source: *Mesoflavibacter zeaxanthinifaciens* DSM 18436

SEQ ID NO: 27

MKTLYWILIFLGTFSIMEFMAWFTHKYIMEGFLWSLHKDHHLKDHDSWFERNDAFFIFYAIVSMTCF

YLWSYEDIWYTLPIGLGIMAYGAAYFLVHDIFIHQRFKMFRNANNWYARGVRRAHKIHHKHIGKED

GENFGMLVVPFKYFKK* crtY_Mz
Source: *Mesoflavibacter zeaxanthinifaciens* DSM 18436
SEQ ID NO: 28

MSQKHYDYIIVGNGLAGLQLALAFAKDSYFNNKSIALIDASTKTENDKTWSFWEQNNSTFSHLTYQS

WQHATIYAEDQKISLNLKPYTYKSIRAIDFYTEAKAQLNQQDNITFLVETVTSVKEKEIVEVTTKTNN

YTTNHVFDSRIPDAFFKDEKATTLIQHFKGWITEAENDVFNENSLTMMDYRLKDNNQTTFMYVLPHT

KNKALVEFTYFTENTVKSDHYDNYLKQYISEYLNINNYNIVETEVGQIPMTTFNFQLFNSSKITKIGTA

GGWVKPSTGYSFKLTEKRVAKIIENIKTNQPTTNGFFKNKYKFYDKVFLQVLKDNNEKGEWVFNQF

YSKNSTPTMFKFLDEESSLFEDIKIMWSLFSFSFIKAFFKTL* crtI_Mz
Source: *Mesoflavibacter zeaxanthinifaciens* DSM 18436
SEQ ID NO: 29

MKNKIAIIGSGFSALSAACYLAKDGFNVSVFEKNDTVGGRCRQFKKDGFTFDMGPSWYWMPDIFDK

FFNDFDKKTSDFYQLDKLSPAYKIFFNDEVITIGDTMEKICEEFERIEKGSSIPLKKFINKAADNYNIAIN

KIVLKPGVSPLELVTKDTVTRLDQFFKTISSDVRRQFKNPKLISTLEFPVLFLGAKPSNTPSFYSFMNYA

DFGLGTWHPKGGMYQIILAMRQLAEELGVSINVNSNVTNINVENNTSTSITVNGKTLKFDVVLSGAD

YHHSETLLDRKYRQYSEKYWNNKTFAPSSLLFYVGFDKKLKNVNHHNLFFDTNFETHAEDIYDNPK

WPKEPLFYANFPSVTDNSMAPNGKENGFFLIPIAPNLEDTPQLREQYFDIIMSRFEKLTQQDVKNSIIFK

ESFCVKDFIEAYNSYKGNAYGMANTLTQTAFLRPNLKSKKVNNLYFTGQLTVPGPGVPPALISGKLV

AELIQKHHQKL* crtB_Mz
Source: *Mesoflavibacter zeaxanthinifaciens* DSM 18436
SEQ ID NO: 30

MKAIFDSVSYNCSKVVTTSYSTSFSLATKMLAKSIRQDIYNIYGFVRFADEIVDTFHDYDKETLFNNFE

NDLELALKNKISLNPILNAFQHTYHKYNIEKHMVDAFMKSMRLDLSKTKYTTDQEYKDYIYGSADV

VGLMCLKVFVKGDNDQYEKLKDTAMSLGSAFQKVNFLRDLKADHELLDRTYFPNTDLNNLTEEDK

LFIINDIENDFKKGLEGIKQLPMEAKFGVFMAYRYYHQLLAKLKKTPALEIKNTRIRVPNYKKAELLT

RSYVKYQLNLL* crtZYIBE-idi, Ev C40 cluster
Source: *Escherichia vulneris*
SEQ ID NO: 31 atggtgagtggcagtaaagcgggcgtttcgcctcatcgcgaaatagaagtaatgagacaatccattgacgatcacctggctggcctgttacctgaaaccgacag ccaggatatcgtcagccttgcgatgcgtgaaggcgtcatggcacccggtaaacggatccgtccgctgctgatgctgctggccgcccgcgacctccgctaccag ggcagtatgcctacgctgctcgatctcgcctgcgccgttgaactgacccataccgcgtcgctgatgctcgacgacatgccctgcatggacaacgccgagctgc gccgcggtcagcccactacccacaaaaaatttggtgagagcgtggcgatccttgcctccgttgggctgctctctaaagcctttggtctgatcgccgccaccggcg atctgccgggggagaggcgtgcccaggcggtcaacgagctctctaccgccgtgggcgtgcagggcctggtactggggcagtttcgcgatcttaacgatgccg ccctcgaccgtaccccttacgctatcctcagcaccaaccacctcaagaccggcattctgttcagcgcgatgctgcagatcgtcgccattgcttccgcctcgtcgc cgagcacgcgagagacgctgcacgccttcgccctcgacttcggccaggcgtttcaactgctggacgatctgcgtgacgatcacccggaaaccggtaaagatc gcaataaggacgcgggaaaatcgacgctggtcaaccggctgggcgcagacgcggcccggcaaaagctgcgcgagcatattgattccgccgacaaacacct cacttttgcctgtccgcagggcggcgccatccgacagtttatgcatctgtggtttggccatcaccttgccgactggtcaccggtcatgaaaatcgcctgataccg ccctttgggttcaagcagtacataacgatggaaccacattacaggagtagtgatgaatgaaggacgagcgccttgttcagcgtaagaacgatcatctggatatc gttctcgaccccgtcgcgccgtaactcaggctagcgcaggttttgagcgctggcgctttacccactgcgccctgccagagctgaattttagcgacatcacgctg gaaaccaccttcctgaatcggcagctacaggctccgctgctgatcagctccatgaccggcggcgttgagcgctcgccatatcaaccgccacctcgccgaggcg gcgcaggtgctaaaaattgcgatgggggtgggctcccagcgcgtcgccattgagagcgacgcgggcttagggctggataaaacccctgcggcagctggctcc -continued

```
ggacgtgccgctgctggcgaacctcggcgcggcgcagctgaccggcagaaaaggtattgattacgcccgacgggccgtggagatgatcgaggcggatgcg
ctgattgtgcacctaaacccgctgcaggaggcgctacagcccggcggcgatcgcgactggcgcggacggctggcggctattgaaactctggtccgcgagct
gcccgttccgctggtggtgaaagaggtgggagccggtatctcccgaaccgtggccgggcagctgatcgatgccggcgttaccgtgattgacgtcgcgggcgc
gggcggcaccagctgggccgccgttgaaggcgagcgggcggccaccgagcagcagcgcagcgtggccaacgtctttgccgactgggggatccccaccg
ctgaggcgctggttgacattgccgaggcctggccgcagatgccccttattgcctcgggcgggattaaaaacggcgtcgacgcggcgaaagcgctgcggctcg
gcgcgtgcatggtagggcaggccgccgccgtgctcggcagcgcaggcgtctccacggagaaggtgatcgatcacttcaacgtgattattgagcagctgcggg
tggcctgcttctgcaccggcagccgcagcctgagcgatctaaagcaggctgatatccgctatgtgcgggatacgccatgagccattttgccattgtggcaccgc
cgctctacagtcatgcggtggcgctgcatgccctggcgctggagatggcccaacgcggccaccgggtgacctttctcaccggcaacgtcgcctcgctggcag
agcaggaaacggagcgggtggcgttctatccacttcccgccagcgtgcaacaggcccagcgcaacgtccagcagcagagtaacggcaacctgctgcggct
gattgcggccatgtcatccctgaccgatgtgctctgccagcagttgcccgctattctacagcggctggcggtggacgcgctgattgtcgatgagatggagcccg
ccggaagcctggtcgccgaggcgctgggactaccatttatctctattgcctgcgcgctgccggtcaaccgcgagccgggtctgccgctgccggtgatgccgttt
cactacgccgaggataagagagccctgcggcgttttcaggtcagcgaacggatctacgatgcgctgatgtacccgcacgggcagacgatcctgcgccacgcc
cagcgctttggtttgccggagcgcaggcgtctcgacgagtgtctctcgccgctggcgcagattagccagtccgttccggccctcgacttcccacgccgggcgct
gccgaactgttttcactacgtgggagcactgcgctatcagccgccgccgcaggtagaacgctcgccacgcagcacgccgcggatctttgcctcgctgggcacc
ctccagggccaccgtctacgcctgtttcagaagatcgcccgcgcctgtgccagcgtgggggcggaggtgaccattgcccactgcgatggcctgacgcccgcc
caggccgactcgctctacgcctgcggcgcgacggaggtggtcagctttgtcgaccagccgcgctacgttgccgaggctaatctggtgatcacccacggcggt
ctcaataccgtactggatgcgctggctgccgcgacgccggtgctggcggtgccactctcttcgaccagcccgccgtggctgcccggctggtctataacgggct
gggtcgccgggtatcgcgctttgccagacagcagacgctggcggatgagattgcccaactgctgggggatgagacgctgcatcagcgtctggcgacggccc
gccagcagcttaacgacgccggggcacgcccgtgcggcgaccctgattgaacaggccatagcagggagtgagagcgtatcgtgagggatctgattttagt
cggcggcggcctggccaacgggctgatcgcctggcgtctgcgccagcgctacccgcagcttaacctgctgctgatcgaggccggggagcagcccggcggg
aaccatacctggtcattccatgaagacgatctgactcccgggcagcacgcctggctggccccgctggtggcccacgcctggccgggctatgaggtgcagtttc
ccgatcttcgccgtcgcctcgcgcgcggctactactccattacctcagagcgctttgccgaggccctgcatcaggcgctgggggagaacatctggctaaactgtt
cggtgagcgaggtgttacccaatagcgtgcgccttgccaacggtgaggcgctgcttgccggagcggtgattgacggacgcggcgtgaccgccagttcggcg
atgcaaaccggctatcagctctttcttggtcagcagtggcggctgacacagccccacggcctgaccgtaccgatcctgatggatgccacggtggcgcagcagc
agggctatcgctttgtctacacgctgccgctctccgccgacacgctgctgatcgaggatacgcgctacgccaatgtcccgcagcgtgatgataatgccctacgc
cagacggttaccgactatgctcacagcaaaggtggcagctggcccagcttgaacgcgaggagaccggctgtctgccgattaccctggcgggtgacatccag
gctctgtgggccgatgcgccgggcgtgccgcgctcgggaatgcgggctggctatttcaccctaccactggctattcgctgccgctggcggtggcccttgccg
acgcgattgccgacagcccgcggctgggcagcgttccgctctatcagctcacccggcagtttgccgaacgccactggcgcaggcagggattcttccgcctgct
gaaccggatgcttttcctggccgggcgcgaggagaaccgctggcgggtgatgcagcgcttttatgggctgccggagcccaccgtagagcgcttttacgccggt
cggctctctctctttgataaggcccgcattttgacgggcaagccaccggttccgctgggcgaagcctggcgggcggcgctgaaccattttcctgacagacgaga
taaaggatgaaaaaaccgttgtgattggcgcaggctttggtggcctggcgctggcgattcgcctgcaggcggcaggatcccaaccgtactgctggagcagc
gggacaagcccggcggtcgggcctacgtctggcatgaccagggctttacctttgacgccgggccgacggtgatcaccgatcctaccgcgcttgaggcgctgtt
cacccctggccgcaggcgcatggaggattacgtcaggctgctgccggtaaaaccttctaccgactctgctgggagtccgggaagaccctcgactatgctaac
gacagcgccgagcttgaggcgcagattacccagttcaaccccgcgacgtcgagggctaccggcgctttctggcttactcccaggcggtattccaggagggat
atttgcgcctcggcagcgtgccgttcctctcttttcgcgacatgctgcgcgccgggccgcagctgcttaagctccaggcgtggcagagcgtctaccagtcggttt
cgcgctttattgaggatgagcatctgcggcaggccttctcgttccactccctgctggtaggcggcaacccttcaccacctcgtccatctacaccctgatccacg
cccttgagcggagtgggggtctggttccctgagggcggcaccggggcgctggtgaacggcatggtgaagctgtttaccgatctgggcggggagatcgaac
tcaacgcccgggtcgaagagctggtggtggccgataaccgcgtaagccaggtccggctggcggatggtcggatctttgacaccgacgccgtagcctcgaac
gctgacgtggtgaacacctataaaaagctgctcggccaccatccggtggggcagaagcgggcggcagcgctggagcgcaagagcatgagcaactcgctgtt
tgtgctctacttcggcctgaaccagcctcattcccagctggcgcaccataccatctgttttggtccccgctaccgggagctgatcgacgagatctttaccggcag
cgcgctggcggatgacttctcgctctacctgcactcgcccctgcgtgaccgatccctcgctcgcgcctcccggctgcgccagcttctacgtgctggccccggtgcc
```

-continued

```
gcatcttggcaacgcgccgctggactgggcgcaggaggggccgaagctgcgcgaccgcatctttgactaccttgaagagcgctatatgcccggcctgcgtag ccagctggtgacccagcggatctttacccgcagacttccacgacacgctggatgcgcatctgggatcggccttctccatcgaccgctgctgacccaaagc gcctggttccgcccgcacaaccgcgacagcgacattgccaacctctacctggtgggcgcaggtactcaccctggggcgggcattcctggcgtagtggcctcg gcgaaagccaccgccagcctgatgattgaggatctgcaatgagccaaccgccgctgcttgaccacgccacgcagaccatggccaacggctcgaaaagttttg ccaccgctgcgaagctgttcgacccggccacccgccgtagcgtgctgatgctctacacctggtgccgccactgcgatgacgtcattgacgaccagacccacg gcttcgccagcgaggccgcggcggaggaggaggccacccagcgcctggcccggctgcgcacgctgaccctggcggcgtttgaaggggccgagatgcag gatccggccttcgctgcctttcaggaggtggcgctgacccacggtattacgcccgcatggcgctcgatcacctcgacggctttgcgatggacgtggctcagac ccgctatgtcacctttgaggatacgctgcgctactgctatcacgtggcgggcgtggtgggtctgatgatggccagggtgatgggcgtgcgggatgagcgggtg ctggatcgcgcctgcgatctggggctggccttccagctgacgaatatcgcccgggatattattgacgatgcggctattgaccgctgctatctgcccgccgagtgg ctgcaggatgccgggctgaccccggagaactatgccgcgcgggagaatcgggccgcgctggcgcgggtggcggagcggcttattgatgccgcagagccgt actacatctcctcccaggccgggctacacgatctgccgccgcgctgcgcctgggcgatcgccaccgcccgcagcgtctaccgggagatcggtattaaggtaa aagcggcggaggcagcgcctgggatcgccgccagcacaccagcaaaggtgaaaaaattgccatgctgatgcggcaccggggcaggttattcgggcga agacgacgagggtgacgccgcgtccggccggtcttggcagcgtcccgtttaggcgggcggccatgacgttcacgcaggatcgcctgtaggtcggcaggctt gcgggcgtaaataaaaccgaaggagacgcagccctcccggccgcgcaccgcgtggtgcaggcggtgggcgacgtagagccgcttcaggtagcccggcg cgggatccagtggaagggccagcgctgatgcaccagaccgtcgtgcaccaggaagtagagcaggccatagaccgtcatgccgcagccaatccactgcagg ggccaaacgcccgcgtgcccacggcaatcagcgcgatagccaccccggcaaacaccaccgcaaagagatcgtttagctcaaatacgcccttgcgcggggt atggtgtgactcatgccagcgccatccccagccgtgcataatgtagcggtgggtaaacgcggcgatgccctccatcgcaataacgctcaagatgacgattaaac tatttactagcat
``` crtZ_Ev
Source: *Escherichia vulneris*

SEQ ID NO: 32

MLVNSLIVILSVIAMEGIAAFTHRYIMEGWGWRWHESHHTPRKGVFELNDLFAVVFAGVAIALIAVG

TAGVWPLQWIGCGMTVYGLLYFLVHDGLVHQRWPFHWIPRRGYLKRLYVAHRLHHAVRGREGCV

SFGFIYARKPADLQAILRERHGRPPKRDAAKDRPDAASPSSSSPE* crtY_Ev
Source: *Escherichia vulneris*

SEQ ID NO: 33

VRDLILVGGGLANGLIAWRLRQRYPQLNLLLIEAGEQPGGNHTWSFHEDDLTPGQHAWLAPLVAHA

WPGYEVQFPDLRRRLARGYYSITSERFAEALHQALGENIWLNCSVSEVLPNSVRLANGEALLAGAVI

DGRGVTASSAMQTGYQLFLGQQWRLTQPHGLTVPILMDATVAQQQGYRFVYTLPLSADTLLIEDTR

YANVPQRDDNALRQTVTDYAHSKGWQLAQLEREETGCLPITLAGDIQALWADAPGVPRSGMRAGL

FHPTTGYSLPLAVALADAIADSPRLGSVPLYQLTRQFAERHWRRQGFFRLLNRMLFLAGREENRWRV

MQRFYGLPEPTVERFYAGRLSLFDKARILTGKPPVPLGEAWRAALNHFPDRRDKG* crtI_Ev
Source: *Escherichia vulneris*

SEQ ID NO: 34

MKKTVVIGAGFGGLALAIRLQAAGIPTVLLEQRDKPGGRAYVWHDQGFTFDAGPTVITDPTALEALF

TLAGRRMEDYVRLLPVKPFYRLCWESGKTLDYANDSAELEAQITQFNPRDVEGYRRFLAYSQAVFQ

EGYLRLGSVPFLSFRDMLRAGPQLLKLQAWQSVYQSVSRFIEDEHLRQAFSPHSLLVGGNPFTTSSIYT

LIHALEREWGVWFPEGGTGALVNGMVKLFTDLGGEIELNARVEELVVADNRVSQVRLADGRIFDTD

AVASNADVVNTYKKLLGHHPVGQKRAAALERKSMSNSLFVLYFGLNQPHSQLAHHTICFGPRYRELI

DEIFTGSALADDFSLYLHSPCVTDPSLAPPGCASFYVLAPVPHLGNAPLDWAQEGPKLRDRIFDYLEE

RYMPGLRSQLVTQRIFTPADFHDTLDAHLGSAFSIEPLLTQSAWFRPHNRDSDIANLYLVGAGTHPGA

GIPGVVASAKATASL crtB_Ev

Source: *Escherichia vulneris*

SEQ ID NO: 35

MSQPPLLDHATQTMANGSKSFATAAKLFDPATRRSVLMLYTWCRHCDDVIDDQTHGFASEAAAEEE

ATQRLARLRTLTLAAFEGAEMQDPAFAAFQEVALTHGITPRMALDHLDGFAMDVAQTRYVTFEDTL

RYCYHVAGVVGLMMARVMGVRDERVLDRACDLGLAFQLTNIARDIIDDAAIDRCYLPAEWLQDAG

LTPENYAARENRAALARVAERLIDAAEPYYISSQAGLHDLPPRCAWAIATARSVYREIGIKVKAAGGS

AWDRRQHTSKGEKIAMLMAAPGQVIRAKTTRVTPRPAGLWQRPV* crtE_Ev
Source: *Escherichia vulneris*

SEQ ID NO: 36

MVSGSKAGVSPHREIEVMRQSIDDHLAGLLPETDSQDIVSLAMREGVMAPGKRIRPLLMLLAARDLR

YQGSMPTLLDLACAVELTHTASLMLDDMPCMDNAELRRGQPTTHKKFGESVAILASVGLLSKAFGLI

AATGDLPGERRAQAVNELSTAVGVQGLVLGQFRDLNDAALDRTPDAILSTNHLKTGILFSAMLQIVA

IASASSPSTRETLHAFALDFGQAFQLLDDLRDDHPETGKDRNKDAGKSTLVNRLGADAARQKLREHI

DSADKHLTFACPQGGAIRQFMELWFGHHLADWSPVMKIA*

Idi_Ev
Source: *Escherichia vulneris*

SEQ ID NO: 37

MKDERLVQRKNDHLDIVLDPRRAVTQASAGFERWRFTHCALPELNFSDITLETTFLNRQLQAPLLISS

MTGGVERSRHINRHLAEAAQVLKIAMGVGSQRVAIESDAGLGLDKTLRQLAPDVPLLANLGAAQLT

GRKGIDYARRAVEMIEADALIVHLNPLQEALQPGGDRDWRGRLAAIETLVRELPVPLVVKEVGAGIS

RTVAGQLIDAGVTVIDVAGAGGTSWAAVEGERAATEQQRSVANVFADWGIPTAEALVDIAEAWPQ

MPLIASGGIKNGVDAAKALRLGACMVGQAAAVLGSAGVSTEKVIDHFNVIIEQLRVACFCTGSRSLS

DLKQADIRYVRDTP* crtZYIBE, Pa C40 cluster
Source: *Pantoea ananatis* ATCC 19321

SEQ ID NO: 38 atgacggtctgcgcaaaaaaacacgttcatctcactcgcgatgctgcggagcagttactggctgatattgatcgacgccttgatcagttattgcccgtggaggga gaacgggatgttgtgggtgccgcgatgcgtgaaggtgcgctggcaccgggaaaacgtattcgccccatgttgctgttgctgaccgcccgcgatctgggttgcgct gtcagccatgacggattactggatttggcctgtgcggtggaaatggtccacgcggcttcgctgatccttgacgatatgccctgcatggacgatgcgaagctgcgg cgcggacgccctaccattcattctcattacggagagcatgtggcaatactggcggcggttgccttgctgagtaaagcctttggcgtaattgccgatgcagatggc ctcacgccgctggcaaaaaatcgggcggtttctgaactgtcaaacgccatcggcatgcaaggattggttcagggtcagttcaaggatctgtctgaagggggataa gccgcgcagcgctgaagctatttgatgacgaatcactttaaaaccagcacgctgttttgtgcctccatgcagatggcctcgattgttgcgaatgcctccagcga agcgcgtgattgcctgcatcgttttcacttgatcttggtcaggcatttcaactgctggacgatttgaccgatggcatgaccgacaccggtaaggatagcaatca ggacgccggtaaatcgacgctggtcaatctgttagggccgagggcggttgaagaacgtctgagacaacatcttcagcttgccagtgagcatctctctgcggcctg ccaacacgggcacgccactcaacatttttattcaggcctggtttgacaaaaaactcgctgccgtcagttaaggatgctgcatgagccatttcgcggcgatcgcacc gcctttttacagccatgttcgcgcattacagaatctcgctcaggaactggtcgcgcgcggtcatcgggtgacctttattcagcaatacgatattaaacacttgat cgatagcgaaaccattggatttcattccgtcgggacagacagccatccccccggcgcgttaacgcgcgtgctacacctggcggctcatcctctgggcgtcaat gctgaagctcatcaatgaaatggcgcgcaccaccgatatgctgtgccgcgaactcccccaggcatttaacgatctggccgtcgatggcgtcattgttgatcaaat ggaaccggcaggcgcgctcgttgctgaagcactgggactgccgtttatctctgtcgcctgcgcgctgcctctcaatcgtgaaccggatatgcccctggcggttat gcctttcgaatacgggaccagcgacgcggctcgcgaacgttatgccgccagtgaaaaaatttatgactggctaatgcgtcgtcatgaccgtgtcattgccgaaca cagccacagaatgggcttagccccccggcaaaagcttcaccagtgttttttcgccactggcgcaaatcagccagcttgttcctgaactggattttcccgcaaagc gttaccggcttgttttcatgccgtcgggcctctgcgcgaaacgcacgcaccgtcaacgtcttcatcccgttattttacatcctcagaaaaacccggattttcgc ctcgctgggcacgcttcagggacaccgttatgggctgtttaaaacgatagtgaaagcctgtgaagaaattgacggtcagctcctgttagcccactgtggtcgtct tacggactctcagtgtgaagagctggcgcgaagccgtcatacacaggtggtggattttgccgatcagtcagccgcgctgtctcaggcgcagctggcgatcaccca cggcggcatgaatacggtactggacgcgattaattaccgacgccccttttagcgcttccgctggcctttgatcagcccggcgtcgcgtcacgcatcgtttatca -continued

```
cggcatcggcaagcgtgcttcccgctttaccaccagccatgctttggctcgtcagatgcgttcattgctgaccaacgtcgactttcagcagcgcatggcgaaaat
ccagacagcccttcgtttggcaggggcaccatggccgctgccgatatcattgagcaggttatgtgcaccggtcagcctgtcttaagtgggagcggctatgcaac
cgcattatgatctgattctcgtgggggctggactcgcgaatggccttatcgccctgcgtcttcagcagcagcaacctgatatgcgtattttgcttatcgacgccg
cacccaggcgggcgggaatcatacgtggtcatttcaccacgatgatttgactgagagccaacatcgttggatagctccgctggtggttcatcactggcccgact
atcaggtacgctttcccacacgccgtcgtaagctgaacagcggctacttttgtattacttctcagcgtttcgctgaggttttacagcgacagtttggcccgcact
tgtggatggataccgcggtcgcagaggttaatgcggaatctgttcggttgaaaaagggtcaggttatcggtgcccgcgcggtgattgacgggcggggttatgcgg
caaattcagcactgagcgtgggcttccaggcgtttattggccaggaatggcgattgagccacccgcatggtttatcgtctcccattatcatggatgccacggtcg
atcagcaaaatggttatcgcttcgtgtacagcctgccgctctcgccgaccagattgttaattgaagacacgcactatattgataatgcgacattagatcctgaat
gcgcgcggcaaaatatttgcgactatgccgcgcaacagggttggcagcttcagacactgctgcgagaagaacagggcgccttacccattactctgtcgggcaatg
ccgacgcattctggcagcagcgcccctggcctgtagtggattacgtgccggtctgttccatcctaccaccggctattcactgccgctggcggttgccgtggccg
accgcctgagtgcacttgatgtctttacgtcggcctcaattcaccatgccattacgcattttgcccgcgagcgctggcagcagcagggcttttccgcatgctga
atcgcatgctgttttagccggacccgccgattcacgctggcgggttatgcagcgtttttatggtttacctgaagatttaattgcccgttttttatgcgggaaaac
tcacgctgaccgatcggctacgtattctgagcggcaagccgcctgttccggtattagcagcattgcaagccattatgacgactcatcgttaaagagcgactacat
gaaaccaactacggtaattggtgcaggcttcggtggcctggcactggcaattcgtctacaagctgcggggatccccgtcttactgcttgaacaacgtgataaacc
cggcggtcgggcttatgtctacgaggatcaggggtttacctttgatgcaggcccgacggttatcaccgatcccagtgccattgaagaactgtttgcactggcagg
aaaacagttaaaagagtatgtcgaactgctgccggttacgccgttttaccgcctgtgttgggagtcagggaaggtctttaattacgataacgatcaaacccggct
cgaagcgcagattcagcagtttaatccccgcgatgtcgaaggttatcgtcagtttctggactattcacgcgcggtgtttaaagaaggctatctaaagctcggtac
tgtcccttttttatcgttcagagacatgcttcgcgccgcacctcaactggcgaaactgcaggcatggagaagcgtttacagtaaggttgccagttacatcgaaga
tgaacatctgcgccaggcgttttctttccactcgctgttggtgggcggcaatcccttcgccacctcatccatttatacgttgatacacgcgctggagcgtgagtg
gggcgtctggtttccgcgtggcggcaccggcgcattagttcagggatgataaagctgtttcaggatctgggtggcgaagtcgtgttaaacgccagagtcagcca
tatgaaacgacaggaaacaagattgaagccgtgcatttagaggacggtcgcaggttcctgacgcaagccgtcgcgtcaaatgcagatgtggttcatacctatcg
cgacctgttaagccagcaccctgccgcggttaagcagtccaacaaactgcagactaagcgcatgagtaactctctgtttgtgctctatttttggtttgaatcacca
tcatgatcagctcgcgcatcacacggtttgtttcggcccgcgttaccgcgagctgattgacgaaatttttaatcatgatggcctcgcagaggacttctcacttta
tctgcacgcgccctgtgtcacggattcgtcactggcgcctgaaggttgcggcagttactatgtgttggcgccggtgccgcatttaggcaccgcgaacctcgactg
gacggttgaggggccaaaactacgcgaccgtatttttgcgtaccttgagcagcattacatgcctggcttacggagtcagctggtcacgcaccggatgtttacgcc
tgtttgattttcgcgaccagcttaatgcctatcaggctcagccttttctgtggagcccgttcttacccagagcgcctggtttcggccgcataaccgcgataaaac
cattactaatctctacctggtcggcgcaggcacgcatcccggcgcaggcattcctggcgtcatcggctcggcaaaagcgacagcaggtttgatgctggaggatct
gatatgaataatccgtcgttactcaatcatgcggtcgaaacgatggcagttggctcgaaaagttttgcgacagcctcaaagttatttgatgcaaaacccggcgc
agcgtactgatgctctacgcctggtgccgccattgtgacgatgttattgacgatcagacgctgggctttcaggcccggcagcctgccttacaaacgcccgaacaa
cgtctgatgcaacttgagatgaaaacgcgccaggcctatgcaggatcgcagatgcacgaaccggcgtttgcggcttttcaggaagtggctatggctcatgatatc
gccccggcttacgcgtttgatcatctggaaggcttcgccatggatgtacgcgaagcgcaatacagccaactggatgatacgctgcgctattgctatcacgttgca
ggcgttgtcggcttgatgatggcgcaaatcatgggcgtgcgggataacgccacgctggaccgcgcctgtgaccttgggctggcatttcagttgaccaatattgct
cgcgatattgtggacgatgcgcatgcgggccgctgttatctgccggcaagctggctggagcatgaaggtctgaacaaagagaattatgcggcacctgaaaaccgt
caggcgctgagccgtatcgcccgtcgtttggtgcaggaagcagaaccttactatttgtctgccacagccggcctggcagggttgcccctgcgttccgcctgggca
atcgctacggcgaagcaggtttaccggaaaataggtgtcaaagttgaacaggccggtcagcaagcctgggatcagcggcagtcaacgaccacgcccgaaaaatta
acgctgctgctggccgcctctggtcaggcccttacttcccggatgcgggctcatcctccccgccctgcgcatctctggcagcgccgctctagcgccatgtcttt
cccgagcgtcgcctgaagttttgacaggggcggcgcatagaggaagccaaaagaaacacaaccttctttgcccctgacggcgtgatgcatacggtgcgccatat
acaaccgtttgaggtagcccttgcgtggaatatagcggaatggccaacgttgatgcaccagcccgtcgtgcaccataaaatagagtaatccatacgcgtcatac
ctgcgccaatccactggagcggccacattcctgtactgcccagataaatcagcaggatcgataatgcagcaaaaccacggcataaagatcgttaacttcaaacg
cacctttacgcggttcatgatgtgaaagatgccatccccaaccccagccgtgcatgatgtatttgtgtgccagtgcagcaatcacttccatgccaatcacggtaa
cgaaaacgatcagggcattccaaatccacaacat
```

-continued crtZ_Pa
Source: *Pantoea ananahs* ATCC 19321

SEQ ID NO: 39

MLWIWNALIVFVTVIGMEVIAALAHKYIMHGWGWGWHLSHHEPRKGAFEVNDLYAVVFAALSILLI

YLGSTGMWPLQWIGAGMTAYGLLYFMVHDGLVHQRWPFRYIPRKGYLKRLYMAHRMHHAVRGK

EGCVSFGFLYAPPLSKLQATLRERHGARAGAARDAQGGEDEPASGK* crtY_Pa
Source: *Pantoea ananatis* ATCC 19321

SEQ ID NO: 40

MQPHYDLILVGAGLANGLIALRLQQQPDMRILLIDAAPQAGGNHTWSFHHDDLTESQHRWIAPLV

VHHWPDYQVRFPTRRRKLNSGYFCITSQRFAEVLQRQFGPHLWMDTAVAEVNAESVRLKKGQVIGA

RAVIDGRGYAANSALSVGFQAFIGQEWRLSHPHGLSSPIIMDATVDQQNGYRFVYSLPLSPTRLLIEDT

HYIDNATLDPECARQNICDYAAQQGWQLQTLLREEQGALPITLSGNADAFWQQRPLACSGLRAGLF

HPTTGYSLPLAVAVADRLSALDVFTSASIHHAITHFARERWQQQGFFRMLNRMLFLAGPADSRWRV

MQRFYGLPEDLIARFYAGKLTLTDRLRILSGKPPVPVLAALQAIMTTHR* crtI_Pa
Source: *Pantoea ananatis* ATCC 19321

SEQ ID NO: 41

MKPTTVIGAGFGGLALAIRLQAAGIPVLLLEQRDKPGGRAYVYEDQGFTFDAGPTVITDPSAIEELFAL

AGKQLKEYVELLPVTPFYRLCWESGKVFNYDNDQTRLEAQIQQFNPRDVEGYRQFLDYSRAVFKEG

YLKLGTVPFLSFRDMLRAAPQLAKLQAWRSVYSKVASYIEDEHLRQAFSFHSLLVGGNPFATSSIYTL

IHALEREWGVWFPRGGTGALVQGMIKLFQDLGGEVVLNARVSHMETTGNKIEAVHLEDGRRFLTQA

VASNADVVHTYRDLLSQHPAAVKQSNKLQTKRMSNSLFVLYFGLNHHHDQLAHHTVCFGPRYRELI

DEIFNHDGLAEDFSLYLHAPCVTDSSLAPEGCGSYYVLAPVPHLGTANLDWTVEGPKLRDRIFAYLE

QHYMPGLRSQLVTHRMFTPFDFRDQLNAYHGSAFSVEPVLTQSAWFRPHNRDKTITNLYLVGAGTH

PGAGIPGVIGSAKATAGLMLEDLI* crtB_Pa
Source: *Pantoea ananatis* ATCC 19321

SEQ ID NO: 42

MNNPSLLNHAVETMAVGSKSFATASKLFDAKTRRSVLMLYAWCRHCDDVIDDQTLGFQARQPALQ

TPEQRLMQLEMKTRQAYAGSQMEEPAFAAFQEVAMAHDIAPAYAFDHLEGFAMDVREAQYSQLDD

TLRYCYHVAGVVGLMMAQIMGVRDNATLDRACDLGLAFQLTNIARDIVDDAHAGRCYLPASWLEH

EGLNKENYAAPENRQALSRIARRLVQEAEPYYLSATAGLAGLPLRSAWAIATAKQVYRKIGVKVEQ

AGQQAWDQRQSTTTPEKLTLLLAASGQALTSRMRAHPPRPAHLWQRPL* crtE_Pa
Source: *Pantoea ananatis* ATCC 19321

SEQ ID NO: 43

MTVCAKKHVHLTRDAAEQLLADIDRRLDQLLPVEGERDVVGAAMREGALAPGKRIRPMLLLLTARD

LGCAVSHDGLLDLACAVEMVHAASLILDDMPCMDDAKLRRGRPTIHSHYGEHVAILAAVALLSKAF

GVIADADGLTPLAKNRAVSELSNAIGMQGLVQGQFKDLSEGDKPRSAEAILMTNHFKTSTLFCASMQ

MASIVANASSEARDCLHRFSLDLGQAFQLLDDLTDGMTDTGKDSNQDAGKSTLVNLLGPRAVEERL

RQHLQLASEHLSAACQHGHATQHFIQAWFDKKLAAVS* crtYIB, Fp US (upstream) cluster
Source: *Fulvimarina pelagi*

SEQ ID NO: 44 ttgacgtctctctgcgaaacagaaggtcgacattgctcttgtgggcggtggacttgccaatgggctgatcgcctggcggcttgccgaattgcggccggatctcagc atcgtcgtcctcgaagccggtgaggcgcctggcggcaaccacacatggtcgtttcacgaacacgaccttacacccgccgctcatcggtggatcgcgcctttcgt cgctcatcgctggaccaccaacgaggtgcaattcccgaccgccatcgtcatctctcgacggggtatttgagcgcgtctccggatctatttcgcgaaaggctgac gacgcgtctcggcttgcgtatccgcaccggctgtccggccgtttctgtcacggcgcgcaaggtgcgactcgaaaacggcgaagtgatcgaggccggctcggt -continued

```
gattgacgggcgcggctaccgatcgagcgaacacctcacgctcggcttcagaagtttctcggtcaggagatcgaattcgaggcaccgcacggcgttgcccga
ccggtcatcatggatgctaccgtcccccaggcggacggctatcggttcgtctatcttcttcccatgacgccgacgcggttgctggtcgaggacacctactatgcc
gatggcgacgccctcgatcgcggaacgatccggcgcaacatcgcggcttaccgggcggcgaagggctggcctgggggaaagtcgttcgcgaagaagatg
gtgtcctgccgatcgcgctcgccggcgatatcgaggccttctggaggagaagcagggcgtccatccagcggcctcaacgctgcgctificcaccccgacga
ctgggtattccttgccggacgccgtgtatctcgccgatctgattgcaggcctgccggactattcggccgcaaccctttatgctgcgacacgccgccactcggtcg
caacgtggaagcggcgcggatcttccgtatgctgaaccgccttctctatctcgccggtgatccgttgaaacgttatgtcatcctccagcattttttatcgcctgcc
cgaaccattggtgtcgcggttctacgctgcgcggctgacccgaggtgacaaggtgcggatcctcaccggcaagccgccggtcagtgttatcagcgcgctcaaagt
tcttccccgagttctgtcgagggagcgcccgcatgaaccagatgccgcgcgaccttcctaacaagacaaagaccgcagtcgttatcggagcaggcttcggcg
gactggcgcttgcgattcgacttcaggcggccggtatccaaacgacgcttctcgaaaagcgcgacaagcccggggacgggcttacgtctacgaggatcagg
gcttcaccttcgatgccggcccaaccgtgatcaccgacccctccgcgctcgaagagctgttcgagacggcgaacgccaagcttcggactatgtcgaactgctt
cccgtcaagcctttctaccgtctcgcctgggaagacggcttcgtcttcgactatgcagacgatcaggaggatctcgaccgccagatcggcgcgaagaacccga
aggatgtcgagggctatcgccgcttcctcgcttattcgcgggacgtgttccacgagggttacgaaaagctcggcaccgtcccttcctgaatttcaaggatatgat
gcgggcagcgccccagctcgttcggctcgaggcctatcgctcggtctattcgaaggtcgcccagttcatcgaggacgaccagnacggcaggccattccttcc
actcgctcctcgtcggcggcaatccgttcgccacttcttcgatctacgcgctcatccacgcgttggagcgcaaatggggcgtcttcttcccgcgcggcggcaccg
gcgcgctggtccgcggcatggccaagctcttcaccgacattggcggggaggatcgaggtgaatgccgaggtcgagaatatcgcgatcgagaacgggcgcgc
gaagtccgtgacgactaagggcggtcaaaccttttcccgcagacttcgtcgcctcgaatgccgacgtcgtccacacctatgccaagctgatgggtcgcagcgag
cgcggcaaaaagcacggcaattcgctgaagaagaagcgcttttccatgtcgctcttcgtcatctatttcggcctgaagacccaccggccggacattgcccatcac
acggtctgtttcggtccgcgctatcgcccgctgatcgacgagattttcaagggcaaagagctcgcgggcgacttctcgctctatctccataacccgtgcgtcacc
gatccctcgctcgccggagggcatgggctccttctacgttctgtccctgtcccccatctcggtaacgccgatatagattgggcggttgaggggccgaaatat
cgcgacaggatcctcgactatctggaagagctgtacatccccggcctgaaggacgatctcgtcaccagccgcatcttcaccccggctgatttcaagaccgaact
gaacgcccatctcggctcggccttctcgctcgatccggtactgacgcagagcgcttggttccgccctcacaatcgcgacgatcagattcccaacctctacgtcgt
cggggctggtacgcatccaggtgccggcgttccgggcgtcgtcggttcggccaaggcgactgccggcctgatgatcgaggacgcgggtctcgcgtgcgtgc
ctgcatgagtttcgccgaccgcctcgacgtaccgatcgtcggcggccttccgttcgaaaagcgcgagcgcgccgcgctggccgccgaagccgaagcgacga
tcgcgcaaggctcgaagagtttcgctgccgccgcccgcctgtttgatccggagatgcgggtcagcgcgcttatgctctatgcctggtgccggcattgcgacgat
gtggtcgatgaccagatccttggttttcgccagccaggccgccgggaccgagccggcgatcgcgcacgtctcgatgaactcgaggccaagacccttgcggcg
gttcgaggccgatccacgggcgaagcaccattcgacgcgatcggcgatgtcgccctgcggcatgagctgccggaatcgctcttgaccgcgcacctcgaagg
cttccggatggatgtcgacggccgggtctacgaggtgattgaggatacgctcgattattgctaccgggtcgcaggtgtcgtcggcgtgatgatggcgcgggtca
tgggcatcagggtcgaaaacggttcgaaattcgacctgacgctgacccctcgatcgagcctgcgacctcggcatggccttcagctcaccaatatcgcacgtgac
atagtcgacgacggcgaggccggacgggtctacgtgccgaagacatggctcgatgcggctggcgtcccgggcagcgccatccaccacccgcgcaatcggg
aggcggcagcggtgttcgctctgcgtctcctcgatctggccgagccatactacgcgtcggcctcgaaggggctagccgcgctgccgcctcgtgccgcatggg
ccgtcgcgactgcgcttggcgtctaccgtgagatcgggaccgtcatccgccggcgtggaagtcaagcctgggacgatcgttcatcgacaagcgcggcgacca
agttcctgcacgccttcaagggtgtcggttggacgatgggatcacgtgtctcaagcaggcgcggcgttcggccgccggagctctggacgcgtcctcgactgctt
gagctcggtgatgcgcccacaacaggtctatcggcctga
``` crtWZ, FP DS (downstream) cluster
Source: *Fulvimarina pelagi*
SEQ ID NO: 45

```
ttaggactggcgagtatgcggcagagcccaccaaggcgtccatggcgccaaatggtgctcatggtggtagccaaaatggaagcaggagaatagcgaggcca
cgtaaccgaattcgctcgaacgtgtgttatgcgcgtcggcaaaggtgcccgattcttcgtgtcgatgcgggcggtaggttccgaagtagaagagctgcaatgac
gaaagcagtgacggcaagccgtaaaatagaaccacgttcgtcacagatgcatccagtatgacgagataaaacgtcacgacggtcgagacgaatgcgaccgat
ctccatccgaaataacgtgagaagaaggtgccgaaccaaggccagaaattctccggatcatctgcgtagaaatccgggtcggccggtgtaccgggtgcgtcgt
ggtgtgcgaagtgagcatctctgatctttttccacgcaaatcccgcgtagacgaacaggatgaacccgccgattacggcattcaaacgcgttcgacccggcgcc
agcgaaccatgcatggcgtcgtgagccaggatgaaaagccccaccgtcaaccagcactgaacaccgtgatcaatggtgcgagaggcaacgtgctgaaatt
```

-continued

```
gatgtcgaggaagaatatcgctgagacgtgtattgcgaaccacgatgccagcagcacggcacagagcgtcaggccaatcgtcgtttggtagggtctgattttgg gtgagtcggcgggtgtggatcgcggtaacgcacttgccgggatcaggcgtgaggttgggctgagggtcatgacctcgcaaataagccgaaccgtccgggtgc aaaatcgtttgccgcctcgtttggcgcggcataacgtcgtccatcctcgctctgtgcgctcgcgagaacacgatcgacggcttctgcagcagcacgcgcaccgc ctgcgttggcgatttccgcctggatcggagcgatccggttcacgaaggctgctcggtttgcaatcaaatcggaaagtgcattcgcaatggttcgcggcttggccc gcttggcggcgatagccttacccacgccgtgatggagtatacgggcaccgacacccggctgatcgtagccaattggcagcgccaacataggcgtaccgaccg ccagacagtcgagaacggtgttgagcccccgtgagtcacgcagacatctgcgcgtgcgagcatcgcgcgttgatcgacgaaactgactacccacttggccg gaagcctcgaagcttgtcgtggcgagagcccccgcaatgcgcgatcatcaattgcacatcgagcgtctcgcaggcggatgcgatctttttgaataaactgtaac gatgaccttgcaccgtgccgagagacgcgaacacgaaggggcgcgtcgggtcgatcgtgagacatgtttccttcgtcagtcttgcgactgaggcactgcggat gggtccaaccggcttcagtttcgtcccctcggtctcggaaagtcgaaaacgctgacggtctgcgacaaacgcaacactggcgagagacaggcaacgtcgtc ctcccgcggccccagtccgaagcgcgtcgcccaggcttggatcaccttccgttgcttgcgcatgaagaatttgccgacacgctccccgccgcgattgcgagca agtccctcttcggtgggatcgtagggccaatcgagaaacggcagaggcatcgccacatcccgttcgattggtagggccgacgccaaggagatgtgtggcagg ccgagataagctgcgaccagaccggcgcctggctcgaattcatctgcgatgattgcatcgatttgcatcgaacgcatgatgtccggagcgatgcgacaaactg atctgtttctcttgctcgatcggcaactgcccgcaagataccgagaatcccggcgccgccgcgtcacgccgacgatgccgaacaccagacatgattgaagca gaagccgctagcgtaacaatctcgatgtcagactggcagaccatcgtctccgcctctttcggcagtatgaagacgacgtcgtggccgcgaaccttgagcgcttg ccccagaacttcgaacgccttgatatggctgtagaacgccggacagaccaaagctatgcgtgccaattacatcaatccctcagccgaaacgaatcgacgcaga caagcaccgccctatcgatagcaaccgaccttaacatagttccgggtgacgatagtcgaggtagggtatgatcaggacattcctgaacggcgatggaagcgttc gggtcgatcgagaaacggcttttaacgtgacgaaagaggattgatgtcggccgcgcgcggttcatgctccctaagcgagatcgctagccgctcggctcggttg cgccgacctcgctcgatcgcgaaagtctggcccgtcgcttcgacacttgcatgcctgttgctgacaaacggcctcgtcgtactctacctctgggcgatcggtaga ccgttcatcgcgccgaccgaacctctcaagctgtttagcgacaacctcgccgctgcgaattcgctttatctctccgatccctactcgcttctgcacgtcatcttc ggaatcggtctcttcctgtatctcgactggatgaaacctttctggccgacgagggaaaaactgattgtcgcggtcttgggagcgcaatctgggaagtcgtcgag aacacgccatatgttgtgggtctgttcaacgacacgagtgacacggcagcttacaacggggacagtgtcgcgaattcgattggcgatacgatctctgcggtaatt ggttttttgttcgcgaatcggacagggcgccgagtttccctgttcgttgcattcgcgcttgaatcaatcgttacagtatggattggcgatggaatcgttattggc acgctcagacttctgggtctgtacccgatctgatcgacgcgactcttgcgcccatcgtcacggccatgtgtgtgccaagatcgagttatatatgtacctcggc ctgaacgactgaaccaaaactagaaacgtcgataagaaacgatgacgatctggactctctactacgtctgtctcaccctcgtcacgatcggtttgatggaggttt atgcatggtgggcgcacaagttcatcatgcatggcaaattcggttggggctggcataagtcccaccacgaggaaaccgaagggtggttcgagaagaacgatctct acgctgtcgtMcgccggottcgcgatagcgctgttcatggtcggacatttcctttctccgaccctgctcgccatcgcctggggcatcacgctttacggattactc tacttcgttgcccatgatggacttgtccatcagcgctggccgttcaactacgtgccgcatcgaggtatgcaaaacgcctggttcaagctcatcgtctgcaccat gcggtggaaggccgcgagcactgcgtctcgttcggctttctctatgcgccgccgattgaaaagctgaagcgcgatttgcgtgagtccggaattctcgaacgggag cgcatcgagcggtctctggaccagcaaggctccgcccacgcgccggttcggtga
``` crtY_Fp
Source: *Fulvimarina pelagi*

SEQ ID NO: 46

LTSSAKQKVDIALVGGGLANGLIAWRLAELRPDLSIVVLEAGEAPGGNHTWSFHEHDLTPAAHRWIA

PFVAHRWTTNEVQFPDRHRHLSTGYLSASSDLFRERLTTRLGLRIRTGCPAVSVTARKVRLENGEVIE

AGSVIDGRGYRSSEHLTLGFQKFLGQEIEFEAPHGVARPVIMDATVPQADGYRFVYLLPMTPTRLLVE

DTYYADGDALDRGTIRRNIAAYRAAKGWPAGKVVREEDGVLPIALAGDIEAFWEEKQGVPSSGLNA

ALFHPTTGYSLPDAVYLADLIAGLPDYSAATLYAATRRHSVATWKRRGFFRMLNRLLYLAGDPLKR

YVILQHFYRLPEPLVSRFYAARLTRGDKVRILTGKPPVSVISALKVLSPSSVEGAPA* crtI_Fp
Source: *Fulvimarina pelagi*

SEQ ID NO: 47

MNQMPRDLPNKTKTAVVIGAGFGGLALAIRLQAAGIQTTLLEKRDKPGGRAYVYEDQGFTFDAGPT

VITDPSALEELFETANAKLSDYVELLPVKPFYRLAWEDGFVFDYADDQEDLDRQIGAKNPKDVEGYR

RFLAYSRDVFHEGYEKLGTVPFLNFKDMMRAAPQLVRLEAYRSVYSKVAQFIEDDQLRQAFSFHSLL

```
VGGNPFATSSIYALIHALERKWGVFFPRGGTGALVRGMAKLFTDIGGRIEVNAEVENIAIENGRAKSV

TTKGGQTFPADFVASNADVVHTYAKLMGRSERGKKHGNSLKKKRFSMSLFVIYFGLKTHRPDIAHH

TVCFGPRYRPLIDEIFKGKELAGDFSLYLHNPCVTDPSLAPEGMGSFYVLSPVPHLGNADIDWAVEGP

KYRDRILDYLEELYIPGLKDDLVTSRIFTPADFKTELNAHLGSAFSLDPVLTQSAWFRPHNRDDQIPNL

YVVGAGTHPGAGVPGVVGSAKATAGLMIEDAGLACVPA*
``` crtB_Fp
Source: *Fulvimarina pelagi*

SEQ ID NO: 48

```
MSFADRLDVPIVGGLPFEKRERAALAAEAEATIAQGSKSFAAAARLFDPEMRVSALMLYAWCRHCD

DVVDDQILGFRQPGRRDRAGDRARLDELEAKTLAAVRGRSTGEAPFDAIGDVALRHELPESLLTAHL

EGFRMDVDGRVYEVIEDTLDYCYRVAGVVGVMMARVMGIRVENGSKFDLTLTLDRACDLGMAFQ

LTNIARDIVDDGEAGRVYVPKTWLDAAGVPGSAIHHPRNREAAAVFALRLLDLAEPYYASASKGLA

ALPPRAAWAVATALGVYREIGTVIRRRGSQAWDDRSSTSAATKFLHAFKGVGWTMGSRVSSRRGVR

PPELWTRPRLLELGDAPTTGLSA*
``` crtW_Fp
Source: *Fulvimarina pelagi*

SEQ ID NO: 49

```
MTLSPTSRLIPASALPRSTPADSPKIRPYQTTIGLTLCAVLLASWFAIHVSAIFFLDINFSTLPLAPLITVF

QCWLTVGLFILAHDAMHGSLAPGRTRLNAVIGGFILFVYAGFAWKKIRDAHFAHHDAPGTPADPDFY

ADDPENFWPWFGTFFSRYFGWRSVAFVSTVVTFYLVILDASVTNVVLFYGLPSLLSSLQLFYFGTYRP

HRHEESGTFADAHNTRSSEFGYVASLFSCFHFGYHHEHHLAPWTPWWALPHTRQS*
``` crtZ_Fp
Source: *Fulvimarina pelagi*

SEQ ID NO: 50

```
MTIWTLYYVCLTLVTIGLMEVYAWWAHKFIMHGKFGWGWHKSHHEETEGWFEKNDLYAVVFAGF

AIALFMVGHFLSPTLLAIAWGITLYGLLYFVAHDGLVHQRWPFNYVPHRGYAKRLVQAHRLHHAVE

GREHCVSFGFLYAPPIEKLKRDLRESGILERERIERSLDQQGSAHAPVR*
```

Flank 3, MEXT_3010
Source: *Methylobacterium extorquens* PA1

SEQ ID NO: 51

```
gtgtcgccagcttcctcttcccggcatcgcccggatgctgttcctgaacccgtgacgcccaaagttttcgcctggagcgccgaccgggcggcggtgcgtcg cctcatcgacggcaccggctcgcgcctcgacccgcaggggctcgacctctaccggcggctgttcacccgccccggccatgtcgcgggcgccctcggcatga tggcgaactggatcttccggcactcgcccgcgacctgccggggctcgaaaccgtacgctgctggtcgtcggcggggacgacaaggcgatcaagcccga cgattccttcgccttgcgcgagcggttgcggagcgcacgcgtagaattgctgcgtgggctcggccacctcgcgcacgaggaggcgccggagcgggtggcg gagatcattctggcagaagcggacgcccttggcgcctcggtatcctgagacgcctcttgcgctgacgaaaatcccagccatagtgtcaacct
```

Flank 3, MEXT_3011
Source: *Methylobacterium extorquens* PA1

SEQ ID NO: 51

```
atgttgacactggccgtcaaaccgactgtcacgtccgactccgatgcccggccgcatgcggtcgtgatcggggccggcttcggcgggctggccgcggcgtt cggctcggcgcccgcggctatcgcgtcaccgttctggaacggctcgaccagcccggcggccgcgcccgcgtccaccgccaggacggcttcaccttcgatgc ggggcccaccatcgtcaccgcgccgttcctgttcgaggagctgtggcggttgtgcgggcgggagatgcgcgaggacgtgactctcgtgccgatgcagccatt ctaccgcattcgcttcgaggatgggcagagcttcgcctatagcggcgaccgcgcggcgatgcgggccgaggtcgcccgcttctcgcccgacgacgtgtccg gctacgaacgcttcatggcccatagcgaggcggtgtgccggatgggcttcgaggaactcggccacgtcccgttcggcagcctcggctcgatgctgcggatcg cgcccgatctgctgcgcttgtcgggccaccgcagcgtctacgacgtggtgtcccgcttcatccgcgacgagcggctgcgcaccatcttcagcttccatccctg ctcatcggcggcaacccgtttcgcgccagcggcatctactgcctgatcgcccatctggagcggcaatggggcgtccatttcgccatgggcggtaccggacgac tggtggacgggctctgcggcttgatccggggcagggaggccgcgtccgctgcggcgaggacgtttcgcgcatccgcgtcgaggatgcgcgggcgacgg gtgtggtgctggcgggcggcgaggtcatccccgccgacaccgtcgtctcgaacgccgattccgccttcacctacggcacgctgctcggcggccggaccccgg cgctggagcgcgcggcgcctggcgcgcgcctcgtcctccatggggctgttcgtctggtatttcggtacccggaagaagtaccggaggtcgatcaccacatga
``` tcctgatgggcccgcgctatcgcggcctgttgcaggacatcttcgaccgcaagcacttggcgaacgatttcagcctctatctccaccgcccgaccgcgaccgac ccgctgctcgccgcccggctgcgacgcgttctacgtgctcgccccggtgccgaacctcgacggcggccaggattgggcacagcttgccgagccctaccg ccagcggatcgcgcgcttcctcgaaggctcggtgctgccggggctgtccgacgccctcgtcacctcgcgggtgacgacgccgcaggacttttccgacgacttc ctgagcttccgcggctccgggttcgggctggagccggtgctgacgcaatcggcgtggttccgtccgcacaaccgctcggaagacgtggccaacctcttcctcg tcggcgcggggacgcatcccggcgccggtctgccgggcgtgctgtcctcggcgcgtgtcctcgattccgtggtgccggatgcccgtgtttgcgcctgaccctttt cgccgccagcgcggcggaccgctctgcctgccgggccgcgatccgcgccggctccaagagcttcttcgcggcctcgctgctgctgccgcccctcagtgcggg tctcggcctacggcctctacgccttctgccgcctttccgacgatgcggtggacgaggcggggggcaaccgtgctgcggccctcgcccgcctggaacgacggc tgacagcggcctgtgccggccggcccgacaaccaccggccgaccgggcgctcgccgaggtgctcgcccgccacgccatcccggaaaagctgccgcgg gcgctgctcgaagggttggcctgggacacgcaaggccggcgctacgacaccctgtcggagctggccgcctatgccgcccgggtcgcgggcgcggtcggg gcgatgatgacactggtgatggggtgcgcgacggccccgcgctcgcccgcgcctgcgatctcggcgtggccatgcaattcaccaacatcgcccgcgatgtc ggcgaggatgcccgcgccgggcgcctctacctgcctcgcgagtggctcgacgcggccggcatcgacccggacgccttcctcgccgagcctcggctcggcc ccagcctgcaacgggtggtggccgagctgctggcggcggccgacgaactctacgcccgcgccgaacccggcatcgccgcgctcccgttgagctgccgccc ggcgatccgcgccgccggcctgatctacgcggagatcggccgtgccgtggaggcgaacgagctcgattcggtcacgcgccgcgcccgcgtcaccggcgc gcgcaaggccgggcttctggccaccgcgatcctgcccgcgggcggcggccagggactatcggcgccgccattgcccgagaccgccttcctcgtggaagcc gtgacgcaccatccggtcccagccgcgcggcgcttgccaccgtggtggaacgtgtcggggcaggtcgtgcgggtgctcgacctgatcgaggtgctggagga gcgcgacgccttccgccgctcggccgcgtcgtaaggaa

We claim:

1. A microorganism comprising a heterologous polynucleotide, comprising a polynucleotide sequence from *Paracoccus zeaxanthinifaciens*, *Escherichia vulneris*, or *Pantoea ananatis* that encodes a polypeptide of a C40 carotenoid biosynthetic pathway or comprising a polynucleotide sequence that has at least 70% sequence identity thereto and that retains the biological activity thereof or comprising a polynucleotide sequence that encodes a polypeptide that has at least 70% sequence identity to the polypeptide of the C40 carotenoid biosynthetic pathway and that retains the biological activity thereof, operably linked to a promoter for expression of said polynucleotide sequence, wherein the microorganism is a bacterial cell from the class Alphaproteobacteria, and wherein the bacterial cell expresses said heterologous polynucleotide sequence to produce at least one C40 carotenoid compound.

2. The microorganism according to claim 1, further comprising a polynucleotide sequence that expresses the heterologous gene sequence idi from *Escherichia vulneris* or comprising a polynucleotide sequence that has at least 70% sequence identity thereto and that retains the biological activity thereof or comprising a polynucleotide sequence that encodes a polypeptide that has at least 70% sequence identity to the encoded idi polypeptide from *Escherichia vulneris* and that retains the biological activity thereof.

3. The microorganism according to claim 1, comprising at least one heterologous polynucleotide comprising polynucleotide sequences that comprise the gene sequences crtZ, crtY, crtI, crtB, and crtE from *Paracoccus zeaxanthinifaciens*, *Escherichia vulneris*, and/or *Pantoea ananatis* or comprising polynucleotide sequences that have at least 70% sequence identity thereto and that retain the biological activity thereof or comprising polynucleotide sequences that that encode polypeptides that have at least 70% sequence identity to the encoded crtZ, crtY, crtI, crtB, and crtE polypeptides from *Paracoccus zeaxanthinifaciens*, *Escherichia vulneris*, and/or *Pantoea ananatis*, and that retain the biological activity thereof, operably linked to a promoter for expression of said polynucleotide sequences, wherein the microorganism produces zeaxanthin.

4. The microorganism according to claim 3, further comprising a heterologous polynucleotide sequence that comprises the gene sequences crtW from *Fulvimarina pelagi* or comprising a polynucleotide sequence that has at least 70% sequence identity thereto and that retains the biological activity thereof or comprising a polynucleotide sequence that encodes a polypeptide that has at least 70% sequence identity to the encoded crtW polypeptide from *Fulvimarina pelagi* and that retains the biological activity thereof, wherein the microorganism produces astaxanthin.

5. The microorganism according to claim 1, comprising at least one heterologous polynucleotide comprising the gene sequences crtY, crtI, crtB, and crtE from *Paracoccus zeaxanthinifaciens*, *Escherichia vulneris*, and/or *Pantoea ananatis* or comprising polynucleotide sequences that have at least 70% sequence identity thereto and that retain the biological activity thereof or comprising polynucleotide sequences that that encode polypeptides that have at least 70% sequence identity to the encoded crtY, crtI, crtB, and crtE polypeptides from *Paracoccus zeaxanthinifaciens*, *Escherichia vulneris*, and/or *Pantoea ananatis*, and that retain the biological activity thereof, operably linked to a promoter for expression of said polynucleotide sequences, wherein the microorganism produces β-carotene.

6. The microorganism according to claim 5, further comprising a heterologous polynucleotide sequence that comprises the gene sequences crtW from *Fulvimarina pelagi* or comprising a polynucleotide sequence that has at least 70% sequence identity thereto and that retains the biological activity thereof or comprising a polynucleotide sequence that encodes a polypeptide that has at least 70% sequence identity to the encoded crtW polypeptide from *Fulvimarina pelagi* and that retains the biological activity thereof, wherein the microorganism produces canthaxanthin.

7. The microorganism according to claim 1, wherein the microorganism is capable of producing the at least one C40 carotenoid compound by consuming at least one C1 compound as a carbon source.

8. The microorganism according to claim 1, wherein the microorganism is capable of producing the at least one C40 carotenoid compound by consuming at least one C2 compound as a carbon source.

9. The microorganism according to claim 1, wherein the microorganism is capable of producing the at least one C40 carotenoid compound by consuming a combination of at least one C1 compound and at least one C2 compound as carbon sources.

10. The microorganism according to claim 1, wherein the microorganism is capable of producing the at least one C40 carotenoid compound by consuming at least one C1 alcohol and/or at least one C2 alcohol as carbon sources.

11. A method for producing biomass that comprises at least one C40 carotenoid compound, comprising culturing the microorganism according to claim 1 in a culture medium under conditions suitable for growth of the microorganism and production of said C40 carotenoid compound, wherein biomass comprising said C40 carotenoid compound is produced in the culture.

12. The method according to claim 11, comprising culturing the microorganism in a medium comprising a C1 compound and/or a C2 compound as a carbon source.

* * * * *